US008828395B2

(12) United States Patent
Watkins et al.

(10) Patent No.: US 8,828,395 B2
(45) Date of Patent: Sep. 9, 2014

(54) ANTIBODIES THAT BIND TYROSYL-TRNA SYNTHETASES

(75) Inventors: Jeffry Dean Watkins, Encinitas, CA (US); Alain P. Vasserot, Carlsbad, CA (US); Rajesh Belani, San Diego, CA (US); Leslie Ann Greene, San Diego, CA (US); Ryan Andrew Adams, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 167 days.

(21) Appl. No.: 13/162,559

(22) Filed: Jun. 16, 2011

(65) Prior Publication Data
US 2012/0064082 A1 Mar. 15, 2012

Related U.S. Application Data

(63) Continuation-in-part of application No. 12/965,655, filed on Dec. 10, 2010.

(60) Provisional application No. 61/285,907, filed on Dec. 11, 2009, provisional application No. 61/304,283, filed on Feb. 12, 2010, provisional application No. 61/334,127, filed on May 12, 2010, provisional application No. 61/359,767, filed on Jun. 29, 2010.

(51) Int. Cl.
A61K 39/395 (2006.01)
C07K 16/40 (2006.01)

(52) U.S. Cl.
CPC ............. C07K 16/40 (2013.01); *C07K 2317/20* (2013.01); *C07K 2317/33* (2013.01); *A61K 39/39533* (2013.01)
USPC .................. 424/146.1; 424/141.1; 424/152.1; 530/388.1; 530/388.25; 530/389.1

(58) Field of Classification Search
None
See application file for complete search history.

(56) References Cited

U.S. PATENT DOCUMENTS

| | | | |
|---|---|---|---|
| 6,013,483 A | 1/2000 | Coleman et al. |
| 6,225,060 B1 | 5/2001 | Clark et al. |
| 6,428,960 B1 | 8/2002 | Clark et al. |
| 6,548,060 B1 | 4/2003 | Kim |
| 6,864,226 B1 | 3/2005 | Coleman et al. |
| 6,903,189 B2 | 6/2005 | Schimmel et al. |
| 7,045,301 B2 | 5/2006 | Coleman et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,413,885 B2 | 8/2008 | Schimmel et al. |
| 7,459,529 B2 | 12/2008 | Kim |
| 7,476,651 B2 | 1/2009 | Schimmel et al. |
| 7,482,326 B2 | 1/2009 | Coleman et al. |
| 7,521,215 B2 | 4/2009 | Schimmel et al. |
| 7,528,106 B2 | 5/2009 | Friedlander et al. |
| 7,786,085 B2 | 8/2010 | Rodgers et al. |
| 7,842,467 B1 | 11/2010 | Heidbrink et al. |
| 7,901,917 B2 | 3/2011 | Schimmel et al. |
| 7,902,165 B2 | 3/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 2002/0182666 A1 | 12/2002 | Schimmel et al. |
| 2003/0017564 A1 | 1/2003 | Schimmel et al. |
| 2003/0215827 A1 | 11/2003 | Yue et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2005/0196754 A1 | 9/2005 | Drmanac et al. |
| 2006/0024288 A1 | 2/2006 | Glidden |
| 2006/0046250 A1 | 3/2006 | Kim |
| 2006/0078553 A1 | 4/2006 | Glidden |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2009/0227662 A1 | 9/2009 | Schimmel et al. |
| 2009/0285792 A1 | 11/2009 | Friedlander et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0138941 A1 | 6/2010 | Kim et al. |
| 2010/0297149 A1 | 11/2010 | Zhou et al. |
| 2010/0310576 A1 | 12/2010 | Adams et al. |

(Continued)

FOREIGN PATENT DOCUMENTS

CN 1341725 3/2002
CN 1341727 3/2002

(Continued)

OTHER PUBLICATIONS

Mihovilovic et al., J Biol Chem. Apr. 15, 1987;262(11):4978-86.*
Ealey et al., Endocrinology. Jan. 1985;116(1):124-31, abstract only.*
Trischitta et al., J Biol Chem. Mar. 25, 1989;264(9):5041-6.*
Algiman et al., Proc Natl Acad Sci U S A. May 1, 1992;89(9):3795-9.*
Colburn, W. A., "Specific antibodies and fab fragments to alter the pharmacokinetics and reverse the pharmacologic/toxicologic effects of drugs," Drug Metabolism Reviews, 1980, vol. 11, No. 2, pp. 223-262.*
Greenberg et al., FASEB J. May 2008;22(5):1597-605. doi: 10.1096/fj.07-9973com. Epub Dec. 28, 2007.*
Rozhko et al., Ukr Biokhim Zh. May-Jun. 1997;69(3):9-16.*
International Preliminary Report on Patentability for International Application No. PCT/US2009/036826, dated Sep. 14, 2010.
International Preliminary Report on Patentability for International Application No. PCT/US2009/048915, dated Jan. 5, 2011.
International Search Report and Written Opinion for International Application No. PCT/US2009/048915, mailed Nov. 2, 2009.

(Continued)

*Primary Examiner* — Michael Szperka

(57) ABSTRACT

Hematopoietic-modulating compositions are provided comprising aminoacyl-tRNA synthetase polypeptides, including active fragments and/or variants thereof, as well as compositions comprising related agents such as antibodies and other binding agents. Also provided are methods of using such compositions in the treatment of conditions that benefit from the modulation of hematopoiesis.

5 Claims, 16 Drawing Sheets

(56) References Cited

U.S. PATENT DOCUMENTS

| | | |
|---|---|---|
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2013/0230508 A1 | 9/2013 | Greene et al. |

FOREIGN PATENT DOCUMENTS

| | | |
|---|---|---|
| CN | 1352242 | 6/2002 |
| CN | 1352252 | 6/2002 |
| EP | 0893494 | 1/1999 |
| EP | 0893496 | 1/1999 |
| EP | 0897004 | 2/1999 |
| EP | 1274834 B1 | 1/2003 |
| EP | 1275720 | 1/2003 |
| EP | 1300468 | 4/2003 |
| EP | 1377305 | 1/2007 |
| EP | 1776138 B1 | 4/2007 |
| WO | WO 97/26351 | 7/1997 |
| WO | WO 97/39017 | 10/1997 |
| WO | WO 99/45130 | 9/1999 |
| WO | WO 01/74841 | 10/2001 |
| WO | WO 01/75067 | 10/2001 |
| WO | WO 01/75078 | 10/2001 |
| WO | WO 01/90330 | 11/2001 |
| WO | WO 01/94568 | 12/2001 |
| WO | WO 02/04611 | 1/2002 |
| WO | WO 02/055663 A2 | 7/2002 |
| WO | WO 02/059323 | 8/2002 |
| WO | WO 02/067970 | 9/2002 |
| WO | WO 03/009813 A2 | 2/2003 |
| WO | WO 03/031589 | 4/2003 |
| WO | WO 03/080648 | 10/2003 |
| WO | WO 03/094862 | 11/2003 |
| WO | WO 2004/023973 | 3/2004 |
| WO | WO 2005/102395 A1 | 11/2005 |
| WO | WO 2005/117954 A2 | 12/2005 |
| WO | WO 2006/016217 | 2/2006 |
| WO | WO 2006/034332 | 3/2006 |
| WO | WO 2006/057500 A1 | 6/2006 |
| WO | WO 2007/064941 | 6/2007 |
| WO | WO 2008/007818 A1 | 1/2008 |
| WO | WO 2008/016356 | 2/2008 |
| WO | WO 2008/021290 | 2/2008 |
| WO | WO 2008/127900 | 10/2008 |
| WO | WO 2008/133359 A1 | 11/2008 |
| WO | WO 2009/114623 | 9/2009 |
| WO | WO 2009/152247 | 12/2009 |
| WO | WO 2009/158649 | 12/2009 |
| WO | WO 2009152247 A2 * | 12/2009 |
| WO | WO 2010/021415 A1 | 2/2010 |
| WO | WO 2010/041892 A2 | 4/2010 |
| WO | WO 2010/041913 A2 | 4/2010 |
| WO | WO 2010/090471 A2 | 8/2010 |
| WO | WO 2010/096170 A2 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2012/027611 | 3/2012 |
| WO | WO 2013/022982 | 2/2013 |

OTHER PUBLICATIONS

Office Action for U.S. Appl. No. 12/482,151, mailed Oct. 11, 2011.
Office Action for U.S. Appl. No. 12/482,151, mailed Mar. 18, 2011.
International Preliminary Report on Patentability for International Application No. PCT/US2009/046910, dated Dec. 13, 2010.
International Search Report and Written Opinion for International Application No. PCT/US2009/046910, mailed Mar. 4, 2010.
Supplementary European Search Report for European Application No. EP06838844, dated Mar. 26, 2009 (10 pages).
Office Action dated Apr. 9, 2009, for European Patent Application No. EP 06838844.6, 10 pages.
Office Action for U.S. Appl. No. 12/085,884, mailed Jan. 20, 2011.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
Office Action for U.S. Appl. No. 13/239,796, mailed Nov. 14, 2012.
International Preliminary Report on Patentability for International Application No. PCT/US2010/025642, dated Aug. 30, 2011.
International Search Report and Written Opinion for International Application No. PCT/US2010/025642, mailed Oct. 29, 2010.
Office Action for U.S. Appl. No. 12/751,358, mailed Oct. 3, 2011.
Office Action for U.S. Appl. No. 12/751,358, mailed Mar. 3, 2011.
International Preliminary Report on Patentability for International Application No. PCT/US2010/029377, dated Oct. 4, 2011.
International Search Report and Written Opinion for International Application No. PCT/US2010/029377, mailed Jan. 26, 2011.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
Office Action for U.S. Appl. No. 12/965,655, dated Mar. 27, 2013.
International Search Report and Written Opinion for International Application No. PCT/US2010/059964, mailed Aug. 25, 2011.
International Preliminary Report on Patentability for International Application No. PCT/US2010/059963, dated Jun. 12, 2012.
International Search Report and Written Opinion for International Application No. PCT/US2010/059963, mailed May 12, 2011.
European Communication Pursuant to Article 94(3) EPC, for EP Application No. 10 793 402.8 dated Mar. 27, 2013.
International Search Report and Written Opinion for International Application No. PCT/US2011/000210, mailed Aug. 12, 2011.
Adams, M. D. et al., "The genome sequence of *Drosophila melanogaster*," Science, 287(5961):2185-2195, 2000.
Aderem, A. et al., "Toll-like receptors in the induction of the innate immune response," Nature, 406:782-787, 2000.
Amaar, Y. G. et al., "Cloning and characterization of the *C.elegans* histidyl-tRNA synthetase gene," Nucleic Acids Research, 21(18):4344-4347, 1993.
Antonellis et al., "Functional Analyses of Glycyl-tRNA Synthetase Mutations Suggest a Key Role for tRNA-Charging Enzymes in Peripheral Axons," The Journal of Neuroscience 26(41):10397-10406, 2006.
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134, 2002.
Ascherman, D. P., "The Role of Jo-1 in the Immunopathogenesis of Polymyositis: Current Hypotheses," Current Rheumatology Reports, 5:425-430, 2003.
Bernstein, R. M. et al., "Anti-Jo-1 antibody: a marker for myositis with interstitial lung disease," British Medical Journal, 289:151-152, 1984.
BIOSIS (Biological Abstracts) Accession No. PREV200300183746, 2003.
BIOSIS (Biological Abstracts) Accession No. PREV200300256685, 2003.
BIOSIS (Biological Abstracts) Accession No. PREV200400442099, 2004.
BIOSIS (Biological Abstracts) Accession No. PREV200700042366, 2007.
BIOSIS (Biological Abstracts) Accession No. PREV200800526912, 2008.
Blum et al., "Extracellular toxicity of 6-hydroxydopamine on PC12 cells," Neurosci. Lett., 283(3):193-196, 2000.

(56) References Cited

OTHER PUBLICATIONS

Brightbill, H. D. et al., "Toll-like receptors: molecular mechanisms of the mammalian immune response," Immunology, 101:1-10, 2000.
Broun, P. et al., "Catalytic plasticity of fatty acid modification enzymes underlying chemical diversity of plant lipids," Science, 282:1315-1317, 1998.
Brown, M. V. et al., "Mammalian aminoacyl-tRNA synthetases: cell signaling functions of the protein translation machinery," Vascular Pharmacology, 52(1-2):21-26, 2010.
Casciola-Rosen, L., et al., "Cleavage by Granzyme B Is Strongly Predictive of Autoantigen Status: Implications for Initiation of Autoimmunity," J. Exp. Med., 190(6):815-825, 1999.
Casciola-Rosen, L., "Histidyl-Transfer RNA Synthetase: A Key Participant in Idiopathic Inflammatory Myopathies," Arthritis and Rheumatism, 63(2):331-333, 2011.
Cheng, G. et al., "Effect of mini-tyrosyl-tRNA synthetase on ischemic angiogenesis, leukocyte recruitment, and vascular permeability," American Journal Physiol. Regul. Integr. Comp. Physiol., 295:1138-1146, 2008.
Chica, R. A. et al., "Semi-rational approaches to engineering enzyme activity: combining the benefits of directed evolution and rational design," Curr. Opin. Biotechnol., 16:378-384, 2005.
Choi et al., "Two Distinct Mechanisms Are Involved in 6-Hydroxydopamine-and MPP+-Induced Dopaminergic Neuronal Cell Death: Role of Caspases, ROS, and JNK," J. Neurosci. Res., 57(1):86-94, 1999.
Copley, "Enzymes with extra talents: moonlighting functions and catalytic promiscuity," Current Opinion in Chemical Biology, 7:265-272, 2003.
DeBruyn et al., "Ex vivo Expansion of Megakaryocyte Progenitor Cells: Cord Blood Versus Mobilized Peripheral Blood," Stem Cells Development, 14:415-424, 2005.
Delgado, C. et al., "The uses and properties of PEG-linked proteins," Critical Reviews in Therapeutic Drug Carrier Systems, 9(3,4):249-304, 1992.
De Pouplana, L. R. et al., "Evidence that two present-day components needed for the genetic code appeared after nucleated cells separated from eubacteria," Proc. Natl. Acad. Sci. USA, 93:166-170, 1996.
Dessypris et al., "Thrombopoiesis-stimulating Factor: Its Effects on Megakaryocyte Colony Formation in vitro and Its Relation to Human Granulocyte-Macrophage Colony-stimulating Factor," Exp. Hematol. 18:754-757, 1990.
Devos, D. et al., "Practical limits of function prediction," Proteins: Structure, Function, and Genetics, 41:98-107, 2000.
Ewalt, K. L. et al., "Activation of Angiogenic Signaling Pathways by Two Human tRNA Synthetases," Biochemistry, 41:13344-13349, 2002.
Froelich et al., "Dominant Intermediate Charcot-Marie-Tooth disorder is not due to a catalytic defect in tyrosyl-tRNA synthetase," Biochemistry, 59 pages, 2011.
Frommhold, D. et al., "Sialyltransferase ST3Gal-IV controls CXCR2-mediated firm leukocyte arrest during inflammation," Journal of Experimental Medicine, 205(6):1435-1446, 2008.
Fu et al., "tRNA-controlled Nuclear Import of a Human tRNA Synthetase," *Journal of Biological Chemistry*, 287(12):9330-9334, 2012.
Garcia-Lozano, J. R. et al., "Detection of anti-PL-12 autoantibodies by ELISA using a recombinant antigen; study of the immunoreactive region," Clin. Exp. Immunol., 114:161-165, 1998.
GenBank Accession No. AA174042, Sep. 30, 1997.
GenBank Accession No. A1963202, Aug. 20, 1999.
GenBank Accession No. AK074524, Mar. 25, 2002.
GenBank Accession No. AU126197, Oct. 23, 2000.
GenBank Accession No. AW976267, Jun. 2, 2000.
GenBank Accession No. B1258770, Jul. 16, 2001.
GenBank Accession No. BP423196, May 27, 2005.
GenBank Accession No. CA314607, Nov. 4, 2002.
GenBank Accession No. DA018291, Nov. 2, 2005.
GenBank Accession No. DA386636, Nov. 5, 2005.
GenBank Accession No. DA478765, Nov. 6, 2005.
GenBank Accession No. DA552410, Nov. 5, 2005.
GenBank Accession No. DA576766, Nov. 5, 2005.
GenBank Accession No. DB488998, Mar. 31, 2006.
GenBank Accession No. DC366890, Apr. 27, 2007.
GenBank Accession No. DB058369, Dec. 10, 2005.
GenBank Accession No. A1352487, Dec. 30, 1998.
GenBank Accession No. A1821854, Jul. 9, 1999.
GenBank Accession No. AJ706186, Jun. 30, 2004.
GenBank Accession No. AK125213, Jul. 3, 2008.
GenBank Accession No. AK126444, Jan. 9, 2008.
GenBank Accession No. AK127182, Jan. 9, 2008.
GenBank Accession No. BC001933, Jul. 15,2006.
GenBank Accession No. BE561651, Aug. 10, 2000.
GenBank Accession No. BF205419, Nov. 3, 2000.
GenBank Accession No. BF308942, Nov. 20, 2000.
GenBank Accession No. BF876481, Jan. 17, 2001.
GenBank Accession No. BG165437, Feb. 5, 2001.
GenBank Accession No. BM917050, Mar. 11, 2002.
GenBank Accession No. BQ231273, May 1, 2002.
GenBank Accession No. BX440782, May 15, 2003.
GenBank Accession No. CX753411, Jan. 22, 2005.
GenBank Accession No. DA119890, Oct. 30, 2005.
GenBank Accession No. DA157534, Oct. 30, 2005.
GenBank Accession No. DA158736, Oct. 30, 2005.
GenBank Accession No. DA269700, Oct. 30, 2005.
GenBank Accession No. DA769799, Nov. 11, 2005.
GenBank Accession No. DA942238, Nov. 13, 2005.
GenBank Accession No. Q7QD89, Nov. 28, 2006.
GenBank Accession No. Z28811, Dec. 14, 1993.
GenBank Accession No. Q9VV60, published May 1, 2000.
GenBank Accession No. Z11518, published Oct. 7, 2008.
GenBank Accession No. Q7QD89, Anopheles gambiae Sequence Committee, submitted Apr. 2002 (Retrieved from the Internet on Apr. 24, 2007): http://www.ncbi.nlm.nih.gov/entrez/viewer.fcgi?db=protein&val=74803944.
GenBank Accession No. U09587, Dec. 9, 1994.
Goldgur, Y. et al., "The crystal structure of phenylalanyl-tRNA synthetase from *Thermus thermophilus* complexed with cognate tRNA," Structure, 5:59-68, 1997.
Greenberg, Y. et al., "The novel fragment of tyrosyl tRNA synthetase, mini-TyrRS, is secreted to induce an angiogenic response in endothelial cells," FASEB Journal, 22(5):1597-1605, 2008.
Guijarro, J. I. et al., "Structure and Dynamics of the Anticodon Arm Binding Domain of *Bacillus stearothermophilus* Tyrosyl-tRNA Synthetase," Structure, 10:311-317, 2002.
Guo, M. et al., "Functional expansion of human tRNA synthetases achieved by structural inventions," FEBS Letters, 584:434-442, 2010.
Guo, M. et al.,"New functions of aminoacyl-tRNA synthetases beyond translation," Nature Reviews Molecular Cell Biology, 11:668-674, 2010.
Guo, R-T. et al., "Crystal structures and biochemical analyses suggest a unique mechanism and role for human glycyl-tRNA synthetase in Ap4A homeostasis," Journal of Biological Chemistry, 284(42):28968-28976, 2009.
Hanrott et al., "6-Hydroxydopamine-induced Apoptosis Is Mediated via Extracellular Auto-oxidation and Caspase 3-dependent Activation of Protein Kinase C8," J. Biol. Chem., 281(9):5373-5382, 2006.
Hausmann et al., "Aminoacyl-tRNA synthetase complexes: molecular multitasking revealed," FEMS Microbiol. Rev., 32(4):705-721, 2008.
Hengstman, G. J. D. et al., "Anti-Jo-1 positive inclusion body myositis with a marked and sustained clinical improvement after oral prednisone," J. Neurol. Neurosurg. Psychiatry, 70:702-710, 2001.
Hou, Y-M. et al., "Sequence determination and modeling of structural motifs for the smallest monomeric aminoacyl-tRNA synthetase," Proc. Nat. Acad. Sci., 88(3):976-980, 1991.
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791, 2002.

(56) References Cited

OTHER PUBLICATIONS

Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255, 2004.

Ivanov et al., "Non-canonical Functions of Aminoacyl-tRNA Synthetases," Biochemistry (Moscow), 65(8):1047-1057, 2000.

Izumi et al., "p-Quinone Mediates 6-Hydroxydopamine-Induced Dopaminergic Neuronal Death and Ferrous Iron Accelerates the conversion of p-Quinone Into Melanin Extracellularly," J. Neurosci. Res., 79(6):849-860, 2005.

Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612, 1989.

Jordanova, A. et al., "Disrupted function and axonal distribution of mutant tyrosyl-tRNA synthetase in dominant intermediate Charcot-Marie-Tooth neuropathy," Nature Genetics, 38(2):197-202, 2006.

Jura, M. et al., "Comprehensive Insight into Human Aminoacyl-tRNA Synthetases as Autoantigens in Idiopathic Inflammatory Myopathies," Critical Reviews in Immunology, 27(6):559-572, 2007.

Kapoor, M. et al., "Mutational separation of aminoacylation and cytokine activities of human tyrosyl-tRNA synthetase," Chemistry & Biology, 16(5):531-539, 2009.

Katsumata, Y. et al., "Species-specific immune responses generated by histidyl-tRNA synthetase immunization are associated with muscle and lung inflammation," Journal of Autoimmunity, 29:174-186, 2007.

Katsumata, Y. et al., "Animal models in myositis," Current Opinion in Rheumatology, 20:681-685, 2008.

Kimchi-Sarfaty, C. et al., "A 'Silent' polymorphism in the MDR1 gene changes substrate specificty," Science, 315:525-528, 2007.

Kise, Y. et al., "A short peptide insertion crucial for angiostatic activity of human tryptophanyl-tRNA synthetase," Nature Structural & Molecular Biology, 11(2):149-156, 2004.

Kleeman, T. A. et al., "Human Tyrosyl-tRNA Synthetase Shares Amino Acid Sequence Homology with a Putative Cytokine," The Journal of Biological Chemistry, 272(22):14420-14425, 1997.

Kochendoerfer, G. G., "Site-specific polymer modification of therapeutic proteins," Current Opinion in Chemical Biology, 9:555-560, 2005.

Kordysh, M. et al., "Conformational Flexibility of Cytokine-Like C-Module of Tyrosyl-tRNA Synthetase Monitored by Trp 144 Intrinsic Fluorescence," J. Fluoresc., 16:705-711, 2006.

Kovaleski, B. J. et al.,"In vitro characterization of the interaction between HIV-1 Gag and human lysyl-tRNA synthetase," J. Bio. Chem., 281(28):9449-9456, 2006.

Lee, J. W. et al., "Editing-defective tRNA synthetase causes protein misfolding and neurodegeneration," Nature, 443:50-55, 2006.

Lee et al., "Uncovering of a Short Internal Peptide Activates a tRNA Synthetase Procytokine," *Journal of Biological Chemistry*, 287(24):20504-20508, 2012.

Leitao-Goncalves, R. et al., "*Drosophila* as a platform to predict the pathogenicity of novel aminoacyl-tRNA synthetase mutations in CMT," Amino Acids, 2011.

Levine, S. M. et al., "Anti-aminoacyl tRNA synthetase immune responses: insights into the pathogenesis of the idiopathic inflammatory myopathies," Current Opinion in Rheumatology, 15(6):708-713, 2003.

Link, A. J. et al., "Discovery of aminoacyl-tRNA synthetase activity through cell-surface display of noncanonical amino acids, " Proc. Nat. Acad. Sci., 103(27):10180-10185, 2006.

Liu, J. et al., "Mutational Switching of a Yeast tRNA Synthetase into a Mammalian-like Synthetase Cytokine," Biochemistry, 41:14232-14237, 2002.

Motley, W. W. et al., "GARS axonopathy: not every neuron's cup of tRNA," Trends Neurosci., 33(2):59, 2010.

Nackley et al., "Human Caechol-O-Methytransferase haplotypes modulate protein expression by altering mRNA secondary structure," Science, 314:1930-1933, 2006.

Nangle, L. A. et al., "Charcot-Marie-Tooth disease-associated mutant tRNA synthetases linked to altered dimer interface and neurite distribution defect," PNAS, 104(27):11239-11244, 2007.

Ngo, J. T. et al., "Computational complexity, protein structure prediction, and the Levinthal paradox," The Protein Folding Problem and Tertiary Structure Prediction, Merz et al. (ed.), Birkhauser, Boston, MA, pp. 433 and 492-495, 1994.

Nichols, R. C. et al., "Human isoleucyl-tRNA synthetase: sequence of the cDNA, alternative mRNA splicing, and the characteristics of an unusually long C-terminal extension," Gene, 155(2):299-304, 1995.

Nishikai, M. et al., "Heterogeneity of Precipitating Antibodies in Polymyositis and Dermatomyositis," Arthritis and Rheumatism, 23(8):881-888, 1980.

Otani, A. et al., "A fragment of human TrpRS as a potent antagonist of ocular angiogenesis," PNAS, 99(1):178-183, 2002.

Park, S. G. et al., "Dose-dependent biphasic activity of tRNA synthetase-associating factor, p43, in angiogenesis," The Journal of Biological Chemistry, 277(47):45243-45248, 2002.

Park, S. G. et al., "Is there an answer? Do aminoacyl-tRNA synthetases have biological functions other than in protein biosynthesis?" IUBMB Life, 58(9):556-558, 2006.

Park, S. G. et al., "Aminoacyl tRNA synthetases and their connections to disease," PNAS, 105(32):11043-11049, 2008.

Parker et al., "Toll-Like Receptor (TLR)2 and TLR4 Agonists Regulate CCR Expression in Human Monocytic Cells," J. Immunol., 172:4977-4986, 2004.

Paukstelis, P. J. et al., "A Tyrosyl-tRNA Synthetase Adapted to Function in Group I Intron Splicing by Acquiring a New RNA Binding Surface," Molecular Cell, 17:417-428, 2005.

Paukstelis, P. J. et al., "NMR Structure of the C-Terminal Domain of a Tyrosyl-tRNA Synthetase That Functions in Group I Intron Splicing," Biochemistry, 50:3816-3826, 2011.

Paukstelis, P. J. et al., "Structure of a tyrosyl-tRNA synthetase splicing factor bound to a group I intron RNA," Nature, 451:94-98, 2008.

Quesniaux, V. F.J. et al., "Hematopoiesis, including lymphocyte developmet and maturation," Principles of Immunopharmacology, pp. 3-17, 2005.

Quinn, C. L. et al., "Species-Specific Microhelix Aminoacylation by a Eukaryotic Pathogen tRNA Synthetase Dependent on a Single Base Pair," Biochemistry, 34(39):12489-12495, 1995.

Reed, V. S. et al., "Characterization of a Novel N-terminal Peptide in Human Aspartyl-tRNA Synthetase," Journal of Biological Chemistry, 269(52):32937-32941, 1994.

Richardson, R. M. et al., "Role of the cytoplasmic tails of CXCR1 and CXCR2 in mediating leukocyte migration, activation, and regulation," Journal of Immunology, 170(6):2904-2911, 2003.

Riley, L. G. et al., "Mutation of the Mitochondrial Tyrosyl-tRNA Synthetase Gene, YARS2, Causes Myopathy, Lactic Acidosis, and Sideroblastic Anemia-MLASA Syndrome," The American Journal of Human Genetics, 87:52-59, 2010.

Rios-Santos, F. et al., "Down-regulation of CXCR2 on Neutrophils in Severe Sepsis Is Mediated by Inducible Nitric Oxide Synthase-derived Nitric Oxide," Am. J. Respir. Crit. Care. Med., 175:490-497, 2007.

Sasarman et al., "A Novel Mutation in YARS2 Causes Myopathy with Lactic Acidosis and Sideroblastic Anemia," *Human Mutation*, 00(0):1-6, 2012.

Sauna, Z. E. et al., "Silent polymorhisms speak: How they affect pharmacogenomics and the treatment of cancer," Cancer Res., 67(20):9609-9612, 2007.

Schluesener, H., "Tyrosyl- tRNA Synthetase: A Housekeeping Protein and an Attractive Harbinger of Cellular Death," Angew. Chem. Int,. Ed. 38(24):3635-3637, 1999.

Seburn, K. L. et al., "An active dominant mutation of glycyl-tRNA synthetase causes neuropathy in a Charcot-Marie-Tooth 2D mouse model," Neuron, 51(6):715-726, 2006.

Sen, S. et al., "Developments in directed evolution for improving enzyme functions," Appl. Biochem. Biotechnol., 143:212-223, 2007.

(56) References Cited

OTHER PUBLICATIONS

Smith, D. F. et al., "Leukocyte phosphoinositide-3 kinase γ is required for chemokine-induced, sustained adhesion under flow in vivo," Journal of Leukocyte Biology, 80(6):1491-1499, 2006.

Soejima, M. et al., "Role of Innate Immunity in a Murine Model of Histidyl-Transfer RNA Snythetase (Jo-1)-Mediated Myositis," Arthritis and Rheumatism, 63(2):479-487, 2011.

Steer, B. A. et al., "Domain-domain communication in a miniature archaebacterial tRNA synthetase," PNAS, 96(24):13644-13649, 1999.

Steer, B. A. et al., "Major Anticodon-binding Region Missing from an Archaebacterial tRNA Synthetase," The Journal of Biological Chemistry, 274(50):35601-35606, 1999.

Storkebaum, E. et al., "Dominant mutations in the tyrosyl-tRNA synthetase gene recapitulate in *Drosophila* features of human Charcot-Marie-Tooth neuropathy," PNAS, 106(28):11782-11787, 2009.

Stum, M. et al., "An assessment of mechanisms underlying peripheral axonal degeneration caused by aminoacyl-tRNA synthetase mutations," Molecular and Cellular Neuroscience, 46:432-443, 2011.

Suzuki, K-I. et al., "Efficient assay for evaluating human thrombopoiesis using NOD/SCID mice transplanted with cord blood CD34 cells," Journal Compilation, 78:123-130, 2006.

Targoff, I. N. et al., "Antibodies to glycyl-transfer RNA synthetase in patients with myositis and interstitial lung disease," Arthritis Rheum., 35(7):821-830, 1992.

Targoff, I. N., "Update on myositis-specific and myositis-associated autoantibodies," Current Opinion in Rheumatology, 12:475-481, 2000.

Traves, S. L. et al., "Specific CXC but not CC chemokines cause elevated monocyte migration in COPD: a role for $CXCR_2$," Journal of Leukocyte Biology, 76(2):441-450, 2004.

Tzima, E. et al., "Inhibition of tumor angiogenesis by a natural fragment of a tRNA synthetase," TRENDS in Biochemical Sciences, 31(1):7-10, 2006.

Tzioufas, A. G. et al., "Antisynthetase syndrome," Orphanet Encyclopedia, http://www.orpha.net/data/patho/GB/uk-antisynthetase. pdf, pp. 1-5 Nov. 2001.

Veronese, F. M. et al., "Preface: Introduction and overview of peptide and protein pegylation," Advanced Drug Delivery Reviews, 54:453-456, 2002.

Vo et al., "Dissociating Quaternary Structure Regulates Cell-signaling Functions of a Secreted Human tRNA Synthetase," The Journal of Biological Chemistry, 286(13):11563-11568, 2011.

Wakasugi, K. et al., "A human aminoacyl-tRNA synthetase as a regulator of angiogenesis," Proc. Natl. Acad. Sci., 99(1):173-177, 2002.

Wakasugi, K. et al., "Induction of angiogenesis by a frament of human tyrosyl-tRNA synthetase," The Journal of Biological Chemistry, 277(23):20124-20126, 2002.

Wakasugi, K. et al., "Two distinct cytokines released from a human aminoacyl-tRNA synthetase," Science, 284:147-151, 1999.

Wakasugi et al., "Highly Differentiated Motifs Responsible for Two Cytokine Activities of a Split Human tRNA Synthetase," The Journal of Biological Chemistry, 274(33):23155-23159, 1999.

Wasenius, V-M et al., "Hepatocyte Growth Factor Receptor, Matrix Metalloproteinase-11, Tissue Inhibitor of Metalloproteinase-1, and Fibronectin Are Up-Regulated in Papillary Thyroid Carcinoma: A cDNA and Tissue Microarray Study," Clin. Cancer Res., 9:68-75, 2003.

Whisstock, J. C. et al., "Prediction of protein function from protein sequence," Q. Rev. Biophysics., 36(3):307-340, 2003.

Wishart, M. J. et al., "A single mutation converts a novel phosphotyrosine binding domain into a dual-specificity phosphatase," J. Biol. Chem., 270(45):26782-26785, 1995.

Witkowski, A. et al., "Conversion of β-ketoacyl synthase to a Malonyl Decarboxylase by replacement of the active cysteine with glutamine," Biochemistry, 38:11643-11650, 1999.

Xie et al., "Crystallization and preliminary X-ray analysis of a native human tRNA synthetase whose allelic variants are associated with Charcot-Marie-Tooth disease," Acta. Cryst., F62:1243-1246, 2006.

Xie, W. et al., "Long-range structural effects of a Charcot-Marie-Tooth disease-causing mutation in human glycyl-tRNA synthetase," PNAS, 104(24):9976-9981, 2007.

Yang, X-L et al., "Crystal structure of a human aminoacyl-tRNA synthetase cytokine," PNAS, 99(24):15369-15374, 2002.

Yang et al., "Crystal structures that suggest late development of genetic code components for differentiating aromatic side chains," PNAS, 100(26): 15376-15380, 2003.

Yang et al., "Gain-of-Function Mutational Activation of Human tRNA Synthetase Procytokine," Chemistry & Biology, 14:1323-1333, 2007.

Yang, X-L et al., "Relationship of two human tRNA synthetases used in cell signaling," Trends in Biochemical Sciences, 29(5):250-256, 2004.

Yu, Y. et al., "Crystal Structure of Human Tryptophanyl-tRNA Synthetase Catalytic Fragment,"The Journal of Biological Chemistry, 279(9):8378-8388, 2004.

Zalipsky, S. et al., "Use of functionalized poly(ethylene glycol)s for modification of polypeptides," Polyethylene glycol chemistry: Biotechnical and Biomedical Applications, pp. 347-370, Plenum Press, New York, 1992.

Zeng et al., "Different angiogenesis effect of mini-TyrRS/mini-TrpRS by systemic administration of modified siRNAs in rats with acute myocardial infarction," Heart Vessels, 25:324-332, 2010.

Zeng et al., "Effect of mini-tyrosyl-tRNA synthetase/mini-tryptophanyl-tRNA synthetase on ischemic angiogenesis in rats: proliferation and migration of endothelial cells," Heart Vessels, 26:69-80, 2011.

Zwijnenburg, P. J. G. et al., "Tyrosyl tRNA synthetase is a chemotactic factor in cerebrospinal fluid from patients with bacterial meningitis," Abstracts of the Interscience Conference on Antimicrobial Agents and Chemotherapy, 42:55, 2002.

Office Action for U.S. Appl. No. 12/482,151, mailed Aug. 13, 2013.
Response to Office Action dated Apr. 18, 2011, for U.S. Appl. No. 12/085,884.
International Preliminary Report on Patentability for International Application No. PCT/US2010/059964, dated Jun. 12, 2012.
International Search Report and Written Opinion for International Application No. PCT/US2011/049223, mailed Mar. 27, 2012.
International Preliminary Report on Patentability for International Application No. PCT/US2011/049223, dated Feb. 26, 2013.
International Search Report for International Application No. PCT/US2012/050012, mailed Feb. 26, 2013.
Hsu, H-C et al., "Circulating levels of thrombopoietic and inflammatory cytokines in patients with clonal and reactive thrombocytosis," J Lab Clin Med., 1999, 134(4):392-397.
Kobos, R. et al., "Overview of thrombopoietic agents in the treatment of thrombocytopenia," Clinical Lymphoma & Myeloma, 2008, 8(1):33-43.
WPI Database Accession No. 2002-090149.
WPI Database Accession No. 2002-501208.
WPI Database Accession No. 2002-501210.
WPI Database Accession No. 2002-692409.
WPI Database Accession No. 2002-714440.

* cited by examiner

| Variant | NCBI | Annotation | mRNA difference from Reference | NCBI ORF prediction |
|---|---|---|---|---|
| SP1 (SEQ ID NO:7) | AK026535 | Homo sapiens cDNA: FLJ22882 fis, clone KAT03587, highly similar to HSU69435 Human tyrosyl-tRNA synthetase Mrna. Signet-ring cell carcinoma | Skip part of Exon 1, 2 nt-gap in Exon 5 | 348aa |
| SP2 (SEQ ID NO:9) | HSU40714 | Human tyrosyl-tRNA synthetase mRNA, complete cds | Skip Exons 12&13 and part of Exons 1&11, 1 nt-gap in Exon 10 | 388aa (Reported) |
| SP3 (SEQ ID NO:11) | CR628320 | full-length cDNA clone CS0DI088YE17 of Placenta Cot 25-normalized | Skip Exons 1-4, no gap | 215aa |
| SP4 (SEQ ID NO:13) | AK127182 | Homo sapiens cDNA FLJ45247 fis, clone BRCOC2018681, highly similar to Tyrosyl-tRNA synthetase, Corpus callosum (Brain) | Skip Exons 1-8, 1214bp of Intron 8-9 extension before Exon 9, no gap | 179aa |
| SP5 (SEQ ID NO:15) | BC35242 | Homo sapiens tyrosyl-tRNA synthetase, Testis mRNA (cDNA clone IMAGE:4837840), with apparent retained intron | Skip Exons 1-9, 958bp of Intron 9-10 extension before Exon 10, no gap | 188aa |

*FIG. 10*

ANTIBODIES THAT BIND TYROSYL-TRNA SYNTHETASES

CROSS REFERENCE TO RELATED APPLICATIONS

This application is a continuation-in-part of U.S. application Ser. No. 12/965,655, filed Dec. 10, 2010, which claims benefit under 35 U.S.C. §119(e) to U.S. Provisional Application No. 61/285,907, filed Dec. 11, 2009; U.S. Provisional Application No. 61/304,283, filed Feb. 12, 2010; U.S. Provisional Application No. 61/334,127, filed May 12, 2010; and U.S. Provisional Application No. 61/359,767, filed Jun. 29, 2010, all of which are incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120161_419C1_SEQUENCE_LISTING.txt. The text file is about 102 KB, was created on Jun. 14, 2011, and is being submitted electronically via EFS-Web.

BACKGROUND

1. Technical Field

The present invention relates generally to compositions comprising hematopoiesis-modulating aminoacyl-tRNA synthetase (AARS) polypeptides, related agents such as antibodies and binding agents that modulate the activity of the AARS polypeptides, and methods of using such compositions and agents for modulating hematopoiesis.

2. Description of the Related Art

Aminoacyl-tRNA synthetases, which catalyze the aminoacylation of tRNA molecules, are essential for decoding genetic information during the process of translation. In higher eukaryotes, some aminoacyl-tRNA synthetases associate with other polypeptides to form supramolecular multi-enzyme complexes. Each of the eukaryotic tRNA synthetases consists of a core enzyme, which is closely related to the prokaryotic counterpart of the tRNA synthetase, and one or more additional domains that are appended to the amino-terminal or carboxyl-terminal end of the core enzyme. Human tyrosyl-tRNA synthetase (YRS), for example, has a carboxyl-terminal domain that is not part of prokaryotic and lower eukaryotic YRS molecules.

Aminoacyl tRNA synthetases, such as tyrosyl-tRNA synthetase, tryptophan-tRNA synthetase, and others, are associated with expanded functions in mammalian cells, including activities in signal transduction pathways, among others.

BRIEF SUMMARY

The present invention stems from the unexpected finding that compositions comprising aminoacyl-tRNA synthetase (AARS) polypeptides, including truncated fragments, splice variants, proteolytic fragments, and variants thereof, are capable of modulating hematopoiesis. In certain instances, these polypeptides reduce erythropoiesis, or the formation of progenitor cells of the erythroid lineage. In certain instances, these polypeptides enhance megakaryopoiesis, thrombopoiesis and/or the formation of megakaryocyte progenitor cells, either in vivo or ex vivo. Other aspects are detailed herein, including the use of agonists and antagonists of these hematopoiesis-modulating AARS polypeptides.

Accordingly, embodiments of the present invention relate to compositions for modulating hematopoiesis, comprising one or more isolated aminoacyl-tRNA synthetase (AARS) polypeptides, or biologically active fragments or variants thereof, wherein the polypeptides modulate hematopoiesis. In certain embodiments, the AARS polypeptide is a tyrosyl-tRNA synthetase (YRS), a tryptophanyl-tRNA synthetase (WRS), a glutaminyl-tRNA synthetase (QRS), a glycyl-tRNA synthetase (GlyRS), a histidyl-tRNA synthetase (HisRS), a seryl-tRNA synthetase, a phenylalanyl-tRNA synthetase, an alanyl-tRNA synthetase, an asparaginyl-tRNA synthetase (AsnRS), an aspartyl-tRNA synthetase (AspRS), a cysteinyl-tRNA synthetase (CysRS), a glutamyl-tRNA synthetase, a prolyl-tRNA synthetase (ProRS), an arginyl-tRNA synthetase, an isoleucyl-tRNA synthetase, a leucyl-tRNA synthetase, a lysyl-tRNA synthetase, a threonyl-tRNA synthetase, a methionyl-tRNA synthetases, or a valyl-tRNA synthetase.

Certain embodiments include a proteolytic fragment of the AARS polypeptide. In certain embodiments, the sequence of the proteolytic fragment is derived by incubating the polypeptide with a protease in vitro. In certain embodiments, the sequence of the proteolytic fragment is derived by recombinantly expressing the AARS polypeptide in a cell, wherein the cell comprises one or more recombinant or endogenous proteases. In certain embodiments, the proteolytic fragment comprises the sequence of an endogenous, naturally-occurring human or mouse AARS proteolytic fragment.

In certain embodiments, the aminoacyl-tRNA synthetase is a YRS polypeptide. In certain embodiments, the YRS polypeptide is truncated at its C-terminus. In certain embodiments, the YRS polypeptide comprises the amino acid sequence of SEQ ID NO: 1, 2, 3, 6, 8, 10, 12, or 14, wherein at least about 1-50, 50-100, 100-150, 150-200, or about 200-250 amino acid residues are truncated from its C-terminus.

In certain embodiments, the YRS polypeptide is truncated at its N-terminus. In certain embodiments, the YRS polypeptide comprises the amino acid sequence of SEQ ID NO: 1, 2, 3, 6, 8, 10, 12, or 14, wherein at least about 1-50, 50-100, 50-100, 100-150, 150-200, or about 200-250 amino acid residues are truncated from its N-terminus.

In certain embodiments, the YRS polypeptide comprises an amino acid sequence at least 80%, 90%, 95%, 98%, or 100% identical to the amino acid sequence set forth in SEQ ID NO:2, wherein the alanine at position 341 is not substituted with a tyrosine. In certain embodiments, the YRS polypeptide comprises an amino acid sequence at least 80%, 90%, 95%, 98%, or 100% identical to the amino acid sequence set forth in SEQ ID NO: 1, 2, 3, 6, 8, 10, 12, or 14.

In certain embodiments, the aminoacyl-tRNA synthetase is a GlyRS polypeptide. In certain embodiments, the GlyRS polypeptide is a fragment of the full-length human glycyl-tRNA synthetase sequence set forth in SEQ ID NO:16. In certain embodiments, the fragment comprises amino acid residues 367-438 of SEQ ID NO:16, or an active variant thereof. In certain embodiments, the GlyRS polypeptide comprises an amino acid sequence at least 80%, 90%, 95%, 98%, or 100% identical to the amino acid sequence set forth in SEQ ID NO:16. In certain embodiments, the GlyRS polypeptide comprises amino acid residues 57-685, 214-685, 239-685, 311-685, 439-685, 511-658, 214-438, 367-438, 214-420, 214-338, 85-127 1-213, 1-61, 85-214, 333-685, 128-685, 265-685, 483-685 or 25-56 of SEQ ID NO:16, or an active fragment thereof.

In certain embodiments, the aminoacyl-tRNA synthetase is a QRS polypeptide. In certain embodiments, the QRS polypeptide comprises an amino acid sequence at least 80%, 90%, 95%, 98%, or 100% identical to the amino acid sequence set forth in SEQ ID NO:25. In certain embodiments, the QRS polypeptide is truncated at its C-terminus. In certain embodiments, the QRS polypeptide comprises the amino acid sequence of SEQ ID NO:25, wherein at least about 1-50, 50-100, 50-100, 100-150, 150-200, 200-250, 250-300, 300-350, 350-400, 400-450, 450-500, or about 500-550 amino acid residues are truncated from its C-terminus. In certain embodiments, the QRS polypeptide comprises amino acid residues 1-183, 1-220, 1-249, or 1-200 of SEQ ID NO:25, or any one or more of SEQ ID NOS:36-108.

In certain embodiments, the aminoacyl-tRNA synthetase is a HisRS polypeptide. Certain embodiments comprise HisRS splice variant polypeptide. In certain embodiments, the HisRS polypeptide comprises at least the WHEP domain of HisRS. In certain embodiments, the HisRS polypeptide comprises at least the anticodon binding domain of HisRS. In certain embodiments, the HisRS polypeptide lacks a functional aminoacylation domain. In certain embodiments, the HisRS polypeptide comprises at least the WHEP domain of HisRS and the anticodon binding domain of HisRS but lacks a functional aminoacylation domain. In certain embodiments, the HisRS polypeptide comprises the sequence set forth in SEQ ID NO:28, 30, or 32. In certain embodiments, the HisRS polypeptide comprises an amino acid sequence at least 80%, 90%, 95%, 98%, or 100% identical to the amino acid sequence set forth in SEQ ID NO:28, 30, or 32. In certain embodiments, the HisRS polypeptide comprises at least 20 contiguous amino acid residues of the sequence set forth in SEQ ID NO:28, 30, or 32.

In certain embodiments, the aminoacyl-tRNA synthetase is a WRS polypeptide. In certain embodiments, the WRS polypeptide comprises an amino acid sequence at least 80%, 90%, 95%, 98%, or 100% identical to the amino acid sequence set forth in any one or more of SEQ ID NOS:33-35. In certain embodiments, the WRS polypeptide comprises a biologically active fragment of any one or more of SEQ ID NOS:33-35.

Certain embodiments include pharmaceutical compositions for modulating hematopoiesis in a subject, comprising an aminoacyl-tRNA synthetase (AARS) polypeptide as described herein and a pharmaceutically acceptable carrier.

Certain embodiments include methods of modulating hematopoiesis, comprising contacting a cell with an effective concentration of an aminoacyl-tRNA synthetase (AARS) polypeptide having a hematopoiesis-modulating activity, thereby modulating hematopoiesis. In certain embodiments, the cell is a stem cell or a progenitor cell. In certain embodiments, the progenitor cell is a megakaryocyte progenitor cell, an erythrocyte progenitor cell, a lymphocyte progenitor cell, a granulocyte progenitor cell, a monocyte, or an endothelial progenitor cell.

Certain embodiments comprise stimulating the production of at least one of megakaryocyte progenitor cells, erythrocyte progenitor cells, lymphocyte progenitor cells, granulocyte progenitor cells, or monocytes. Certain embodiments comprise stimulating the production of at least one of megakaryocytes, platelets, erythrocytes, lymphocytes, granulocytes, or macrophages. Certain embodiments comprise reducing the production of at least one of megakaryocyte progenitor cells, erythrocyte progenitor cells, lymphocyte progenitor cells, granulocyte progenitor cells, or monocytes. Certain embodiments comprise reducing the production of at least one of megakaryocytes, platelets, erythrocytes, lymphocytes, granulocytes, or macrophages.

Certain embodiments comprise contacting the cell in vitro or ex vivo. Certain embodiments comprise administering the contacted cells to a subject. Certain embodiments comprise contacting the cell in a subject by directly administering the AARS polypeptide to the subject.

In certain embodiments, the subject is about to undergo, is undergoing, or has undergone a transplant therapy. In certain embodiments, the transplant therapy is a bone marrow transplant, a cord blood transplant, a hematopoietic stem cell transplant, an autologous peripheral blood cell progenitor transplant, or a liver transplant.

In certain embodiments, the subject is about to undergo, is undergoing, or has undergone chemotherapy or radiotherapy. In certain embodiments, chemotherapy comprises treatment with an agent selected from chlorambucil, cyclophosphamide, lomustine (CCNU), melphalan, procarbazine, thiotepa, carmustine (BCNU), busulfan, daunorubicin, doxorubicin, idarubicin, epirubicin, mitoxantrone, bleomycin, cisplatin, carboplatin, oxaliplatin, camptothecins, irinotecan, topotecan, amsacrine, etoposide, etoposide phosphate, teniposide, vincristine, vinblastine, vinorelbine, vindesine, paclitaxel, mechlorethamine, ifosfamide, nitrosurea, dactinomycin, plicomycin, mitomycin, tamoxifen, raloxifene, estrogen receptor binding agents, gemcitabien, navelbine, farnesyl-protein transferase inhibitors, transplatinum, 5-fluorouracil, methotrexate, and temazolomide. In certain embodiments, chemotherapy comprises high-dose chemotherapy. In certain embodiments, high-dose chemotherapy further comprises a transplant therapy.

In certain embodiments, the transplant therapy is a bone marrow transplant, a cord blood transplant, a hematopoietic stem cell transplant, or an autologous peripheral blood cell progenitor transplant.

In certain embodiments, the subject has a condition that is associated with increased red blood cell count. In certain embodiments, the conditions is living at a high altitude, smoking, congenital heart disease, failure of the right side of the heart, pulmonary fibrosis, polycythemia vera, dehydration, kidney disease, kidney, cancer, exposure to carbon monoxide, anabolic steroid use, COPD, or erythropoietin (EPO) doping. In certain embodiments, the subject has a condition that is associated with decreased red blood count.

In certain embodiments, the subject has a condition that is associated with increased lymphocyte count. In certain embodiments, the subject has a condition that is associated with decreased lymphocyte count. In certain embodiments, the subject has a condition that is associated with increased granulocyte count. In certain embodiments, the subject has a condition that is associated with decreased granulocyte count. In certain embodiments, the subject has a condition that is associated with increased platelet count. In certain embodiments, the subject has a condition that is associated with decreased platelet count.

Certain embodiments include methods of modulating hematopoiesis in a subject, comprising administering to the subject an effective concentration of an aminoacyl-tRNA synthetase (AARS) polypeptide, thereby modulating hematopoiesis in the subject.

Certain embodiments comprise increasing the hematopoiesis-stimulatory activity of at least one of an osteoblast cell or a vascular cell. Certain embodiments comprise reducing the hematopoiesis-stimulatory activity of at least one of an osteoblast cell or a vascular cell. Certain embodiments comprise increasing the hematopoiesis-inhibitory activity of at least one of an osteoblast cell or a vascular cell. Certain embodiments comprise reducing the hematopoiesis-inhibitory activity of at least one of an osteoblast cell or a vascular cell.

Certain embodiments comprise increasing the mobilization of hematopoietic cells from the bone marrow to the periphery of the subject. In certain embodiments, the subject is a peripheral blood cell donor.

In certain embodiments, the subject is about to undergo, is undergoing, or has undergone a transplant therapy. In certain embodiments, the subject is about to undergo, is undergoing, or has undergone chemotherapy or radiotherapy. In certain embodiments, the subject has a condition that is associated with at least one of increased red blood cell, increased lymphocyte count, increased granulocyte count, or increased platelet count. In certain embodiments, the subject has a condition that is associated with at least one of decreased red blood cell count, decreased lymphocyte count, decreased granulocyte count, or decreased platelet count.

Also included are methods of co-administering to the subject one or more thrombopoiesis-stimulatory agents, such as thrombopoietin (TPO), a TPO agonist, a TPO mimetic, an mpl-signaling agonist, a cytokine, a chemokine, a chemokine receptor ligand, or an adhesion molecule. In some embodiments, the co-administration of the agent achieves a synergistic effect. In particular embodiments, the agent is TPO, a TPO agonist, a TPO mimetic, or an mpl-signaling agonist, and the synergistic effect comprises increased thrombopoiesis. In specific embodiments, the agent is eltrombopag or romiplostim. In certain embodiments, the AARS polypeptide is a YRS polypeptide comprising the sequence set forth in SEQ ID NO:2 (Y341A).

Also included are compositions, comprising an AARS polypeptide and one or more thrombopoiesis-stimulatory agents, such as thrombopoietin (TPO), a TPO agonist, a TPO mimetic, an mpl-signaling agonist, a cytokine, a chemokine, a chemokine receptor ligand, or an adhesion molecule. In some embodiments, the agent is TPO, a TPO agonist, a TPO mimetic, or an mpl-signaling agonist. In specific embodiments, the agent is eltrombopag or romiplostim. In certain embodiments, the AARS polypeptide is a YRS polypeptide comprising the sequence set forth in SEQ ID NO:2 (Y341A).

Certain embodiments include isolated polynucleotides encoding an AARS polypeptide provided herein. Certain embodiments include vectors comprising said polynucleotides. Certain embodiments include host cells comprising said vectors. Certain embodiments include fusion polypeptides comprising an AARS polypeptide provided herein and a heterologous fusion partner.

Also included are antibodies that exhibit binding specificity for an isolated YRS polypeptide of SEQ ID NO:2 or 3, a cellular binding partner of the YRS polypeptide, or both. In specific embodiments, affinity of the antibody for the YRS polypeptide of SEQ ID NO:2 or 3 is at least about 10× stronger than its affinity for the YRS polypeptide of SEQ ID NO:1.

Also included are binding agents that exhibit binding specificity for an isolated YRS polypeptide of SEQ ID NO:2 or 3, a cellular binding partner of the YRS polypeptide, or both. In specific embodiments, affinity of the binding agent for the YRS polypeptide of SEQ ID NO:2 or 3 is at least about 10× stronger than its affinity for the YRS polypeptide of SEQ ID NO:1. In certain embodiments, the binding agent is selected from a peptide, a soluble receptor, an adnectin, a small molecule, and an aptamer.

In some embodiments, the antibody or binding agent antagonizes a hematopoiesis-modulating activity of the YRS polypeptide of SEQ ID NO:2 or 3. In other embodiments, the antibody or binding agent agonizes a hematopoiesis-modulating activity of the YRS polypeptide of SEQ ID NO:2 or 3.

In certain embodiments, the hematopoiesis-modulating is a thrombopoietic activity.

Also included are methods of reducing platelet count in a subject, comprising administering to the subject an antibody or binding agent that antagonizes the thrombopoietic activity of a YRS polypeptide, such as the YRS polypeptides of SEQ ID NOS:2 or 3, thereby reducing platelet count in the subject. In some embodiments, the subject has thrombocythemia or thrombocytosis. Specific embodiments include methods of reducing cell division of one or more platelets, comprising contacting the platelet(s) with an antibody or binding agent that antagonizes the thrombopoietic activity of a YRS polypeptide, such as the YRS polypeptides of SEQ ID NOS:2 or 3, thereby reducing cell division of the platelet(s).

As noted above, also included are methods of reducing platelet count in a subject, comprising administering to the subject an AARS polypeptide, wherein the AARS polypeptide reduces thrombopoiesis or megakaryopoiesis, thereby reducing platelet count in the subject. In some embodiments, the AARS polypeptide is a WRS polypeptide or a selected YRS polypeptide. In specific embodiments, the YRS polypeptide is a variant of SEQ ID NO:2 which reduces thrombopoiesis or megakaryopoiesis.

Certain embodiments include an antibody that exhibits binding specificity for an isolated YRS polypeptide of SEQ ID NO:1, 2 or 3, a cellular binding partner of the YRS polypeptide, or both. In some embodiments, affinity of the antibody for the YRS polypeptide of SEQ ID NO:2 or 3 is at least about 10× stronger than its affinity for the YRS polypeptide of SEQ ID NO:1. In particular embodiments, affinity of the antibody for the YRS polypeptide of SEQ ID NO:2 or 3 is at least about 1.5× stronger than its affinity for the YRS polypeptide of SEQ ID NO:1. In certain embodiments, the antibody is a monoclonal antibody. In some embodiments, the antibody is a polyclonal antibody. In specific embodiments, the antibody is a rabbit antibody.

In certain embodiments, the antibody antagonizes a hematopoiesis-modulating activity of the YRS polypeptide of SEQ ID NO:2 or 3. In some embodiments, the antibody agonizes a hematopoiesis-modulating activity of the YRS polypeptide of SEQ ID NO:2 or 3.

Also included are methods of reducing platelet count in a subject, comprising administering to the subject an antibody described herein, where the antibody antagonizes a thrombopoiesis-stimulatory activity of a YRS polypeptide, thereby reducing platelet count in the subject. In specific embodiments, the subject has thrombocythemia or thrombocytosis.

Also included are methods of increasing platelet count in a subject, comprising administering to the subject an antibody described herein, where the antibody agonizes a thrombopoiesis-stimulatory activity of a YRS polypeptide, thereby increasing platelet count in the subject. In some embodiments, the subject has thrombocytopenia. In specific embodiments, the subject has a myelodysplastic syndrome.

Also included are methods of reducing platelet count in a subject, comprising administering to the subject a monoclonal antibody, or antibody fragment to a YRS polypeptide of SEQ ID NO:2 or 3, wherein affinity of the antibody or antibody fragment for the YRS polypeptide of SEQ ID NO:2 or 3 is at least about 1.5× stronger than their affinity for the YRS polypeptide of SEQ ID NO:1, and wherein the antibody, or antibody fragment reduces thrombopoiesis or megakaryopoiesis, thereby reducing platelet count in the subject. In certain embodiments, the subject has thrombocythemia or thrombocytosis.

Also included are methods of increasing platelet count in a subject, comprising administering to the subject a monoclonal antibody, or antibody fragment to a YRS polypeptide of SEQ ID NO:2 or 3, wherein affinity of the antibody or antibody fragment for the YRS polypeptide of SEQ ID NO:2 or 3 is at least about 1.5× stronger than their affinity for the YRS polypeptide of SEQ ID NO:1, and wherein the antibody, or antibody fragment increases thrombopoiesis or megakaryopoiesis, thereby reducing platelet count in the subject. In certain embodiments, the subject has thrombocytopenia. In specific embodiments, the subject has a myelodysplastic syndrome.

Sequence Listing

SEQ ID NO:1 is the full-length amino acid sequence of human tyrosyl-tRNA synthetase (YRS).

SEQ ID NO:2 is the amino acid sequence of a Y341A variant of full-length human YRS.

SEQ ID NO:3 is the amino acid sequence of a C-terminally truncated (amino acids 1-364) human YRS.

SEQ ID NO:4 is a polynucleotide sequence that encodes the full-length amino acid sequence of human YRS (SEQ ID NO:1).

SEQ ID NO:5 shows the sequence of an eight amino acid tag.

SEQ ID NO:6 is the amino acid sequence of the SP1 human YRS splice variant.

SEQ ID NO:7 is the polynucleotide sequence that encodes the SP1 human YRS splice variant (SEQ ID NO:6).

SEQ ID NO:8 is the amino acid sequence of the SP2 human YRS splice variant.

SEQ ID NO:9 is the polynucleotide sequence that encodes the SP2 human YRS splice variant (SEQ ID NO:8)

SEQ ID NO:10 is the amino acid sequence of the SP3 human YRS splice variant.

SEQ ID NO:11 is the polynucleotide sequence that encodes the SP3 human YRS splice variant (SEQ ID NO:10).

SEQ ID NO:12 is the amino acid sequence of the SP4 human YRS splice variant.

SEQ ID NO:13 is the polynucleotide sequence that encodes the SP4 human YRS splice variant (SEQ ID NO:12).

SEQ ID NO:14 is the amino acid sequence of the SP5 human YRS splice variant.

SEQ ID NO:15 is the polynucleotide sequence that encodes the SP5 human YRS splice variant (SEQ ID NO:14).

SEQ ID NO:16 is the full-length amino acid sequence of human cytoplasmic glycyl-tRNA synthetase (GlyRS).

SEQ ID NO:17 is a nucleic acid sequence encoding the GlyRS polypeptide of SEQ ID NO:16.

SEQ ID NOS:18-24 represent illustrative peptide sequences analyzed in determining GlyRS fragment boundaries (see Example 9 & Table 1).

SEQ ID NO:25 is the full-length amino acid sequence of human glutaminyl-tRNA synthetase (QRS).

SEQ ID NOS:26 and 27 represent illustrative peptide sequences analyzed in determining QRS fragment boundaries (see Example 10 & Table 2).

SEQ ID NO:28 is the full-length amino acid sequence of the histidyl-tRNA synthetase (HisRS) protein (NP_002100.2).

SEQ ID NO:29 is a nucleic acid coding sequence of the HisRS-SV9 splice variant.

SEQ ID NO:30 is the amino acid sequence of the HisRS-SV9 splice variant polypeptide encoded by SEQ ID NO:29.

SEQ ID NO:31 is a nucleic acid coding sequence of the HisRS-SV11 splice variant.

SEQ ID NO:32 is the amino acid sequence of the HisRS-SV11 splice variant polypeptide encoded by SEQ ID NO:31.

SEQ ID NO:33 is the amino acid sequence of the main isoform of human tryptophanyl-tRNA synthetase (WRS).

SEQ ID NO:34 is the amino acid sequence of a fragment (T2) of human WRS.

SEQ ID NO:35 is the amino acid sequence of a fragment (Toltrup) of human WRS.

SEQ ID NOS:36-103 represent various endogenous peptide fragments of human QRS.

SEQ ID NO:104 is the amino acid sequence of a human phenylalanyl-tRNA synthetase (PheRS) splice variant (PheRS_SV1P).

SEQ ID NO:105 is the amino acid sequence of a full-length human aspartyl-tRNA synthetase (AspRS) polypeptide.

SEQ ID NO:106 is the amino acid sequence of an N-terminal fragment (F1; amino acids 1-471) of human WRS.

SEQ ID NO:107 is the amino acid sequence of a splice variant (mini-WRS; amino acids 48-471) of human WRS.

SEQ ID NO:108 is the amino acid sequence of a fragment (T1; amino acids 71-471) of human WRS).

BRIEF DESCRIPTION OF THE DRAWINGS

FIG. 1 (A-B) shows the in vivo effects on platelet production following administration of a C-terminally truncated human-tyrosyl-tRNA synthetase polypeptide (SEQ ID NO:3) having an eight amino acid C-terminal tag, L-E-H-H-H-H-H-H (SEQ ID NO:5).

FIG. 10 provides the NCBI annotation of the cDNA sequences for human tyrosyl-tRNA synthetase splice variants SP1 to SP5.

FIG. 12 illustrates mRNA transcripts of wild-type, full-length HisRS, HRS-SV9 and HRS-SV11.

FIG. 14A shows the relative binding of the full-length YRS selective polyclonal antibody sera to full-length YRS (squares) and mini-YRS (crosses). FIG. 14 B shows the relative binding of the mini-YRS selective polyclonal antibody sera to full-length YRS (squares) and mini-YRS (triangles).

DETAILED DESCRIPTION

Figure 1A:
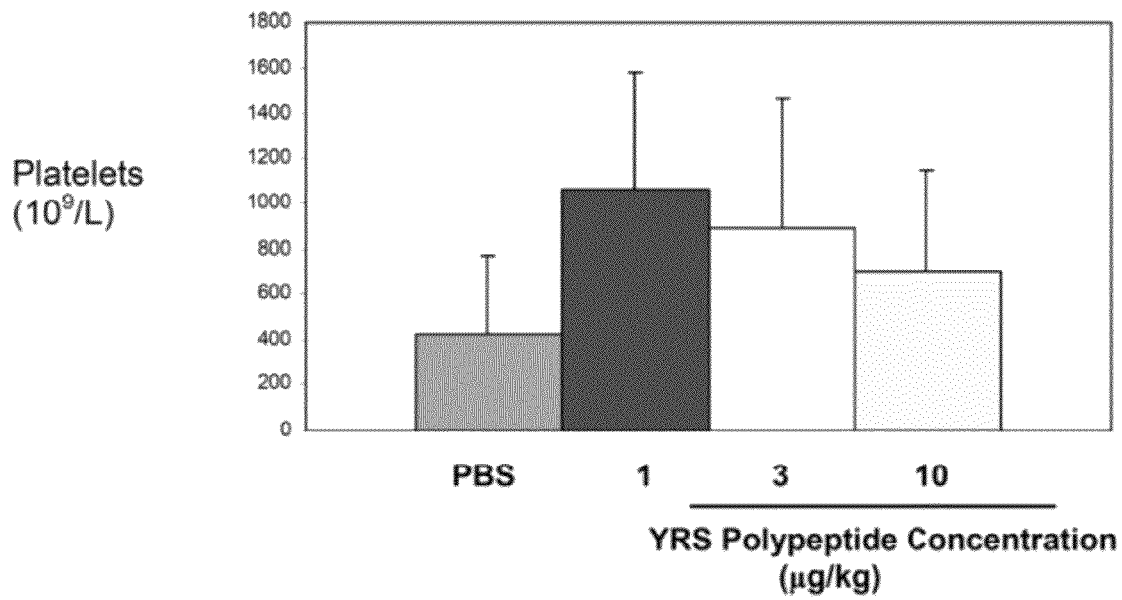
FIG. 1(A) shows the platelet count for the experiment in which mice were injected with 1, 3, and 10 µg/kg of the truncated tyrosyl-tRNA synthetase polypeptide, as compared to a phosphate-buffer saline (PBS) control.

The present invention stems from the discovery that aminoacyl-tRNA synthetases (AARS) and certain polypeptides derived therefrom possess non-canonical biological activities of therapeutic relevance. Therefore, according to one aspect, the present invention provides isolated AARS polypeptides having at least one non-canonical biological activity, as well as active fragments and variants thereof which substantially retain said non-canonical activity.

"Non-canonical" activity," as used herein, refers generally to an activity possessed by an AARS polypeptide of the invention that is other than the addition of an amino acid onto a tRNA molecule. As detailed herein, in certain embodiments, a non-canonical biological activity exhibited by an AARS polypeptide of the invention may include, but is not limited to, the modulation of hematopoiesis. Examples of hematopoietic-modulating activities include increasing or reducing any one or more of megakaryopoiesis, thrombopoiesis, erythropoiesis, granulopoiesis, or lymphopoiesis. Hence, embodiments of the present invention include aminoacyl-tRNA synthetase polypeptides, including truncations, splice variants, proteolytic fragments, and variants thereof, which regulate or modulate hematopoiesis, and thereby possess therapeutically beneficial activity.

Advantages of the use of AARS polypeptides over other treatments include, for example, a different mechanism of action than traditional treatments, synergism with hematopoietic-based signaling, higher potency, and the benefits associated with using a de-immunized molecule, which possibly possesses homeostasis functions. Other advantages will be apparent to a person skilled in the art.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken N.J., John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005).

All publications, patents and patent applications cited herein are hereby incorporated by reference in their entirety.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An "agonist" refers to a molecule that intensifies or mimics a hematopoiesis-modulating activity of an AARS. Agonists may include antibodies and other binding agents such as proteins, nucleic acids, carbohydrates, small molecules, or any other compound or composition that modulates the activity of an AARS either by directly interacting with the AARS or its binding partner, or by acting on components of the biological pathway in which the AARS participates. Included are partial and full agonists.

The term "antagonist" refers to a molecule that reduces or attenuates a hematopoiesis-modulating activity of an AARS. Antagonists may include antibodies and other binding agents such as proteins, nucleic acids, carbohydrates, small molecules, or any other compound or composition that modulates the activity of an AARS or its binding partner, either by directly interacting with the AARS or its binding partner or by acting on components of the biological pathway in which the AARS participates. Included are partial and full antagonists.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 420, 440, 460, 480, 500 or more contiguous nucleotides or amino acid residues in length, including all integers in between, which comprise or encode a hematopoietic-modulating activity of a reference aminoacyl tRNA transferase polynucleotide or polypeptide, such as the exemplary reference polypeptide sequences of SEQ ID NOS: 1, 2, 3, 6, 8, 10, 12, 14, 16, 25, 28, 30, and 32-108, or exemplary the reference nucleotide sequences of SEQ ID NOS: 4, 7, 9, 11, 13, 15, 17, 19, and 31.

Biologically active fragments also include naturally occurring splice variants of a reference AARS sequence, as well as proteolytic fragments of AARS polypeptides.

"Proteolytic fragments," or the sequence of proteolytic fragments, can be identified or derived according to a variety of techniques. For instance, as exemplified herein, proteolytic fragments can be identified in vitro, such as by incubating QRS polypeptides with selected proteases, or they can be identified endogenously (i.e., in vivo). In certain embodiments, endogenous proteolytic fragments can be generated or identified, for instance, by recombinantly expressing QRS polypeptides in a selected microorganism or eukaryotic cell that has been either modified to contain one or more selected proteases, or that naturally contains one or more proteases that are capable of acting on a QRS polypeptide, and isolating and characterizing the endogenously produced proteolytic fragments therefrom. Examples of such proteolytic fragments include Q1-Q4, as described herein, as well as the proteolytic fragments illustrated in Tables C-G, including variants thereof.

In certain embodiments, naturally-occurring endogenous proteolytic fragments can be generated or identified, for instance, from various cellular fractions (e.g., cytosolic, membrane, nuclear) and/or growth medium of various celltypes, including, for example, macrophages such as RAW macrophages (e.g., RAW 264.7 macrophages; see Example 5), T-cells, including primary T-cells and T-cell lines such as Jurkats, and natural killer (NK) cells, among others. In certain embodiments, endogenous proteolytic fragments, however generated, can be identified by techniques such as massspectrometry, or equivalent techniques. Once an in vitro or endogenously identified proteolytic fragment has been generated or identified, then it can be sequenced and cloned into an expression vector for recombinant production, or produced synthetically.

Representative biologically active fragments generally participate in an interaction, e.g., an intramolecular or an inter-molecular interaction. An inter-molecular interaction can be a specific binding interaction or an enzymatic interaction. An inter-molecular interaction can be between an AARS polypeptide and target molecule, such as another AARS polypeptide or a target molecule involved in modulating the process of hematopoiesis (e.g., megakaryopoiesis, erythropoiesis). Biologically active fragments of an AARS polypeptide include polypeptide fragments comprising amino acid sequences with sufficient similarity or identity to, or which are derived from, the amino acid sequences of any of SEQ ID NOS: 1, 2, 3, 6, 8, 10, 12, 14, 16, 25, 28, 30, or 32-108, including biologically active portions thereof, or are encoded by a nucleotide sequences of SEQ ID NOS: 4, 7, 9, 11, 13, 15, 17, 19, or 31.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference AARS polynucleotide sequence or polynucleotides that hybridize to an AARS reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Polynucleotide variants include, for example, polynucleotides having at least 50% (and at least 51% to at least 99% and all integer percentages in between) sequence identity with the sequence set forth in SEQ ID NO:4, 7, 9, 11, 13, 15, 17, 19, or 31, or portions thereof that encode a biologically active fragment of an AARS polypeptide. The terms "polynucleotide variant" and "variant" also include naturally occurring allelic variants.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "aminoacyl-tRNA synthetase" (AARS) refers generally to enzymes that in their natural or wild-type form are capable of catalyzing the esterification of a specific amino acid or its precursor to one of all its compatible cognate tRNAs to form an aminoacyl-tRNA. In this "canonical" activity, aminoacyl-tRNA synthetases catalyse a two-step reaction: first, they activate their respective amino acid by forming an aminoacyl-adenylate, in which the carboxyl of the amino acid is linked in to the alpha-phosphate of ATP by displacing pyrophosphate, and then, when the correct tRNA is bound, the aminoacyl group of the aminoacyl-adenylate is transferred to the 2' or 3' terminal OH of the tRNA.

Class I aminoacyl-tRNA synthetases typically have two highly conserved sequence motifs. These enzymes aminoacylate at the 2'-OH of an adenosine nucleotide, and are usually monomeric or dimeric. Class II aminoacyl-tRNA synthetases typically have three highly conserved sequence motifs. These enzymes aminoacylate at the 3'-OH of the same adenosine, and are usually dimeric or tetrameric. The active sites of class II enzymes are mainly made up of a seven-stranded anti-parallel β-sheet flanked by α-helices. Although phenylalanine-tRNA synthetase is class II, it aminoacylates at the 2'-OH.

AARS polypeptides include tyrosyl-tRNA synthetases (YRS), tryptophanyl-tRNA synthetases (WRS), glutaminyl-tRNA synthetases (QRS), glycyl-tRNA synthetases (GlyRS), histidyl-tRNA synthetases, seryl-tRNA synthetases, phenylalanyl-tRNA synthetases, alanyl-tRNA synthetases, asparaginyl-tRNA synthetases (AsnRS), aspartyl-tRNA synthetases (AspRS), cysteinyl-tRNA synthetases (CysRS), glutamyl-tRNA synthetases, prolyl-tRNA synthetases (ProRS), arginyl-tRNA synthetases, isoleucyl-tRNA synthetases, leucyl-tRNA synthetases, lysyl-tRNA synthetases, threonyl-tRNA synthetases, methionyl-tRNA synthetases, and valyl-tRNA synthetases. The full-length wild-type sequences of these AARS polypeptides are known in the art.

Also included within the meaning of AARS polypeptides are aminoacyl tRNA synthetase-interacting multifunctional proteins (AIMPs), including AIMP-1 (or p43), AIMP-2 (or p38), and AIMP-3 (or p18).

The recitations "polypeptides" "polypeptide fragments," "truncated polypeptides" or "variants thereof" encompass, without limitation, polypeptides having the amino acid sequence that shares at least 50% (and at least 51% to at least 99% and all integer percentages in between) sequence identity with a reference AARS sequence, such as the amino acid sequence of a human AARS polypeptide, including biologically active fragments thereof, such as fragments having at least about 10, 20, 30, 40, 50, 60, 70, 80, 90, 100, 120, 140, 160, 180, 200, 220, 240, 260, 280, 300, 350, 400, 450, 500, 550, 600, 650, 700 or more contiguous amino acids of the reference sequences, including all integers in between. These recitations further encompass natural allelic variation of AARS polypeptides that may exist and occur from one genus or species to another. Illustrative reference sequences include those set forth in any one of SEQ ID NOS: 1, 2, 3, 6, 8, 10, 12, 14, 16, 25, 28, 30, and 32-108.

AARS polypeptides, including truncations, fragments, and/or variants thereof, encompass polypeptides that exhibit at least about 10%, 20%, 30%, 40%, 50%, 60%, 70%, 80%, 90%, 100%, 110%, 120%, 130%, 140%, 150%, 200%, 300%, 400%, 500%, 600%, 700%, 800%, 900%, 1000% or more of the specific biological activity of a reference AARS polypeptide (e.g., a hematopoietic-modulating activity in a subject or in vitro). Merely by way of illustration, AARS-related biological activity may be quantified, for example, by measuring the ability of an AARS polypeptide to increase the megakaryocyte number in a subject (see, e.g., Example 1), or to impact the formation of megakaryocyte progenitor cells (see, e.g., Example 11). Suitable in vitro models for assaying megakaryocyte colony formation are described herein, and exemplified in Dessypris et al., *Exp Hematol.* 18:754-7, 1990. AARS polypeptides, including truncations and/or variants thereof, having substantially reduced biological activity relative to a reference AARS polypeptide are those that exhibit less than about 25%, 10%, 5% or 1% of the specific activity of a reference AARS polypeptide (i.e., having a non-canonical biological activity).

The recitation polypeptide "variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length AARS polypeptides (e.g., a full-length YRS polypeptide having a Y341A substitution), truncated fragments of full-length AARS polypeptides, splice variants, proteolytic fragments, including endogenous proteolytic fragments, and variants of such fragments, as well as their related biologically active fragments. Biologically active fragments of an AARS polypeptide include peptides comprising amino acid sequences sufficiently similar to, or derived from, the amino acid sequences of a (putative) full-length AARS polypeptide sequence, such as SEQ ID NO:1, or portions thereof, such as the polypeptides of SEQ ID NOS: 3, 6, 8, 10, 12, and 14.

Typically, biologically active fragments comprise a domain or motif with at least one activity of an AARS polypeptide and may include one or more (and in some cases all) of the various active domains, and include fragments having a hematopoietic-modulating activity. In some cases, biologically active fragments of an AARS polypeptide have a biological activity (e.g., megakaryopoiesis-modulating activity, erythropoiesis-modulating activity) that is unique to the particular, truncated fragment, such that the full-length AARS polypeptide may not have that activity. In certain cases, the biological activity may be revealed by separating the biologically active AARS polypeptide fragment from the other full-length AARS polypeptide sequences, or by altering certain residues (e.g., Y341A of the YRS polypeptide) of the full-length AARS wild-type polypeptide sequence to unmask the biologically active domains. A biologically active fragment of a truncated AARS polypeptide can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 550, 600, 650, 700, 750 or more contiguous or non-contiguous (e.g., splice variants may not be contiguous) amino acids, including all integers in between, of the amino acid sequences set forth in any one of SEQ ID NOS: 1, 2, 3, 6, 8, 10, 12, 14, 16, 25, 28, 30, or 32-108, or the known amino acid sequences of the various human AARS polypeptides. In certain embodiments, a biologically active fragment comprises a hematopoiesis modulating sequence, domain, or motif. Suitably, the biologically-active fragment has no less than about 1%, 10%, 25%, or 50% of an activity of the biologically-active (i.e., non-canonical activity) polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "subject," as used herein, includes any animal that exhibits a symptom, or is at risk for exhibiting a symptom, which can be treated with an AARS polypeptide of the invention, cells (e.g., bone marrow stem cells) that have been treated ex vivo or in vitro with an AARS polypeptide, such as to increase the proportion or number of megakaryocyte progenitors, or both. Suitable subjects (patients) include laboratory animals (such as mouse, rat, rabbit, or guinea pig), farm animals, and domestic animals or pets (such as a cat or dog). Non-human primates and, preferably, human patients, are included. Typical subjects include animals that exhibit, or are at risk for exhibiting increased or reduced platelet count, increased or reduced red blood cell count, increased or reduced lymphocyte or granulocyte count, or other hematopoietic-related symptom. As one example, a "subject" may also be about to undergo, is undergoing, or has undergone, a transplant procedure, such as a stem cell or bone marrow transplant.

An "effective concentration" of an aminoacyl-tRNA synthetase polypeptide refers to an amount that is capable of modulating or regulating hematopoiesis in any desired way, as compared to a control polypeptide or no polypeptide, whether in one or more cells in vitro or ex vivo, or in subject. One example of a hematopoiesis-modulating activity includes increasing megakaryopoiesis, as typically measured by increased platelet levels, maintained platelet levels, increased megakaryocyte numbers, and/or increased neutrophil production. Another example of a hematopoiesis-modulating activity includes reducing or increasing erythropoiesis, as typically measured by the formation of erythroid progenitor cells or erythrocytes (red blood cells). Other examples will be apparent from the description provided herein and the understanding in the art.

A "megakaryocyte" refers generally to a bone marrow cell that is responsible for the production of blood thrombocytes (i.e., platelets), which are necessary for normal blood clotting. Megakaryocytes typically account for 1 out of 10,000 bone marrow cells. Megakaryocytes are derived from pluripotent hematopoietic stem cell precursor cells in the bone marrow. Thrombopoietin (TPO) is the primary regulator of megakaryocyte production, i.e., TPO is sufficient but not absolutely necessary for inducing differentiation of progenitor cells in the bone marrow towards a final megakaryocyte phenotype. Other factors regulating megakaryocyte differentiation include GM-CSF, IL-3, IL-6, IL-11, chemokines (SDF-1; FGF-4), and erythropoietin.

Megakaryocytes are believed to develop through the following lineage: CFU-Me (pluripotential hematopoietic stem cell or hemocytoblast) →megakaryoblast→promegakaryocyte→megakaryocyte. At the megakaryoblast stage, the cell loses its ability to divide, but is still able to replicate its DNA and continue development, becoming polyploid. Upon maturation, megakaryocytes begin the process of producing platelets, or thrombocytes. Thrombopoietin plays a role in inducing the megakaryocyte to form small proto-platelet processes, or cytoplasmic internal membranes for storing platelets prior to release. Upon release, each of these proto-platelet processes can give rise to 2000-5000 new platelets. Overall, about ⅔ of the newly-released platelets will remain in circulation and about ⅓ will be sequestered by the spleen. After releasing the platelets, the remaining cell nucleus typically crosses the bone marrow barrier to the blood and is consumed in the lung by alveolar macrophages. Megakaryocytopenia, also referred to as megakaryophthisis, is a scarcity of megakaryocytes in the bone marrow.

An "erythrocyte" refers to a red blood cell that consists mainly of hemoglobin, a complex metalloprotein containing heme groups whose iron atoms temporarily link to oxygen molecules ($O_2$) in the lungs. Erythrocytes are produced by a process called erythropoiesis, in which they develop from committed stem cells through reticulocytes to mature erythrocytes in about 7 days and live a total of about 100-120 days. "Polycythemias" (or erythrocytoses) are diseases characterized by a surplus of erythrocytes, in which the increased viscosity of the blood can cause a number of symptoms. "Anemias" are diseases characterized by low oxygen transport capacity of the blood, because of low red cell count or some abnormality of the red blood cells or the hemoglobin.

A "granulocyte" refers to a white blood cell that is characterized by the presence of granules in its cytoplasm. Granulocytes are also referred to as polymorphonuclear leukocytes (PMN or PML), because of the varying shapes of the nuclei. Examples of granulocytes include neutrophils, eosinophils, and basophils.

A "neutrophil," or neutrophil granulocyte, refers generally to an abundant type of white blood cells in humans, which, together with basophils and eosinophils, form part of the polymorphonuclear cell family (PMNs). Neutrophils can be readily identified according to their unique staining characteristics on hematoxylin and eosin (H&E) histological or cytological preparations. Neutrophils are normally found in the blood stream, but are one of the first group of inflammatory cells to migrate toward inflammation sites during the beginning (i.e., acute) phase of inflammation, mainly as a result of infection or cancer. Typically, neutrophils first migrate through the blood vessels, and then through interstitial tissues, following chemical signals (e.g., interleukin-8 (IL-8), interferon-gamma (IFN-gamma), and C5a) that originate at the site of inflammation. "Neutropenia" refers to the presence of low neutrophil counts, which may result from a congenital (genetic) disorder, or may develop due to other conditions, as in the case of aplastic anemia or some kinds of leukemia. "Neutrophilia" refers to an abnormally high neutrophil count.

"Eosinophils," also called eosinophilic leukocytes, refer to leukocytes that have coarse round granules of uniform size within their cytoplasm, and which typically have a bilobate (two-lobed) nucleus. The cytoplasmic granules of eosinophils stain red with the dye eosin. Eosinophils normally constitute about 1% to about 3% of the peripheral blood leukocytes, at a count of about 350 to 650 per cubic millimeter.

Eosinophil counts in blood often rise above the normal range during allergic reactions and parasitic infections, such as worms. "Eosinopenia" refers to a form of agranulocytosis in which the number of eosinophil granulocyte is lower than expected. "Eosinophilia" refers to an abnormally high number of eosinophils in the blood. For example, eosinophilia can be categorized as mild (less than about 1500 eosinophils per cubic millimeter), moderate (about 1500 to about 5000 per cubic millimeter), or severe (more than about 5000 per cubic millimeter). In primary eosinophilia, the increased production of eosinophils is typically due to an abnormality in hematopoietic stem cells, such as in eosinophilic leukemia. In secondary eosinophilia, the increased production of eosinophils is typically due to a reactive process driven by cytokines Basophils, also called basophilic leukocytes, refer to leukocytes that have coarse bluish-black granules of uniform size within the cytoplasm, and which typically have a bilobate (two-lobed) nucleus. The cytoplasmic granules of basophils stain with basic dyes. Basophils normally constitute about 0.5% to 3% of the peripheral blood leukocytes. Basophils store and release histamine and serotonin, among other chemicals. Basophils are capable of ingesting foreign particles, and also produce, store and release heparin, serotonin, and histamine. The release of inflammatory chemicals such as heparin and histamine is often associated with asthma and allergies. Basophils are produced continually by stem cells in the bone marrow. "Basopenia" refers to a low basophil count (e.g., less than about $0.01 \times 10^9$ per liter of blood), and "basophilia" refers to a high basophil count (e.g., more than about $10^{10}$ per liter of blood).

"Lymphocytes" refer generally to white blood cells of the vertebrate immune system, and include B-cells, T-cells (e.g., helper T-cells, cytotoxic T-cells, yδ T-cells), and natural killer (NK) cells. Generally, and merely for illustrative purposes, B-cells produce and secrete antibodies, T-helper cells release cytokines and growth factors that regulate other immune cells, cytotoxic T-cells (CTLs) lyse virally infected cells, tumour cells and allografts, and NK cells lyse virally infected cells and tumour cells. "Lymphocytopenia" is characterized by abnormally low level of lymphocytes in the blood. The normal total lymphocyte count is typically about 1000 to 4800/μL in adults, and about 3000 to 9500/μL in children younger than 2 years. At age 6, the lower limit of normal total lymphocyte count is about 1500/μL. Lymphocytopenia is often characterized by a total lymphocyte count of <1000/μL in adults or <3000/μL in children younger than 2 years. Specific examples of lymphocytopenia include T-lymphocytopenia, in which there are too few T-cells (e.g., CD4+ T-cell counts below about 300 cells/μL) but often normal numbers of other lymphocytes, B lymphocytopenia, in which there are too few B lymphocytes but often normal numbers of other lymphocytes, and NK lymphocytopenia, in which there are there are too few natural killer cells but often normal numbers of other lymphocytes.

"Lymphocytosis" refers to an abnormally high lymphocyte count, often characterized by a total lymphocyte count that is more than 40% above normal. In adults, absolute lymphocytosis is typically present when the absolute lymphocyte count is greater than 4000 per microliter, in older children greater than 7000 per microliter, and in infants greater than 9000 per microliter. Relative lymphocytosis may occur when there is a higher proportion (greater than 40%) of lymphocytes among the white blood cells, and when lymphocyte count (ALC) is normal (less than about 4000 per microliter).

The term "modulating" includes "increasing" or "stimulating," as well as "decreasing" or "reducing," typically in a statistically significant or a physiologically significant amount.

The terms "enhance" or "enhancing," or "increase" or "increasing," or "stimulate" or "stimulating," refer generally to the ability of one or agents or compositions to produce or cause a greater physiological response (i.e., downstream effects) in a cell, as compared to the response caused by either no AARS polypeptide or a control molecule/composition. A measurable physiological response may include greater cell growth, expansion, migration, or faster differentiation, among others apparent from the understanding in the art and the description herein. Among other methods known in the art, in vitro colony formation assays represent one way to measure cellular responses to agents provided herein. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1), e.g., 1.5, 1.6, 1.7. 1.8, etc.) the amount produced by no AARS polypeptide (the absence of an agent) or a control composition.

The term "reduce" may relate generally to the ability of one or more AARS polypeptides of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art. A "decrease" in a response may be statistically significant as compared to the response produced by no AARS polypeptide or a control composition, and may include, for example, a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

"Migration" refers to cellular migration, a process that can be measured according to routine in vitro assays, as described herein and known in the art (see, e.g., Example 8). Migration also refers to in vivo migration, such as the migration of cells from one tissue to another tissue (e.g., from bone marrow to peripheral blood, or from peripheral blood to lung tissue), or from a site within one tissue to another site within the same tissue. Migration in vivo (e.g., chemotaxis) often occurs in a response to infection or damaged/irritated tissue.

"Differentiation" refers to the process by which a less specialized (e.g., pluripotent, totipotent, multipotent, etc.) cell becomes a more specialized cell type.

"Treatment" or "treating," as used herein, includes any desirable effect on the symptoms or pathology of a disease or condition associated with the modulation of hematopoiesis (e.g., reduced platelet levels), or on the outcome of other primary treatments (e.g., transplants) that may benefit from the modulation of hematopoiesis, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general. Also included are "prophylactic" treatments, which reduce the risk of developing a relevant disease or condition, or of developing symptoms associated with the disease or condition. Exemplary markers of clinical improvement include either increased platelet counts, maintenance of normal platelet counts, and/or increased megakaryocyte numbers, whether following administration of an AARS polypeptide, following administration of cells that have been treated ex vivo or in vitro with an AARS polypeptide, or both. Other exemplary clinical markers will be apparent to persons skilled in the art.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

Aminoacyl-tRNA Polypeptides and Variants Thereof

The present invention relates in part to the unexpected observation that aminoacyl-tRNA synthetase (AARS) polypeptides, including truncations and variants thereof, modulate the hematopoietic process both in vivo and ex vivo (or in vitro). Accordingly, polypeptides of the present invention include full-length aminoacyl-tRNA synthetases, including any biologically active fragments, variants, or modifications thereof, wherein the polypeptides are capable of modulating hematopoiesis, such as by modulating the differentiation or growth of cells from the myeloid, megakaryocyte, erythrocyte, lymphoid and/or endothelial progenitor (EPC) lineages.

Aminoacyl-tRNA synthetases typically catalyze the aminoacylation of tRNA with their cognate amino acid. Because of their central role in linking amino acids with nucleotide triplets contained in tRNAs, aminoacyl-tRNA synthetases are thought to be among the first proteins that appeared in evolution.

As noted above, examples of aminoacyl-tRNA synthetases include tyrosyl-tRNA synthetases (YRS), tryptophanyl-tRNA synthetases (WRS), glutaminyl-tRNA synthetases (QRS), glycyl-tRNA synthetases (GlyRS), histidyl-tRNA synthetases (HisRS), seryl-tRNA synthetases (SRS), phenylalanyl-tRNA synthetases (PheRS), alanyl-tRNA synthetases (AlaRS), asparaginyl-tRNA synthetases (AsnRS), aspartyl-tRNA synthetases (AspRS), cysteinyl-tRNA synthetases (CysRS), glutamyl-tRNA synthetases (ERS), prolyl-tRNA synthetases (ProRS), arginyl-tRNA synthetases (RRS), isoleucyl-tRNA synthetases (IRS), leucyl-tRNA synthetases (LRS), lysyl-tRNA synthetases (KRS), threonyl-tRNA synthetases (TRS), methionyl-tRNA synthetases (MRS), and valyl-tRNA synthetases (VRS).

Tyrosyl-tRNA synthetases belong to the class I tRNA synthetase family, which has two highly conserved sequence motifs at the active site, HIGH and KMSKS. Class I tRNA synthetases aminoacylate at the 2'-OH of an adenosine nucleotide, and are usually monomeric or dimeric (one or two subunits, respectively).

The human tyrosyl-tRNA synthetase is composed of three domains: 1) an amino-terminal Rossmann fold domain that is responsible for formation of the activated E•Tyr-AMP intermediate and is conserved among bacteria, archeae, and eukaryotes; 2) a tRNA anticodon recognition domain that has not been conserved between bacteria and eukaryotes; and 3) a carboxyl-terminal domain that is unique to the human tyrosyl-tRNA synthetase, and whose primary structure is 49% identical to the putative human cytokine endothelial monocyte-activating protein II, 50% identical to the carboxyl-terminal domain of methionyl-tRNA synthetase from *Caenorhabditis elegans*, and 43% identical to the carboxyl-terminal domain of Arc1p from *Saccharomyces cerevisiae*.

The first two domains of the human tyrosyl-tRNA synthetase are 52, 36, and 16% identical to tyrosyl-tRNA synthetases from *S. cerevisiae, Methanococcus jannaschii*, and *Bacillus stearothermophilus*, respectively. Nine of fifteen amino acids known to be involved in the formation of the tyrosyl-adenylate complex in *B. stearothermophilus* are conserved across all of the organisms, whereas amino acids involved in the recognition of tRNA$^{Tyr}$ are not conserved. Kinetic analyses of recombinant human and *B. stearothermophilus* tyrosyl-tRNA synthetases expressed in *Escherichia coli* indicate that human tyrosyl-tRNA synthetase aminoacylates human but not *B. stearothermophilus* tRNA$^{Tyr}$, and vice versa. It is believed that the carboxyl-terminal domain of human tyrosyl-tRNA synthetase evolved from gene duplication of the carboxyl-terminal domain of methionyl-tRNA synthetase and may direct tRNA to the active site of the enzyme.

Biological fragments of eukaryotic tyrosyl-tRNA synthetases connect protein synthesis to cell-signaling pathways, such as megakaryopoiesis. These fragments may be produced naturally by either alternative splicing or proteolysis, or by artificial proteolytic treatment. For example, as provided in the present invention, the N-terminal fragment mini-YRS is capable of modulating hematopoiesis in vivo. In addition, certain mutations in the full-length YRS polypeptide sequence confer increased hematopoietic-modulating activity on the wild-type reference sequence (e.g., Y341A). Examples of truncated splice variants of the full-length YRS polypeptide sequence include the SP1-SP5 polypeptides.

The full-length amino acid sequence of human tyrosyl-tRNA synthetase is set forth in SEQ ID NO:1. The structure of human mini-YRS (i.e., SEQ ID NO:3; or mini-Tyr), which contains both the catalytic and the anticodon recognition domain, has been reported to a resolution of 1.18 Å. Whereas the catalytic domains of the human and bacterial enzymes superimpose, the spatial disposition of the anticodon recognition domain relative to the catalytic domain is unique in mini-YRS relative to the bacterial orthologs. Without wishing to be bound by any one theory, the unique orientation of the anticodon-recognition domain may explain why the fragment mini-YRS is more active in various cell-signaling pathways.

Specific examples of YRS polypeptide variants include full-length YRS polypeptides, or truncations or splice variants thereof, having one or more amino acid substitutions selected from an R93Q substitution, an I14L substitution, an N17G substitution, an L27I substitution, an A85S substitution, and a V156L substitution, in addition to combinations thereof. Particular examples of YRS polypeptide variants include, but are not limited to, a YRS polypeptide having amino acids 1-364 of SEQ ID NO:1 with an R93Q substitution, a YRS polypeptide having amino acids 1-353 of SEQ ID NO:1 with an I14L substitution, a YRS polypeptide having amino acids 1-353 of SEQ ID NO:1 with an N17G substitution, a YRS polypeptide having amino acids 1-353 of SEQ ID NO:1 with an L27I substitution, a YRS polypeptide having amino acids 1-353 of SEQ ID NO:1 with an A85S substitution, and a YRS polypeptide having amino acids 1-353 of SEQ ID NO:1 with a V156L substitution.

Particular examples of biologically active YRS fragments include, but are not limited to, C-terminally truncated tyrosyl-tRNA synthetase polypeptides comprising or consisting of amino acids 1-343, amino acids 1-344, amino acids 1-350, amino acids 1-353, or amino acids 1-364 of the amino acid sequence set forth in SEQ ID NO:1, in addition to the polypeptides of SEQ ID NOS:3 and 6. Additional examples of biologically active fragments include, but are not limited to, N-terminally truncated tyrosyl-tRNA synthetase polypeptides comprising or consisting of the amino acid sequences set forth in SEQ ID NOS: 6, 10, 12, and 14. These and other YRS polypeptides are included within the AARS polypeptides of the present invention.

Histidyl-tRNA synthetases (HisRS) are α2 dimers that belong to the class IIa tRNA synthetase family. A compilation of primary structures of HisRSs shows that the subunits of these homo-dimeric enzymes consist of 420-550 amino acid residues. This represents a relatively short chain length among AARSs, whose peptide chain sizes range from about 300 to 1100 amino acid residues. SEQ ID NO:28 is the amino acid sequence of the full-length HisRS protein (NP_002100.2). SEQ ID NO:30 is the amino acid sequence of the HRS-SV9 splice variant, and SEQ ID NO:32 is the amino acid sequence of the HRS-SV11 splice variant.

Examples of histidyl-tRNA synthetase polypeptides, and variants or truncations thereof, include HisRS fragments comprising at least the WHEP domain of HisRS, e.g., amino acid residues 3-43 of the human full-length HisRS protein and HisRS fragments comprising at least the anticodon binding domain of HisRS, e.g., amino acid residues 406-501 of the full-length human HisRS protein. Further examples include HisRS fragments that lack a functional aminoacylation domain, e.g., amino acid residues 54-398 of the human full-length HisRS protein or HisRS splice variant polypeptides that comprise at least the WHEP domain and the anticodon binding domain but lack a functional aminoacylation domain.

In certain embodiments, the HisRS polypeptide of the invention comprises a sequence set forth in SEQ ID NOS:28, 30, or 32, or is a contiguous or non-contiguous (e.g., splice variants are sometimes non-contiguous) fragment of a polypeptide set forth in SEQ ID NOS:28, 30, or 32. Illustratively, the fragments may be of essentially any length, provided they retain at least one non-canonical biological activity of interest. For example, as further described herein, such a fragment may comprise at least about 5, 10, 15, 20, 25, 50, 75 or 80, or more, contiguous amino acid residues of SEQ ID NOS:28, 30, or 32.

In further embodiments of the invention, an HisRS polypeptide comprises an active variant (i.e., retains at least one non-canonical biological activity of interest) of a sequence set forth in SEQ ID NOS:28, 30, or 32. In certain embodiments, the active variant is a polypeptide having at least 70%, 80%, 90%, 95% or 99% identity along its length to a sequence set forth in SEQ ID NOS:28, 30, or 32. In certain embodiment, the HisRS polypeptide of the invention is not a polypeptide consisting of residues 1-48 of the full-length human HisRS protein. These and other HisRS polypeptides are included within the AARS polypeptides of the present invention.

Tryptophanyl-tRNA synthetases (WRS), also referred to as tryptophan-tRNA ligases, belong to the class I tRNA synthetase family. Tryptophanyl-tRNA synthetase catalyzes the aminoacylation of tRNA$^{trp}$ with tryptophan, an essential function in protein synthesis. Human WRS has a kinase domain in the N-terminal region and a serine phosphorylation site near the C-terminus.

Two main forms of human tryptophanyl-tRNA synthetase are produced in vivo through alternative mRNA splicing, to yield the full-length protein (SEQ ID NO: 33), and a fragment thereof, often designated mini-WRS (SEQ ID NO:107). Also included are human T1-WRS (SEQ ID NO:108) and T2-WRS (SEQ ID NO:34), alternate splice variants that are produced from an IFN-gamma-sensitive promoter, the latter being an N-terminally truncated fragment of WRS, as well as an N-terminal fragment (F1; SEQ ID NO:106) and fragment of WRS referred to as "Tolstrup" (SEQ ID NO:35). Other splice variants of human WRS are known in the art (see, e.g., Liu et al., *Nucleic Acids Research*, 32(2):719-27, 2004, herein incorporated by reference).

Structurally, full-length WRS contains three parts, a canonical dinucleotide-binding fold, a dimer interface, and a helical domain. This enzyme has enough structural homology to tyrosyl-tRNA synthetase (YRS) that the two enzymes can be described as conformational isomers. Structural elements interacting with the activated amino acid, tryptophanyl-5' AMP, are almost exactly as seen in the tyrosyl-5' AMP complex. Also, side chains that recognize indole are also highly conserved, and require reorientation of a "specificity-determining" helix containing a conserved aspartate to assure selection of tryptophan versus tyrosine. The carboxy terminus, which is disordered and therefore not seen in YRS, forms part of the dimer interface in WRS (see Doublie et al., *Structure*. 3:17-31, 1995).

The crystal structure of human T2-WRS has been reported at 2.5 Å resolution. This variant shares a very low sequence homology of 22% with *Bacillus stearothermophilus* WRS (bWRS), however their overall structures are strikingly similar. Structural comparison of T2-WRS with bWRS reveals substantial structural differences in the substrate-binding pocket and at the entrance to the pocket that play important roles in substrate binding and tRNA binding. T2-WRS has a wide opening to the active site and adopts a compact conformation similar to the closed conformation of bWRS. Modeling studies indicate that tRNA binds with the dimeric enzyme and interacts primarily with the connective polypeptide 1 of human WRS via its acceptor arm and the α-helical domain of WRS via its anticodon loop.

The amino acid sequence of the full-length WRS polypeptide (or the main splice variant) is shown in SEQ ID NO:33. The amino acid sequence of various splice variants or fragments are shown in SEQ ID NOS:34-35 and 106-108 Accordingly, these and other variants or fragments of WRS polypeptides are included within the AARS polypeptides of the present invention.

Glutaminyl-tRNA synthetases (QRS) belong to the class I tRNA synthetase family, and the human protein is one of several mammalian aminoacyl-tRNA synthetases that form a macromolecular protein complex. The eukaryote-specific N-terminal appendix of QRS appears to stabilize the association of other components in the multi-ARS complex, whereas the C-terminal catalytic domain is necessary for QRS association with the multi-AARS complex.

The human QRS enzyme differs from both the bacterial and yeast enzymes, suggesting that a considerable part of human QRS has evolved to perform functions other than the charging of tRNA. For instance, at least two distinct regions (part I and part II) within the eukaryotic QRS (EC 6.1.1.18) N-terminal region have no counterpart in *Escherichia coli*. Even though these regions are thought to bind RNA in a non-specific manner, enhancing interactions between the tRNA and enzyme, they are not essential for enzyme function (see, e.g., Wang et al., *J. Biol. Chem.* 274:16508-12, 1999). Further, human and mouse cells express at least one QRS variant that contains a deletion in part 1 of the N-terminal region, possibly due to an alternate start codon or alternate splicing. However, the available sequence data for yeast suggests that these microorganisms do not express such a QRS variant, but rather only express a QRS polypeptide that contains both part I and part II of the N-terminal region.

Molecular phylogenetic studies of QRS suggest that it has relatively recently evolved from the closely related enzyme glutamyl-tRNA synthetase. As evidence, selected glutaminyl-tRNA synthetase mutants display enhanced glutamic acid recognition. For instance, mutagenesis of two residues proximal to the active site, Phe-90 and Tyr-240, improves glutamic acid recognition 3-5-fold in vitro and results in the misacylation of tRNA$^{gln}$ with glutamic acid.

QRS has been crystallised in a variety of complexes, most importantly with its cognate tRNA$^{gln}$. The enzyme makes extensive contacts with the concave face of the tRNA, and makes specific interactions with the CUG anticodon at positions 34 to 36, and with the base pairs between the 5' end and the 3' end of the tRNA, just before the aminoacyl acceptor.

Certain QRS polypeptides possess anti-apoptotic activities. For instance, human QRS interacts with Fas ligation activated apoptosis signal-regulating kinase 1 (ASK1) in a glutamine-dependent manner. This interaction involves the catalytic domains of the two enzymes, and is dissociated by Fas ligand. This interaction also inhibits both ASK1 activity, as measured by in vitro kinase and transcription assays, and cell death induced by ASK1, an effect that is weakened by glutamine deprivation. The anti-apoptotic interaction of QRS with ASK1 is therefore enhanced by the cellular concentration of glutamine and reduced by Fas ligation. This anti-apoptotic activity is believed to lie in the C-terminal 539 amino acids of human QRS.

The amino acid sequence of the full-length QRS polypeptide is shown in SEQ ID NO:25. Certain specific examples of QRS variants, truncations, or fragments include QRS polypeptides that comprise or consist essentially of amino acids 1-183 (QRS1 or Q1), 1-220 (QRS2 or Q2), 1-249 (QRS3 or Q3), 1-200 (QRS4 or Q4), 1-(181-293), e.g., 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, etc., of SEQ ID NO:25 (see Table 2). Accordingly, these and other variants of QRS polypeptides are included within the AARS polypeptides of the present invention.

Glycyl-tRNA synthetase (GlyRS) is an α2 dimer that belongs to the class II family of tRNA synthetases (see, e.g., U.S. application Ser. No. 12/492,925, herein incorporated by reference). The approximately 2462 bp cDNA for this gene contains a large open reading frame (ORF) encoding 685 amino acids with predicted M(r)=77,507 Da. The protein sequence of human GlyRS has approximately 60% identity with *B. mori* GlyRS and 45% identity with *S. cerevisiae* GlyRS, and contains motifs 2 and 3 characteristic of Class II tRNA synthetases The amino acid sequence of the full-length GlyRS polypeptide is shown in SEQ ID NO:16. SEQ ID NOS:18-24 represent illustrative peptide sequences analyzed in determining GlyRS fragment boundaries (see Example 9 & Table 1).

Certain examples of GlyRS proteolytic fragments include polypeptides that comprise, consist essentially of, or consist of amino acid residues 57-685, 214-685, 239-685, 311-685, 439-685, 511-658, 214-438, 367-438, 214-420, 214-338, 85-127 1-213, 1-61, 85-214, 333-685, 128-685, 265-685, 483-685 or 25-56 of SEQ ID NO:16 (see Table 1), including biologically active truncations or variants thereof (e.g., variants having about 80%, 85%, 90%, 95%, 98% sequence identity to the fragments) that substantially retain at least one non-canonical biological activity of interest. In certain specific embodiments, the GlyRS polypeptide is not a polypeptide as set forth in any one of NCBI # CR594947, U09587 and/or U09510. Accordingly, these and other variants of GlyRS polypeptides are included within the AARS polypeptides of the present invention.

Additional examples of AARS polypeptides having non-canonical activities include phenylalanyl-tRNA synthetase (PheRS) splice variant polypeptides (PheRS_SV1P) (SEQ ID NO:104), which have a unique amino acid sequence in the C-terminal end that is different from the full-length human PheRS protein sequence, including variants and fragments of those PheRS polypeptides; and aspartyl-tRNA synthetase (AspRS) polypeptides (SEQ ID NO:105), including fragments thereof that consist essentially of amino acid residues 1-154, 1-174, 1-31, 399-425, 413-476 or 397-425 of SEQ ID NO:105.

Embodiments of the present invention contemplate the use of compositions comprising hematopoiesis-modulating AARS polypeptides, including truncated fragments, splice variants, proteolytic fragments, and variants and/or modified polypeptides thereof, for modulating hematopoiesis in a subject. Variant proteins encompassed by the present application are biologically active, that is, they continue to possess the hematopoietic-modulating activity of a reference AARS polypeptide sequence (e.g., SEQ ID NOS: 1, 2, 3, 6, 8, 10, 12, 14, 16, 25, 28, 30, and 32-108). Such variants may result from, for example, genetic polymorphism or from human manipulation. Biologically active variants of a reference AARS polypeptide fragment will have at least 40%, 50%, 60%, 70%, generally at least 75%, 80%, 85%, usually about 90% to 95% or more, and typically about 98% or more sequence similarity or identity with the amino acid sequence for a reference protein as determined by sequence alignment programs described elsewhere herein using default parameters. A biologically active variant of a reference AARS polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, an AARS polypeptide differs from the reference sequences in SEQ ID NOS: 1, 2, 3, 6, 8, 10, 12, 14, 16, 25, 28, 30, or 32-108 by at least one but by less than 15, 10 or 5 amino acid residues. In other embodiments, it differs from the reference sequences in SEQ ID NOS: 1, 2, 3, 6, 8, 10, 12, 14, 16, 25, 28, 30, or 32-108 by at least one residue but less than 20%, 15%, 10% or 5% of the residues.

An AARS polypeptide may be altered in various ways including amino acid substitutions, deletions, truncations, and insertions. Methods for such manipulations are generally known in the art. For example, amino acid sequence variants of a truncated and/or variant AARS polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of AARS polypeptides. Recursive ensemble mutagenesis (REM), a technique which enhances the frequency of functional mutants in the libraries, can be used in combination with the screening assays to identify AARS polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Biologically active truncated and/or variant AARS polypeptides may contain conservative amino acid substitutions at various locations along their sequence, as compared to a reference AARS amino acid sequence (e.g., SEQ ID NOS: 1, 2, 3, 6, 8, 10, 12, 14, 16, 25, 28, 30, and 32-108). A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant AARS polypeptide can readily be determined by assaying its activity, as described herein (see, e.g., Examples 1, 2, 10, and 11). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a truncated and/or variant AARS polypeptide is typically replaced with another amino acid residue from the same side chain family. Alternatively, mutations can be introduced randomly along all or part of an AARS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of the reference AARS sequence. An "essential" amino acid residue is a residue that, when altered from the reference sequence of an AARS polypeptide, results in abolition of an activity of the parent molecule such that less than 20% of the reference activity is present. For example, such essential amino acid residues include those that are conserved in AARS polypeptides across different species, including those sequences that are conserved in the active binding site(s) or motif(s) of AARS polypeptides from various sources.

Accordingly, the present invention also contemplates variants of the naturally-occurring AARS polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference AARS polypeptide sequence, for example, as set forth in SEQ ID NOS: 1, 2, 3, 6, 8, 10, 12, 14, 16, 25, 28, 30, and 32-108. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of a parent or reference AARS polypeptide sequence are contemplated. In certain embodiments, the C-terminal or N-terminal region of any AARS polypeptide, including the AARS polypeptides of SEQ ID NOS: 1, 2, 3, 6, 8, 10, 12, 14, 16, 25, 28, 30, or 32-108, may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, or 700 or more amino acids, or by about 10-50, 20-50, 50-100, 100-150, 150-200, 200-250, 250-300, 300-350, 350-400, 400-450, 450-500, 500-550, 550-600, 600-650, 650-700 or more amino acids, including all integers and ranges in between (e.g., 101, 102, 103, 104, 105), so long as the truncated AARS polypeptide is capable of modulating hematopoiesis, either in vivo, in vitro, or ex vivo (e.g., stimulating megakaryocyte progenitor accumulation, stimulating neutrophil proliferation, reducing erythroid progenitor cell formation).

In some embodiments, variant polypeptides differ from a reference AARS sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NOS: 1, 2, 3, 6, 8, 10, 12, 14, 16, 25, 28, 30, or 32-108 by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution.

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of an AARS polypeptide as, for example, set forth in SEQ ID NOS: 1, 2, 3, 6, 8, 10, 12, 14, 16, 25, 28, 30, or 32-108 and has the ability to modulate hematopoiesis in a subject, such as by reducing the proliferation of progenitor cells of the erythroid lineage, stimulating the proliferation and/or differentiation of megakaryocytes in a subject, and/or stimulating the proliferation of neutrophils in a subject.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of an AARS polypeptide can be identified by screening combinatorial libraries of mutants of an AARS polypeptide. Libraries or fragments e.g., N terminal, C terminal, or internal fragments, of AARS protein coding sequence can be used to generate a variegated population of fragments for screening and subsequent selection of variants of an AARS polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of AARS polypeptides.

Also included are proteolytic fragments of AARS polypeptides. In certain illustrative embodiments, proteolytic fragments of AARS polypeptides may be produced using a variety of proteolytic enzymes or proteolytic chemical agents, according to techniques known and available in the art. Proteolytic fragments can be produced in vitro, such as by incubating AARS polypeptides with one or more proteases (as described herein and known in the art) under controlled conditions and isolating and characterizing the fragments produced therefrom. Proteolytic fragments can also be produced in vivo, or endogenously, such as by recombinantly expressing the AARS polypeptides in a selected cell (e.g., bacterial cell, eukaryotic cell), and isolating and characterizing the endogenous fragments produced therefrom (see, e.g., Example 10).

Proteases are usually classified according to three major criteria: (i) the reaction catalysed, (ii) the chemical nature of the catalytic site, and (iii) the evolutionary relationship, as revealed by the structure. General examples of proteases or proteinases, as classified by mechanism of catalysis, include aspartic proteases, serine proteases, cysteine proteases, and metalloproteases.

Most aspartic proteases belong to the pepsin family. This family includes digestive enzymes, such as pepsin and chymosin, as well as lysosomal cathepsins D and processing enzymes such as renin, and certain fungal proteases (e.g., penicillopepsin, rhizopuspepsin, endothiapepsin). A second family of aspartic proteases includes viral proteinases such as the protease from the AIDS virus (HIV), also called retropepsin.

Serine proteases include two distinct families. First, the chymotrypsin family, which includes the mammalian enzymes such as chymotrypsin, trypsin, elastase, and kallikrein, and second, the substilisin family, which includes the bacterial enzymes such as subtilisin. The general 3D structure between these two families is different, but they have the same active site geometry, and catalysis proceeds via the same mechanism. The serine proteases exhibit different substrate specificities, differences which relate mainly to amino acid substitutions in the various enzyme subsites (substrate residue interacting sites). Some serine proteases have an extended interaction site with the substrate whereas others have a specificity that is restricted to the P1 substrate residue.

The cysteine protease family includes the plant proteases such as papain, actinidin, and bromelain, several mammalian lysosomal cathepsins, the cytosolic calpains (calcium-activated), as well as several parasitic proteases (e.g., *Trypanosoma, Schistosoma*). Papain is the archetype and the best studied member of the family. Recent elucidation of the X-ray structure of the Interleukin-1-beta Converting Enzyme has revealed a novel type of fold for cysteine proteinases.

The metalloproteases are one of the older classes of proteases, found in bacteria, fungi, and higher organisms. They differ widely in their sequences and their 3D structures, but the great majority of enzymes contain a zinc atom that is catalytically active. In some cases, zinc may be replaced by another metal such as cobalt or nickel without loss of proteolytic activity. Bacterial thermolysin has been well characterized and its crystallographic structure indicates that zinc is bound by two histidines and one glutamic acid. Many metalloproteases contain the sequence motif HEXXH, which provides two histidine ligands for the zinc. The third ligand is either a glutamic acid (thermolysin, neprilysin, alanyl aminopeptidase) or a histidine (astacin, serralysin).

Illustrative proteases include, for example, achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

Tables C-G illustrate the type of proteolytic fragments that can be produced in vitro by incubating AARS polypeptides with various proteases. In certain embodiments, the incubation conditions can be controlled so that only certain cleavage sites are cleaved by the indicated protease, to achieve only partial cleavage, followed by isolation of the desired proteolytic fragment according to techniques known in the art (e.g., chromatography). Once a desired fragment has been isolated and characterized (e.g., sequenced) according to routine techniques in the art, it can be cloned and produced recombinantly, or produced synthetically, as desired.

Hence, included within the AARS polypeptides of the invention are any proteolytic fragments that can be produced by the exemplary proteases in Tables C-G, in addition to the proteases listed elsewhere herein, including any combination of proteases (e.g., Caspase 1 and hydroxylamine), or any combination of individual cleavage sites. Also, the residue position of cleavage sites may be approximate. Merely by way of illustration, an AARS proteolytic fragment may include about residues 1-165, about residues 166-445, about residues 166-455, about residues 166-716, about residues 445-716, or about residues 455-716 of GlyRS that has been cleaved or partially cleaved by incubation with iodosobenzoic acid (see Table C). As an additional illustration, an AARS proteolytic fragment may include about residues 1-98, about residues 1-135, about residues 98-135, about residues 1-234, about residues 98-234, about residues 1-379, about residues 234-674, or about residues 135-737 of QRS that has been cleaved or partially cleaved by proline-endopeptidase (see Table D). As a further illustrative example, an AARS polypeptide may include about residues 1-210, about residues 1-273, about residues 1-295, about residues 210-273, about residues 210-295, about residues 273-295 of QRS that has been cleaved or partially cleaved by hydroxylamine. Similar patterns can be applied to any of the AARS polypeptides and any of the proteases in Tables C-G, or to the other proteases listed herein or known in the art.

TABLE C

| Glycyl-tRNA synthetase (EC 6.1.1.14) (Glycine-tRNA ligase) (GlyRS) | |
|---|---|
| Protease | Position of cleavage sites (Residue No.) |
| Arg-C proteinase | 5 10 13 23 27 33 34 52 68 72 79 101 103 121 130 131 166 213 297 310 331 337 342 344 388 391 412 428 430 464 474 560 583 596 602 640 656 657 660 687 689 693 696 722 |
| Asp-N endopeptidase | 55 75 83 89 91 115 116 119 125 134 148 178 195 199 204 214 227 246 255 270 355 360 369 393 424 442 445 462 467 510 522 553 598 647 648 661 672 674 687 689 707 717 |
| Asp-N endopeptidase + N-terminal Glu | 55 60 61 75 82 83 89 91 96 105 108 115 116 119 124 125 134 148 171 172 176 178 185 195 199 204 209 214 227 233 237 239 246 252 255 270 298 312 332 344 349 351 355 358 360 369 393 396 424 433 435 442 445 447 456 462 467 482 487 497 510 516 522 523 528 530 535 538 542 544 553 567 568 575 589 596 598 599 625 632 635 647 648 661 662 672 674 687 689 697 700 707 717 719 726 729 734 737 738 |
| BNPS-Skatole | 165 445 455 716 |
| CNBr | 1 55 124 182 202 226 239 281 292 348 390 433 437 516 530 532 555 585 628 692 |

TABLE C-continued

Glycyl-tRNA synthetase (EC 6.1.1.14) (Glycine-tRNA ligase) (GlyRS)

| Protease | Position of cleavage sites (Residue No.) |
|---|---|
| Caspase 1 | 215 |
| Chymotrypsin-high specificity (C term to [FYW], not before P) | 132 133 134 138 141 148 150 165 169 198 201 212 249 258 261 278 282 285 295 305 308 314 321 330 346 354 365 374 376 408 409 414 416 429 440 445 453 455 467 497 508 518 526 540 549 561 566 579 586 589 593 604 605 614 627 630 658 668 674 716 726 |
| Clostripain | 5 10 13 23 27 33 34 52 68 72 79 101 103 121 130 131 166 213 297 310 331 337 342 344 388 391 412 428 430 464 474 560 583 596 602 640 656 657 660 687 689 693 696 722 |
| Formic acid | 56 76 84 90 92 116 117 120 126 135 149 179 196 200 205 215 228 247 256 271 356 361 370 394 425 443 446 463 468 511 523 554 599 648 649 662 673 675 688 690 708 718 |
| Glutamyl endopeptidase | 61 62 83 97 106 109 125 172 173 177 186 210 234 238 240 253 299 313 333 345 350 352 359 397 434 436 448 457 483 488 498 517 524 529 531 536 539 543 545 568 569 576 590 597 600 626 633 636 663 698 701 720 727 730 735 738 739 |
| Hydroxylamine | 208 711 |
| Iodosobenzoic acid | 165 445 455 716 |
| LysC | 80 82 85 93 99 102 108 115 123 129 158 190 197 204 207 219 224 229 230 235 236 264 283 309 318 360 364 379 389 419 426 450 477 484 487 490 501 506 509 510 513 537 547 553 559 563 615 632 646 679 733 734 |
| LysN | 79 81 84 92 98 101 107 114 122 128 157 189 196 203 206 218 223 228 229 234 235 263 282 308 317 359 363 378 388 418 425 449 476 483 486 489 500 505 508 509 512 536 546 552 558 562 614 631 645 678 732 733 |
| NTCB (2-nitro-5-thiocyanobenzoic acid) | 40 154 179 210 230 441 443 460 465 470 521 524 615 |
| Proline-endopeptidase | 6 28 298 363 485 |
| Staphylococcal peptidase I | 61 83 97 106 109 125 172 177 186 210 234 238 240 253 299 313 333 345 350 352 359 397 434 436 448 457 483 488 498 517 524 529 531 536 539 543 545 568 576 590 597 600 626 633 636 663 698 701 720 727 730 735 738 |
| Trypsin | 10 13 23 33 34 52 68 72 79 80 82 85 93 99 101 102 103 108 115 121 123 129 130 131 158 166 190 197 204 207 213 219 224 229 230 235 236 264 283 309 310 318 331 337 342 344 360 364 379 388 389 391 412 419 426 428 430 450 464 474 477 487 490 501 506 509 510 513 537 547 553 559 560 563 583 596 602 615 632 640 646 656 657 660 679 687 689 693 696 722 733 734 |

TABLE D

Glutaminyl-tRNA synthetase (EC 6.1.1.18) (Glutamine-tRNA ligase) (QRS)

| Protease | Positions of cleavage sites (Residue No.) |
|---|---|
| Arg-C proteinase | 21 34 62 64 67 68 95 109 132 134 141 154 195 201 202 225 265 267 301 351 352 361 376 378 391 403 419 427 463 464 486 497 509 515 523 524 525 538 558 567 576 616 629 639 666 667 690 694 745 764 |
| Asp-N endopeptidase | 4 48 64 99 102 105 160 169 183 199 205 214 302 303 319 336 339 376 409 413 429 438 445 474 509 511 512 558 562 588 597 617 668 702 713 723 728 738 751 753 770 |
| Asp-N endopeptidase + N-terminal Glu | 4 16 21 34 48 64 83 91 99 102 105 107 109 119 122 123 126 139 151 160 167 169 181 183 185 196 197 199 205 208 211 214 221 226 235 257 270 302 303 307 309 310 319 336 339 347 362 363 376 380 381 387 396 398 408 409 413 429 438 445 448 458 474 482 509 511 512 529 548 553 558 562 572 588 597 598 614 617 620 621 623 645 658 661 668 671 687 692 701 702 705 713 723 728 738 743 751 753 769 770 |
| BNPS-Skatole | 159 324 345 375 432 469 482 511 632 680 |
| CNBr | 1 146 150 164 171 221 250 321 380 390 404 408 413 548 569 686 |
| Caspase1 | 184 |
| Chymotrypsin-high specificity (C-term to [FYW], not before P) | 10 57 71 75 93 107 142 144 159 189 231 238 243 286 288 290 299 302 314 315 324 327 330 334 338 339 343 345 356 375 387 395 418 422 432 438 440 460 467 468 469 477 482 484 491 511 517 535 603 608 613 619 627 632 643 677 680 692 696 711 738 741 743 748 749 762 |
| Clostripain | 21 34 62 64 67 68 95 109 132 134 141 154 195 201 202 225 265 267 301 351 352 361 376 378 391 403 419 427 463 464 486 497 509 515 523 524 525 538 558 567 576 616 629 639 666 667 690 694 745 764 |
| Formic acid | 5 49 65 100 103 106 161 170 184 200 206 215 303 304 320 337 340 377 410 414 430 439 446 475 510 512 513 559 563 589 598 618 669 703 714 724 729 739 752 754 771 |
| Glutamyl endopeptidase | 17 22 35 84 92 108 110 120 123 124 127 140 152 168 182 186 197 198 209 212 222 227 236 258 271 308 310 311 348 363 364 381 382 388 397 399 409 449 459 483 530 549 554 573 599 615 621 622 624 646 659 662 672 688 693 702 706 744 770 |

TABLE D-continued

Glutaminyl-tRNA synthetase (EC 6.1.1.18) (Glutamine-tRNA ligase) (QRS)

| Protease | Positions of cleavage sites (Residue No.) |
| --- | --- |
| Hydroxylamine | 210 273 295 |
| Iodosobenzoic acid | 159 324 345 375 432 469 482 511 632 680 |
| LysC | 19 25 50 79 80 158 163 166 180 187 188 190 193 205 230 233 239 254 282 292 309 313 331 366 392 394 405 412 421 431 458 496 498 586 601 620 628 652 673 675 699 736 740 759 769 774 |
| LysN | 18 24 49 78 79 157 162 165 179 186 187 189 192 204 229 232 238 253 281 291 308 312 330 365 391 393 404 411 420 430 457 495 497 585 600 619 627 651 672 674 698 735 739 758 768 773 |
| NTCB (2-nitro-5-thiocyanobenzoic acid) | 110 297 318 357 432 442 444 455 470 477 535 555 656 664 686 729 |
| Proline-endopeptidase | 98 135 234 379 674 737 |
| Staphylococcal peptidase I | 17 22 35 84 92 108 110 120 123 127 140 152 168 182 186 197 209 212 222 227 236 258 271 308 310 348 363 381 388 397 399 409 449 459 483 530 549 554 573 599 615 621 624 646 659 662 672 688 693 702 706 744 770 |
| Thrombin | 567 |
| Trypsin | 19 21 25 34 50 62 64 67 68 79 80 95 109 132 141 154 158 163 166 180 187 188 190 193 195 201 202 205 225 230 239 254 265 267 282 292 301 309 313 331 351 352 361 366 376 391 392 394 403 405 412 419 421 427 431 458 463 464 486 496 497 498 509 515 523 525 538 558 567 576 586 601 616 620 628 629 639 652 666 667 675 690 694 699 740 745 759 764 769 774 |

TABLE E

Tryptophanyl-tRNA synthetase, cytoplasmic (EC 6.1.1.2) (Tryptophan-tRNA ligase) (WRS) (Interferon-induced protein 53) (IFP53) (hWRS)

| Protease | Positions of cleavage sites (Residue No.) |
| --- | --- |
| Arg-C proteinase | 24 106 119 122 127 133 134 141 162 298 300 318 321 326 381 388 417 448 449 464 |
| Asp-N endopeptidase | 33 36 56 60 75 82 85 98 100 112 141 147 184 196 197 204 208 220 227 236 238 270 272 298 301 311 313 321 353 362 381 394 396 408 409 410 418 453 468 |
| Asp-N endopeptidase + N-terminal Glu | 4 10 20 33 34 36 55 56 60 75 78 80 81 82 85 98 100 112 114 120 141 147 150 166 184 196 197 198 204 208 216 220 227 236 238 270 272 298 301 311 313 321 353 362 381 384 385 394 396 407 408 409 410 413 418 428 435 443 450 453 454 458 468 |
| BNPS-Skatole | 88 182 203 |
| CNBr | 1 42 48 143 169 195 241 243 319 350 401 425 461 |
| Caspase1 | 61 363 |
| Chymotrypsin-high specificity (C-term to [FYW], not before P) | 13 50 58 84 88 100 107 131 137 138 150 156 157 159 177 179 182 187 201 203 212 214 227 233 235 240 247 248 260 267 269 289 297 316 317 339 360 377 390 400 402 405 406 420 460 468 470 |
| Clostripain | 24 106 119 122 127 133 134 141 162 298 300 318 321 326 381 388 417 448 449 464 |
| Enterokinase | 200 412 |
| Formic acid | 34 37 57 61 76 83 86 99 101 113 142 148 185 197 198 205 209 221 228 237 239 271 273 299 302 312 314 322 354 363 382 395 397 409 410 411 419 454 469 |
| Glutamyl endopeptidase | 5 11 21 35 56 79 81 82 115 121 151 167 199 217 385 386 408 414 429 436 444 451 455 459 |
| Iodosobenzoic acid | 88 182 203 |
| LysC | 27 33 41 47 51 59 96 102 111 114 153 154 181 200 204 220 231 249 253 256 264 277 331 349 366 369 371 374 412 418 431 432 450 458 465 |
| LysN | 26 32 40 46 50 58 95 101 110 113 152 153 180 199 203 219 230 248 252 255 263 276 330 348 365 368 370 373 411 417 430 431 449 457 464 |
| NTCB (2-nitro-5-thiocyanobenzoic acid) | 61 224 273 304 308 393 |
| Proline-endopeptidase | 128 155 332 |
| Staphylococcal peptidase I | 5 11 21 35 56 79 81 115 121 151 167 199 217 385 408 414 429 436 444 451 455 459 |
| Thrombin | 162 326 |
| Trypsin | 24 27 33 41 47 51 59 96 102 106 111 114 119 122 133 134 141 153 162 181 200 204 220 231 249 253 256 264 277 298 300 318 321 326 349 366 369 371 374 381 388 412 417 418 431 432 448 449 450 458 464 465 |

TABLE F

Tyrosyl-tRNA synthetase (EC 6.1.1.1) (Tyrosyl-tRNA ligase) (YRS)

| Protease | Positions of cleavage sites (Residue No.) |
|---|---|
| Arg-C proteinase | 16 34 93 135 189 207 237 279 325 367 371 400 418 432 450 |
| Asp-N endopeptidase | 2 60 74 80 121 131 143 172 179 186 232 235 239 279 293 297 307 321 342 368 382 384 392 416 455 477 493 |
| Asp-N endopeptidase + N-terminal Glu | 2 7 8 19 23 24 28 32 34 60 67 74 80 87 90 97 105 112 121 127 131 143 150 156 172 173 174 179 186 195 226 227 228 232 235 238 239 250 255 273 279 280 293 295 297 301 307 313 321 325 342 358 360 361 368 378 382 384 389 392 395 397 412 413 416 434 445 452 455 464 472 477 478 479 488 493 498 499 |
| BNPS-Skatole | 40 87 283 505 |
| CNBr | 1 56 83 104 211 214 223 350 431 439 511 |
| Caspase1 | 75 494 |
| Chymotrypsin-high specificity (C-term to [FYW], not before P) | 39 40 52 53 62 73 79 87 96 97 117 123 129 134 176 183 192 194 198 204 249 263 275 283 289 292 299 328 388 409 468 472 488 495 505 510 |
| Clostripain | 16 34 93 135 189 207 237 279 325 367 371 400 418 432 450 |
| Formic acid | 3 61 75 81 122 132 144 173 180 187 233 236 240 280 294 298 308 322 343 369 383 385 393 417 456 478 494 |
| Glutamyl endopeptidase | 8 9 20 24 25 29 33 35 68 88 91 98 106 113 128 151 157 174 175 196 227 228 229 239 251 256 274 281 296 302 314 326 359 361 362 379 390 396 398 413 414 435 446 453 465 473 479 480 489 499 500 |
| Hydroxylamine | 258 |
| Iodosobenzoic acid | 40 87 283 505 |
| LysC | 10 26 28 32 37 47 58 64 84 102 114 116 119 127 146 147 154 178 190 197 206 222 231 238 242 243 244 246 247 265 272 282 287 297 310 319 327 334 335 346 348 352 356 374 380 391 412 427 430 470 474 482 484 485 486 490 496 506 513 520 523 |
| LysN | 9 25 27 31 36 46 57 63 83 101 113 115 118 126 145 146 153 177 189 196 205 221 230 237 241 242 243 245 246 264 271 281 286 296 309 318 326 333 334 345 347 351 355 373 379 390 411 426 429 469 473 481 483 484 485 489 495 505 512 519 522 |
| NTCB (2-nitro-5-thiocyanobenzoic acid) | 66 249 423 441 500 518 |
| Proline-endopeptidase | 48 159 306 349 382 428 483 |
| Staphylococcal peptidase I | 8 20 24 29 33 35 68 88 91 98 106 113 128 151 157 174 196 227 239 251 256 274 281 296 302 314 326 359 361 379 390 396 398 413 435 446 453 465 473 479 489 499 |
| Trypsin | 10 16 26 28 32 34 37 58 64 84 93 102 114 116 119 127 135 146 147 154 178 189 190 197 206 207 222 231 237 238 242 243 244 246 247 265 272 279 282 287 297 310 319 325 327 334 335 346 352 356 367 371 374 380 391 400 412 418 430 432 450 470 474 484 485 486 490 496 506 513 520 523 |

TABLE G

Histidyl-tRNA synthetase (EC 6.1.1.21) (Histidine-tRNA ligase) (HisRS)

| Protease | Positions of cleavage sites (Residue No.) |
|---|---|
| Arg-C proteinase | 4 17 19 63 68 73 82 86 128 137 149 157 158 165 167 169 214 215 232 266 326 362 375 388 396 405 424 479 484 490 491 500 501 |
| Asp-N endopeptidase | 47 63 77 92 109 115 118 129 158 174 176 182 187 205 212 217 227 238 241 264 268 285 300 314 315 320 328 363 370 432 472 487 492 |
| Asp-N endopeptidase + N-terminal Glu | 2 7 8 15 28 31 32 33 47 48 63 73 77 89 92 97 100 108 109 115 118 122 129 158 169 174 176 182 187 189 196 205 212 217 227 238 241 246 247 251 255 261 264 268 280 285 296 300 306 314 315 320 328 336 348 349 363 370 386 393 397 400 401 407 421 422 429 432 438 455 456 467 469 472 484 485 487 491 492 495 496 |
| BNPS-Skatole | 246 432 |
| CNBr | 1 70 104 141 163 185 195 220 253 369 |
| Chymotrypsin high specificity (C term to [FYW], not before P) | 54 65 77 84 97 107 115 129 135 138 150 156 168 171 172 176 182 207 221 231 246 270 306 308 312 320 330 331 336 363 370 390 432 442 454 |
| Clostripain | 4 17 19 63 68 73 82 86 128 137 149 157 158 165 167 169 214 215 232 266 326 362 375 388 396 405 424 479 484 490 491 500 501 |
| Formic acid | 48 64 78 93 110 116 119 130 159 175 177 183 188 206 213 218 228 239 242 265 269 286 301 315 316 321 329 364 371 433 473 488 493 |
| Glutamyl endopeptidase | 3 8 9 16 29 32 33 34 49 74 90 98 101 109 123 170 190 197 247 248 252 256 262 281 297 307 337 349 350 387 394 398 401 402 408 422 423 430 439 456 457 468 470 485 486 492 496 497 |
| Iodosobenzoic acid | 246 432 |
| LysC | 12 22 25 37 40 42 51 53 57 60 75 85 100 106 112 118 143 148 154 193 210 230 240 243 250 257 288 293 303 317 373 376 403 418 419 426 437 443 444 447 472 477 499 |

TABLE G-continued

Histidyl-tRNA synthetase (EC 6.1.1.21) (Histidine-tRNA ligase) (HisRS)

| Protease | Positions of cleavage sites (Residue No.) |
|---|---|
| LysN | 11 21 24 36 39 41 50 52 56 59 74 84 99 105 111 117 142 147 153 192 209 229 239 242 249 256 287 292 302 316 372 375 402 417 418 425 436 442 443 446 471 476 498 |
| NTCB (2-nitro-5-thiocyanobenzoic acid) | 82 173 190 195 223 234 378 454 506 508 |
| Staphylococcal peptidase I | 3 8 16 29 32 49 74 90 98 101 109 123 170 190 197 247 252 256 262 281 297 307 337 349 387 394 398 401 408 422 430 439 456 468 470 485 492 496 |
| Trypsin | 4 12 17 19 22 25 37 40 42 51 53 57 60 63 68 73 75 82 85 86 100 106 112 118 128 137 143 148 149 154 157 158 165 167 169 193 210 214 215 230 232 240 243 250 257 266 288 293 303 317 326 362 373 375 376 388 396 403 405 418 419 424 426 437 443 444 447 472 477 479 484 490 491 499 500 501 |

Certain embodiments relate to isolated AARS polypeptides, comprising, consisting essentially of, or consisting of amino acid sequences that have been derived from endogenous, naturally-occurring AARS polypeptide fragments, and pharmaceutical compositions comprising said fragments, and methods of use thereof. In certain embodiments, as noted above, the sequences of naturally-occurring endogenous proteolytic fragments can be generated or identified, for instance, from various cellular fractions (e.g., cytosolic, membrane, nuclear) and/or conditioned medium from various cell-types, including primary cells and cell lines. Examples of such cell types include, without limitation, immune cells such as dendritic cells, monocytes/macrophages (e.g., RAW 264.7 macrophages; see Example 5), neutrophils, eosinophils, basophils, and lymphocytes, such as B-cells and T-cells (e.g., CD4+ helper and CD8+ killer cells), including primary T-cells and T-cell lines such as Jurkat T-cells, as well as natural killer (NK) cells.

In certain embodiments, endogenous proteolytic fragments can be identified by techniques such as mass-spectrometry, or equivalent techniques. Merely by way of illustration and not limitation, in certain embodiments the proteomes from various cell types or fractions thereof may be separated by 1D SDS-PAGE and the gel lanes cut into bands at fixed intervals; after which the bands may be optionally digested with an appropriate protease, such as trypsin, to release the peptides, which may then be analyzed by 1D reverse phase LC-MS/MS. The resulting proteomic data may be integrated into so-called peptographs, which plot, in the left panel, sequence coverage for a given protein in the horizontal dimension (N to C terminus, left to right) versus SDS-PAGE migration in the vertical dimension (high to low molecular weight, top to bottom). The specific peptide fragments can then be sequenced or mapped. Table H provides a set of illustrative mouse QRS polypeptide fragments that were identified from RAW macrophages according to these exemplary techniques. Table I provides the corresponding set of human QRS polypeptide fragments.

TABLE H

Mouse QRS Polypeptide Fragments

| PEPTIDE SEQUENCE | SEQ ID NO: |
|---|---|
| ETLKNEALSTQLR | 36 |
| EAATQAHQILGSTIDKATGVLLYDLVSR | 37 |
| ETLKNEALSTQLREAATQAHQILGSTIDKATGVLLYDLVSR | 38 |

TABLE H-continued

Mouse QRS Polypeptide Fragments

| PEPTIDE SEQUENCE | SEQ ID NO: |
|---|---|
| DFEQECGVGVVVTPEQIEEAVESTINK | 39 |
| FNMGLLMGEAR* | 40 |
| MIKNEVDMQVLHLLGPK* | 41 |
| NEVDMQVLHLLGPK* | 42 |
| TPGYVITPYTMDLLK | 43 |
| FDDTNPEKEEAK* | 44 |
| VEELKGHNPLPSPWR | 45 |
| DRPKEESLLLFEAMR | 46 |
| VEELKGHNPLPSPWRDRPKEESLLLFEAMR | 47 |
| LVMEDGKMDPVAYR* | 48 |
| VYCPVQWEYGR* | 49 |
| ILQLVAAGAVR | 50 |
| DVLNDAAPRAMAVLEPLQVVITNFPAPK | 51 |
| GFHQVPFASTVFIERSDFKEESEPGYKRLASGQPVGLR | 52 |
| AFIHWVSQPLVCEIR | 53 |
| LGYFSVDPDSHQGQIVFNR | 54 |
| TPGYVITPYTMDLLK | 55 |
| AINFNFGYAK* | 56 |
| FDDTNPEKEEAK* | 57 |
| FFTAIYDMVTWLGYTPYK | 58 |
| FDDTNPEKEEAKFFTAIYDMVTWLGYTPYK | 59 |
| DRPKEESLLLFEAMR | 60 |
| VYCPVQWEYGR* | 61 |
| LNLHYAVVSK* | 62 |
| VYCPVQWEYGRLNLHYAVVSK* | 63 |
| ILQLVAAGAVR | 64 |

TABLE H-continued

Mouse QRS Polypeptide Fragments

| PEPTIDE SEQUENCE | SEQ ID NO: |
|---|---|
| AMAVLEPLQVVITNFPAPK | 65 |
| PLDIRVPNFPADETK | 66 |
| AMAVLEPLQVVITNFPAPKPLDIRVPNFPADETK | 67 |
| SDFKEESEPGYKRLASGQPVGLRHTGYVIELQNIVR | 68 |
| AFIHWVSQPLVCEIR | 69 |
| LGYFSVDPDSHQGQIVFNR | 70 |
| KATGVLLYDLVSR | 71 |
| SFLVSYIANK | 72 |
| DFEQECGVGVVVTPEQIEEAVESTINK | 73 |
| MIKNEVDMQVLHLLGPK* | 74 |
| EAATQAHQILGSTIDKATGVLLYDLVSR | 75 |

*The mouse and human sequences are identical.

TABLE I

Human QRS Polypeptide Fragments

| PEPTIDE SEQUENCE | SEQ ID NO: |
|---|---|
| ETLKNSALSAQLR | 76 |
| EAATQAQQTLGSTIDKATGILLYGLASR | 77 |
| ETLKNSALSAQLREAATQAQQTLGSTIDKATGILLYGLASR | 78 |
| DFERECGVGVIVTPEQIEEAVEAAINR | 79 |
| TPGYVVTPHTMNLLK | 80 |
| GEELKGHNTLPSPWR | 81 |
| DRPMEESLLLFEAMR | 82 |
| GEELKGHNTLPSPWRDRPMEESLLLFEAMR | 83 |
| ILQLVATGAVR | 84 |
| DVLNDTAPRAMAVLESLRVIITNFPAAK | 85 |
| GFHQVPFAPIVFIERTDFKEEPEPGFKRLAWGQPVGLR | 86 |
| AFIHWVSQPLMCEVR | 87 |
| LGYFSVDPDSHQGKLVFNR | 88 |
| TPGYVVTPHTMNLLK | 89 |
| FFTAICDMVAWLGYTPYK | 90 |
| FDDTNPEKEEAKFFTAIYDMVTWLGYTPYK | 91 |
| DRPMEESLLLFEAMR | 92 |
| ILQLVATGAVR | 93 |
| AMAVLESLRVIITNFPAAK | 94 |

TABLE I-continued

Human QRS Polypeptide Fragments

| PEPTIDE SEQUENCE | SEQ ID NO: |
|---|---|
| SLDIQVPNFPADETK | 95 |
| AMAVLESLRVIITNFPAAKSLDIQVPNFPADETK | 96 |
| TDFKEEPEPGFKRLAWGQPVGLRHTGYVIELQHVVK | 97 |
| AFIHWVSQPLMCEVR | 98 |
| LGYFSVDPDSHQGKLVFNR | 99 |
| KATGILLYGLASR | 100 |
| SFLVSYIASK | 101 |
| DFERECGVGVIVTPEQIEEAVEAAINR | 102 |
| EAATQAQQTLGSTIDKATGILLYGLASR | 103 |

Hence, certain specific embodiments include isolated QRS polypeptides that comprise, consist essentially of, or consist of any one or more of SEQ ID NOS:36-103 (in Tables H and I above), which modulate hematopoiesis, including variants thereof. In certain embodiments, these isolated QRS polypeptide fragments may further comprise 1, 2, 3, 4, 5, 6, 7, 8, 9, 10, 11, 12, 13, 14, 15, 16, 17, 18, 19, or 20 or more of the C-terminal and/or N-terminal residues that surround them, as characterized by their location within the full-length QRS polypeptide. In certain embodiments, these isolated QRS polypeptide fragments may be truncated to contain 1, 2, 3, 4, 5, 6, 7, 8, 9, 10, 11, 12, 13, 14, 15, 16, 17, 18, 19, or 20 fewer of their C-terminal and/or N-terminal residues. Also included are pharmaceutical compositions comprising such QRS polypeptide fragments, and methods of using said polypeptides or compositions to treat a subject in need thereof.

The present invention also contemplates the use of AARS chimeric or fusion proteins for modulating hematopoiesis. As used herein, an AARS "chimeric protein" or "fusion protein" includes an AARS polypeptide or polypeptide fragment linked to either another AARS-polypeptide (e.g., to create multiple fragments), to a non-AARS polypeptide, or to both. A "non-AARS polypeptide" refers to a "heterologous polypeptide" having an amino acid sequence corresponding to a protein which is different from an AARS protein, and which is derived from the same or a different organism. The AARS polypeptide of the fusion protein can correspond to all or a portion of a biologically active AARS amino acid sequence. In certain embodiments, an AARS fusion protein includes at least one (or two) biologically active portion of an AARS protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the hematopoietic-modulating activity of the polypeptide. For example, in one embodiment, a fusion partner may comprise a sequence that assists in expressing the protein (an expression enhancer) at higher yields than the native recombinant protein. Other fusion partners may be selected so as to increase the solubility of the protein or to enable the protein to be targeted to desired intracellular compartments.

The fusion protein can include a moiety which has a high affinity for a ligand. For example, the fusion protein can be a GST-AARS fusion protein in which the AARS sequences are fused to the C-terminus of the GST sequences. As another example, an AARS polypeptide may be fused to an eight amino acid tag at the C-terminus, such as an L-E-H-H-H-H-H-H (SEQ ID NO:5) tag. In certain specific embodiments, amino acids 1-364 of a YRS polypeptide are fused to a 365-L-E-H-H-H-H-H-H-372 (SEQ ID NO:5) tag at the C-terminus. Such fusion proteins can facilitate the purification and/or identification of an AARS polypeptide. Alternatively, the fusion protein can be an AARS protein containing a heterologous signal sequence at its N-terminus. In certain host cells, expression and/or secretion of AARS proteins can be increased through use of a heterologous signal sequence.

More generally, fusion to heterologous sequences, such as an Fc fragment, may be utilized to remove unwanted characteristics or to improve the desired characteristics (e.g., pharmacokinetic properties) of an AARS polypeptide. For example, fusion to a heterologous sequence may increase chemical stability, decrease immunogenicity, improve in vivo targeting, and/or increase half-life in circulation of an AARS polypeptide.

Fusion to heterologous sequences may also be used to create bi-functional fusion proteins, such as bi-functional proteins that are not only capable of modulating hematopoiesis (e.g., modulating cells from the myeloid, megakaryocyte, erythrocyte, lymphoid and/or endothelial progenitor (EPC) lineages), through the AARS polypeptide, but are also capable of modifying (i.e., stimulating or inhibiting) other pathways through the heterologous polypeptide. Examples of such pathways include, but are not limited to, various immune system-related pathways, such as innate or adaptive immune activation pathways, or cell-growth regulatory pathways, such as angiogenesis. In certain aspects, the heterologous polypeptide may act synergistically with the AARS polypeptide to modulate hematopoietic-related pathways in a subject. Examples of heterologous polypeptides that may be utilized to create a bi-functional fusion protein include, but are not limited to, thrombopoietin (TPO) or TRP peptide agonists, mpl-ligands, cytokines (e.g., IL-11, SDF-1, CXCL-12), chemokines, chemokine receptor ligands (e.g., CXCR-1, CXCR-2, CXCR-4 ligands), adhesion molecules (e.g., NCAM, ICAM-1, VCAM-1, PECAM-1, L1, CHL1, MAG, Nectins), and various hematopoietic growth factors (e.g., vascular endothelial growth factor (VEGF), fibroblast growth factors (FGF) such as FGF-1, FGF-2, and FGF-4, and other FGFR ligands), in addition to biologically active fragments and/or variants thereof. In certain embodiments, these heterologous polypeptides achieve additive or synergistic effects. Without wishing to be bound by any one theory, certain particular embodiments, such as fusion polypeptides of an AARS polypeptide (e.g., YRS) and TPO or other TPO peptide agonist, may achieve synergistic effects in increasing thrombopoiesis because certain AARS polypeptides are believed to increase thrombopoiesis by a TPO-independent mechanism; hence, the two thrombopoietic-stimulatory mechanisms may cooperate synergistically.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are typically located 5' to the DNA sequence encoding the first polypeptide. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Certain embodiments also encompass dimers of AARS polypeptides. Dimers may include, for example, homodimers between two identical AARS polypeptides, heterodimers between two different AARS polypeptides (e.g., a full-length YRS polypeptide and a truncated YRS polypeptide; a truncated YRS polypeptide and a truncated WRS polypeptide), and/or heterodimers between an AARS polypeptide and a heterologous polypeptide. Certain heterodimers, such as those between an AARS polypeptide and a heterologous polypeptide, may be bi-functional, as described herein. Also included are monomers of AARS polypeptides, including isolated AARS polypeptides monomers that do not substantially dimerize with a second AARS polypeptide, whether due to one or more substitutions, truncations, deletions, additions, chemical modifications, or a combination of these alterations. In certain embodiments, monomeric AARS polypeptides possess biological activities, including hematopoiesis-modulating activities, which are not possessed by dimeric or multimeric AARS polypeptide complexes.

Certain embodiments of the present invention also contemplate the use of modified AARS polypeptides, including modifications that improved the desired characteristics of an AARS polypeptide, as described herein. Modifications of AARS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of an AARS-polypeptide (see, e.g., Veronese and Harris, *Advanced Drug Delivery Reviews* 54: 453-456, 2002, herein incorporated by reference).

In certain aspects, chemoselective ligation technology may be utilized to modify truncated AARS polypeptides of the invention, such as by attaching polymers in a site-specific and controlled manner. Such technology typically relies on the incorporation of chemoselective anchors into the protein backbone by either chemical or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The truncated and/or variant AARS polypeptides of the invention may be prepared by any suitable procedure known to those of skill in the art, such as by recombinant techniques. For example, AARS polypeptides may be prepared by a procedure including the steps of: (a) preparing a construct comprising a polynucleotide sequence that encodes a truncated AARS polypeptide and that is operably linked to a regulatory element; (b) introducing the construct into a host cell; (c) culturing the host cell to express the truncated AARS polypeptide; and (d) isolating the truncated and/or variant AARS polypeptide from the host cell. In illustrative examples, the nucleotide sequence encodes at least a biologically active portion of a polypeptide sequence set forth in, or derived from, SEQ ID NOS:1, 2, 3, 6, 8, 10, 12, or 14, or a biologically active variant or fragment thereof. Recombinant AARS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the aminoacyl-tRNA synthetase polypeptides of the invention, including truncations and/or variants thereof, as well as compositions comprising such polynucleotides.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an aminoacyl-tRNA synthetase or a portion thereof) or may comprise a variant, or a biological functional equivalent of such a sequence. Polynucleotide variants may contain one or more substitutions, additions, deletions and/or insertions, as further described below, preferably such that the hematopoietic-modulating activity of the encoded polypeptide is not substantially diminished relative to the unmodified polypeptide. The effect on the hematopoietic-modulating activity of the encoded polypeptide may generally be assessed as described herein.

In additional embodiments, the present invention provides isolated polynucleotides comprising various lengths of contiguous stretches of sequence identical to or complementary to an aminoacyl-tRNA synthetase, wherein the isolated polynucleotides encode a truncated aminoacyl tRNA synthetase as described herein.

Exemplary nucleotide sequences that encode the AARS polypeptides of the application encompass coding sequences, such as the polynucleotide sequences of SEQ ID NOS:4, 7, 9, 11, 13, 15, 17, 19, and 31, as well as portions of the full-length or substantially full-length nucleotide sequences of the AARS genes or their transcripts or DNA copies of these transcripts.

Portions of an AARS nucleotide sequence may encode polypeptide portions or segments that retain the biological activity of the reference polypeptide, including the polypeptides of SEQ ID NOS:1, 2, 3, 6, 8, 10, 12, 14, 16, 25, 28, 30, and 32-108, or polypeptides having an amino acid sequence that is at least 80%, 85%, 90%, 95%, 97%, or 98% identical to these sequences. A portion of an AARS nucleotide sequence that encodes a biologically active fragment of an AARS polypeptide may encode at least about 20, 21, 22, 23, 24, 25, 30, 40, 50, 60, 70, 80, 90, 100, 120, 150, 300 or 400 contiguous amino acid residues, or almost up to the total number of amino acids present in a full-length AARS polypeptide. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the AARS nucleotide sequences. Nucleic acid variants can be naturally-occurring, such as allelic variants (same locus), homologs (different locus), and orthologs (different organism) or can be non naturally-occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference AARS polypeptide, such as the sequences set forth in SEQ ID NOS: 1, 2, 3, 6, 8, 10, 12, 14, 16, 25, 28, 30, or 32-108. Variant nucleotide sequences also include synthetically derived nucleotide sequences, such as those generated, for example, by using site-directed mutagenesis but which still encode an AARS polypeptide. Generally, variants of a particular AARS nucleotide sequence will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

AARS nucleotide sequences can be used to isolate corresponding sequences and alleles from other organisms, particularly other organisms or microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other AARS-coding sequences present in a population of cloned genomic DNA fragments or cDNA fragments (i.e., genomic or cDNA libraries) from a chosen organism.

Accordingly, the present invention also contemplates polynucleotides that hybridize to reference AARS nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, an AARS polypeptide is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6 (\log_{10} M)+0.41 (\% G+C)-0.63 (\%$ formamide$)-(600/$length$)$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a truncated and/or variant aminoacyl-tRNA synthetase polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer or immediate/early cytomegalovirus (CMV) enhancer/promoter region, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk– or aprt– cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

Antibodies

According to another aspect, the present invention further provides antibodies that exhibit binding specificity for an AARS polypeptide or its cellular binding partner as disclosed herein, or to a portion, variant or derivative thereof, and methods of using same. The term antibody includes the various variations of the same, such as FABs, human antibodies, modified human antibodies, single chains, nonhuman antibodies, and other derivatives of the immunoglobulin fold that underly immune system ligands for antigens, as described herein and known in the art. Antibodies can be used in any of the therapeutic, diagnostic, drug discovery, or protein expression/purification methods and compositions provided herein.

Certain antibodies of the present invention differ from certain previously made antibodies because they can distinguish between certain AARS protein fragments/variants and their corresponding full-length AARS, typically by binding with greater affinity to the AARS protein fragments/variants than to the corresponding full-length AARS. Generally, such antibodies may bind to unique sequences or structures generated or revealed by splice variations, proteolysis, mutation, or other cellular processing that generates an AARS protein fragment/variant of the invention (e.g., post translational processing, including but not limited to phosphorylation and other modifications that change protein structure). For example, such antibodies may have binding specificity to one or more non-solvent exposed faces that are exposed in the AARS protein fragment/variant but not in the full-length AARS, or sequences that are not found or are otherwise inaccessible in the full-length AARS. Antibodies may also bind to unique three-dimensional structures that result from differences in folding between the AARS protein fragment/variant and the full-length AARS. Such differences in folding may be localized (e.g., to a specific domain or region) or globalized. As one example, folding of AARS protein fragments or variants may generate unique continuous or discontinuous epitopes that are not found in the corresponding or parent AARS. Examples also include antibodies that specifically bind to N- or C-termini generated by splice variations, proteolysis, or other cellular processing; such termini may be unique compared to the full-length AARS or may not be exposed for antibody binding in the full-length versions due to their termini being completely or partially buried in the overall structure of the larger AARS parent molecule.

In some embodiments, antibodies provided herein do not form aggregates, have a desired solubility, and/or have an immunogenicity profile that is suitable for use in humans, as described herein and known in the art. Also included are antibodies that are suitable for production work, such as to purify the AARS protein fragments/variants described herein. Preferably, active antibodies can be concentrated to at least about 10 mg/ml and optional formulated for biotherapeutic uses.

In certain embodiments, antibodies are effective for modulating one or more of the hematopoiesis-modulating activities mediated by an AARS polypeptide of the invention, or the full-length protein. In certain embodiments, for example, the antibody is one that binds to an AARS polypeptide and/or its binding partner, inhibits their ability to interact with each other, and/or antagonizes the hematopoiesis-modulating of the AARS polypeptide. In certain embodiments, for example, the antibody binds to the cellular binding partner of an AARS polypeptide, and mimics the AARS polypeptide activity, such as by increasing or agonizing the hematopoiesis-modulating activity of the AARS polypeptide. Specific embodiments include antibodies that antagonize the thrombopoietic activity of certain YRS polypeptides, such as the exemplary YRS polypeptides of SEQ ID NOS:1, 2 and 3. Accordingly, antibodies may be used to diagnose, treat, or prevent diseases, disorders or other conditions that are mediated by an AARS polypeptide of the invention (or its full-length parent), such as by antagonizing or agonizing its non-canonical activity (e.g., hematopoietic modulating activity) partially or fully.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably in a statistically significant manner with unrelated polypeptides under similar conditions. In certain instances, an antibody or binding agent does not significantly interact with a full-length version of the AARS polypeptide. In some instances, an antibody or binding agent recognizes both the AARS polypeptide and the full length AARS. In certain embodiments, an antibody or binding agent selectively interacts with a full-length version of the AARS polypeptide.

Immunological binding, as used in this context, generally refers to the non-covalent interactions of the type which occur between an immunoglobulin molecule and an antigen for which the immunoglobulin is specific. The strength, or affinity of binding such as immunological binding interactions can be expressed in terms of the dissociation constant ($K_d$) of the interaction, wherein a smaller $K_d$ represents a greater affinity. Immunological binding properties of selected polypeptides can be quantified using methods well known in the art. See, e.g., Davies et al. (1990) Annual Rev. Biochem. 59:439-473. In certain illustrative embodiments, an antibody has an affinity for an AARS polypeptide of the invention of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, the affinity of the antibody for an AARS protein fragment is stronger than its affinity for a corresponding full-length AARS polypeptide, typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between). In certain embodiments, an antibody as an affinity for a corresponding full-length or parental AARS protein of at least about 0.05, 0.1, 0.25, 0.5, 0.75, 1, 2, 3, 4, 5, 6, 7, 8, 9, 10, 11, 12, 13, 14, 15, 16, 17, 18, 19, or 20 μM. In certain embodiments, an antibody binds weakly or substantially undetectably to a full-length AARS protein.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Antibodies may be prepared by any of a variety of techniques known to those of ordinary skill in the art. Methods for immunizing non-human animals such as rabbits, mice, rats, sheep, goats, pigs, cattle and horses are well known in the art. See, e.g., Harlow and Lane, *Antibodies: A Laboratory Manual*, Cold Spring Harbor Laboratory, 1988 and U.S. Pat. No. 5,994,619. In some embodiments, an AARS polypeptide fragment (for example, such as miniYRS (SEQ. ID. No. 3)), a splice variant, or a full length AARS protein with a conformationally active mutation, (for example, such as YRS comprising Y341A (SEQ. ID. No. 2)) is administered with an adjuvant to stimulate the immune response to generate antibodies that are selective for the AARS polypeptide fragment. Exemplary adjuvants include complete or incomplete Freund's adjuvant, RIBI (muramyl dipeptides) or ISCOM (immunostimulating complexes). Such adjuvants may protect the protein from rapid dispersal by sequestering it in a local deposit, or they may contain substances that stimulate the host to secrete factors that are chemotactic for macrophages and other components of the immune system. Typically, the immunization schedule will involve two or more administrations of the protein, spread out over several weeks.

Rabbits are known to produce antibodies to many antigens that are not especially immunogenic in mice, and are particularly well suited for the production of conformationally specific antibodies. Direct comparisons of rabbit and mouse antibodies have shown that rabbit and mouse antibodies often recognize different epitopes and that rabbit antibodies are generally of higher affinity than mouse antibodies. These differences enable the development of antibodies with better cross reactivity and improved specificity to particular AARS polypeptide fragments compared to mouse monoclonal antibodies.

Accordingly in one aspect the present invention includes a method for selecting an an AARS polypeptide fragment selective antibody comprising the steps of; a) immunizing a rabbit with a human AARS polypeptide fragment, a splice variant, or a full length AARS protein with a conformationally active mutation, b) screening the rabbit for an AARS polypeptide fragment specific antibodies, and; c) isolating sera from the rabbit comprising the AARS polypeptide specific antibodies. In some embodiments, the method may additionally involve the step of isolating or amplifying one or more nucleic acids derived from the rabbit's antibody-producing cells encoding an antibody heavy or light chain, or portion thereof, that binds to an AARS polypeptide fragment In some aspects, after immunization, rabbits with high titers against human AARS polypeptide fragments are selected for the subsequent generation of rabbit monoclonal antibodies. Such monoclonal antibodies may be generated via the creation of immortalized cell fusions, such as the creation of hybridomas, or by direct cloning or amplification of the antibody genes using recombinant DNA technology as described herein.

Exemplary AARS protein fragments for immunization include for example, any of the peptide fragments listed in Tables C-G. Exemplary YRS polypeptide variants for immunization include, for example, full-length YRS polypeptides, or truncations or splice variants thereof, having one or more amino acid substitutions selected from an R93Q substitution, an I14L substitution, an N17G substitution, an L271 substitution, an A85S substitution, and a V156L substitution, in addition to combinations thereof. Particular examples of YRS polypeptide variants include, but are not limited to, a YRS polypeptide having amino acids 1-364 of SEQ ID NO:1 with an R93Q substitution, a YRS polypeptide having amino acids 1-353 of SEQ ID NO:1 with an I14L substitution, a YRS polypeptide having amino acids 1-353 of SEQ ID NO:1 with an N17G substitution, a YRS polypeptide having amino acids 1-353 of SEQ ID NO:1 with an L271 substitution, a YRS polypeptide having amino acids 1-353 of SEQ ID NO:1 with an A85S substitution, and a YRS polypeptide having amino acids 1-353 of SEQ ID NO:1 with a V156L substitution.

Particular examples of biologically active YRS fragments include, but are not limited to, C-terminally truncated tyrosyl-tRNA synthetase polypeptides comprising or consisting of amino acids 1-343, amino acids 1-344, amino acids 1-350, amino acids 1-353, or amino acids 1-364 of the amino acid sequence set forth in SEQ ID NO:1, in addition to the polypeptides of SEQ ID NOS:3 and 6. Additional examples of biologically active fragments include, but are not limited to, N-terminally truncated tyrosyl-tRNA synthetase polypeptides comprising or consisting of the amino acid sequences set forth in SEQ ID NOS: 6, 10, 12, and 14.

Exemplary HRS polypeptide variants for immunization include, for example, full length HisRS protein (NP_002100.2), the HRS-SV9 splice variant, (SEQ ID NO:30) and the HRS-SV11 splice variant (SEQ ID NO:32).

Particular examples of biologically active HRS fragments include, but are not limited to, HisRS fragments comprising at least the WHEP domain of HisRS, e.g., amino acid residues 3-43 of the human full length HisRS protein and HisRS fragments comprising at least the anticodon binding domain of HisRS, e.g., amino acid residues 406-501 of the full length human HisRS protein. Further examples include HisRS fragments that lack a functional aminoacylation domain, e.g., amino acid residues 54-398 of the human full length HisRS protein or HisRS splice variant polypeptides that comprise at least the WHEP domain and the anticodon binding domain but lack a functional aminoacylation domain.

Exemplary WRS polypeptide variants for immunization include, for example, the full-length protein (SEQ ID NO: 33), and a fragment thereof, often designated mini-WRS (SEQ ID NO:107). Also included are human T1-WRS (SEQ ID NO:108) and T2-WRS (SEQ ID NO:34), as well as an N-terminal fragment (F1; SEQ ID NO:106) and fragment of WRS referred to as "Tolstrup" (SEQ ID NO:35). Other splice variants of human WRS are known in the art (see, e.g., Liu et al., *Nucleic Acids Research*, 32(2):719-27, 2004, herein incorporated by reference).

Exemplary QRS polypeptide variants for immunization include, for example, the full-length QRS polypeptide is shown in SEQ ID NO:25. Certain specific examples of QRS variants, truncations, or fragments include QRS polypeptides that comprise or consist essentially of amino acids 1-183 (QRS1 or Q1), 1-220 (QRS2 or Q2), 1-249 (QRS3 or Q3), 1-200 (QRS4 or Q4), 1-(181-293), e.g., 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, etc., of SEQ ID NO:25 (see Table 2).

Exemplary GRS polypeptide variants for immunization include, for example, the full-length GlyRS polypeptide is shown in SEQ ID NO:16 (see Example 9 & Table 1).

Particular examples of GlyRS proteolytic fragments for use in immunization include polypeptides that comprise, consist essentially of, or consist of amino acid residues 57-685, 214-685, 239-685, 311-685, 439-685, 511-658, 214-438, 367-438, 214-420, 214-338, 85-127 1-213, 1-61, 85-214, 333-685, 128-685, 265-685, 483-685 or 25-56 of SEQ ID NO:16 (see Table 1).

Other Exemplary AARS polypeptide variants for immunization also include, phenylalanyl-tRNA synthetase (PheRS) splice variant polypeptides (PheRS_SV1P) (SEQ ID NO:104), and aspartyl-tRNA synthetase (AspRS) polypeptides (SEQ ID NO:105), including fragments thereof that consist essentially of amino acid residues 1-154, 1-174, 1-31, 399-425, 413-476 or 397-425 of SEQ ID NO:105.

Monoclonal antibodies specific for any of the AARS polypeptide fragments of interest may be prepared, for example, using the technique of Kohler and Milstein, *Eur. J. Immunol.* 6:511-519, 1976, and improvements thereto. For further descriptions of rabbit monoclonal antibodies and methods of making the same from rabbit-rabbit and rabbit-mouse fusions, see, e.g., U.S. Pat. No. 5,675,063 (rabbit-rabbit); U.S. Pat. No. 4,859,595 (rabbit-rabbit); U.S. Pat. No. 5,472,868 (rabbit-mouse); and U.S. Pat. No. 4,977,081 (rabbit-mouse). For a description of the production of conventional mouse monoclonal antibodies, see, e.g., Kohler and Milstein, *Nature* (1975) 256:495-497. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VelocImmune® platform by Regernerex® (see, e.g., U.S. Pat. No. 6,596,541).

AARS polypeptide fragment specific antibodies can be recovered directly from antibody producing cells, such as peripheral B-cells, immortalized antibody producing cells, or hybridomas derived from antibody producing cells by, single cell RT-PCR for the selected B cells (SLAM) (See, e.g., Babcook et al., *Proc. Natl. Acad. Sci. USA* (1996) 93:7843-7848), or via antibody display technologies and by a variety of standard recombinant cloning strategies known in the art. (See generally, Poul M A et al., (1995) Eur J. Immunol. 25(7):2005-9; Jovelin F et al., (1995) Biotechniques. 19(3): 378-80; Heinrichs A et al., (1995) J Immunol Methods. 178 (2):241-51; Essono S et al., (2003) J Immunol Methods. 279(1-2):251-66). These technologies can also be used for further structural and functional characterization and optimization of therapeutic antibodies (Kim S J et al., (2005) Mol Cells. 20(1):17-29. Aires da Silva F, et al., (2008) BioDrugs. 22(5):301-14), or for generating vectors allowing the stable in vivo delivery of monoclonal antibodies Antibodies can also be generated or identified by the use of phage display or yeast display libraries (see, e.g., U.S. Pat. No. 7,244,592; Chao et al., *Nature Protocols.* 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art. The polypeptides of this invention may be used in the purification process in, for example, an affinity chromatography step.

The term "antigen-binding portion of an antibody," "antigen-binding fragment," "antigen-binding domain," "antibody fragment" or a "functional fragment of an antibody" are used interchangeably in the present invention to include one or more fragments of an antibody that retain the ability to specifically bind to an antigen (see, e.g., Holliger et al., *Nature Biotech.* 23 (9): 1126-1129 (2005)). Non-limiting examples of antibody fragments include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., *Nature* 341:544-546, 1989), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 242:423-426, 1988; and Huston et al., *PNAS USA* 85:5879-5883, 1988; and Osbourn et al., *Nat. Biotechnol.* 16:778, 1998). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed.

An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. See, e.g., Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) *PNAS USA.* 85 (16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

Certain embodiments include single domain antibody (sd-Abs or "nanobodies"), which refer to an antibody fragment consisting of a single monomeric variable antibody domain (see, e.g., U.S. Pat. Nos. 5,840,526; 5,874,541; 6,005,079, 6,765,087, 5,800,988; 5,874,541; and 6,015,695). Such sdABs typically have a molecular weight of about 12-15 kDa. In certain aspects, sdABs and other antibody molecules can be derived or isolated from the unique heavy-chain antibodies of immunized camels and llamas, often referred to as camelids. See, e.g., Conrath et al., *JBC.* 276:7346-7350, 2001.

A number of "humanized" antibody molecules comprising an antigen-binding site derived from a non-human (donor) immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) *J Immunol.* 138: 4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

For the most part, humanized antibodies are human immunoglobulins (recipient antibody) in which residues from a hyper-variable region of the recipient are replaced by residues from a hypervariable region of a non-human species (donor antibody) such as mouse, rat, rabbit, or non-human primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., *Nature* 321:522-525 (1986); Riechmann et al., *Nature* 332: 323-329 (1988); and Presta, *Curr. Op. Struct. Biol.* 2:593-596 (1992), WO 92/02190, U.S. Patent Application 2006/0073137, and U.S. Pat. Nos. 6,750,325; 6,632,927; 6,639, 055; 6,548,640; 6,407,213; 6,180,370; 6,054,297; 5,929,212; 5,895,205, 5,886,152; 5,877,293; 5,869,619; 5,821,337; 5,821,123; 5,770,196; 5,777,085; 5,766,886; 5,714,350; 5,693,762; 5,693,761; 5,530,101; 5,585,089; and 5,225,539.

The antibodies and antibody fragments of the present invention can be used in any of the therapeutic, diagnostic, drug discovery, protein purification, and analytical methods and compositions described herein.

Antibody Alternatives and Other Binding Agents

According to another aspect, the present invention further provides antibody alternatives or other binding agents, such as soluble receptors, adnectins, peptides, peptide mimetics, small molecules, aptamers, etc., that exhibit binding specificity for an AARS polypeptide or its cellular binding partner as disclosed herein, or to a portion, variant or derivative thereof, and compositions and methods of using same. Binding agents can be used in any of the therapeutic, diagnostic, drug discovery, or protein expression/purification, and analytical methods and compositions described herein. Biologic-based binding agents such as adnectins, soluble receptors, avimers, and trinectins are particularly useful.

In certain embodiments, such binding agents are effective for modulating one or more of the hematopoiesis-modulating activities mediated by an AARS polypeptide of the invention. In some embodiments, for example, the binding agent is one that binds to an AARS polypeptide and/or its binding partner, inhibits their ability to interact with each other, and/or antagonizes the hematopoiesis-modulating activity of the AARS polypeptide. In specific embodiments, the binding agent binds to and/or antagonizes the thrombopoietic activity of certain YRS polypeptides, such as the polypeptides of SEQ ID NOS:1, 2 or 3. In certain embodiments, for example, the binding agent binds to the cellular binding partner of an AARS polypeptide, and mimics the AARS polypeptide activity, such as by increasing or agonizing the hematopoiesis-modulating activity mediated by the AARS polypeptide. Accordingly, such binding agents may be used to diagnose, treat, or prevent diseases, disorders or other conditions that are mediated by an AARS polypeptide of the invention, such as by antagonizing or agonizing its non-canonical activity (e.g., hematopoiesis-modulating activity) partially or fully.

A binding agent is said to "specifically bind" to an AARS polypeptide of the invention, or its cellular binding partner, if it reacts at a detectable level (within, for example, an ELISA assay) with the polypeptide or its cellular binding partner, and does not react detectably in a statistically significant manner with unrelated polypeptides under similar conditions. In certain instances, a binding agent does not significantly interact with a full-length version of the AARS polypeptide. In certain illustrative embodiments, a binding agent has an affinity for a hematopoiesis-modulating AARS polypeptide of the invention or its cellular binding partner of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, the affinity of the binding agent for an AARS protein fragment is stronger than its affinity for a corresponding full-length AARS polypeptide, typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between). In certain embodiments, a binding agent has an affinity for a corresponding full-length AARS protein of at least about 0.5, 1, 2, 3, 4, 5, 6, 7, 8, 9, 10, 11, 12, 13, 14, 15, 16, 17, 18, 19, or 20 µM.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with an AARS polypeptide, its cellular binding partner, or both. Peptides can be composed of naturally-occurring amino acids and/or non-naturally occurring amino acids, as described herein.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Luthman, et al., *A Textbook of Drug Design and Development*, 14:386-406, 2nd Ed., Harwood Academic Publishers (1996); Joachim Grante, *Angew. Chem. Int. Ed. Engl.*, 33:1699-1720 (1994); Fauchere, J., *Adv. Drug Res.*, 15:29 (1986); Veber and Freidinger TINS, p. 392 (1985); and Evans, et al., *J. Med. Chem.* 30:229 (1987)). A peptidomimetic is a molecule that mimics the biological activity of a peptide but is no longer peptidic in chemical nature. Peptidomimetic compounds are known in the art and are described, for example, in U.S. Pat. No. 6,245,886.

The present invention also includes peptoids. Peptoid derivatives of peptides represent another form of modified peptides that retain the important structural determinants for biological activity, yet eliminate the peptide bonds, thereby conferring resistance to proteolysis (Simon, et al., *PNAS USA*. 89:9367-9371, 1992). Peptoids are oligomers of N-substituted glycines. A number of N-alkyl groups have been described, each corresponding to the side chain of a natural amino acid. The peptidomimetics of the present invention include compounds in which at least one amino acid, a few amino acids or all amino acid residues are replaced by the corresponding N-substituted glycines. Peptoid libraries are described, for example, in U.S. Pat. No. 5,811,387.

A binding agent may also include one or more small molecules. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Small molecule libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or on phage (Cwirla et al., 1990; Devlin et al., 1990; Felici et al., 1991; Ladner et al., U.S. Pat. No. 5,223,409, 1993; Scott and Smith, 1990). Embodiments of the present invention encompass the use of different libraries for the identification of small molecule modulators of one or more AARS protein fragments, their cellular binding partners, and/or their related hematopoiesis-modulating activities. Libraries useful for the purposes of the invention include, but are not limited to, (1) chemical libraries, (2) natural product libraries, and (3) combinatorial libraries comprised of random peptides, oligonucleotides and/or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. See, e.g., Cane et al., *Science* 282: 63-68, 1998. Combinatorial libraries may be composed of large numbers of peptides, oligonucleotides or organic compounds as a mixture. They are relatively easy to prepare by traditional automated synthesis methods, PCR, cloning or proprietary synthetic methods.

More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

For a review of combinatorial chemistry and libraries created therefrom, see, e.g., Huc, I. and Nguyen, R. (2001) Comb. Chem. High Throughput Screen 4:53-74; Lepre, C A. (2001) Drug Discov. Today 6:133-140; Peng, S. X. (2000) Biomed. Chromatogr. 14:430-441; Bohm, H. J. and Stahl, M. (2000) Curr. Opin. Chem. Biol. 4:283-286; Barnes, C. and Balasubramanian, S. (2000) Curr. Opin. Chem. Biol. 4:346-350; Lepre, Enjalbal, C, et al., (2000) Mass Septrom Rev. 19:139-161; Hall, D. G., (2000) Nat. Biotechnol. 18:262-262; Lazo, J. S., and Wipf, P. (2000) J. Pharmacol. Exp. Ther. 293:705-709; Houghten, R. A., (2000) Ann. Rev. Pharmacol. Toxicol. 40:273-282; Kobayashi, S. (2000) Curr. Opin. Chem. Biol. (2000) 4:338-345; Kopylov, A. M. and Spiridonova, V. A. (2000) Mol. Biol. (Mosk) 34:1097-1113; Weber, L. (2000) Curr. Opin. Chem. Biol. 4:295-302; Dolle, R. E. (2000) J. Comb. Chem. 2:383-433; Floyd, C D., et al., (1999) Prog. Med. Chem. 36:91-168; Kundu, B., et al., (1999) Prog. Drug Res. 53:89-156; Cabilly, S. (1999) Mol. Biotechnol. 12:143-148; Lowe, G. (1999) Nat. Prod. Rep. 16:641-

651; Dolle, R. E. and Nelson, K. H. (1999) J. Comb. Chem. 1:235-282; Czarnick, A. W. and Keene, J. D. (1998) Curr. Biol. 8:R705-R707; Dolle, R. E. (1998) Mol. Divers. 4:233-256; Myers, P. L., (1997) Curr. Opin. Biotechnol. 8:701-707; and Pluckthun, A. and Cortese, R. (1997) Biol. Chem. 378: 443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

Aptamers are also included as binding agents (see, e.g., Ellington et al., *Nature*. 346, 818-22, 1990; and Tuerk et al., *Science*. 249, 505-10, 1990). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620 Hence, included are nucleic acid aptamers that bind to the AARS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys- loop in the wild protein), with the two cysteines lateral chains being able to form a disulfide bridge. Methods for identifying peptide aptamers are described, for example, in U.S. Application No. 2003/0108532. Hence, included are peptide aptamers that bind to the AARS polypeptides described herein and/or their cellular binding partners. Peptide aptamer selection can be performed using different systems known in the art, including the yeast two-hybrid system.

Also included are Adnectins™, Avimers™, and anticalins that specifically bind to an AARS protein fragment of the invention. Adnectins™ refer to a class of targeted biologics derived from human fibronectin, an abundant extracellular protein that naturally binds to other proteins. See, e.g., U.S. Application Nos. 2007/0082365; 2008/0139791; and 2008/0220049. Adnectins™ typically consists of a natural fibronectin backbone, as well as the multiple targeting domains of a specific portion of human fibronectin. The targeting domains can be engineered to enable an Adnectin™ to specifically recognize a therapeutic target of interest, such as an AARS protein fragment of the invention.

Avimers™ refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., *Nature Biotechnology*. 23:1556-1561, 2005; U.S. Pat. No. 7,166,697; and U.S. Application Nos. 2004/0175756, 2005/0048512, 2005/0053973, 2005/0089932 and 2005/0221384.

Also included are designed ankyrin repeat proteins (DARPins), which include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins. See, e.g., Stumpp et al., *Curr Opin Drug Discov Devel*. 10:153-159, 2007; U.S. Application No. 2009/0082274; and PCT/EP2001/10454.

Certain embodiments include "monobodies," which typically utilize the 10th fibronectin type III domain of human fibronectin (FNfn10) as a scaffold to display multiple surface loops for target binding. FNfn10 is a small (94 residues) protein with a β-sandwich structure similar to the immunoglobulin fold. It is highly stable without disulfide bonds or metal ions, and it can be expressed in the correctly folded form at a high level in bacteria. The FNfn10 scaffold is compatible with virtually any display technologies. See, e.g., Batori et al., *Protein Eng*. 15:1015-20, 2002; and Wojcik et al., *Nat Struct Mol Biol.*, 2010; and U.S. Pat. No. 6,673,901.

Anticalins refer to a class of antibody mimetics, which are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, *FEBS J*. 275:2677-83, 2008, herein incorporated by reference.

Modulation of Hematopoiesis and Methods of Use

Embodiments of the present invention relate to the discovery that aminoacyl-tRNA synthetase (AARS) polypeptides, and fragments and variants thereof, modulate hematopoiesis in a variety of useful ways, both in vitro and in vivo. For instance, in certain embodiments, the AARS polypeptides, antibodies and antibody fragments thereto, and related agents of the present invention modulate or reduce erythropoiesis, such as by leading to a reduction in the formation of erythroid progenitor cells. As a further example, in certain embodiments, the AARS polypeptides, and antibodies and antibody fragments thereto, of the present invention modulate or stimulate megakaryopoiesis and/or thrombopoiesis. More generally, AARS polypeptides, and antibodies and antibody fragments thereto, are capable of modulating cells from the myeloid, megakaryocyte, erythrocyte, granulocyte, lymphoid, thrombocytes, and/or endothelial progenitor (EPC) lineages, among others described herein.

The AARS polypeptides of the present invention may therefore be used to treat various diseases or conditions that benefit from the modulation of hematopoietic processes. Likewise, related agents such as antibodies and other binding agents that interact with these hematopoiesis-regulating AARS polypeptides may also be used to modulate hematopoietic process, and thereby treat or manage diseases and conditions associated with the same, as described herein and known in the art.

"Hematopoiesis" refers generally to the process of cellular differentiation or formation of particular, specialized blood cells from a stem cell or hematopoietic stem cell (HSC). Examples of hematopoietic processes that may be modulated by the AARS polypeptides of the invention include, without limitation, the formation of myeloid cells (e.g., erythroid cells, mast cells monocytes/macrophages, myeloid dendritic cells, granulocytes such as basophils, neutrophils, and eosinophils, megakaryocytes, platelets) and lymphoid cells (e.g., natural killer cells, lymphoid dendritic cells, B-cells, and T-cells).

The methods of modulating hematopoiesis may be practiced in vivo, in vitro, ex vivo, or in any combination thereof. These methods can be practiced on any biological sample, cell culture, or tissue that contains hematopoietic stem cells, hematopoietic progenitor cells, or other stem or progenitor cells that are capable of differentiating along the hematopoietic lineage (e.g., adipose tissue derived stem cells). For in vitro and ex vivo methods, stem cells and progenitor cells, whether of hematopoietic origin or otherwise, can be isolated and/or identified according to the techniques and characteristics described herein and known in the art.

AARS polypeptides and related agents (e.g., antibodies, antibody fragments, binding agents) may modulate hematopoiesis in a variety of ways. For instance, AARS polypeptides and related agents may modulate hematopoiesis by directly interacting with a hematopoietic cell or a cell that has the potential to enter the hematopoietic lineage, such as a stem cell. AARS polypeptides and related agents may also modulate hematopoiesis by indirectly altering the tissue microenvironment surrounding a hematopoietic cell or stem cell. In certain embodiments, these relatively indirect mechanisms may involve modulating the activity of any combination of osteoblast cells, vascular cells, and immune cells. For instance, certain embodiments include methods of increasing the hematopoiesis-stimulatory activity of at least one of an osteoblast cell or a vascular cell, reducing the hematopoiesis-stimulatory activity of at least one of an osteoblast cell or a vascular cell, increasing the hematopoiesis-inhibitory activity of at least one of an osteoblast cell or a vascular cell, and reducing the hematopoiesis-inhibitory activity of at least one of an osteoblast cell or a vascular cell. Without wishing to be bound by any one theory, it is believed that the vascular niche, including vascular cells such as endothelial cells, smooth muscle cells, and fibroblasts may play a role in modulating hematopoiesis, and that the osteoblast niche, including osteoblast cells, may also play a role in hematopoietic cell differentiation.

In certain embodiments, AARS polypeptides and related agents remodel the vasculature and/or regulate the necessary interactions between blood vessels and hematopoietic progenitor cells. In these and related embodiments, AARS polypeptides and related agents may be used to treat or manage bone marrow abnormalities, such as those associated with the stroma, the vasculature, bone, blood cells, or bone-marrow micro-environment. As one non-illustrative example, certain bone marrow conditions such as myelodysplastic syndrome involve the abnormal development of hematopoietic progenitors, and antagonistic AARS polypeptides and related agents may reduce or manage this abnormal development. In certain embodiments, WRS polypeptides, and antibodies and antibody fragments thereto, reduce the abnormal development of hematopoietic progenitors in bone marrow abnormalities such as myelodysplastic syndrome. Additional illustrative bone marrow abnormalities are discussed below.

Also included are methods of increasing the hematopoiesis-stimulatory activity of immune cells such as neutrophils. In these and related embodiments, AARS polypeptides and related agents increase the neutrophil-mediated effect on the release of hematopoietic stem cells and other progenitor cells from the stem cell niche in the bone marrow. Without wishing to be bound by any one theory, it is believed that AARS polypeptides such as YRS and variants (e.g., Y431 mutants, mini-YRS) may stimulate the release of neutrophil proteases which degrade the molecules responsible for anchoring hematopoietic stem cells in the stem cell niche, and thereby facilitate their mobilization into the periphery. Also included are methods of decreasing the hematopoiesis-stimulatory activity of neutrophils. In these and related embodiments, AARS polypeptides such as WRS and variants may decrease the neutrophil-mediated effect on the release of hematopoietic stem cells and other progenitor cells from the stem cell niche in the bone marrow, and thereby reduce their mobilization into the periphery.

Also included are methods of modulating the trafficking or mobilization of hematopoietic cells, including hematopoietic stem cells, progenitor cells, erythrocytes, granulocytes, lymphocytes, megakaryocytes, and thrombocytes. In certain embodiments, these methods increase the trafficking of one or more selected hematopoietic cells between the bone marrow and periphery, and thereby increase the concentration of the one or more selected hematopoietic cells in the periphery. These methods can be practiced in vivo, in vitro, and ex vivo. For instance, in certain embodiments, AARS polypeptides and related agents may be used to increase the concentration of selected peripheral hematopoietic cells in a bone marrow, stem cell, or blood donor prior to removal of those cells from the donor. In certain embodiments, AARS polypeptides and related agents may be used to increase the number of (stem) cells that can be collected for transplantation before a subject undergoes myeloablative radiation treatment.

Certain specific hematopoietic processes include erythropoiesis, granulopoiesis, lymphopoiesis, megakaryopoiesis, thrombopoiesis, and others. "Erythropoiesis" refers generally to the process by which red blood cells (erythrocytes) are produced from HSCs, and includes the formation of erythroid progenitor cells. "Granulopoiesis" refers to generally to the development of the granulocytic white blood cells, neutrophils, eosinophils, and basophils, and includes the formation of granulocyte progenitor cells, such as myelocytes and promelyocytes. "Lymphopoiesis" refers to process by which lymphocytes, such as T-cells and B-cells are produced from HSCs, and includes the formation lymphocyte progenitor cells, such as lymphoblasts. "Megakaryopoiesis" refers generally to the process by which HSCs in the bone marrow differentiate into mature megakaryocytes, and includes the formation of megakaryocyte progenitor cells. "Thrombopoiesis" refers generally to the formation of blood platelets.

"Erythropoiesis" is a carefully ordered sequence of events. Initially occurring in fetal hepatocytes, the process is taken over by the bone marrow in the child and adult. Although multiple cytokines and growth factors are dedicated to the proliferation of the red blood cell, the primary regulator is erythropoietin (EPO). Red blood cell development is initially regulated by stem cell factor (SCF), which commits hematopoietic stem cells to develop into erythroid progenitors. Subsequently, EPO continues to stimulate the development and terminal differentiation of these progenitors. In the fetus, EPO is produced by monocytes and macrophages found in the liver. After birth, EPO is produced in the kidneys; however, Epo messenger RNA (mRNA) and EPO protein are also found in the brain and in red blood cells (RBCs), suggesting the presence of paracrine and autocrine functions.

Erythropoiesis escalates as increased expression of the EPO gene produces higher levels of circulating EPO. EPO gene expression is known to be affected by multiple factors, including hypoxemia, transition metals ($Co^{2+}$, $Ni^{2+}$, $Mn^{2+}$), and iron chelators. However, the major influence is hypoxia, including factors of decreased oxygen tension, red blood cell loss, and increased oxygen affinity of hemoglobin. For instance, EPO production may increase as much as 1000-fold in severe hypoxia.

In certain embodiments, the AARS polypeptides and related agents of the present invention reduce erythropoiesis, and may be used to treat a condition associated with increased red blood cells. In certain embodiments, the AARS polypeptides, and antibodies and antibody fragments thereto, of the present invention increase erythropoiesis, and may be used to treat a condition associated with reduced red blood cells, such as anemia.

In certain embodiments, the AARS polypeptides and related agents of the present invention may modulate erythropoiesis by reducing formation of erythroid progenitors or by reducing the formation of red blood cells. In certain embodiments, the AARS polypeptides and related agents may modulate erythropoiesis by increasing or stimulating the formation (i.e., production) of erythroid progenitors or by increasing the formation of red blood cells.

In certain embodiments, these methods may utilize particular AARS polypeptides or selected dosages or forms (e.g., monomers, dimers, oligomers) of AARS polypeptides that both reduce erythropoiesis and increase megakaryopoiesis, including thrombopoiesis (i.e., the formation of platelets). In certain embodiments, depending on the condition to be treated, these methods may utilize particular AARS polypeptides or related agents or selected dosages of AARS polypeptides or related agents that reduce erythropoiesis without significantly enhancing megakaryopoiesis.

The methods of modulating erythropoiesis may be practiced in vivo, in vitro, ex vivo, or in any combination thereof. In vitro and ex vivo methods can be practiced on any biological sample or cell culture that contains hematopoietic stem cells, or other stem or progenitor cells that are capable of differentiating along the hematopoietic lineage (e.g., adipose tissue derived stem cells). Examples of biological samples include bone marrow, cord blood, and enriched stem cells, in addition to others described herein and known in the art. In certain instances, it may be advantageous to reduce the formation of erythroid progenitor cells in such biological samples or cell cultures.

In certain erythropoiesis-reducing embodiments, merely by way of non-limiting example, AARS polypeptides and related agents may be administered directly to a subject to reduce red blood count, if desired. In this regard, a normal red blood cell count typically ranges from about 4.7 to about 6.1 million red blood cells per µl in men, and about 4.2 to about 5.4 million red blood cells per µl in women. A high red blood cell count is generally defined as more than about 5.72 million red blood cells per µl of blood for men and about 5.03 million red blood cells per µl of blood for women. In children, the threshold for high red blood cell count varies with age and sex. Red blood count may also be reflected by a person's hematocrit (i.e., packed cell volume (PCV) or erythrocyte volume fraction (EVF)), which is the proportion or percentage of blood volume that is occupied by red blood cells. A normal hematocrit is normally about 46% for men and about 38% for women. A higher hematocrit value indicates a greater number of red blood cells. In severe cases, a high red blood cell count can impair circulation and lead to abnormal clotting, among other problems.

Hence, certain embodiments of the present invention relate to methods of administering an AARS polypeptide or a related agent to a subject in need thereof, wherein the subject has an increased red blood count (e.g., greater than about 5.72 million red blood cells per µl of blood for men and about 5.03 million red blood cells per µl of blood for women, often by a clinically or statistically significant amount), or an increased hematocrit (e.g., greater than about 46% for men or about 38% for women, often by a clinically or statistically significant amount). In certain embodiments, administration of an AARS polypeptide or related agent to such a subject reduces their red blood cell count or hematocrit. Also included are methods of reducing red blood cells in a subject, and methods of reducing hematocrit in a subject, including a subject that has a higher than normal red blood cell count or hematocrit, or is at risk for developing such a condition, comprising administering to the subject an AARS polypeptide or a related agent of the present invention, and thereby reducing red blood cell count or hematocrit in the subject.

There are many general diseases or conditions that increase the red blood cell count or hematocrit of a subject, and which may be improved or treated by the AARS polypeptides and related agents of the present invention. As one general, illustrative example, high red blood cell count may result from increases in red blood cell production, mainly to compensate for low oxygen levels, which may be caused by poor heart or lung function. Also, high red blood cell count may result from increased release of erythropoietin (EPO) from the kidneys (EPO enhances red blood cell production), production of too many red blood cells by the bone marrow, impairment of the oxygen-carrying capacity of red blood cells (leading to overproduction), compensation for a limited oxygen supply in higher altitudes, and the loss of blood plasma (i.e., the liquid component of blood), which may create relatively high levels of red blood cells, volume-wise.

Further examples of conditions that are associated with high red blood cell count include, without limitation, living at a high altitude, smoking, congenital heart disease, failure of the right side of the heart (i.e., cor pulmonale), scarring and thickening of the lung tissue (i.e., pulmonary fibrosis), bone marrow disorders (e.g., polycythemia vera), dehydration, such as from severe diarrhea or excessive sweating, kidney disease/cancer, exposure to carbon monoxide, anabolic steroid use, COPD or other lung diseases, such as pulmonary fibrosis, and EPO doping, mainly to enhance athletic performance. Hence, the AARS polypeptides and related agents can be used to treat or reduce the risk of developing high red blood cell count or volume as it is associated with these or any other conditions known in the art.

Polycythemia refers to an increase in the red blood cell count, hemoglobin, and total red blood cell volume, typically accompanied by an increase in total blood volume. Polycythemia can be distinguished from relative erythrocytosis secondary to fluid loss or decreased intake, because polycythemia results in increased total blood volume, and relative erythrocytosis does not. Two basic categories of polycythemia are typically recognized: primary polycythemias, which are due to factors intrinsic to red cell precursors and include the diagnoses of primary familial and congenital polycythemia (PFCP) and polycythemia vera (PV), and secondary polycythemias, which are caused by factors extrinsic to red cell precursors.

Primary polycythemia refers to a variety of myeloproliferative syndromes that include, for example, polycythemia vera, essential thrombocythemia, agnogenic myeloid metaplasia, and myelofibrosis.

Polycythemia vera has a significant genetic component. For instance, an activating mutation in the tyrosine kinase JAK2 (JAK2$^{V617F}$) now appears to cause most primary cases in adults. Several other mutations of JAK2 have also been described (e.g., exon 12, JAK2$^{H538-K539delinsI}$). These and possibly other JAK2 mutations are thought to cause hypersensitivity to EPO via the EPO receptor. Familial clustering suggests a genetic predisposition. Also, the clonality of polycythemia vera is well established. Studies also suggest hypersensitivity of the myeloid progenitor cells to growth factors, including EPO, IL-3, SCF, GM-CSF, and insulin-like growth factor (IGF)-1, whereas other studies show defects in programmed cell death.

PFCP is caused by a hypersensitivity of erythroid precursors to EPO. Several mutations (approximately 14) have been identified in the Epo receptor (EPOR) gene. Most of the identified EPOR mutations (11) cause truncation of the c-terminal cytoplasmic receptor domain of the receptor. These truncated receptors have heightened sensitivity to circulating Epo due to a lack of negative feedback regulation.

Secondary polycythemia may result from functional hypoxia induced by lung disease, heart disease, increased altitude (hemoglobin increase of 4% for each 1000-m increase in altitude), congenital methemoglobinemia, and other high-oxygen affinity hemoglobinopathies stimulating increased EPO production. Secondary polycythemia may also result from increased EPO production secondary to benign and malignant EPO-secreting lesions. Secondary polycythemia may also be a benign familial polycythemia. Chuvash polycythemia, a congenital polycythemia first recognized in an endemic Russian population, has mutations in the von Hippel-Lindau (VHL) gene, which is associated with a perturbed oxygen dependent regulation of EPO synthesis. Secondary polycythemia of the newborn is fairly common and may result from either chronic or acute fetal hypoxia or delayed cord clamping and stripping of the umbilical cord. Accordingly, AARS polypeptides and related agents may be used in treating or reducing the risk of primary polycythemia, such as polycythemia vera, or secondary polycythemia.

Also, certain primary treatment regimes may lead to an undesirably increase in red blood cells. For instance, the drugs gentamicin and methyldopa have been associated with increasing the number of red blood cells in a subject. Hence, the AARS polypeptides and related agents may be used in conjunction or combination with one or more of gentamicin, methyldopa, or other drug that leads to increased production of red blood cells, mainly to off-set the undesired effects of producing too many red blood cells. In certain embodiments, by reducing their undesirable side effects, combination therapy with AARS polypeptides may allow the use of higher concentrations of gentamicin, methyldopa, or related drugs.

Accordingly, in certain embodiments, the AARS polypeptides or related agents may be used to reduce erythropoiesis, and also to reduce the formation of erythroid progenitors, red blood cells, or both. In certain embodiments, methods of reducing erythropoiesis or red blood cell formation may be used to treat a subject that has or is at risk for having increased red blood cell count, increased hemoglobin levels, or increased total red blood cell volume, as described herein and known in the art.

In certain erythropoiesis-stimulating embodiments, merely by way of non-limiting example, AARS polypeptides and related agents may be administered directly to a subject to increase or maintain red blood count, if desired, such as to treat a condition associated with reduced blood count or risk of reduced blood count. Typically, conditions associated with reduced blood count are referred to as anemias. Hence, certain embodiments may include the use or administration of AARS polypeptides to treat or reduce the risk of anemia, or to treat a condition associated with anemia. Certain embodiments may include the use of AARS polypeptides or related agents to increase erythropoiesis in vitro or ex vivo, such as to increase the number of erythrocyte progenitor cells or red blood cells in a population of hematopoietic cells, which may then be optionally administered to a subject in need thereof.

Anemia may be associated with any one or more of excessive bleeding, reduced production of red blood cells, or increased destruction of red blood cells. For example, aplastic anemia is typically caused by the inability of the bone marrow to produce blood cells, and pure red cell aplasia is typically caused by the inability of the bone marrow to produce only red blood cells. Aplastic anemia can be inherited, can occur without apparent cause, or can occur when the bone marrow is injured by medications, radiation, chemotherapy, or infection. Also included is thalassemia, a condition that occurs when the red cells fail to mature and grow properly. Thalassemia is an inherited condition that typically affects people of Mediterranean, African, Middle Eastern, and Southeast Asian descent. This condition can range in severity from mild to life-threatening; the most severe form is called Cooley's anemia. As a further example, anemia may be caused by lead exposure, which is toxic to the bone marrow, and reduces red blood cell production. Also included are iatrogenic bone marrow disorders.

Hemolytic anemia is typically caused by excessive breakdown of red blood cells. Causes of hemolytic anemia may include any one or more of inherited conditions, such as sickle cell anemia and thalassemia, stressors such as infections, drugs, snake or spider venom, or certain foods, toxins from advanced liver or kidney disease, inappropriate attack by the immune system (called hemolytic disease of the newborn when it occurs in the fetus of a pregnant woman), vascular grafts, prosthetic heart valves, tumors, severe burns, chemical exposure, severe hypertension, and clotting disorders. In certain cases, an enlarged spleen can trap red blood cells and destroy them before they enter the circulation.

Anemia also associates with excessive bleeding, whether acute or chronic. Red blood cells can be lost through bleeding, which can occur slowly over a long period of time, and can often go undetected. Chronic bleeding associated with anemia may result from any one or more of gastrointestinal conditions such as ulcers, hemorrhoids, gastritis (inflammation of the stomach) and cancer, use of nonsteroidal anti-inflammatory drugs (NSAIDS) such as aspirin or Motrin®, as well as menstruation and childbirth in women, especially if menstrual bleeding is excessive and if there are multiple pregnancies.

Certain types of anemia associate with vitamin deficiencies or iron deficiencies. For instance, vitamin deficiency anemia may occur when vitamin B-12 and folate are deficient. These two vitamins are needed to make red blood cells. Conditions leading to anemia caused by vitamin deficiency include any one or more of megaloblastic anemia, in which vitamin B-12 or folate or both are deficient, pernicious anemia, in which poor vitamin B-12 absorption is caused by conditions such as Crohn's disease, an intestinal parasite infection, surgical removal of part of the stomach or intestine, or infection with HIV, dietary deficiency, in which eating little or no meat may cause a lack vitamin B12, or overcooking or eating too few vegetables may cause a folate deficiency, and other causes, such as pregnancy, certain medications, alcohol abuse, and intestinal diseases such as tropical sprue and gluten-sensitive enteropathy (celiac disease). During early pregnancy, sufficient folic acid can prevent the fetus from developing neural tube defects such as spina bifida.

Anemia also associates with other conditions, and usually occurs when there are too few of the hormones required for red blood cell production. Conditions causing this type of anemia include, for example, advanced kidney disease, hypothyroidism, cancer, infection (e.g., bacterial, viral, parasitic), and autoimmune disorders such as lupus and rheumatoid arthritis.

Certain embodiments may include combination therapies for treating anemias, including the administration of one or more AARS polypeptides, or antibodies and antibody fragments thereto, in combination with other anemia-based therapeutic agents or treatment modalities. Examples of combination therapies included, without limitation, any one or more of iron supplementation with ferrous sulfate, ferrous gluconate, or vitamin C, the latter of which may aid in the body's ability to absorb iron, vitamin supplements given orally (e.g., folic acid) or subcutaneously (e.g., vitamin B-12), administration of recombinant erythropoietin or epoetin alfa, blood transfusion, or hyperbaric oxygenation.

In certain embodiments, AARS polypeptides and related agents may be used to modulate granulopoiesis. These embodiments may be practiced in vitro, ex vivo, and in vivo. In certain embodiments, the AARS polypeptides and related agents of the present invention may stimulate granulopoiesis, and may be used to treat a condition associated with any one or more of neutropenia, eosinopenia, or basopenia. In certain embodiments, the AARS polypeptides and related agents of the present invention may reduce granulopoiesis, and may be used to treat a condition associated with any one or more of neutrophilia, eosinophilia, or basophilia. In certain in vitro or ex vivo embodiments, AARS polypeptides and related agents may increase or reduce the number of granulocytes (e.g., neutrophils, eosinophils, basophils) in a population of hematopoietic cells, which may then be optionally administered to a subject in need thereof.

Neutropenia can develop if neutrophils are used up or destroyed in the bloodstream faster than the bone marrow can make new neutrophils. Neutrophils are destroyed faster than they are produced in certain bacterial infections, allergic disorders, and drug treatments. Certain autoimmune diseases may lead to the production of antibodies that destroy neutrophils, and thereby associate with neutropenia. Low neutrophil count may also result from an enlarged spleen, because the enlarged spleen traps and destroys neutrophils.

Neutropenia can also develop if the production of neutrophils in the bone marrow is reduced. Examples of conditions associated with reduced neutrophil production include cancer, viral infections such as influenza, bacterial infections such as tuberculosis, myelofibrosis, and deficiencies of vitamin $B_{12}$ or folate (folic acid). Radiation therapy may also associate with neutropenia, especially if targeted to the bone marrow. Certain drugs, including phenyloin, chloramphenicol, sulfa drugs, chemotherapeutic agents, as well as certain toxins (benzene and insecticides) can also impair the bone marrow's ability to produce neutrophils, and thereby associate with neutropenia. Neutropenia can also result from the colonization of intracellular neutrophilic parasites. Aplastic anemia and various leukemias may also associate with neutropenia. Also included are congenital neutropenia, autosomal recessive Kostmann's syndrome, cyclic neutropenia, and myelokathexis.

Neutrophilia may associate with bacterial infections, any form of acute inflammation, including after a heart attack or other infarct, and the administration of certain drugs, such as prednisone and cortisol, which cause marginated neutrophils to enter the blood stream. Nervousness or emotional stress may also slightly raise the neutrophil count because of this same effect. Neutrophilia also associates with malignancies. For instance, chronic myelogenous leukemia (CML or chronic myeloid leukemia) is characterized by excessive blood cell proliferation, including excessive neutrophil proliferation. Neutrophilia may also associate with eclampsia, gout, thyroiditis, rheumatic fever, appendicitis, vasculitis, trauma, surgery, burns, blood loss, steroids, fungal infection, pregnancy, connective tissue disease, arthritis, dermatitis, hemolytic anemia, and essential thrombocythemia, among other conditions known in the art.

Eosinopenia may associate with steroid use (e.g., Cushing's syndrome), infections (e.g., bacterial infections and sepsis, for which eosinophil count can be a valuable predictor), and psychological stress, among other conditions known in the art. Eosinophilia may be characterized as primary or secondary, or it may be characterized as reactive (i.e., in response to other stimuli such as allergy or infection) or non reactive. Generally, eosinophilia may associate with neoplasia (e.g., lymphoma such as Hodgkin lymphoma and non-Hodgkin lymphoma, human T-cell lymphotropic virus I (HTLV-I) infection, adult T-cell leukemia/lymphoma (ATLL), eosinophilic leukemia, gastric or lung carcinoma), Addison Disease, allergy/asthma, collagen vascular diseases, cholesterol emboli, and parasites. Particular examples of conditions that associate with eosinophilia include, without limitation, coccidioidomycosis fungal infection, hypereosinophilic syndrome, parasitic infections (intestinal helminthiasis), allergic disorders (including eosinophilic esophagitis), certain drug reactions (e.g., DRESS syndrome), cholesterol embolization, Churg-Strauss syndrome, certain forms of chronic myeloid leukemia, Hodgkin's lymphoma, Gleich's syndrome, Addison's disease, Clonorchis sinensis (a flatworm infection), eosinophilia-myalgia syndrome, often caused by contaminated tryptophan supplements, Job's Syndrome, typically caused by increased levels of Immunoglobulin E, and certain forms of colitis, such as eosinophilic colitis.

Basopenia may associate with autoimmune urticaria, a chronic itching condition, and may be an indicator of ovulation. Basophilia may associate with myeloproliferative disorders, such as certain forms of leukemia and lymphoma, including chronic granulocytic leukemia and acute basophilic leukemia, a form of acute myeloid leukemia in which blasts are accompanied by abnormal basophils in all stages of differentiation. Increased basophil counts advanced may be found in advanced anemia, malaria, and chronic lead poisoning. Basophilia may also cause or associate with leukocytosis, or the destruction of white blood cells.

Certain embodiments may include combination therapies for treating any one or more of neutropenia, neutrophilia, eosinopenia, eosinophilia, basopenia, or basophilia, including the administration of one or more AARS polypeptides or related agents in combination with other granulocyte-based therapeutic agents or treatment modalities. Examples include the administration of recombinant G-CSF (granulocyte-colony stimulating factor), typically used in treating neutropenia, corticosteroids and interferon (IFN)-alpha, hydroxyurea, chlorambucil, vincristine, cytarabine, 2-chlorodeoxyadenosine (2-CdA), and etoposide, typically used in treating primary eosinophilia.

In certain embodiments, AARS polypeptides and related agents may be used to modulate lymphopoiesis. These embodiments may be practiced in vitro, ex vivo, and in vivo. In certain embodiments, the AARS polypeptides and related agents of the present invention may stimulate lymphopoiesis, and may be used to treat a condition associated with lymphocytopenia. Certain embodiments may be used to treat any one or more of T-lymphocytopenia, B lymphocytopenia, and NK lymphocytopenia. In certain embodiments, the AARS polypeptides of the present invention may reduce lymphopoiesis, and may be used to treat a condition associated with lymphocytosis. In certain in vitro or ex vivo embodiments, AARS polypeptides and related agents may increase or reduce the number of lymphocytes (e.g., B-cells, T-cells, NK cells) in a population of hematopoietic cells, which may then be optionally administered to a subject in need thereof.

Various disorders and conditions, including infection with human immunodeficiency virus (HIV), the virus that causes AIDS, associate with decreased numbers of lymphocytes in the blood. Other viral, bacterial, and fungal agents may associate with lymphocytopenia, such as viral hepatitis, tuberculosis, and typhoid fever. Sepsis may also associate with reduced lymphocytes. Lymphocytopenia may associate with starvation, malnutrition, severe stress, intense or prolonged physical exercise, often due to increased cortisol release, autoimmune disorders such as lupus and rheumatoid arthritis, bone marrow or blood malignancies (e.g., leukemia, Hodgkin's disease, aplastic anemia), use of corticosteroids (such as prednisone), use of chemotherapeutics (e.g., cytotoxic agents, immunosuppressive drugs), and radiation therapy or exposure. Severe reduction in lymphocytes can also occur in certain hereditary or congenital disorders, which are often X-linked disorders, such as DiGeorge anomaly, Wiskott-Aldrich syndrome, severe combined immunodeficiency syndrome, and ataxia-telangiectasia.

Lymphocytosis may associate with any one or more of chronic bacterial infections such as pertussis, chronic lymphocytic leukemia, acute lymphoblastic leukemia, multiple myeloma, mumps, ulcerative colitis, vasculitis, Crohn's disease, and whooping cough. Also included are viral infections, such as infectious mononucleosis (glandular fever), Epstein-Barr virus infection, cytomegalovirus (CMV), and hepatitis, protozoal infections, such as toxoplasmosis and American trypanosomiasis (Chagas disease), and chronic intracellular bacterial infections such as tuberculosis and brucellosis. Certain medications, including corticosteroids, lithium and beta agonists, may also cause lymphocytosis.

In certain embodiments, AARS polypeptides and related agents may be used to modulate megakaryopoiesis, thrombopoiesis, or both. These embodiments may be practiced in vitro, ex vivo, and in vivo. In certain embodiments, the AARS polypeptides and related agents of the present invention may stimulate megakaryopoiesis, stimulate thrombopoiesis, or both, and may be used to treat a condition associated with megakaryocytopenia, thrombocytopenia, or both. In certain embodiments, the AARS and related agents polypeptides of the present invention may reduce megakaryopoiesis, reduce thrombopoiesis, or both, and may be used to treat a condition associated with excess megakaryocytes, excess thrombocytes (e.g., thrombocythemia, thrombocytosis), or both. In certain in vitro or ex vivo embodiments, AARS polypeptides and related agents may increase or reduce the number of megakaryocytes, megakaryocyte progenitors, or platelets in a population of hematopoietic cells, which may then be optionally administered to a subject in need thereof. In certain embodiments, AARS polypeptides and related agents increase thrombopoiesis by a thrombopoietin (TPO)-independent mechanism. In certain preferred embodiments, YRS-based polypeptides, such as those that comprise a Y341A mutation or that comprise or consist essentially of the sequence of mini-YRS (SEQ ID NO:3), increase thrombopoiesis by a TPO-independent mechanism. In certain embodiments, antagonists to Y341A or mini-YRS may be used to reduce thrombopoiesis, or to reduce platelet levels, and thereby treat conditions such as thrombocythemia or thrombocytosis. Examples of antagonists include various antibodies and other binding agents that antagonize the thrombopoietic or megakaryopoeitic activities of Y341A and/or mini-YRS, as described elsewhere herein.

In certain embodiments, these methods may be utilized to either enhance or reduce the growth, differentiation, migration, or accumulation of megakaryocyte progenitor cells, including early progenitor cells, i.e., the most primitive lineage-restricted progenitors of the megakaryocyte lineage, late progenitor cells, or both. In certain embodiments, the methods provided herein may impact (i.e., enhance or reduce) the proliferation, cell cycle changes, mobilization, migration, attachment, cell-cell contacts, endomitosis, or polyploidy of megakaryocyte precursors, megakaryoblasts, or megakaryocytes. In certain embodiments, depending on the particular AARS polypeptides, related agents, or dosages, these methods may selectively enhance the formation of early megakaryocyte progenitor cells. In certain embodiments, these methods may selectively enhance the formation of late megakaryocyte progenitor cells. In certain embodiments, depending on the particular AARS polypeptides, related agents, or dosages, these methods may selectively reduce the formation of early megakaryocyte progenitor cells. In certain embodiments, these methods may selectively modulate (e.g., reduce) the formation of late megakaryocyte progenitor cells. The methods may be practiced in vivo, in vitro, ex vivo, or in any combination thereof.

The methods provided herein may also enhance or reduce platelet formation or cell division. For instance, certain methods relate to modulating the transition from pro-platelets (i.e., compartmentalization of mature megakaryocytes) to platelets, and their release into the circulation. Certain AARS polypeptides and related agents may increase the transition from pro-platelets to platelets, and thereby increase the release of platelets into the circulation. In certain embodiments, YRS polypeptides increase the transition from pro-platelets to platelets. Certain AARS polypeptides and related agents may reduce the transition from pro-platelets to platelets, and thereby reduce the release of platelets into the circulation. In certain embodiments, WRS polypeptides, WRS antibodies, WRS antibody fragments, or YRS polypeptide antagonists reduce the transition from pro-platelets to platelets.

Also, certain methods relate to modulating the cell division of platelets, which are believed to undergo cell division even in the absence of a nucleus. Certain embodiments therefore relate to the use of AARS polypeptides and related agents to increase the cell division of platelets. In certain embodiments, a YRS polypeptide, or YRS antibody or antibody fragment thereto, increases platelet cell division. These methods can be used, for example, to increase the number of platelets in a platelet transfusion prior to administration to a donor, and/or to treat or manage a condition associated with reduced platelet levels. Certain embodiments relate to the use of AARS polypeptides, or related agents, to reduce the cell division of platelets. In certain embodiments, a WRS polypeptide or a YRS polypeptide antagonist, such as an antibody or antibody fragment, reduces platelet division. The methods may be practiced in vivo, in vitro, ex vivo, or in any combination thereof.

Included are in vitro or ex vivo methods of modulating megakaryopoiesis. In certain embodiments, these methods relate to stimulating the proliferation or accumulation of megakaryocyte progenitor cells, comprising incubating a culture of hematopoietic stem cells or other blood cells with an aminoacyl-tRNA synthetase polypeptide (i.e., contacting a cell with an AARS polypeptide or related agent), typically for a time sufficient to allow proliferation or accumulation of megakaryocyte progenitor cells, thereby stimulating megakaryopoiesis. In certain embodiments, the progenitor cells include early megakaryocyte progenitor cells, and in certain embodiments they include late megakaryocyte progenitor cells. In these and related embodiments, the AARS polypeptides and related agents of the invention may be incubated with purified HSCs, partially purified HSCs, whole bone marrow cultures (e.g., for bone marrow transplants), cord blood, or other types of blood or marrow-based cultures, such as those used in hematopoietic graft therapies. Such methods may result in a culture that is enriched for early megakaryocyte progenitor cells, late progenitor cells, or both, and which may be administered to a subject in need thereof (e.g., transplant subject), if desired.

Growth or proliferation (or lack thereof) of megakaryocyte progenitor cells (e.g., early, intermediate, late, etc.) can be measured according to routine techniques known in the art and described herein (see, e.g., Example 10). For instance, among other characteristics, early megakaryocyte progenitors may be identified by immuno-staining as $Lin^-c-Kit^+CD41^+$, and later stage megakaryocyte progenitors may be identified as $Lin^-c-Kit^-CD41^+$ (see, e.g., Perez et al., *PLoS ONE*. 3:e3565, 2008; and Lefebvre et al., *Journal of Hematotherapy & Stem Cell Research*. 9:913-921, 2000, each of which is incorporated by reference in its entirety).

Megakaryocyte progenitor cells are positive for CD34 expression. CD34 is a monomeric cell surface antigen with a molecular mass of approximately 110 kD that is selectively expressed on human hematopoietic progenitor cells. The gene is expressed by small vessel endothelial cells in addition to hematopoietic progenitor cells and is a single-chain 105-120 kDa heavily O-glycosylated transmembrane glycoprotein.

Megakaryocyte progenitor cells also typically express the tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. CD9 interacts with the integrin family and other membrane proteins, and is postulated to participate in cell migration and adhesion.

Megakaryocyte progenitor cells may also express CD41, also referred to as the glycoprotein IIb/IIIa integrin, which is the platelet receptor for fibrinogen and several other extracellular matrix molecules. GP IIIa is a protein of 788 amino acids, including a 26-residue amino terminal signal peptide, a 29-residue transmembrane domain near the carboxy terminus, and 4 tandemly repeated cysteine-rich domains of 33-38 residues.

Megakaryocyte progenitor cells are typically positive for expression of CD117. CD117 is also known as the receptor tyrosine kinase c-Kit. This receptor has been particularly implicated with stem cells, including hematopoietic stem cells. Multiple isoforms of c-Kit also exist as a result of alternate mRNA splicing, proteolytic cleavage and the use of cryptic internal promoters in certain cell types. Structurally, c-Kit contains five immunoglobulin-like domains extracellularly and a catalytic domain divided into two regions by a 77 amino acid insert intracellularly.

Megakaryocyte progenitor cells are typically positive for expression of CD38. CD38 is a 300-amino acid type II transmembrane protein with a short N-terminal cytoplasmic tail and 4 C-terminal extracellular N-glycosylation sites. This marker is also generally associated with lymphocytes, myeloblasts, and erythroblasts.

Megakaryocyte progenitor cells may also have the phenotype of lacking expression of certain lineage specific markers. For staining purposes a cocktail of binding reagents, herein designated "lin" may be used. A "lin" panel may comprise binding reagents (e.g., antibodies and functional binding fragments thereof, ligands, peptidomimetics) that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells. Lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. Megakaryocyte progenitor cells are also typically negative for expression of Thy-1 (CD90), which is a 25-35 kD molecule expressed on 1-4% of human fetal liver cells, cord blood cells, and bone marrow cells.

"Hematopoietic stem cells (HSCs)" relate generally to either pluripotent or multipotent "stem cells" that give rise to the blood cell types, including myeloid (e.g., monocytes/macrophages, neutrophils, basophils, eosinophils, erythrocytes, megakaryocytes/platelets, dendritic cells), and lymphoid lineages (e.g., T-cells, B-cells, NK-cells), and others known in the art. "Stem cells" are typically defined by their ability to form multiple cell types (i.e., multipotency) and their ability to self-renew. In certain embodiments, however, oligopotent and unipotent progenitors may be included.

HSCs may be obtained according to known techniques in the art. For instance, HSCs may be found in the bone marrow of adults, which includes femurs, hip, ribs, sternum, and other bones. HSCs may be obtained directly by removal from the hip using a needle and syringe, or from the blood, often following pre-treatment with cytokines, such as G-CSF (granulocyte colony-stimulating factors), that induce cells to be released from the bone marrow compartment. Other sources for clinical and scientific use include umbilical cord blood, placenta, and mobilized peripheral blood. For experimental purposes, fetal liver, fetal spleen, and AGM (Aorta-gonad-mesonephros) of animals are also useful sources of HSCs.

HSCs may be identified according to certain phenotypic or genotypic markers. For example, HSCs may be identified by their small size, lack of lineage (lin) markers, low staining (side population) with vital dyes such as rhodamine 123 ($rhodamine^{DULL}$, also called $rho^{lo}$) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSCs are mainly negative for the markers that are typically used to detect lineage commitment, and, thus, are often referred to as lin(−) cells. Most human HSCs may be characterized as $CD34^+$, $CD59^+$, Thy1/$CD90^+$, $CD38^{lo/-}$, C-kit/$CD117^+$, and lin(−). However, not all stem cells are covered by these combinations, as certain HSCs are $CD34^-/CD38^-$. Also some studies suggest that earliest stem cells may lack c-kit on the cell surface. For human HSCs, CD133 may represent an early marker, as both CD34+ and CD34− HSCs have been shown to be CD133+.

For purification of lin(−) HSCs by flow cytometry, or FACS, an array of mature blood-lineage marker antibodies may be used to deplete the lin(+) cells or late multipotent progenitors (MPP), including, for example, antibodies to CD13 and CD33 for human myeloid cells, CD71 for human erythroid cells, CD19 for human B cells, CD61 for human megakaryocytic cells, Mac-1 (CD11b/CD18) for monocytes, Gr-1 for Granulocytes, Il7Ra, CD3, CD4, CD5, and CD8 for T cells, among others known in the art. Other purification methods are known in the art, such as those methods that use the particular signature of the 'signaling lymphocyte activation molecules' (SLAM) family of cell surface molecules.

HSCs, whether obtained from, or present in, cord blood, bone marrow, peripheral blood, or other source, may be grown or expanded in any suitable, commercially available or custom defined medium, with or without serum, as desired (see, e.g., Hartshorn et al., *Cell Technology for Cell Products*, pages 221-224, R. Smith, Editor; Springer Netherlands, 2007, herein incorporated by reference in its entirety). For instance, in certain embodiments, serum free medium may utilize albumin and/or transferrin, which have been shown to be useful for the growth and expansion of CD34+ cells in serum free medium. Also, cytokines may be included, such as Flt-3 ligand, stem cell factor (SCF), and thrombopoietin (TPO), among others. HSCs may also be grown in vessels such as bioreactors (see, e.g., Liu et al., *Journal of Biotechnology* 124:592-601, 2006, herein incorporated by reference in its entirety). A suitable medium for ex vivo expansion of HSCs may also comprise HSC supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of HSCs, as well as their progeny.

HSC growth or expansion can be measured in vitro or in vivo according to routine techniques known in the art. For example, WO 2008/073748, herein incorporated by references for these methods, describes methods for measuring in vivo and in vitro expansion of HSCs, and for distinguishing between the growth/expansion of HSCs and the growth/expansion of other cells in a potentially heterogeneous population (e.g., bone marrow), such as intermediate progenitor cells. The administering or incubation step that results in the growth or expansion can occur in vivo, ex vivo, or in vitro, though in certain embodiments, the administration or incubation occurs during ex vivo treatment of HSCs.

"Cord blood" or "umbilical cord blood" relates generally to the relatively small amount of blood (up to about 180 mL) from a newborn baby that returns to the neonatal circulation if the umbilical cord is not prematurely clamped. Cord blood is rich in HSCs, and may be harvested and stored for later use according to techniques known in the art (see, e.g., U.S. Pat. Nos. 7,147,626 and 7,131,958, herein incorporated by reference for such methodologies). Also, if the umbilical cord is ultimately not clamped, a physiological clamping occurs upon interaction with cold air, wherein the internal gelatinous substance, called Wharton's jelly, swells around the umbilical artery and veins. Nonetheless, Wharton's jelly can still serve as a source of HSCs.

However, delayed platelet recovery is an inherent problem with cord blood cell transplantation. In this regard, rapid platelet recovery after transplant reduces the cost of supportive therapy and reduces the risk of fatal bleeding due to severe thrombocytopenia. Delayed platelet recovery in cord blood transplantation is associated with low numbers of megakaryocyte progenitor cells in cord blood grafts (see, e.g., Kanamaru et al., *Stem Cells*. 18:190-195, 2000). Hence, methods of ex vivo pre-treatment of cord blood grafts with AARS polypeptides, antibodies and antibody fragments thereto, methods of in vivo administration of AARS polypeptides or related agents prior to, during, or after cord blood transplantation, or both methods in combination, may increase the number of megakaryocyte progenitor cells, increase platelet recovery in cord blood transplantation, and thereby reduce secondary costs and improve the therapeutic outcome of such transplant procedures.

As noted above, "ex vivo" refers generally to activities that take place outside an organism, such as experimentation or measurements done in or on living tissue in an artificial environment outside the organism, preferably with minimum alteration of the natural conditions. Most commonly, "ex vivo" procedures involve living cells or tissues taken from an organism and cultured in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The terms "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure to expand the stem cells (e.g., an ex vivo administration step that involves incubating the cells with a composition of the present invention to enhance expansion of desirable cells, such as HSCs or megakaryocyte progenitors), and then administered to the same or different living subject after that optional treatment or procedure. As one example, thrombocytopenia may be alleviated by infusion of megakaryocyte progenitor cells (see, e.g., De Bruyn et al., *Stem Cells Dev.* 14:415-24, 2005, herein incorporated by reference).

Such ex vivo therapeutic applications may also include an optional in vivo treatment or procedural step, such as by administering an AARS polypeptide, or antibody or antibody fragment thereto, one or more times to the living subject prior to, during, or after administration of the organ, cells, or tissue. Both local and systemic administration are contemplated for these embodiments, according to well-known techniques in the art. The amount of AARS polypeptide or related agent administered to a subject will depend on the characteristics of that subject, such as general health, age, sex, body weight, and tolerance to drugs, as well as the degree, severity, and type of reaction to the polypeptide and/or cell transplant.

Megakaryocytic progenitors can be generated ex vivo, as described herein, and administered to any subject in need thereof, including, for example, subjects having or at risk for developing reduced platelet or thrombocytopenia. Thrombocytopenia is generally characterized by reduced platelet counts, as compared to a normal range of platelet counts for a typical subject. For example, thrombocytopenia refers generally to a decrease in the platelet count to about 150,000/$mm^3$ or lower compared to a normal platelet count. A normal platelet count generally ranges from about 150,000 $mm^3$ to about 450,000 $mm^3$ in a subject.

Thrombocytopenia often causes no signs or symptoms, but may be identified by routine blood tests. If present, possible signs and symptoms of thrombocytopenia include easy bruising and/or excessive bleeding. For example, bleeding in the skin may be the first sign of a low platelet count. Many tiny red dots (petechiae) often appear in the skin on the lower legs, and minor injuries may cause small scattered bruises. In addition, the gums may bleed, and blood may appear in the stool or urine. Menstrual periods may be unusually heavy. Bleeding may be hard to stop.

Bleeding typically worsens as the number of platelets decreases. People who have very few platelets may lose large amounts of blood into the digestive tract or may develop life-threatening bleeding in the brain even though they have not been injured. The rate at which symptoms develop can vary depending on the cause of thrombocytopenia.

Thrombocytopenia may be congenital, acquired, and/or iatrogenic, and may stem from a variety of underlying physiological causes or conditions. For example, thrombocytopenia may result generally from decreased production of platelets, increased destruction of platelets, consumption of platelets, entrapment/sequestration of platelets due to hypersplenism (i.e., enlarged spleen) or hypothermia, and/or from the side-effects of certain medications (i.e., medication induced thrombocytopenia). In addition, idiopathic forms of thrombocytopenia occur, especially in children, transient forms may follow viral infections (e.g., Epstein-Barr or infectious mononucleosis), and pregnant women may develop mild thrombocytopenia, often when close to delivery.

Examples of congenital conditions associated with the decreased production (i.e., diminished or defective production) of platelets include Wiskott-Aldrich syndrome, maternal ingestion of thiazides, congenital amegakaryocytic thrombocytopenia, thrombocytopenia absent radius syndrome, Fanconi anemia, Bernard-Soulier syndrome, May-Hegglin anomaly, Grey platelet syndrome, Alport syndrome, and neonatal rubella. Examples of acquired conditions associated with the decreased production of platelets include aplastic anemia, myelodysplastic syndrome, marrow infiltration (e.g., acute and chronic leukemias, tumors, cancer of the bone marrow), lymphomas, nutritional deficiencies (e.g., $B_{12}$, folic acid), the use of myelosuppressive agents, the use of drugs that directly influence platelet production (e.g., thiazides, alcohol, hormones), radiation exposure (e.g., radiation therapy), exposure to toxic chemicals (e.g., pesticides, arsenic, benzene), decreased production of thrombopoietin by the liver in liver failure, bacterial sepsis, and certain viral infections (e.g., chickenpox, mumps, parvovirus, measles, dengue, HIV, HCV). AARS polypeptides and ex vivo expanded megakaryocyte progenitors generated therefrom, as described herein, may be used to treat or manage any of these conditions.

Examples of congenital conditions associated with increased peripheral platelet destruction include nonimmune conditions, such as prematurity, erythroblastosis fetalis, infection; and immune conditions, such as drug sensitivity, idiopathic thrombocytopenic purpura (ITP), and maternal ITP. Examples of acquired conditions associated with increased peripheral platelet destruction include nonimmune conditions, such as hemolytic-uremic syndrome, disseminated intravascular coagulation, thrombotic thrombocytopenic purpura (TTP); immune conditions, such as drug-induced thrombocytopenia (e.g., especially with quinine and quinidine), post-transfusion purpura, systemic lupus erythematosus, rheumatoid arthritis, neonatal alloimmune thrombocytopenia, paroxysmal nocturnal hemoglobinuria, acute and chronic ITP, sepsis, and alcohol; in addition to the use of invasive lines and devices (e.g., arterial or central venous catheters), intra-aortic ballon pumps, prosthetic heart valves, as well as the use of heparin-related therapies. AARS polypeptides and ex vivo expanded megakaryocyte progenitors generated therefrom, as described herein, may be used to treat or manage any of these conditions.

Medication-induced thrombocytopenia may result in particular from certain drugs, such as chemotherapeutic agents, nonsteroidal anti-inflammatory agents, sulfonamides, vancomycin, clopidogrel, glycoprotein IIb/IIIa inhibitors, interferons, valproic acid, abciximab, linezolid, famotidine, mebeverine, histamine blockers, alkylating agents, heparin, alcohol, antibiotic chemotherapeutic agents, carbapenems, ureidopenicillins, cefazolin, among others known in the art. Particular examples of chemotherapeutic agents include, but are not limited to, cisplatin (CDDP), carboplatine, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, temazolomide (an aqueous form of DTIC), or any analog or derivative variant of the foregoing. AARS polypeptides and ex vivo expanded megakaryocyte progenitors generated therefrom, as described herein, may be used to treat or manage any of these medication-induced conditions.

The present invention relates generally to methods of treating, or reducing the risks of developing, thrombocytopenia (i.e., decreased platelet count) in a subject, such as in a subject having one or more of the exemplary diseases or conditions provided herein, among others known in the art, by administering to the subject a composition comprising a therapeutically effective concentration of an AARS polypeptide, or by expanding megakaryocyte progenitor cells ex vivo in the presence of AARS polypeptides, and administering those cells to the subject. In one aspect, the subject has been diagnosed with a myelodysplastic syndrome (MDS) (formerly known as "preleukemia"). In some embodiments, the myelodysplastic syndrome is selected from Refractory Anemia (RA)(ICD-O code M9980/3), Refractory Anemia with Ring Sideroblasts (RARS) (ICD-O code M9982/3), Refractory Anemia with Excess Blasts (RAEB) (ICD-O code M9983/3), Refractory Anemia with Excess Blasts in Transformation (RAEB-T) (ICD-O code M9984/3), Chronic Myelomoncytic Leukemia (CMML) (ICD-O code M9945/3), 5q-syndrome, Myelodyplasia unclassificable, and refractory cytopenia of childhood.

Embodiments of the present invention encompass methods of treatment intended not only to increase or improving the platelet count in a subject having a reduced, decreased, abnormal, or low platelet count, but to maintain a normal platelet count in a subject at risk for developing a low platelet count. Certain embodiments also contemplate the use of AARS polypeptides or related agents to increase the platelet count in a platelet donor, including an otherwise healthy donor (i.e., a donor with a normal platelet count), such as administering an AARS polypeptide to the donor prior to, during, and/or after the platelet donation or apheresis process, or by administering ex vivo expanded megakaryocyte progenitor cells, or both.

Accordingly, certain embodiments include methods for increasing the platelet count in a subject, comprising administering to the subject a composition comprising an AARS polypeptide or related agent, or by administering ex vivo or in vitro expanded megakaryocyte progenitor cells (e.g., early or late progenitor cells), thereby increasing the platelet count in the subject. Other embodiments include methods of maintaining a normal platelet count in subject, comprising administering to the subject a composition comprising an AARS polypeptide or related agent, or by administering ex vivo or in vitro expanded megakaryocyte progenitor cells, such as wherein the subject is at risk for developing a low platelet count. Certain embodiments may include methods of stimulating thrombopoiesis in a subject, such as by administering to the subject a composition comprising an AARS polypeptide or related agent, or by administering ex vivo or in vitro expanded megakaryocyte progenitor cells, or both. In certain aspects, the subject has a reduced, lowered, or abnormal platelet count, such as a platelet count of about 100,000/mm$^3$ or less. In certain aspects, the ARS polypeptides, or related agents provided herein may be utilized to stimulate the proliferation and/or differentiation of megakaryocytes and/or neutrophils in the subject.

A subject having a reduced platelet count may also be at risk for developing other problems associated with thrombocytopenia, such as bleeding or bruising, hemorrhage, gastrointestinal bleeding, eptistaxis (i.e., nose bleeds), or intracranial hemorrhage (i.e., bleeding in the brain). As one particular example, septic patients with thrombocytopenia have increased bleeding. Accordingly, certain aspects of the invention may utilize the thrombopoietic compositions provided herein to reduce the risk of developing these types of thrombocytopenia associated problems, among others. In other aspects, the subject may be at risk for developing a reduced, lowered, or otherwise abnormal platelet count, such as from an acquired condition associated with lowered platelet levels (e.g., certain medical therapies, leukemias, among others). Also included are surgical patients. For instance, AARS polypeptides or related agents may be administered prophylactically, for instance before surgery, to reduce blood loss.

In certain aspects, the methods of treatments described herein may be employed independently of other therapeutic modalities, and may be the only or primary therapeutic modality relied upon to manage a thrombocytopenic condition and/or otherwise reduce the risk not only of developing thrombocytopenia, but of developing other medical problems associated therewith, such as bleeding. For example, a subject having thrombocytopenia for which there is no known, underlying cause (e.g., idiopathic thrombocytopenic purpura), may benefit from the methods of treatment provided herein to increase and/or manage platelet levels.

In certain aspects, the methods and compositions of the present invention may be employed as part of a combination therapy, such as by administration with other agents that may impact thrombopoietic and/or hematopoietic pathways in a subject. Examples of other agents that may be used as part of a combination therapy include thrombopoietin (TPO) and TPO agonists/mimetics, mpl-signaling agonists, cytokines (e.g., IL-11, SDF-1, CXCL-12), chemokines, chemokine receptor ligands (e.g., CXCR-1, CXCR-2, CXCR-4 ligands), adhesion molecules (e.g., NCAM, ICAM-1, VCAM-1, PECAM-1, L1, CHL1, MAG, Nectins), and/or growth factors (e.g., vascular endothelial growth factor (VEGF), fibroblast growth factors (FGF) such as FGF-1, FGF-2, FGF-4, and other FGFR ligands) or other signaling molecules involved in thrombopoiesis or hematopoiesis, including biologically active fragments or variants thereof. In certain embodiments, these combination therapies achieve additive or synergistic effects. Without wishing to be bound by any one theory, certain particular embodiments, such as the combination of an AARS polypeptide (e.g., YRS) and TPO or other TPO peptide agonist or mimetic, achieve synergistic effects in increasing thrombopoiesis because certain AARS polypeptides are believed to increase thrombopoiesis by a TPO-independent mechanism; hence, the two independent thrombopoietic-stimulatory mechanisms may cooperate synergistically to increase thrombopoiesis.

In certain aspects, the methods of the present invention may be employed in conjunction with other therapeutic modalities, such as those involved in treating the underlying condition that causes the condition associated with thrombocytopenia. For example, a subject having congenital amegakaryocytic thrombocytopenia (CAMT) may ultimately undergo a bone marrow transplantation procedure, but may also benefit from a separate treatment, as provided herein, to either enhance platelet levels and/or to maintain platelet levels within a normal range. The thrombopoietic polypeptides of the present invention may be employed in this and similar regards.

In certain aspects, the methods provided herein may be employed in combination with a subject undergoing other medical treatments, such as treatments that either cause thrombocytopenia or increase the risk of developing thrombocytopenia. For example, the methods provided herein may be employed with a subject undergoing, a subject about to undergo, and/or a subject who has undergone, radiation therapy, chemotherapy, or other type of treatment, including various types of pharmaceutical treatments, as described herein and known in the art, since such treatments are known to reduce the platelet count in a subject. Accordingly, the methods provided herein may be utilized before, during, and/or after other medical treatments to reduce the risk of developing thrombocytopenia resulting from such treatments, and/or to manage or improve thrombocytopenia resulting from such treatments. For instance, in certain embodiments, megakaryocytic progenitors can be generated ex vivo and administered to autologous peripheral blood progenitor cell transplant subjects, bone marrow transplant subjects, stem cell transplant subjects, or any other transplant subjects. Examples of such subjects include cancer patients (e.g., breast cancer, non-Hodgkin's lymphoma) undergoing autologous peripheral blood progenitor cell transplant. In these and other embodiments, administration of enriched megakaryocyte progenitors may abrogate the need for allogeneic platelet transfusion support in autologous transplantation (see, e.g., Bertolini et al, *Blood.* 89:2679-2688, 1997).

As noted above, transfusion of ex vivo expanded megakaryocyte progenitor cells may also be used to shorten the time of platelet recovery in the thrombocytopenia induced by radiotherapy or chemotherapy. In this regard, it has been shown that transfusion of CD34+ cells expanded with TPO+ IL-11+ heparin (to increase the number of megakaryocyte progenitor cells) into irradiated nonobese diabetic/severe combined immunodeficient mice significantly accelerated platelet recovery (see, e.g., Feng, et al., *Experimental Hematology.* 33:1537-1543, 2005). In certain embodiments, hematopoietic stem cells (or other biological samples having cells that are capable of differentiating along the hematopoietic lineage) may be expanded ex vivo in the presence of AARS polypeptides, to increase the formation of megakaryocyte progenitors, and then administered to a subject prior to, during, or after radiotherapy or chemotherapy, to increase platelet recovery in the subject. In certain embodiments, AARS polypeptides may be administered directly to such subjects, either separately or in combination with ex vivo treatments.

Accordingly, whether ex vivo or in vitro, AARS polypeptides and related agents may be used in the treatment of cancer. For instance, as noted above, AARS polypeptide-based treatments may be used in combination with chemotherapy, radiotherapy, autologous peripheral blood progenitor cell transplant, bone marrow transplants, or other cancer therapies that impact platelet formation. "Cancer" relates generally to a class of diseases or conditions in which a group of cells display one or more of uncontrolled growth (i.e., division beyond normal limits), invasion (i.e., intrusion on and destruction of adjacent tissues), and metastasis (i.e., spread to other locations in the body via lymph or blood). These malignant properties of cancers differentiate them from benign cancers, which are self-limited, and typically do not invade or metastasize. Also included are myelodysplastic syndromes.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. Examples of cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma. Also included are "cancer stem cells," a small population of tumor cells that behave like stem cells (i.e., potential for indefinite self renewal), which are often refractory to therapeutic agents due to their dormancy, and which may contribute to the recurrence of cancer. Specific examples of cancer stem cells include "blast cells," the circulating precursor cells leading to leukemia (AML). In certain embodiments, AARS polypeptides modulate the growth or differentiation of these and other circulating cells, including circulating immune or hematopoietic cells such as hematopoeitic stem cells.

As noted above, AARS polypeptides or AARS polypeptide-expanded megakaryocyte progenitor cells may be administered in combination with chemotherapeutic agents, for instance, to increase platelet recovery. In certain embodiments, the chemotherapy is high-dose chemotherapy, which is often used in conjunction with CD34+ stem cell transplants (or other hematopoietic progenitor cell transplants). Merely by way of illustration, ex vivo expansion of megakaryocyte progenitor cells may provide a complementary transplant product able to enhance platelet production in patients with neuroblastoma (or other cancer) who undergo transplantation with CD34(+) cells following high-dose chemotherapy. Otherwise, these patients show prolonged delays in platelet recovery. Administration protocols for increasing platelet recovering in chemotherapy can be optimized according to techniques in the art.

Examples of general classes of chemotherapeutic or cytotoxic agents included, without limitation, alkylating agents, anti-metabolites, anthracyclines, anti-tumor antiobiotics, platinums, type I topoisomerase inhibitors, type II topoisomerase inhibitors, vinca alkaloids, and taxanes. Examples of particular chemotherapeutic or cytotoxic agents include, without limitation, chlorambucil, cyclophosphamide, lomustine (CCNU), melphalan, procarbazine, thiotepa, carmustine (BCNU), busulfan, daunorubicin, doxorubicin, idarubicin, epirubicin, mitoxantrone, bleomycin, cisplatin, carboplatin, oxaliplatin, camptothecins, irinotecan, topotecan, amsacrine, etoposide, etoposide phosphate, teniposide, vincristine, vinblastine, vinorelbine, vindesine, paclitaxel, and others described herein and known in the art.

AARS polypeptides and ex vivo expanded megakaryocyte progenitor cells may also be used in other tissue transplant therapies associated with reduced platelet levels. For instance, reduced platelets are common after liver transplantation due to platelet sequestration secondary to hypersplenism, and increasing platelet levels may improve post-transplant recovery. Liver transplants may be used to treat chronic active hepatitis and cirrhosis (from alcoholism, unknown cause, or biliary), biliary atresia, which is an incomplete development of the bile duct, and end-stage liver disease, among other liver-related diseases. Since liver transplantation is often a successful treatment for patients with liver related diseases, AARS polypeptides or ex vivo expanded megakaryocyte progenitor cells produced therefrom (or both) can be used in combination with liver transplants for treating these and other liver diseases. The treatment of other types of liver damage is also contemplated, whether by transplant or by direct treatment with AARS polypeptides, including liver damage related to hepatitis virus infection (e.g., HCV).

As noted above, certain embodiments relate to the use of AARS polypeptides and related agents to reduce the number of megakaryocytes, megakaryocyte progenitors, or platelets, whether in a subject in vivo or in tissue culture in vitro or ex vivo. These and related embodiments may be used to treat conditions associated with increased numbers of any one or more of megakaryocytes, megakaryocyte progenitors, or platelets, such as by reducing thrombopoiesis. Particular embodiments include the use of certain WRS polypeptides to reduce thrombopoiesis or megakaryopoiesis. Specific embodiments include the use of variants of YRS (Y341A) to reduce thrombopoiesis or megakaryopoiesis, particularly those that have been converted from having a thrombopoietic-stimulatory activity to having a thrombopoiesis-reducing activity.

Included are conditions associated with thrombocythemia or thrombocytosis, myeloproliferative conditions in which excess platelets are produced, often due to an increased number of megakaryocytes, leading to abnormal blood clotting or bleeding. In essential thrombocythemia, the platelet count is usually 2 to 4 or more times higher than normal. Thrombocythemia is typically characterized as either primary, for which the cause is not known, or secondary, for which the cause is known. Occasionally, primary thrombocythemia changes into a more serious disorder, such as polycythemia vera or certain types of leukemia. Secondary thrombocythemia may associate with bleeding, removal of the spleen, infections, rheumatoid arthritis, certain cancers, premature destruction of red blood cells (hemolysis), iron deficiency, and sarcoidosis, among other conditions known in the art.

As noted above, also included are direct in vivo methods of modulating hematopoiesis. These direct in vivo methods may be used alone or in combination with other treatments, including in combination with the ex vivo treatments described above. For in vivo treatment of human and non-human subjects, the subject is usually administered a pharmaceutical formulation comprising an AARS polypeptide or a related agent of the present invention. When used for in vivo therapy, the polypeptides of the subject invention are administered to the patient in therapeutically effective amounts (e.g., amounts that modulate hematopoiesis). The polypeptides may be administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The polypeptides may be administered parenterally, when possible, at the target cell site, or intravenously. Intravenous or subcutaneous administration of the polypeptide is preferred in certain embodiments.

For parenteral administration, the polypeptides or related agents may be formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The polypeptides will typically be formulated in such vehicles at concentrations of about 0.01 mg/ml to about 1 mg/ml to about 10 mg/ml, or more.

Generally, a therapeutically effective amount of polypeptide is administered to a subject or patient. In particular embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

Formulations and Pharmaceutical Compositions

The compositions of the invention comprise aminoacyl-tRNA synthetase polypeptides, including truncations and/or variants thereof and related agents, formulated in pharmaceutically-acceptable or physiologically-acceptable solutions for administration to a cell or an animal, either alone, or in combination with one or more other modalities of therapy. Also included are pharmaceutical compositions that comprise antibodies, antibody fragments, or alternative binding agents, typically those that agonize or antagonize a hematopoiesis-modulating activity of an AARS polypeptide. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the hematopoietic-modulating or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Stimulation of Thrombopoiesis and Megakaryopoiesis In Vivo

The effects of a tyrosyl-tRNA synthetase polypeptide on thrombopoiesis were measured in vivo. The tyrosyl-tRNA synthetase polypeptide utilized in the experiments described below is a C-terminal truncation that comprises amino acids 1-364 of the full-length human tyrosyl-tRNA. This C-terminally truncated polypeptide was fused to an eight amino acid C-terminal tag (365-L-E-H-H-H-H-H-H-372) (SEQ ID NO:5). The amino acid sequence of the full-length human tyrosyl-tRNA synthetase is set forth in SEQ ID NO:1.

To measure the effects of tyrosyl-tRNA synthetase polypeptides on thrombopoiesis, in a first set of experiments, mice were injected subcutaneously twice daily for seven days with 3 µg/kg of the C-terminally truncated tyrosyl-tRNA synthetase polypeptide. In a second set of experiments, mice were injected twice daily for seven days with 1, 3, and 10 µg/kg of the C-terminally truncated tyrosyl-tRNA synthetase polypeptide. In a third set of experiments, mice were injected subcutaneously twice daily for six days with (i) 3 and 300 µg/kg of the C-terminally truncated tyrosyl-tRNA synthetase polypeptide, and one single daily injection of (ii) 90 µg/kg thrombopoietin (TPO), and (iii) 250 µg/kg G-CSF.

For the first and second set of experiments described above, the platelet count for each animal was determined upon completion of the administration protocol. For the third set of experiments, bone marrow and spleen histology were examined at the end of the administration protocol.

Figure 1B:
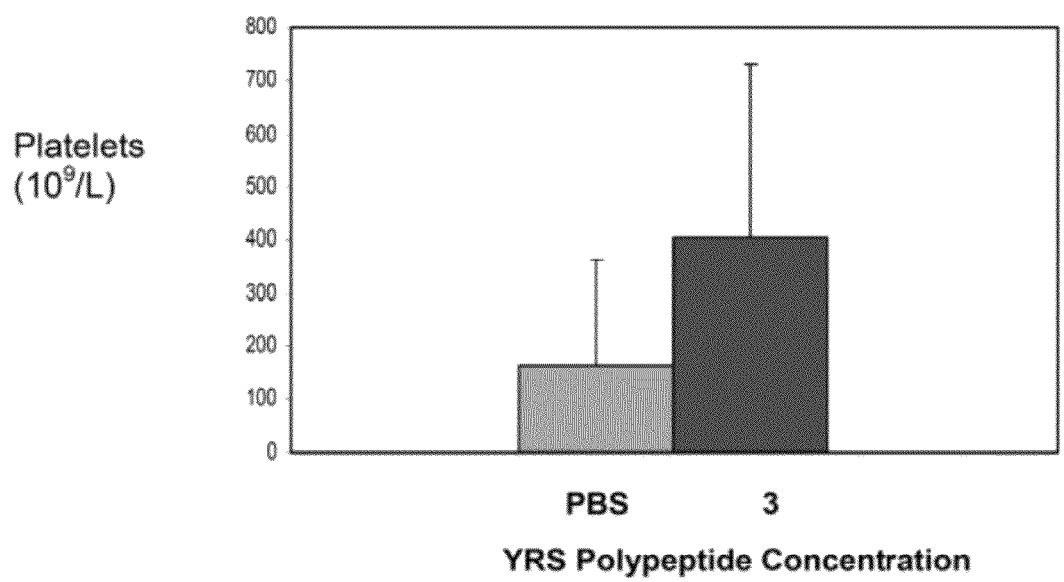
FIG. 1(B) shows the platelet count for the experiment in which mice were injected with 3 µg/kg of the truncated tyrosyl-tRNA synthetase polypeptide, as compared to a PBS control. See Example 1.

Administration of a truncated tyrosyl-tRNA synthetase for about one week showed a reproducible, in vivo increase in thrombopoietic activity, as measured by either increased platelet count or increased megakaryocyte numbers. FIG. 1(a) shows the platelet count for the experiment in which mice were injected with 1, 3, and 10 µg/kg of the truncated tyrosyl-tRNA synthetase polypeptide, as compared to a phosphate-buffer saline (PBS) control. FIG. 1(b) shows the platelet count for the experiment in which mice were injected with 3 µg/kg of the truncated tyrosyl-tRNA synthetase polypeptide, as compared to a PBS control. In both experiments, mice showed an increase in platelet counts over control in response to treatment with a tyrosyl-tRNA polypeptide of the invention.

Figure 2:
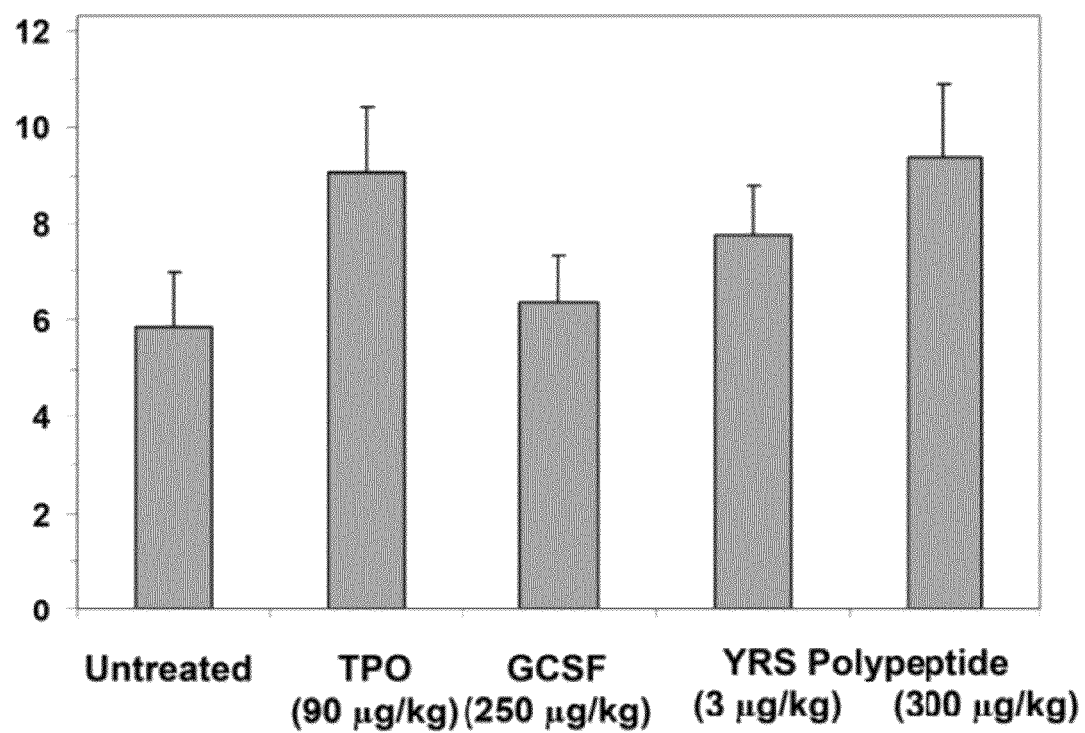
FIG. 2 shows the in vivo effects on megakaryocyte number following administration of a C-terminally truncated human-tyrosyl-tRNA synthetase polypeptide (SEQ ID NO:3) having an eight amino acid C-terminal tag, L-E-H-H-H-H-H-H (SEQ ID NO:5). See Example 1.

In addition, FIG. 2 shows an increase in megakaryocyte numbers in response to administration of the truncated tyrosyl-tRNA synthetase polypeptide, as compared to untreated animals, which is comparable to the increased numbers observed after administration with TPO. These results show that tyrosyl-tRNA synthetase polypeptide fragments, and in particular C-terminally truncated fragments, are capable of stimulating thrombopoiesis and megakaryopoiesis in vivo.

Example 2

In Vitro Measurements of Thrombopoiesis and Megakaryopoiesis

Effects on thrombopoiesis may also be measured in vitro. Stem cells are treated in vitro with a tyrosyl-tRNA synthetase polypeptide of the invention to determine its effect on hematopoietic progenitors of the erythroid, myeloid and megakaryocyte lineages using colony-forming cell (CFC) assays (e.g., inhibition, stimulation, toxicity, synergism with other cytokines, hematopoietic defects). In addition, CD34+ megakaryocyte progenitor cells are treated in vitro with a tyrosyl-tRNA synthetase polypeptide of the invention to monitor megakaryocyte expansion and differentiation (e.g., increase in number of progenitor cells, stimulation of differentiation, increase in polyploidy). Similar experiments are performed using bone marrow and spleen cells derived from mice treated with a tyrosyl-tRNA synthetase polypeptide.

Example 3

Combination Therapy Stimulates Thrombopoiesis

To assess whether a tyrosyl-tRNA synthetase polypeptide of the present invention has a synergistic and/or additive effect on the proliferation and differentiation of megakaryocytes in vitro, CD34+ cord blood cells are grown in liquid culture medium in the presence of optimal or sub-optimal formulations of cytokines (StemCell Technologies, Vancouver), such as IL-11, and treated with increasing concentrations of a tyrosyl-tRNA synthetase polypeptide. Additivity or synergism can be determined by monitoring the growth and differentiation of the progenitor cells in the two formulation conditions.

Similarly, in a protocol comparable to that described in Example 1, mice are injected with a limiting amount of thrombopoietin and with increasing amounts of a tyrosyl-tRNA synthetase polypeptide and the effects of the combination therapy on thrombopoiesis in vivo can be determined by platelet and megakaryocyte counts. In addition, combination therapy with limited amounts of other cytokines, chemokines and/or growth factors involved in hematopoiesis can be evaluated using the same type of regimen.

Example 4

Thrombopoietic Activity of Tyrosyl-tRNA Synthetase Polypeptides in Rats

The effects of two tyrosyl-tRNA synthetase polypeptides on thrombopoiesis were measured in rats. The tyrosyl-tRNA synthetase polypeptides utilized in the experiments described below are: i) a C-terminal truncation that comprises amino acids 1-364 of the full-length human tyrosyl-tRNA (SEQ ID NO:3) fused to an eight amino acid C-terminal histidine tag (SEQ ID NO:5) and; ii) a mutant of the full-length human tyrosyl-tRNA synthetase with a single, tyrosine to alanine, amino acid substitution at position 341, referred to as "Y341A" (SEQ ID NO: 2).

To measure the effects of tyrosyl-tRNA synthetase polypeptides on thrombopoiesis, platelet count for each rat was determined one day before the first scheduled injection and animals were grouped in seven cohorts according to their initial platelet counts. Three groups of rats were injected intravenously once daily for seven days with 0.1, 10, and 1000 μg/kg of the C-terminally truncated tyrosyl-tRNA synthetase polypeptide, respectively. Three additional groups were administered with the same dosages of Y341A. One control group received a daily injection of buffer only (0.5× PBS, 2 mM DTT) and an additional control group was injected daily with 90 μg/kg of thrombopoietin (R&D Systems, Minneapolis, Minn.).

Figure 3:
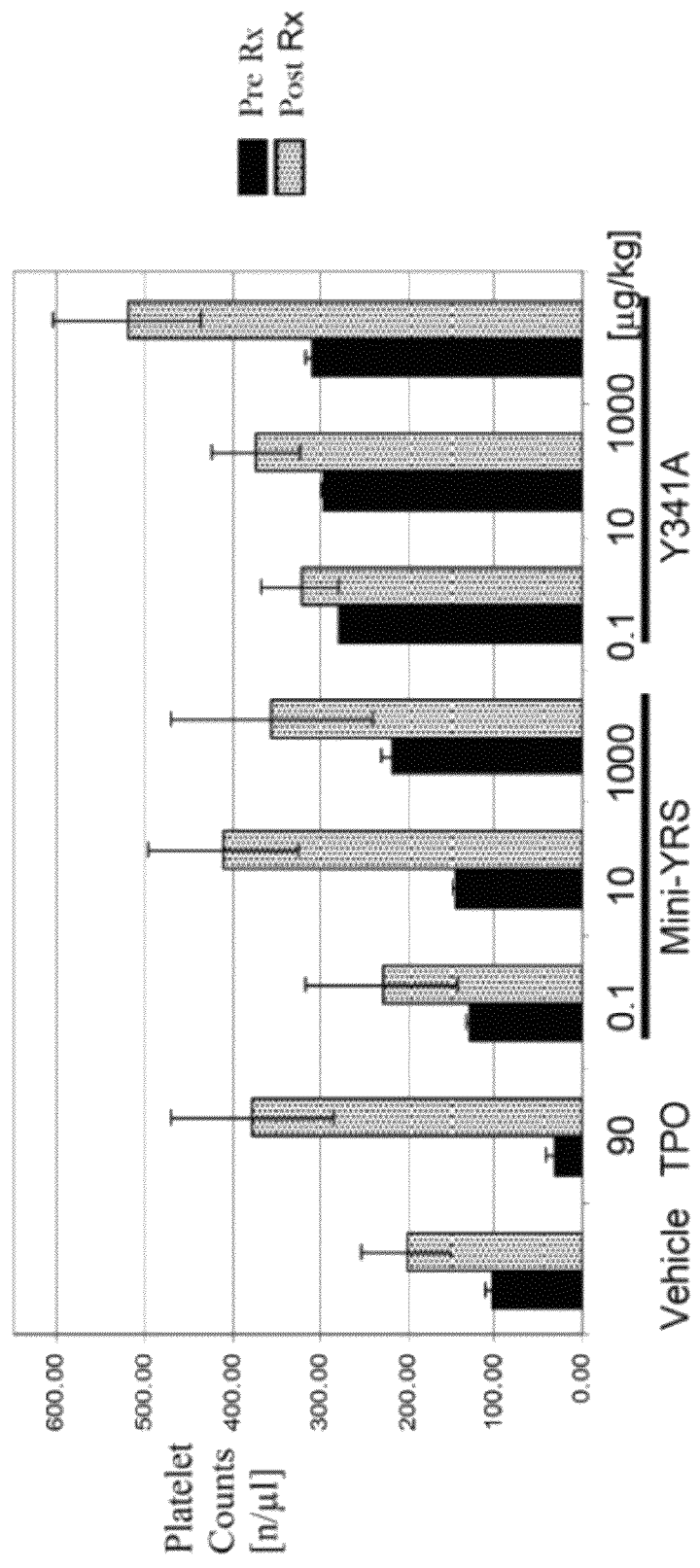
FIG. 3 shows the in vivo effects on platelet production following administration of two YRS polypeptide variants, mini-YRS and Y341A.

Administration of the two tyrosyl-tRNA synthetase polypeptides resulted in a marked elevation in platelet counts, comparable or superior to that observed in the thrombopoietin group (See FIG. 3). These results show that tyrosyl-tRNA synthetase polypeptides are capable of stimulating thrombopoiesis in vivo.

Example 5

Tyrosyl-tRNA Synthetase Polypeptides are Chemoattractants for Megakaryocytes

MO7e cells (DSMZ, Braunschweig, Germany) were cultured in RPMI-1640 medium supplemented with 20% heat-inactivated FBS and 10 ng/ml IL-3 (R&D Systems, Minneapolis, Minn.). Cells were maintained at a density of $2 \times 10^5$ to $1 \times 10^6$/ml and RPMI-1640 medium with 0.1% BSA was used as migration buffer. Before the migration assay, cells were serum-starved for 30 minutes in migration buffer and loaded with 8 μg/ml calcein AM (Invitrogen, Carlsbad, Calif.). Cells were spun down at 200 g for 5 minutes without brake and washed once with migration buffer to remove free calcein AM. Cell density was adjusted to $1 \times 10^7$/ml and 100 μl were added to 6.5 mm transwell 8.0 μm pore filter inserts (Costar, Cambridge, Mass.). 600 μl migration buffer containing either PBS, a control chemokine, or the tyrosyl-tRNA synthetase polypeptides were added to the lower chamber and cells were allowed to migrate for 4 to 16 hours (for the 16-hour migration time, cells were stained after migration). Cells that migrated to the lower chamber were collected and resuspended in 100 μl PBS, transferred into 384-well opaque Greiner plate and counted by fluorescence in a plate reader. Tyrosyl-tRNA synthetase polypeptides stimulated migration of MO7e megakaryoblasts.

Example 6

Tyrosyl-tRNA Synthetase Polypeptides Promote Cell Adhesion to Endothelial Monolayers The ability of YRS polypeptides to stimulate adhesion of THP-1 cells to endothelial monolayers of HUVEC-2 cells was tested. HUVEC-2 cells (BD Biosciences, San Jose, Calif.) were cultured in EGM-2 medium (Lonza, Allendale, N.J.) and used before they reached 10 passages. THP-1 cells (ATCC, Manassas, Va.) were cultured in RPMI-1640 medium supplemented with 10% heat-inactivated FBS and maintained at a density of $2-4 \times 10^5$/ml. Cells were seeded at approximately $1 \times 10^4$ cells/well into fibronectin-coated (10 μg/ml, 2 hours at 37° C.), opaque 96-well plates.

HUVEC-2 cells were grown until a monolayer was formed and then stimulated overnight in EGM-2 medium with either PBS, IL-1 or the tyrosyl-tRNA synthetase polypeptides. THP-1 cells were collected and incubated for 30 minutes in RPMI-1640 serum-free medium containing 0.1% BSA and calcein AM (6 µl/ml). The cells were then washed in RPMI-1640 serum-free medium containing 0.1% BSA and resuspended at a density of $1.5 \times 10^5$ cells/ml in RPMI medium containing 10% FBS. 100 µl THP-cells were added to the HUVEC monolayer and incubated for 15 minutes. Unbound THP-1 cells were washed with PBS twice and the remaining cells were fixed with 2% formaldehyde and counted by fluorescence in a plate reader.

Adhesion molecule expression in endothelial monolayers was measured following exposure to tyrosyl-tRNA synthetase polypeptides. $1 \times 10^4$ HUVEC-2 cells were seeded into a 96-well plate and grown for 48 hours as described in the previous paragraph. Tyrosyl-tRNA synthetase polypeptides, diluted in growth media, were added to the wells and incubated for 16 hours. The culture medium was removed and cells were fixed with 50 µl of Z fix (Anatech Ltd, Battle Creek, Mich.) for 15 minutes at room temperature. Wells were subsequently blocked with 50 µl of casein for 1 hour followed by multiple 200 µl washes with PBS. All subsequent reagents were diluted in casein and all steps were performed at room temperature. Antibodies directed against VCAM-1 and E-selectin (Santa Cruz Biotech, Santa Cruz, Calif.) were added for 1 hour. Wells were then washed as above and an HRP-labeled secondary antibody (Jackson Immunoresearch, West Grove, Pa.) was added for 1 hour. Wells were washed and the substrate for HRP was added. 15 minutes later, an equal volume of 2 M sulfuric acid was added and absorbance determined at 450 nm. VCAM-1 expression was increased following stimulation of the endothelial cells with tyrosyl-tRNA synthetase polypeptides.

Example 7

Tyrosyl-tRNA Synthetase Polypeptides Stimulate Migration of 293 and CHO Cell Lines Transfected with the CXCR-2 Receptor The effects of tyrosyl-tRNA synthetase polypeptides on CXCR-2 signaling was tested by measuring the migration of CXCR-2 expressing cells in response to said polypeptides. 293/CXCR-2 cells were maintained in DMEM medium supplemented with 10% heat-inactivated FBS, 1% Penicillin-Streptomycin and 800 µg/ml Geneticin, all purchased from Invitrogen, Carlsbad, Calif. DMEM medium with 0.1% BSA was used as migration buffer. Prior to migration assay, cells were serum-starved for 30 minutes in migration buffer, centrifuged at 200 g for 5 minutes and resuspended in migration buffer at a final density of $1 \times 10^6$ cells/ml. 100 µl were added to 6.5 mm transwell filter inserts (Costar, Cambridge, Mass.) and 600 µl migration buffer containing a control chemokine, the tyrosyl-tRNA synthetase polypeptides or buffer only were added to the plate lower chambers. Cells were allowed to migrate for 4 hours and the remaining cells in the upper chamber (transwell filter inserts) were removed with a cotton swap. The filter inserts were then transferred to a new 24-well plate containing 500 µl cell dissociation buffer (Invitrogen, Carlsbad, Calif.) and 12 µg/ml Calcein AM (Invitrogen, Carlsbad, Calif.). After 1 hour incubation at 37° C., cells were collected and resuspended in 100 µl PBS, transferred into a 384-well opaque Greiner plate, and counted by fluorescence in a plate reader.

CHO-K1/CXCR-2 cells were maintained in F12 medium supplemented with 10% heat-inactivated FBS, 1% Penicillin-Streptomycin-Glutamine and 800 µg/ml Geneticin. F12 medium with 0.5% BSA was used as migration buffer. Prior to migration, cells were serum-starved for 30 minutes in migration buffer, collected by using cell dissociation buffer, spun down at 200 g for 5 minutes and resuspended in migration buffer at the final density of $1 \times 10^6$ cells/ml. 100 µl were added to 6.5 mm transwell filter inserts and 600 µl migration buffer containing a control chemokine, the tyrosyl-tRNA synthetase polypeptides or buffer only were added to the plate lower chambers. Cells were allowed to migrate for 3 hours and the remaining cells in the upper chamber (transwell filter inserts) were removed with a cotton swap. The filter inserts were then transferred to a new 24-well plate containing 500 µl PBS and 12 µg/ml Calcein AM. After 30 minutes incubation at 37° C., filters were transferred again into a new 24-well plate containing 500 µl phenol/red-free trypsin. After 2 to 5 minutes incubation, detached cells were collected and resuspended in 100 µl PBS, transferred into a 384 well opaque Greiner plate and counted by fluorescence in a plate reader. Tyrosyl-tRNA synthetase polypeptides induced migration of CXCR-2 transfected cells.

Example 8

Tyrosyl-tRNA Synthetase Polypeptides Stimulate Polymorphonuclear (PMN) Cell Migration To test the effects of YRS polypeptides on PMN cell migration, human granulocyte cells were purified from fresh human peripheral blood using RosetteSep® Human Granulocyte Enrichment Kit (StemCell Technologies, Vancouver, BC) according to the manufacturer's instructions. Serum-free RPMI medium supplemented with 0.5% FBS was used as migration buffer. $4 \times 10^7$ cells were resuspended in 1 ml migration buffer and incubated for 30 minutes with 8 µl of a 1 mg/ml Calcein AM solution (Invitrogen, Carlsbad, Calif.). Cells were collected, spun down at 200 g for 5 minutes without brake, washed once with migration buffer and resuspended in the same buffer at a final density of $1 \times 10^7$/ml.

100 µl were added to 6.5 mm transwell filter inserts (Costar, Cambridge, Mass.) and 600 µl migration buffer containing a control chemokine, the tyrosyl-tRNA synthetase polypeptides or buffer only were added to the plate lower chambers. Cells were allowed to migrate for 45 minutes in the incubator and cells that migrated to the lower chamber were collected, resuspended in 100 µl PBS, transferred into a 384-well opaque Greiner plate and counted by fluorescence in a plate reader.

The tyrosyl-tRNA synthetase polypeptides induced a biphasic migration of PMN both at low pM and at higher µM concentrations, as illustrated by a bell-shaped migration curve typically observed with chemokines Example 9

Generation and Identification of Human Glycyl-tRNA Synthetase (GlyRS) Proteolytic Fragments Full-length recombinant human GlyRS having an amino acid sequence as set forth in SEQ ID NO:16 was expressed and purified from *E. coli* using nickel IMAC chromatography. To generate fragments of GlyRS by controlled proteolysis, the full-length protein was treated with 167 nM human neutrophil elastase for 30 minutes before separation of the fragments by SDS-PAGE. Fragments generated by cleavage with neutrophil elastase were analyzed using LC/MS/MS to determine accurate masses for each fragment. In addition individual fragments were excised from an SDS-PAGE gel and subjected to in-gel trypsin digestion followed by LC/MS/MS analysis to identify the portion of the full-length protein from which the fragment was generated and to identify non-trypsin cleavage sites that could be attributed to neutrophil elastase.

The identity of these peptide boundaries is summarized in Table 1; residues in bold are non-trypsin cleavage sites indicating that the exact cleavage site of elastase (thus exact N- or C-terminus) of that fragment has been identified.

LC/MS/MS. Without wishing to be bound by any one theory, it is believed that these fragments are indicative of those that would be created in human cells through the process of natural proteolysis.

To identify the residues at which proteolysis occurs for human QRS, the proteins were separated by SDS-PAGE run in 4-12% MOPS, gel slices containing the fragments were excised and subjected to in-gel trypsin digestion followed LC/MS/MS analysis. This process allowed the identification of both the portion of the full-length protein from which the fragments were generated and the non-tryptic cleavage sites that could be attributed to endogenous proteolytic cleavage.

TABLE 1

GlyRS proteolytic fragments

| | Whole mass (Da) | Protease used | N-term. boundary | C-term. boundary | Non-tryptic peptide found |
|---|---|---|---|---|---|
| 1 | 71384 | No protease | A57 | E685 | |
| 2 | 50782 | No protease | P239 | E685 | PGYLRPETAQGIFLNFK (SEQ ID NO: 18) |
| 3 | 53406 | elastase | T214 | E685 | TGNDLSPPVSFNLMFK (SEQ ID NO: 19) |
| 4 | 41000-43000 | elastase | F311-L338 | E685 | |
| 5 | 28096 | elastase | N439 | E685 | 439NVVQFEPSK (SEQ ID NO: 20) |
| 6 | 25328 | elastase | T214 | V438 | TGNDLSPPVSFNLMFK (SEQ ID NO:19) 439NVVQFEPSK (SEQ ID NO: 20) |
| 7 | 22398 | elastase | T214 | R420 | TGNDLSPPVSFNLMFK (SEQ ID NO: 19) |
| 8 | 19783 | elastase | L511 | E685 | LYVEEVVPNVIEPSFGLGR (SEQ ID NO: 21) |
| 9 | | elastase | T214 | 325-338 | TGNDLSPPVSFNLMFK (SEQ ID NO: 19) |
| 10 | 4841 | elastase | A85 | T127 | AIYGGVSGLYDFGPVGCALK (SEQ ID NO: 22) QHFIQEEQILEIDCT (SEQ ID NO: 23) |
| 11 | 3675 | elastase | R25 | I56 | |

Figure 4:
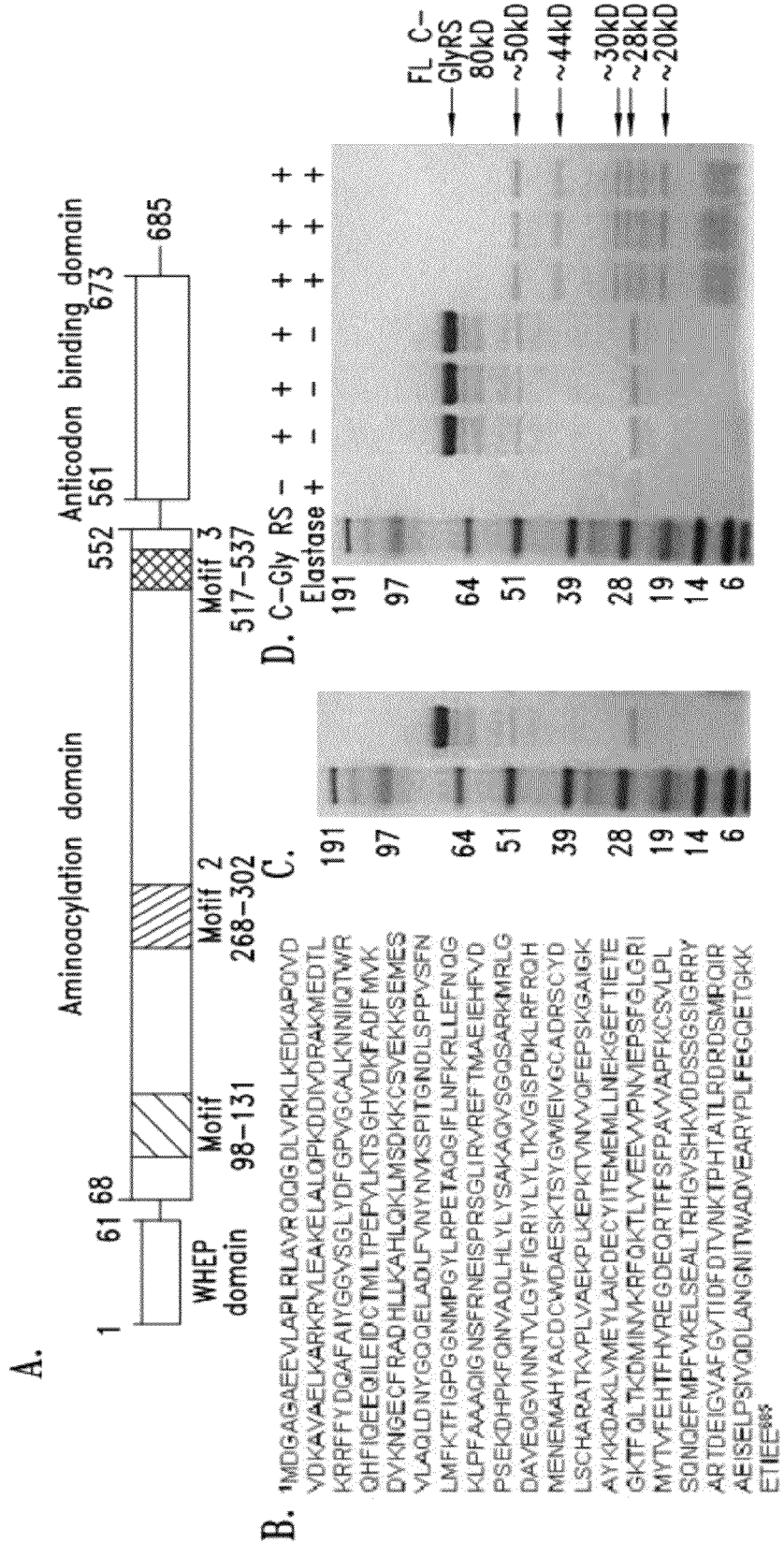
FIG. 4 (A-D) shows the domain structure and amino acid sequence of GlyRS (SEQ ID NO:16), and illustrates the SDS-PAGE separation of fragments of GlyRS generated by controlled proteolysis of the full-length GlyRS protein with human neutrophil elastase. See Example 9.

FIG. 4 (A-D) shows the domain structure and amino acid sequence of GlyRS, and illustrates the SDS-PAGE separation of fragments of GlyRS generated by controlled proteolysis of the full-length GlyRS protein with human neutrophil elastase. As described below, certain of these fragments were tested for the hematopoietic-modulating activities. Included are variants and biologically active fragments of the above GlyRS polypeptides.

Example 10

Generation and Identification of Endogenous Human Glutaminyl-tRNA Synthetase (QRS) Fragments Full-length recombinant human QRS (SEQ ID NO:25) was expressed and purified from *E. coli* using nickel IMAC chromatography. Endogenous proteolytic fragments were generated, purified, and subsequently characterized using LC/MS/MS. Without wishing to be bound by any one theory, it is believed that these fragments are indicative of those that would be created in human cells through the process of natural proteolysis.

Figure 5:
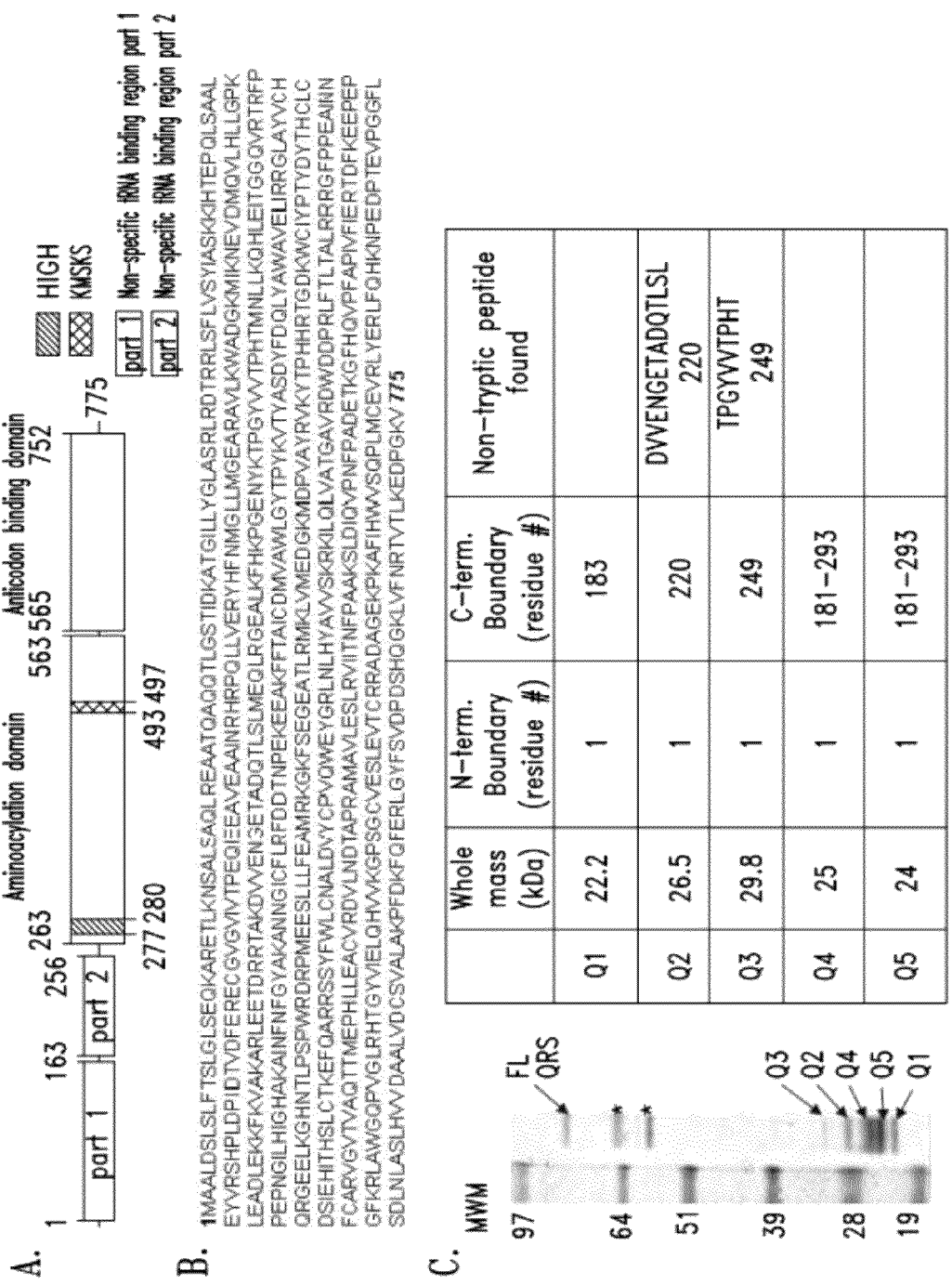
FIG. 5 (A-C) shows the domain structure and amino acid sequence of QRS (SED ID NO:25), and illustrates the SDS-PAGE separation of fragments of QRS (SEQ ID Nos. 26 and 27) generated by endogenous or controlled proteolysis of the full-length QRS. See Example 10.

All protein fragments identified represented the N-terminal portion of QRS. See Table 2 below, and FIG. 5 (A-D).

TABLE 2

Endogenous QRS proteolytic fragments

| | Whole mass (Da) | N-term. boundary | C-term. boundary | Non-tryptic peptide found |
|---|---|---|---|---|
| Q1 | 22200 | 1 | 183 | |
| Q2 | 26500 | 1 | 220 | DVVENGETADQTLSL220 (SEQ ID NO: 26) |
| Q3 | 29800 | 1 | 249 | TPGYVVTPHT249 (SEQ ID NO: 27) |

TABLE 2-continued

Endogenous QRS proteolytic fragments

| Whole mass (Da) | N-term. boundary | C-term. boundary | Non-tryptic peptide found |
|---|---|---|---|
| Q4 25000 | 1 | 181-293 (200) | |
| Q5 24000 | 1 | 181-293 | 439NVVQFEPSK (SEQ ID NO: 20) |

Figure 6:
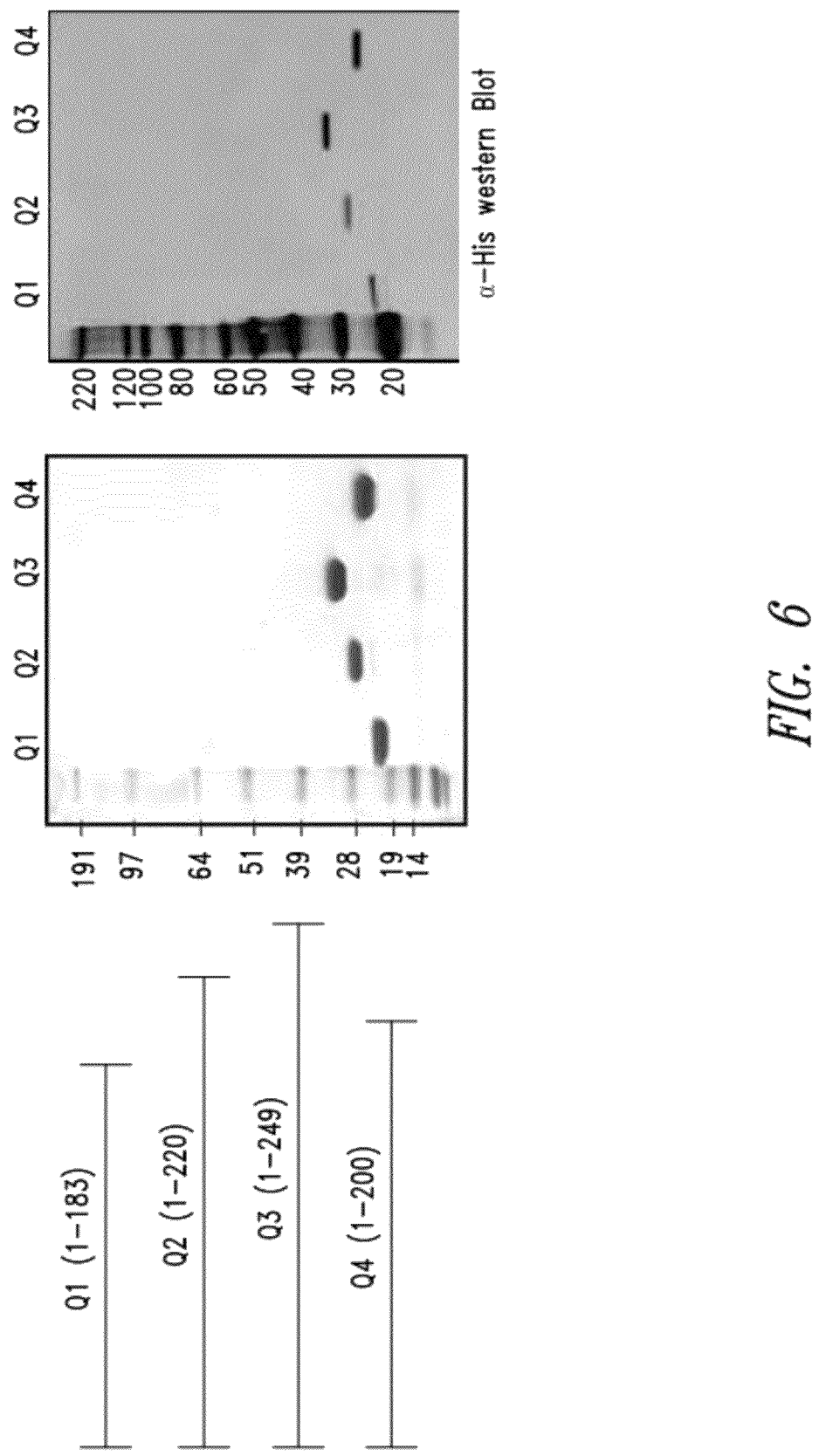
FIG. 6 shows the QRS fragments that were cloned into an *E. coli* protein expression vector for over-expression and purification. See Example 10.

QRS fragments closely matching those identified by LC/MS/MS in Table 2 above were cloned into an E. coli protein expression vector for overexpression and purification. Proteins were purified using Nickel IMAC chromatography and contaminants were removed using a Sartobind Q membrane (Sartorius). See FIG. 6.

Example 11

Aminoacyl-tRNA Synthetase Polypeptides Impact Megakaryocyte Progenitor Cells in Bone Marrow Cell Cultures To test the effects of YRS polypeptides on megakaryocyte progenitor cells in bone marrow cell cultures, clonogenic progenitors of the megakaryocyte (CFU-Mk; Colony Forming Unit-Megakaryocyte) lineage were assessed in serum-free, collagen-based media MegaCult-C® 4950 supplemented with proprietary concentrations of cytokines (StemCell Technologies, Vancouver, BC). Normal human bone marrow light density cells (Lonza, Allendale, N.J.) were stored at −152° C. until required for the assay. On the day of the experiment, cells were thawed rapidly at 37° C., the contents of the vial were diluted in 10 mL of Iscove's modified Dulbecco's medium (IMDM) containing 2% fetal bovine serum (FBS) and washed by centrifugation (1200 rpm for 10 minutes, room temperature). The supernatant was discarded and the cell pellet resuspended in a known volume of IMDM containing 2% FBS. A cell count (3% glacial acetic acid) and viability assessment (trypan blue exclusion test) were performed.

The aminoacyl-tRNA synthetase polypeptides (stored in 50% glycerol/0.5×PBS/2 mM DTT) were dialyzed in 0.5× PBS/2 mM DTT for a total of 5 hours, with one change of buffer after 3 hours in order to remove glycerol. After dialysis, proteins and buffer sample were sterile filtered and concentration was adjusted to compensate for the increase in volume.

Test proteins (AARS polypeptides) were added to tubes of serum-free, collagen-based media MegaCult-C® 4950 supplemented with cytokines (rhTpo, rhIL-3, and rhIL-6). Standard control cultures (containing no test protein) and solvent control cultures (containing no test protein but equivalent concentrations of buffer) were also initiated. Bone marrow cells were then added to each tube of media to give a final concentration of $1\times10^5$ cells per slide. Bovine collagen was then added, tubes were vortexed, and contents dispensed into triplicate double chamber slides. All cultures were incubated for 10-12 days at 37° C., 5% $CO_2$.

Following incubation, cultures were assessed microscopically for colony formation prior to dehydration and fixation of the slide. Using an antibody staining protocol to detect GPIIa/IIIb (CD41) expression, the colonies on the slide were stained using an alkaline phosphatase detection system as described in the StemCell Technical Manual, "Assays for the Quantitation of Human and Murine Megakaryocytic Progenitors", Section 7, herein incorporated by reference in its entirety. Colony numbers were scored and assessed by trained StemCell personnel. The colonies were divided into the following categories, based on size and morphology: i) CFU-Mk (2-20)—the small megakaryocytic colony derived from this more mature progenitor cell contains 2-20 cells; ii) CFU-Mk—the medium megakaryocytic colony derived from this more primitive progenitor cell contains 21-49 cells and; iii) CFU-Mk (>50)—the large megakaryocytic colony derived from this most primitive lineage-restricted progenitor cell contains >50 cells.

Figure 7A:
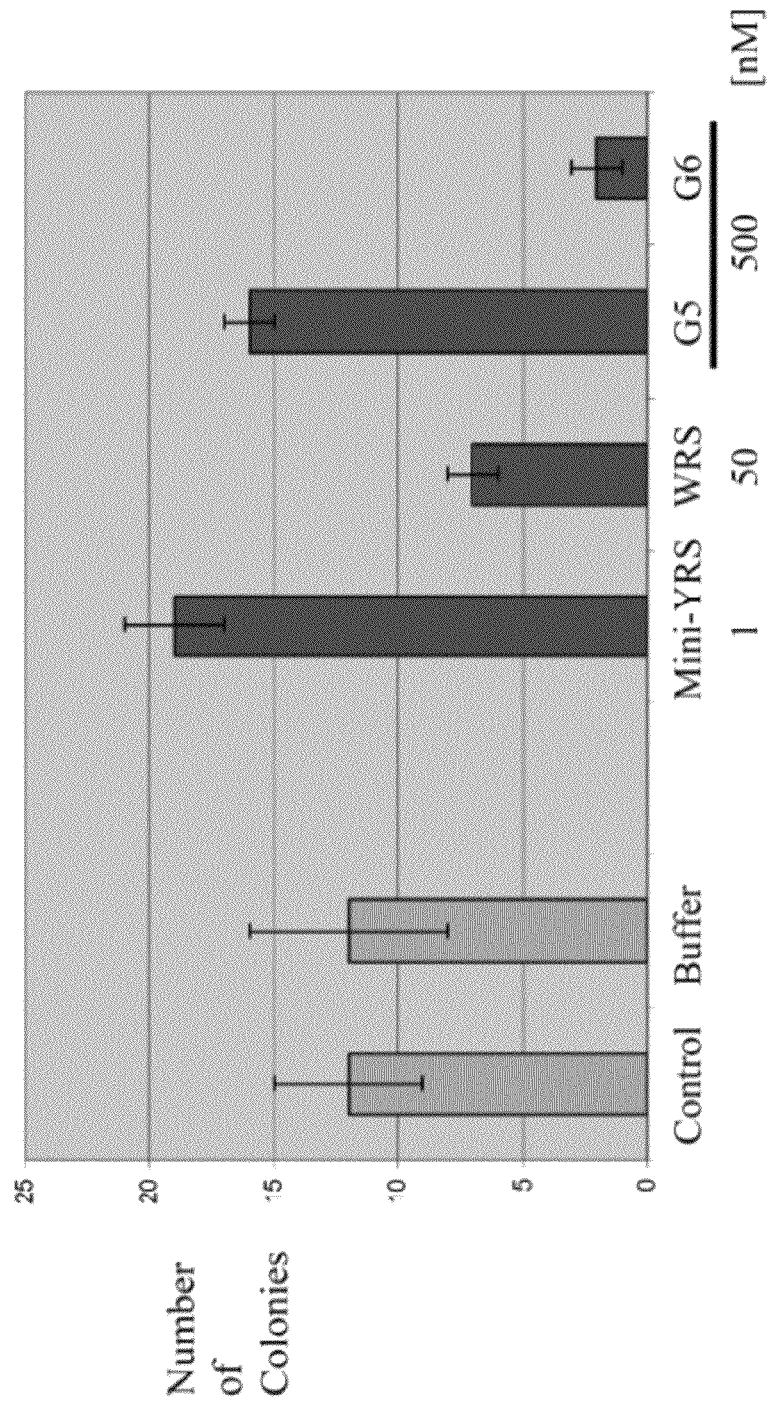
FIG. 7 shows the impact of a variety of AARS polypeptide on the in vitro formation of the most primitive lineage-restricted (early) megakaryocyte progenitors (FIG. 7(A)), and the more mature (late) megakaryocyte progenitors (FIG. 7(B)). See Example 11.
Figure 7B:
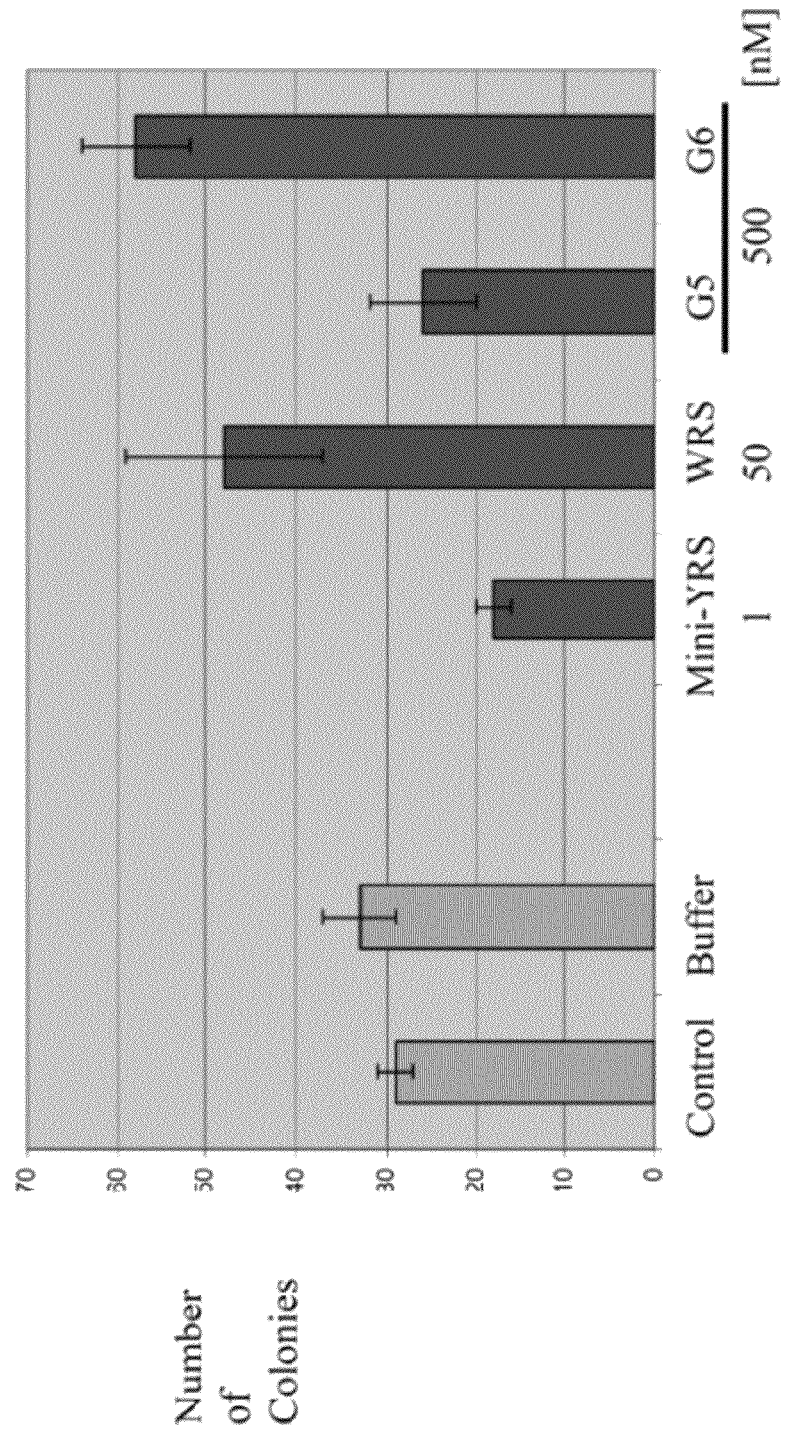

FIG. 7 shows the impact of a variety of AARS polypeptide on the most primitive lineage-restricted (early) progenitors (FIG. 7(A)), and on the more mature progenitors (FIG. 7(B)). Mini-YRS and the G5 fragment of GlyRS (amino acids 439-685 of human GlyRS) increase the number of early progenitors and decrease the number of late progenitors. A WRS fragment (see, e.g., SEQ ID NOS:34 and 35) and the G6 fragment of GlyRS (amino acids 214-438 of human GlyRS) decrease the number of early progenitors and increase the number of late progenitors.

Example 12

Aminoacyl-tRNA Synthetase Polypeptides Impact Erythrocyte Progenitor Cell Formation in Bone Marrow Cultures To test the effects of AARS polypeptides on erythrocyte progenitor cells in bone marrow cultures, clonogenic progenitors of the erythroid (CFU-E; Colony Forming Unit-Erythrocyte) lineage were assessed in the methylcellulose-based medium MethoCult® 84434 (StemCell Technologies, Vancouver, BC). Normal human bone marrow light density cells (Lonza, Allendale, N.J.; lot #07B21195) were stored at −152° C. until required for the assay. On the day of the experiment, the cells were thawed rapidly at 37° C., the contents of the vial were diluted in 10 mL of Iscove's modified Dulbecco's medium (IMDM) containing 2% fetal bovine serum (FBS) and washed by centrifugation (1200 rpm for 10 minutes, room temperature). The supernatant was discarded and the cell pellet resuspended in a known volume of IMDM containing 2% FBS. A cell count (3% glacial acetic acid) and viability assessment (trypan blue exclusion test) were performed.

The AARS polypeptides (stored in 50% glycerol/0.5× PBS/2 mM DTT) were dialyzed in 0.5×PBS/2 mM DTT for a total of 5 hours, with one change of buffer after 3 hours in order to remove glycerol. After dialysis, proteins and buffer sample were sterile filtered and concentration was adjusted to compensate for the changes in volume. Dialyzed proteins were added directly into the methylcellulose media to achieve the final test concentrations.

Test proteins (tRNA synthetase polypeptides) were added to tubes of methylcellulose-based media MethoCult® 84434, which contains optimal proprietary concentrations of cytokines (StemCell Technologies, Vancouver, BC). Standard control cultures (containing no test protein) and solvent control cultures (containing no test protein but equivalent concentrations of dialyzed 50% glycerol/0.5×PBS/2 mM DTT buffer) were also initiated. Bone marrow cells were then added to each tube of media and cultures plated in triplicate at $1\times10^4$ cells per dish. Following 14 days in culture at 37° C., 5% $CO_2$, the colonies were assessed and scored by trained StemCell personnel.

The mean+/−1 standard deviation was calculated for triplicate cultures. Standard t-tests were performed to assess if there was a difference in the number of colonies generated between solvent control and treated cultures. Due to the potential subjectivity of colony enumeration, a p-value of less than 0.01 is deemed significant. Photographs were taken of representative erythroid progenitor derived colonies from solvent controls and various test protein concentrations illustrating normal colonies and colonies where the growth was impacted due to the activity of the test proteins.

Figure 8:
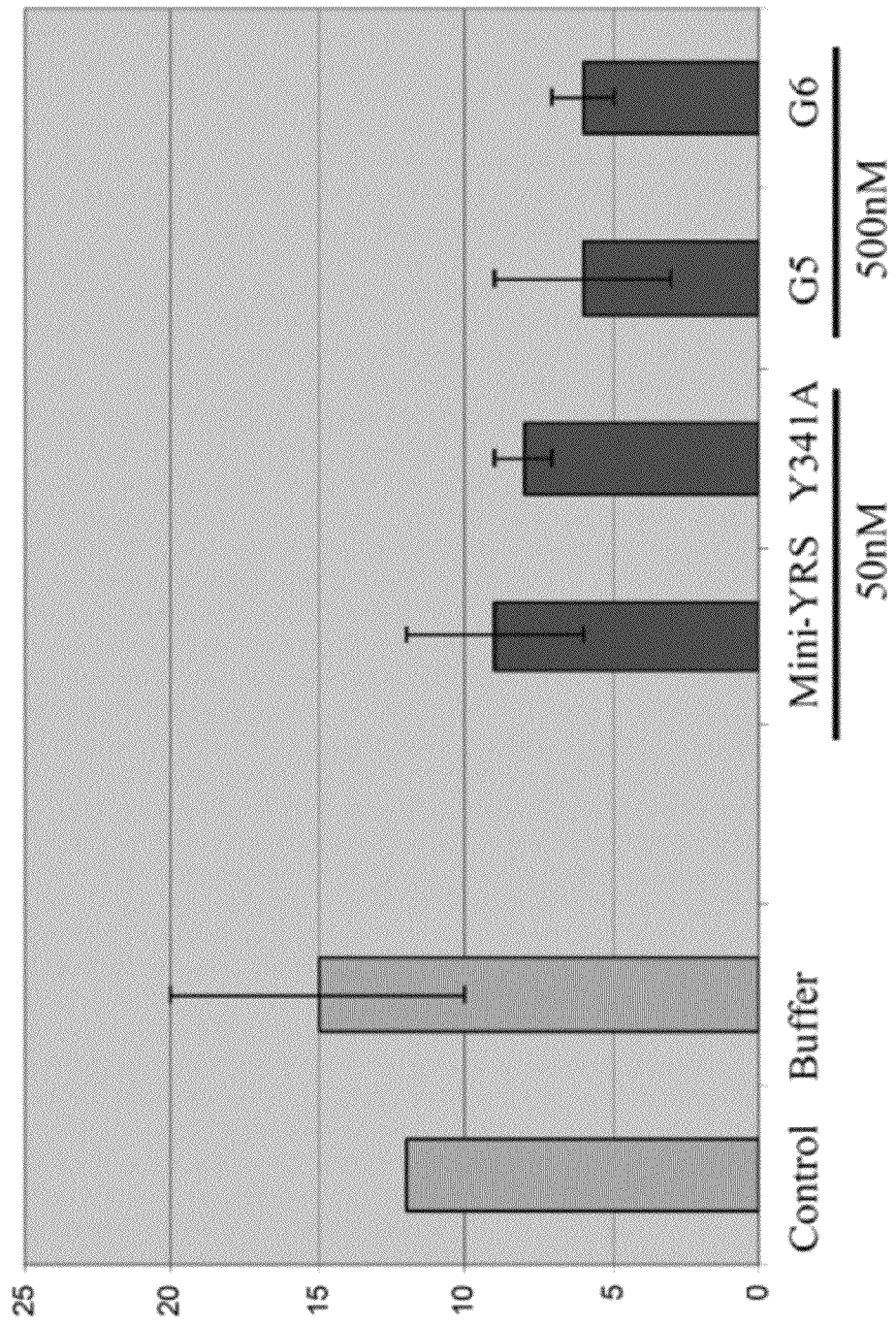
FIG. 8 shows the impact of a variety of AARS polypeptides on the formation of erythroid progenitor cells (CFU-E). See Example 12.
Figure 9:
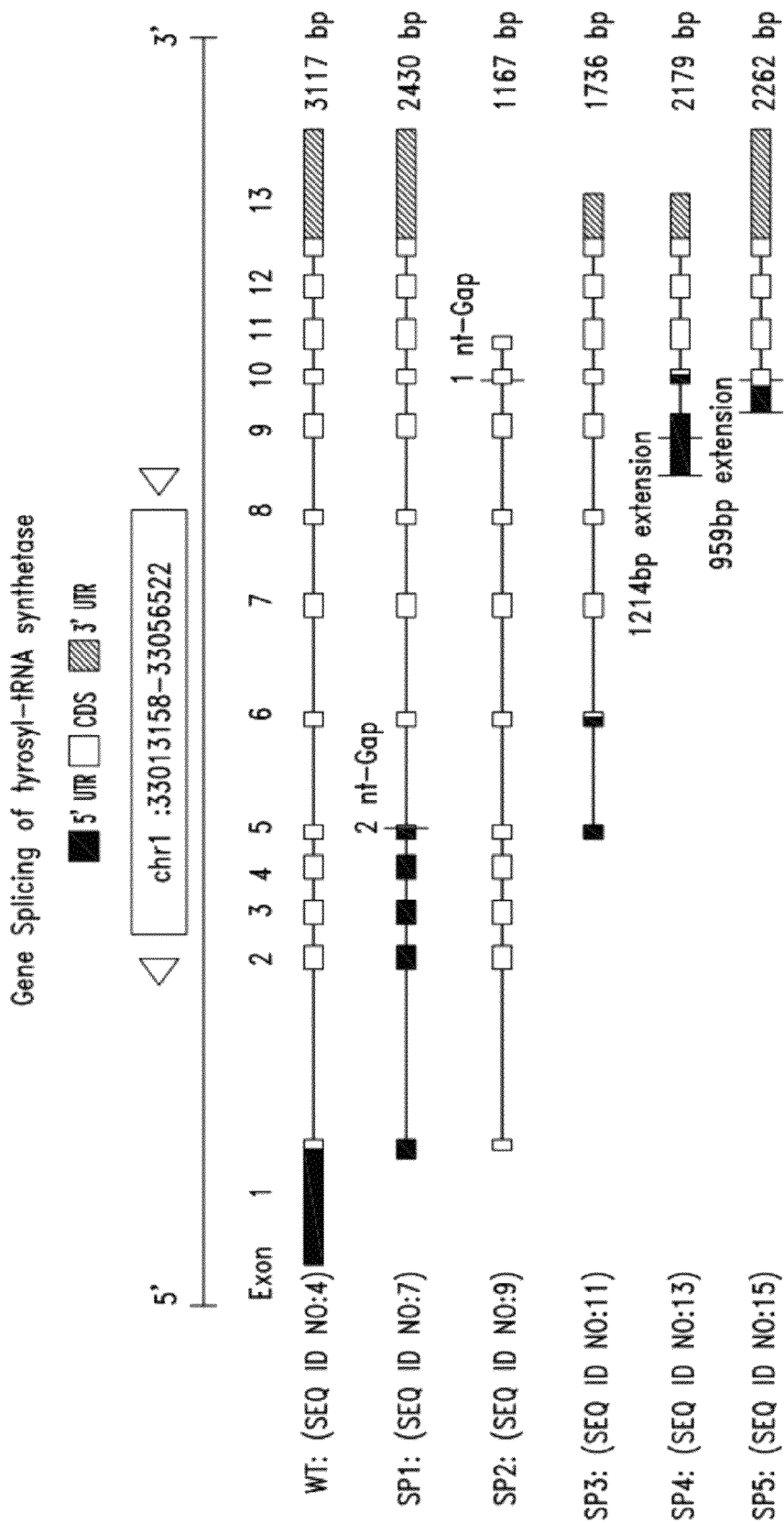
FIG. 9 illustrates the alternate gene splicing of wild-type (WT) human tyrosyl-tRNA synthetase, as represented by the cDNA sequence of alternate splice variants SP1 to SP5.
Figure 11:
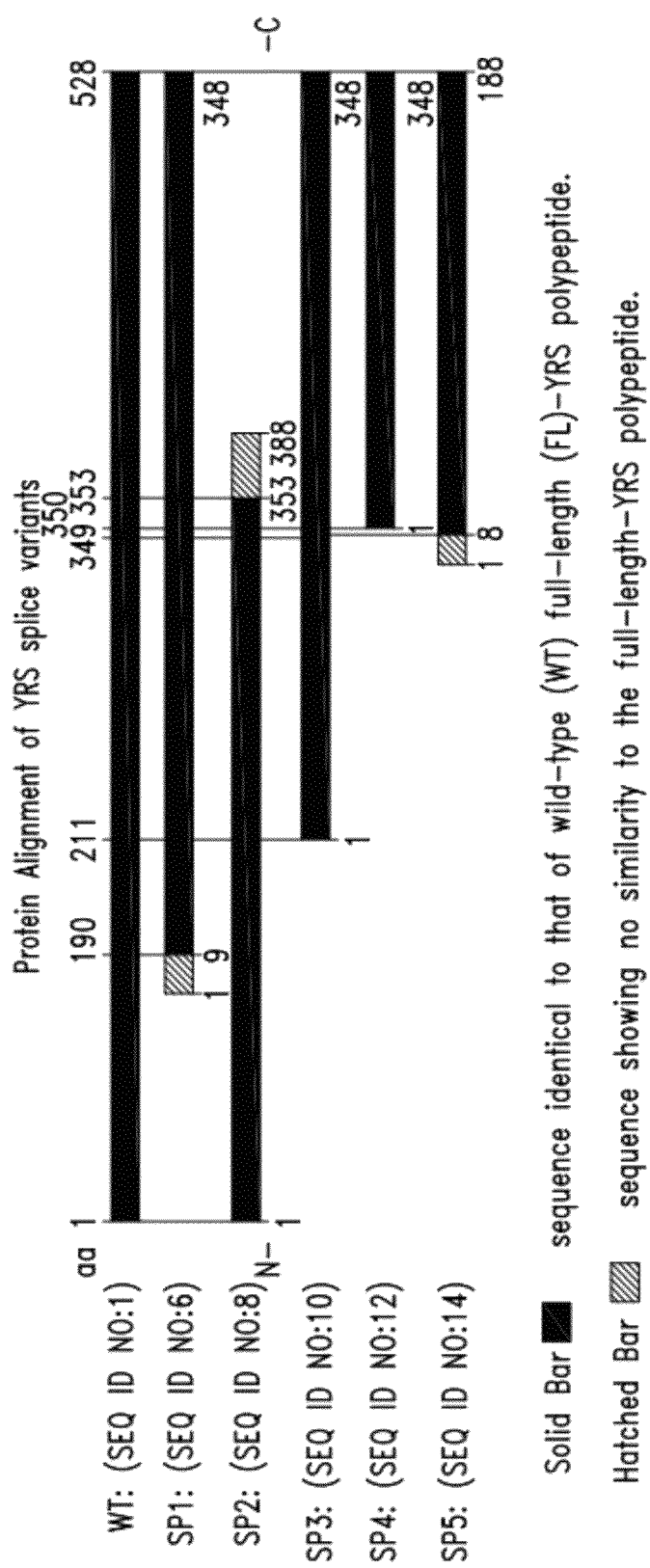
FIG. 11 depicts the protein sequence alignment of the predicted and reported open reading frames for the SP1 to SP5 YRS polypeptides as compared to the full-length human YRS polypeptide.
Figure 12A:
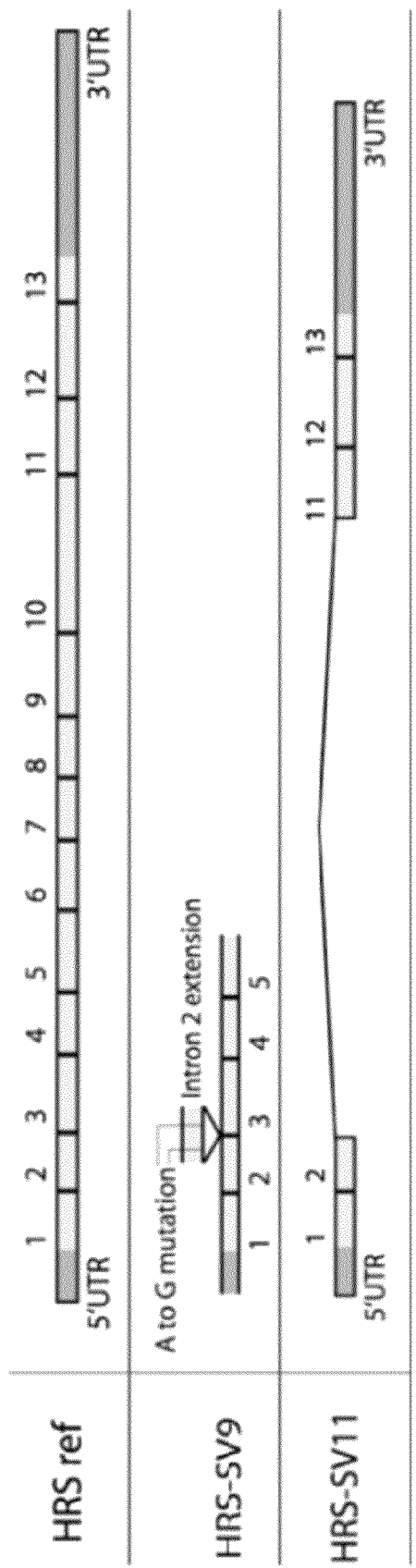
FIG. 12A shows an illustration of mRNA transcripts showing that HRS-SV9 has an insertion from Intron 2 and HRS-SV11 has a deletion from Exon 3 to Exon 10.
Figure 12B:
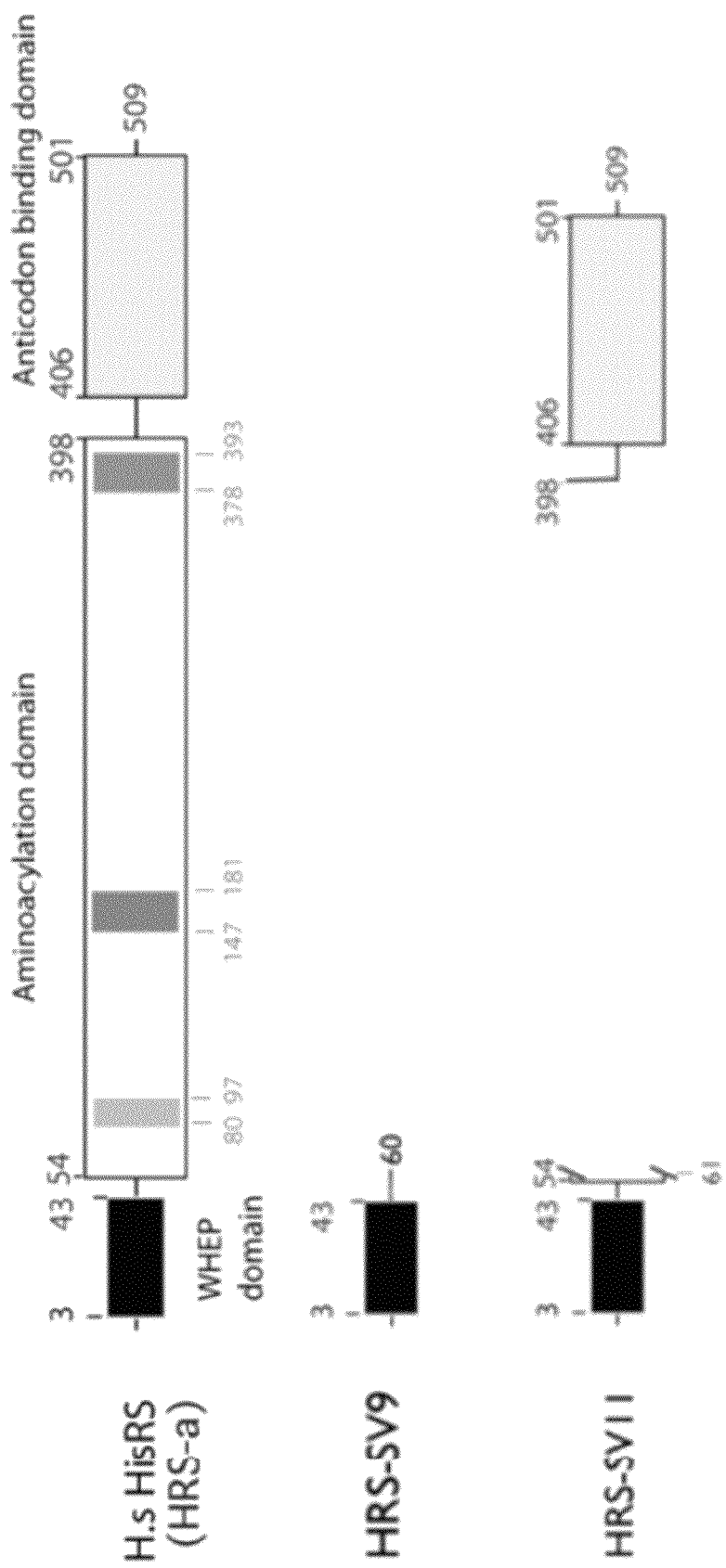
FIG. 12B shows protein structural information encoded by the mRNA transcripts, showing that HRS-SV9 has only the first 60 amino acids of HisRS, including the intact WHEP domain, whereas HRS-SV11 has a deletion of the whole aminoacylation domain, leaving only the WHEP and anticodon domains.

FIG. 8 shows the impact of a variety of AARS polypeptides on erythropoiesis, as illustrated by the reduced formation of erythroid progenitor cells. G5 and G6 are active fragments of human GlyRS (amino acids 439-685 and amino acids amino acids 214-438, respectively). The y-axis represents the number of colonies (CFU-E).

Example 13

Tyrosyl-tRNA Synthetase Polypeptides Increase Platelet Counts by Mechanisms Distinct from Those of Thrombopoietin Thpo$^{-/-}$ and/or Mpl$^{-/-}$ mice are injected intravenously with recombinant tyrosyl-tRNA synthetase polypeptides, daily, for 7 days. Included are tyrosyl-tRNA synthetase polypeptides having a Y341A mutation, and mini-YRS. Blood is collected by retro-orbital bleeding using capillary pipettes and platelet levels are determined using a blood analyzer or a hematocytometer. Thpo$^{-/-}$ and/or Mpl$^{-/-}$ mice have typically 85% fewer platelets than normal mice.

In this Example, platelets counts are increased and/or restored to normal or near normal levels after administration of tyrosyl-tRNA synthetase polypeptides demonstrating that these polypeptides exert their thromobopoietic effects by thrombopoietin-independent and/or thrombopoietin receptor-independent mechanisms.

Example 14

Tyrosyl-tRNA Synthetase Polypeptides Impact Cells Present in the Bone Marrow

Thpo$^{-/-}$ and/or Mpl$^{-/-}$ and/or normal mice are injected intravenously with recombinant tyrosyl-tRNA synthetase polypeptides (e.g., Y341A, mini-YRS), daily, for 7 days. Blood is collected by retro-orbital bleeding using capillary pipettes and platelet levels are determined using a blood analyzer or a hematocytometer. Bone marrow samples are prepared to determine the effects of the tyrosyl-tRNA synthetase polypeptides.

In this Example, administration of the tyrosyl-tRNA synthetase polypeptides results: i) in a change in the number and/or activity of neutrophils and, in turn, this results in a change in the distribution of stem cells in the bone marrow (e.g., an increase in the number of neutrophils and/or activation of the neutrophils resulting in the redistribution or mobilization of stem cells to a more permissive environment where they can proliferate and differentiate); ii) in a change in the number and/or activity of hematopoietic progenitor/precursor cells that, ultimately, results in an increase in platelet counts; iii) in a change in the development, cell cycle, proliferation, distribution, mobilization, differentiation, migration, attachment, cell-cell interactions, maturation, endomitosis, and/or polyploidy of megakaryocytes precursors and/or megakaryocytes; iv) in a change (e.g., stimulation) in the transition from pro-platelet to platelets and in their release in the bone marrow blood vessels; and/or v) in a change in platelet progeny. In this Example, some or all of the effects of the tyrosyl-tRNA synthetase polypeptides are discovered using in vitro assays.

Example 15

Tyrosyl-tRNA Synthetase Polypeptides Impact Bone Marrow Environment and/or Vasculature Normal mice are treated with intravenous injection of 5-fluorouracil, sublethal irradiation or lethal irradiation (either alone or followed by bone marrow transplant) to study hematopoietic maintenance and recovery/regeneration after myelosuppression. Recombinant tyrosyl-tRNA synthetase polypeptides are administered to mice either prophylactically or after myelosuppression and their impact on the maintenance, homeostasis and/or regeneration of the bone marrow environment, osteoblastic niche, stem cell niche, and vasculature is determined using histology staining, immunohistochemistry, fluorescent microscopy, enzyme and reporter gene activity, imaging, flow cytometry and cell enumeration techniques. In this Example, the tyrosyl-tRNA synthetase polypeptides demonstrate an impact on bone marrow structures and/or cells leading to an increase in platelet counts (e.g., stimulation of blood vessel regeneration after myelosuppression, other changes in the marrow microenvironment [osteoblastic, stem cell, vasculature niches] promoting interactions between the vasculature, or other niches, and hematopoietic stem and progenitor cells, resulting in the stimulation of hematopoiesis and/or contributing to homeostasis).

Example 16

Tyrosyl-tRNA Synthetase Polypeptides Improve Chemotherapy- and/or Radiation-Induced Thrombocytopenia Normal mice are treated with intravenous injection of 5-fluorouracil, sublethal irradiation or lethal irradiation (either alone or followed by bone marrow transplant) to recapitulate thrombocytopenia observed in patients receiving chemotherapy and radiation treatment. Recombinant tyrosyl-tRNA synthetase polypeptides are administered to mice either prophylactically or after myelosuppression and their impact on thrombocytopenia is determined using the techniques of Example 13-15. In this Example, administration of tyrosyl-tRNA synthetase polypeptides results in an increase in platelet counts and demonstrates their therapeutic potential in the treatment of thrombocytopenia in cancer patients. The methods and reagents described in Example 15 are used to discover and define the biological effect of the tyrosyl-tRNA synthetase polypeptides and their mechanism of action in platelet count recovery, as well as the protective effects enabling enhanced/optimized chemotherapy/radiation regimens in the management of cancer patients.

In this Example, chemotherapy and/or radiation treatment results in bone marrow damages that mimic or recapitulate (aspects of) human diseases characterized by marrow failures (e.g., myelodysplatic syndromes, cytopenia, etc.). The tyrosyl-tRNA synthetase polypeptides or tryptophanyl-tRNA synthetase polypeptides are administered to the animals and any beneficial effect on the bone marrow environment and/or on the production of blood cells that has potential therapeutic benefit in the treatment of (aspects of) bone marrow failures is examined/determined using methods and techniques similar to those described in Example 15.

Example 17

Combination Treatment/Therapy with Tyrosyl-tRNA Synthetase Polypeptides

Methods and techniques described in Examples 13-16 are used to determine whether synergism, additivity or enhanced therapeutic benefits can be derived from combining tyrosyl-tRNA synthetase polypeptides with other molecules involved in hematopoiesis, including, but not limited to, thrombopoietin, thrombopoietin receptor agonists and mimetics, molecules binding to the Mpl receptor, IL-11 and other interleukins, SDF-1, FGF-4 and other members of the FGF family, VEGF and other angiogenic molecules, ligands binding to CXCR-1, CXCR-2, CXCR-4 and other chemokine receptors involved in hematopoiesis, and/or adhesion molecules.

Example 18

Other tRNA Synthetase Polypeptides

Methods and techniques described in Examples 13-17 are used to identify other tRNA synthetase polypetides and molecules with similar effects, as well as other tRNA synthetase polypeptides and molecules that oppose or modulate the effects of the tyrosyl-tRNA synthetase polypeptides. For instance, tryptophanyl-tRNA synthetase polypetides or glycyl-tRNA synthetase polypetides are used in the above Examples to characterize their angiostatic properties and their potential effects in reducing, inhibiting or modulating hematopoiesis. In certain instances, tyrosyl-tRNA synthetase polypeptides are shown to have the opposite effects described above for tyrosyl-tRNA synthetase polypeptides.

Example 19

Tyrosyl-tRNA Synthetase Polypeptides Impact Platelet Progeny

Platelets are isolated from human blood by mixing 45 ml of fresh blood with 5 ml 2% EDTA followed by centrifugation at 200 g for 10 minutes at room temperature. The platelet-rich phase is transferred to a new tube and centrifuged at 1500 g for 5 minutes. The pellet is washed twice with 30 ml of reagent I and II in a 49:1 ratio (Reagent I: NaCl 8.1 g, KCl 0.4 g, Tris 1.83 g in 1000 ml water, pH 7.4; Reagent II: 2% EDTA in 0.7% NaCl, pH 7.4). Washed platelets are resuspended at a density of 100,000/µl in serum-free M199 medium and cultured at 37° C. under gentle rotation. Platelets are counted using a blood analyzer or a hematocytometer before and after treatment with tyrosyl-tRNA synthetase polypeptides.

In this Example, the addition of tyrosyl-tRNA synthetase polypeptides directly to the culture medium results in an increase in the number of functional platelets generated by the production of new cell bodies indistinguishable from the parent platelets. Standard molecular biology methods are used to determine whether the tyrosyl-tRNA synthetase polypeptides can also confer protection from cell death and extend the life of platelets.

Example 20

Generation of Antibodies to AARS Polypeptides

To generate monoclonal antibodies with selectivity for an AARS polypeptide fragment compared to the full-length AARS, phage displayed recombinant bivalent Fab mini antibodies (AbD Serotech, USA) were screened against full-length tyrosyl-tRNA synthetase comprising the Y341A mutation (SEQ ID NO:2), and then profiled against the full-length wild-type tyrosyl-tRNA synthetase (SEQ ID NO:1), and against the YRS AARS polypeptide fragment YRS 1-364 (mini-YRS) (SEQ ID NO:3).

Antigen production: Codon-optimized (GeneArt, Regensburg, Germany) DNA encoding C-terminally his tagged Y341A (SEQ ID NO:2), and full-length C-terminally His tagged versions of YRS and mini-YRS (without codon optimization) were cloned in bacterial expression vectors (pET24 derivatives) and produced in a Bioreactor using a fed-batch fermentation process. Expressed proteins were purified from bacterial cell pellets using nickel chelate chromatography as described below:

Affinity Purification: The *E. coli* pellet was resuspended in binding buffer (20 mM sodium phosphate, 500 mM sodium chloride and 10 mM imidazole, pH 7.5). An EDTA-free protease inhibitor is added to prevent degradation (Roche cat. no. 1 836 170). The sample was passed through a microfluidizer (Microfluidics, M-110L) at 14,000 psi to disrupt cells. The lysate was centrifuged at 10,000 g for 30 minutes to remove insoluble cell debris. The supernatant was passed through a Sartobran 300 filter (Sartorius, cat. no. 5231307H). A chromatographic column, "Econo column" (B10-rad, cat. no. 737-4250) was loaded with Ni-NTA Superflow slurry (Qiagen, cat. no. 30450) and then equilibrated by adding 100 ml binding buffer. The clarified cell lysate was then loaded onto the column using a peristaltic pump, "Masterflex® L/S® Digital Drive" (Cole-Parmer cat. no. 07523). The resin was first washed with binding buffer plus 0.1% Triton X-100 and then washed with binding buffer without Triton. The bound 6×His-tagged protein was eluted with elution buffer (20 mM sodium phosphate, 500 mM sodium chloride and 500 mM imidazole, pH 7.5) and stored at 4° C.

Desalting and Polishing Steps: The eluate from Ni-NTA was dialyzed against 1×PBS at pH 7.4 overnight using Slide-A-Lyzer Dialysis Cassettes (Pierce, cat. no. 66810). To remove endotoins, an anion exchanger column, HiTrap Q HP 5 ml (GE, 17-1154-01) was flushed with 50 ml 1×PBS and the dialyzed sample is slowly passed through the membrane using a syringe. The flow-through fraction containing the polished protein was collected and store at −80° C.

Antibody Screening: Phage Libraries (HUCAL®, Morphosys) were selected against recombinant Y341A with three rounds of enrichment, following standard screening protocols (see, e.g., U.S. Pat. Nos. 6,300,064; 6,696,248; 6,706,484; and 7,264,963). Antibodies displaying greater than a 5-fold ELISA signal for the Y341A antigen over background were selected for further evaluation.

Figure 13:
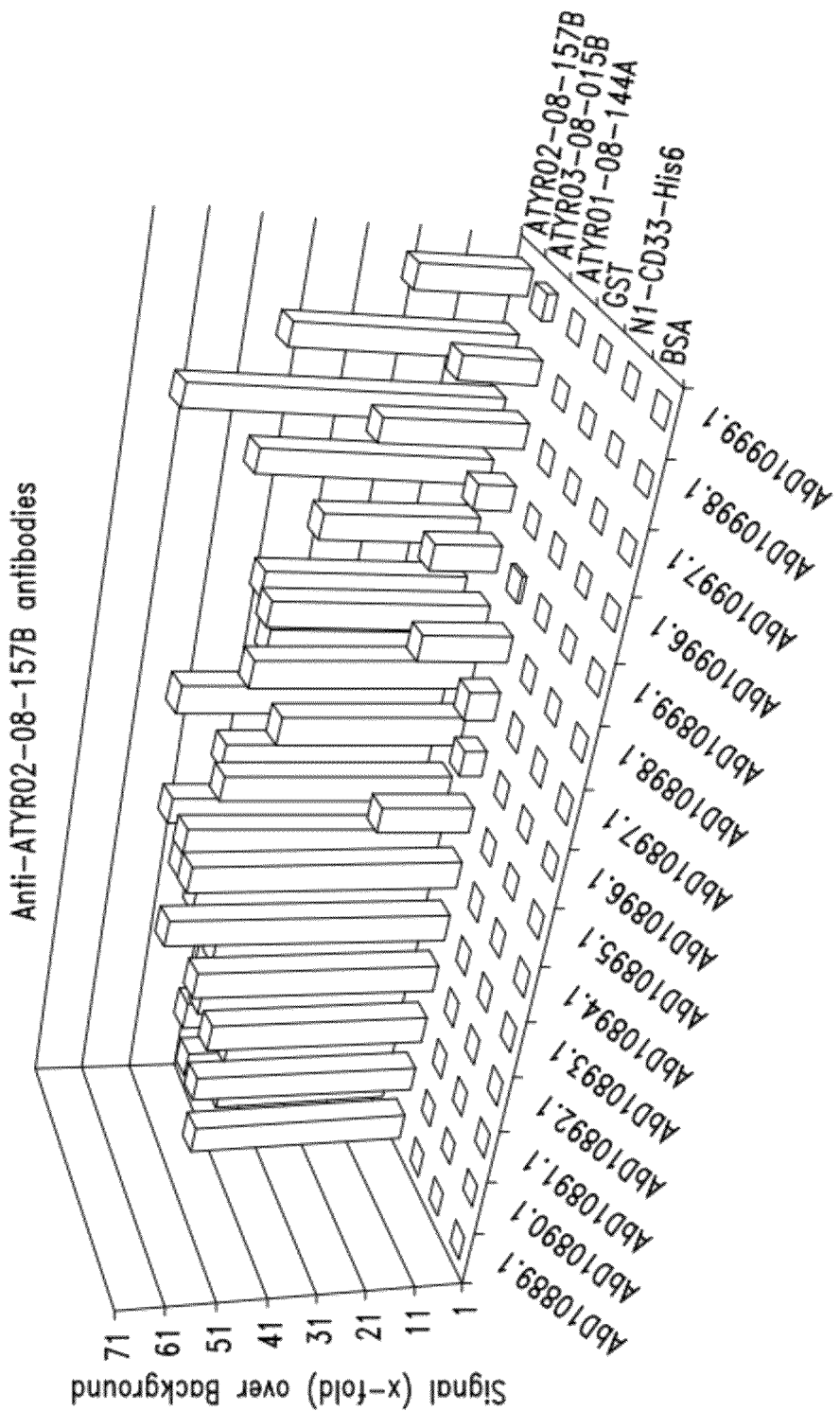
FIG. 13 shows the results of ELISA screening of candidate monoclonal antibodies (Fab mini bodies) for binding against full-length YRS (SEQ ID NO:1)(aTyr03 in FIG. 13), full-length YRS Y341A (SEQ ID NO:2)(aTyr02 in FIG. 13), and mini-YRS (1-364) (SEQ ID NO:3)(aTyr01 in FIG. 13).

Selected antibodies were screened in an ELISA format using the full-length Y341A, as well as YRS 1-364 (mini-YRS) and the full-length wild-type YRS proteins in parallel. Up to 20 positive antibodies were selected for sequencing to find unique clones. 15 unique clones were expressed and purified. The reactivity profile of these antibodies toward the 3 antigens is shown in FIG. 13. The data in FIG. 13 shows that antibodies were obtained that exhibited selectivity for full-length YRS (aTyr03 in FIG. 13) alone, full-length Y341A (aTyr02 in FIG. 13) alone, and mini-YRS (aTyr01 in FIG. 13). Moreover, various antibodies were obtained that exhibited a range of relative affinities for each of these protein isoforms.

Generation of polyclonal antibodies: To generate polyclonal antibodies with selectivity for an AARS polypeptide fragment compared to the full-length AARS, rabbits were immunized with either full-length tyrosyl-tRNA synthetase comprising the Y341A mutation (SEQ ID NO:2), or with the YRS AARS polypeptide fragment YRS 1-364 (mini-YRS) (SEQ ID NO:3) in complete Freunds adjuvant. Immunizations and test bleeds were conducted by Lampire Biological Laboratories (PA), using recombinant proteins prepared essentially as described above, and screened via ELISA assays.

To assess the relative binding of each polyclonal antibody to full-length YRS and the AARS protein fragment (mini-YRS), samples of each polyclonal antibody were incubated with equal amounts of both proteins at a range of different concentrations. In these experiments, proteins were captured using the pan selective monoclonal antibody 10894.1 (Morphosys), and rabbit antibody binding was detected using a goat anti-rabbit HRP conjugated antibody (Jackson Immunoresearch Cat No. 111-035-045).

Figure 14A:
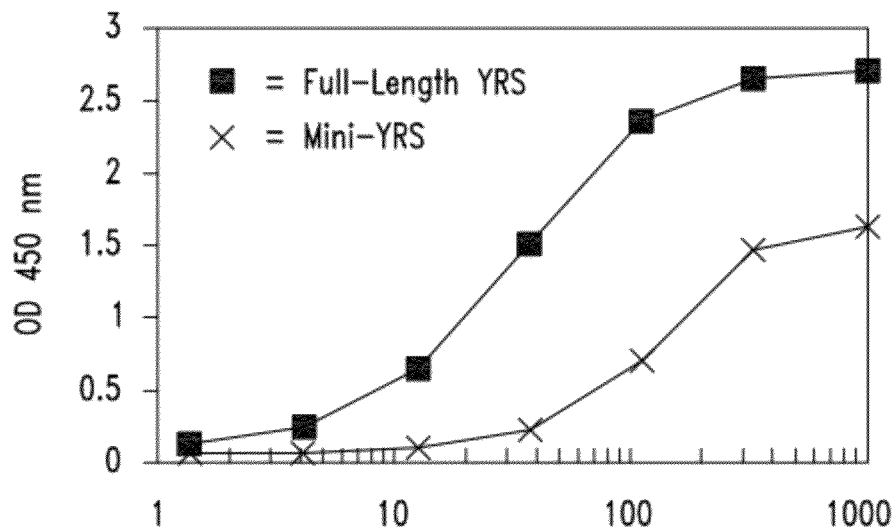
FIGS. 14A-B show the relative binding to full-length YRS and mini-YRS (1-364) for two different samples of rabbit polyclonal antibodies raised against either full-length YRS (FIG. 14A) or mini-YRS (FIG. 14B).
Figure 14B:
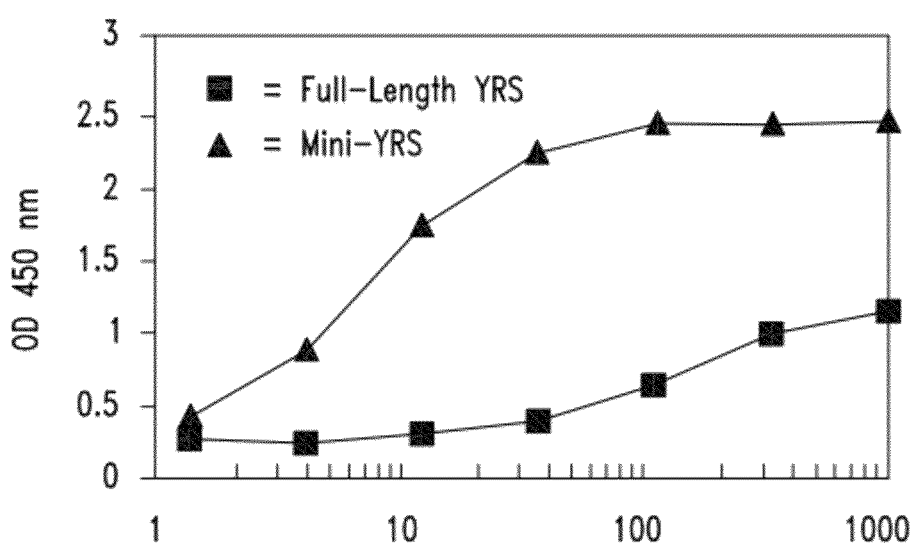

FIGS. 14A-B show the relative binding to full-length YRS (SEQ ID NO:1) and mini-YRS (SEQ ID NO:3) for two samples of rabbit polyclonal antibodies raised against full-length YRS (SEQ ID NO:1) (FIG. 14A) and mini-YRS (SEQ ID NO:3) (FIG. 14B). FIG. 14A shows the relative binding of the full-length selective polyclonal antibody sera to full-length YRS (squares) and mini-YRS (crosses). FIG. 14 B shows the relative binding of the mini-YRS selective polyclonal antibody sera to full-length YRS (squares) and mini-YRS (triangles). The results show that antibodies 4 to 10 times more selective for either the full length YRS or mini YRS may be readily generated by standard immunization procedures, using either the mini-YRS, full-length YRS, or the conformationally active mutant full-length YRS, Y341A.

The invention claimed is:

1. An isolated antibody that exhibits binding specificity for an isolated tyrosyl-tRNA synthetase (YRS) polypeptide of SEQ ID NO:1, 2 or 3, wherein affinity of the antibody for the YRS polypeptide of SEQ ID NO:2 or 3 is at least about 1.5× stronger than its affinity for the YRS polypeptide of SEQ ID NO:1.

2. The antibody of claim 1, wherein affinity of the antibody for the YRS polypeptide of SEQ ID NO:2 or 3 is at least about 10× stronger than its affinity for the YRS polypeptide of SEQ ID NO:1.

3. The antibody of claim 1, wherein the antibody is a monoclonal antibody.

4. The antibody of claim 1, wherein the antibody is a polyclonal antibody.

5. The antibody of claim 4, wherein the antibody is a rabbit antibody.

* * * * *

```
                        SEQUENCE LISTING

<160> NUMBER OF SEQ ID NOS: 108

<210> SEQ ID NO 1
<211> LENGTH: 528
<212> TYPE: PRT
<213> ORGANISM: Homo sapiens

<400> SEQUENCE: 1

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255
```

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
        435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
            500                 505                 510

Lys Leu Gly Ser Ile Ser Cys Lys Ser Leu Lys Gly Gly Asn Ile Ser
        515                 520                 525

<210> SEQ ID NO 2
<211> LENGTH: 528
<212> TYPE: PRT
<213> ORGANISM: Homo sapiens

<400> SEQUENCE: 2

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

```
Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
    130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Tyr
            165                 170                 175

Leu Lys Val Asp Ala Gln Phe Gly Gly Ile Asp Gln Arg Lys Ile Phe
    180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
    275                 280                 285

Tyr Thr Ala Tyr Val Asp Leu Glu Lys Asp Phe Ala Ala Glu Val Val
290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
            325                 330                 335

Ala Ser Ala Ala Ala Pro Asp Pro Ser Lys Gln Lys Pro Met Ala Lys
                340                 345                 350

Gly Pro Ala Lys Asn Ser Glu Pro Glu Glu Val Ile Pro Ser Arg Leu
        355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
        435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
            485                 490                 495

Ile Ser Glu Glu Cys Ile Ala Gln Trp Lys Gln Thr Asn Phe Met Thr
        500                 505                 510

Lys Leu Gly Ser Ile Ser Cys Lys Ser Leu Lys Gly Gly Asn Ile Ser
    515                 520                 525
```

<210> SEQ ID NO 3
<211> LENGTH: 364
<212> TYPE: PRT
<213> ORGANISM: Homo sapiens

<400> SEQUENCE: 3

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile
        355                 360

<210> SEQ ID NO 4

<211> LENGTH: 1683
<212> TYPE: DNA
<213> ORGANISM: Homo sapiens

<400> SEQUENCE: 4

```
atggggacg ctcccagccc tgaagagaaa ctgcacctta tcacccggaa cctgcaggag      60
gttctggggg aagagaagct gaaggagata ctgaaggagc gggaacttaa aatttactgg    120
ggaacggcaa ccacgggcaa accacatgtg gcttactttg tgcccatgtc aaagattgca    180
gacttcttaa aggcagggtg tgaggtaaca attctgtttg cggacctcca cgcatacctg    240
gataacatga agccccatg ggaacttcta gaactccgag tcagttacta tgagaatgtg    300
atcaaagcaa tgctggagag cattggtgtg cccttggaga agctcaagtt catcaaaggc    360
actgattacc agctcagcaa agagtacaca ctagatgtgt acagactctc ctccgtggtc    420
acacagcacg attccaagaa ggctggagct gaggtggtaa agcaggtgga gcaccctttg    480
ctgagtggcc tcttataccc cggactgcag gctttggatg aagagtattt aaaagtagat    540
gcccaatttg gaggcattga tcagagaaag attttcacct ttgcagagaa gtacctccct    600
gcacttggct attcaaaacg ggtccatctg atgaatccta tggttccagg attaacaggc    660
agcaaaatga gctcttcaga agaggagtcc aagattgatc tccttgatcg gaaggaggat    720
gtgaagaaaa aactgaagaa ggccttctgt gagccaggaa atgtggagaa caatggggtt    780
ctgtccttca tcaagcatgt cctttttccc cttaagtccg agtttgtgat cctacgagat    840
gagaaatggg gtggaaacaa aacctacaca gcttacgtgg acctggaaaa ggactttgct    900
gctgaggtta tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg gccaaaggcc ctgccaagaa ttcagaacca   1080
gaggaggtca tcccatcccg gctggatatc cgtgtgggga aatcatcac tgtggagaag   1140
cacccagatg cagacagcct gtatgtagag aagattgacg tggggaagc tgaaccacgg   1200
actgtggtga gcggcctggt acagttcgtg cccaaggagg aactgcagga caggctggta   1260
gtggtgctgt gcaacctgaa accccagaag atgagaggag tcgagtccca aggcatgctt   1320
ctgtgtgctt ctatagaagg gataaaccgc caggttgaac ctctggaccc tccggcaggc   1380
tctgctcctg gtgagcacgt gtttgtgaag ggctatgaaa agggccaacc agatgaggag   1440
ctcaagccca agaagaaagt cttcgagaag ttgcaggctg acttcaaaat ttctgaggag   1500
tgcatcgcac agtggaagca aaccaacttc atgaccaagc tgggctccat ttcctgtaaa   1560
tcgctgaaag gggggaacat tagctagcca gcccagcatc ttcccccctt cttccaccac   1620
tgagtcatct gctgtctctt cagtctgctc catccatcac ccatttaccc atctctcagg   1680
aca                                                                  1683
```

<210> SEQ ID NO 5
<211> LENGTH: 8
<212> TYPE: PRT
<213> ORGANISM: Artificial Sequence
<220> FEATURE:
<223> OTHER INFORMATION: C-terminal tag

<400> SEQUENCE: 5

Leu Glu His His His His His His
 1               5

<210> SEQ ID NO 6

```
<211> LENGTH: 348
<212> TYPE: PRT
<213> ORGANISM: Homo sapiens
<220> FEATURE:
<221> NAME/KEY: VARIANT
<222> LOCATION: 1, 2, 3, 4, 5, 6, 7, 8, 9
<223> OTHER INFORMATION: Xaa = Any Amino Acid

<400> SEQUENCE: 6
```

| | | | | | | | | | | | | | | |
|---|---|---|---|---|---|---|---|---|---|---|---|---|---|---|
| Xaa | Xaa | Xaa | Xaa | Xaa | Xaa | Xaa | Xaa | Lys | Ile | Phe | Thr | Phe | Ala | Glu |
| 1 | | | | 5 | | | | | 10 | | | | | 15 |
| Lys | Tyr | Leu | Pro | Ala | Leu | Gly | Tyr | Ser | Lys | Arg | Val | His | Leu | Met | Asn |
| | | | 20 | | | | | 25 | | | | | 30 | |
| Pro | Met | Val | Pro | Gly | Leu | Thr | Gly | Ser | Lys | Met | Ser | Ser | Glu | Glu |
| | | 35 | | | | | 40 | | | | | 45 | | |
| Glu | Ser | Lys | Ile | Asp | Leu | Leu | Asp | Arg | Lys | Glu | Asp | Val | Lys | Lys |
| | 50 | | | | | 55 | | | | | 60 | | | |
| Leu | Lys | Lys | Ala | Phe | Cys | Glu | Pro | Gly | Asn | Val | Glu | Asn | Asn | Gly | Val |
| 65 | | | | | 70 | | | | | 75 | | | | | 80 |
| Leu | Ser | Phe | Ile | Lys | His | Val | Leu | Phe | Pro | Leu | Lys | Ser | Glu | Phe | Val |
| | | | | 85 | | | | | 90 | | | | | 95 | |
| Ile | Leu | Arg | Asp | Glu | Lys | Trp | Gly | Gly | Asn | Lys | Thr | Tyr | Thr | Ala | Tyr |
| | | | 100 | | | | | 105 | | | | | 110 | | |
| Val | Asp | Leu | Glu | Lys | Asp | Phe | Ala | Ala | Glu | Val | Val | His | Pro | Gly | Asp |
| | | 115 | | | | | 120 | | | | | 125 | | | |
| Leu | Lys | Asn | Ser | Val | Glu | Val | Ala | Leu | Asn | Lys | Leu | Leu | Asp | Pro | Ile |
| | 130 | | | | | 135 | | | | | 140 | | | | |
| Arg | Glu | Lys | Phe | Asn | Thr | Pro | Ala | Leu | Lys | Lys | Leu | Ala | Ser | Ala | Ala |
| 145 | | | | | 150 | | | | | 155 | | | | | 160 |
| Tyr | Pro | Asp | Pro | Ser | Lys | Gln | Lys | Pro | Met | Ala | Lys | Gly | Pro | Ala | Lys |
| | | | | 165 | | | | | 170 | | | | | 175 | |
| Asn | Ser | Glu | Pro | Glu | Glu | Val | Ile | Pro | Ser | Arg | Leu | Asp | Ile | Arg | Val |
| | | | 180 | | | | | 185 | | | | | 190 | | |
| Gly | Lys | Ile | Ile | Thr | Val | Glu | Lys | His | Pro | Asp | Ala | Asp | Ser | Leu | Tyr |
| | | 195 | | | | | 200 | | | | | 205 | | | |
| Val | Glu | Lys | Ile | Asp | Val | Gly | Glu | Ala | Glu | Pro | Arg | Thr | Val | Val | Ser |
| | 210 | | | | | 215 | | | | | 220 | | | | |
| Gly | Leu | Val | Gln | Phe | Val | Pro | Lys | Glu | Glu | Leu | Gln | Asp | Arg | Leu | Val |
| 225 | | | | | 230 | | | | | 235 | | | | | 240 |
| Val | Val | Leu | Cys | Asn | Leu | Lys | Pro | Gln | Lys | Met | Arg | Gly | Val | Glu | Ser |
| | | | | 245 | | | | | 250 | | | | | 255 | |
| Gln | Gly | Met | Leu | Leu | Cys | Ala | Ser | Ile | Glu | Gly | Ile | Asn | Arg | Gln | Val |
| | | | 260 | | | | | 265 | | | | | 270 | | |
| Glu | Pro | Leu | Asp | Pro | Pro | Ala | Gly | Ser | Ala | Pro | Gly | Glu | His | Val | Phe |
| | | 275 | | | | | 280 | | | | | 285 | | | |
| Val | Lys | Gly | Tyr | Glu | Lys | Gly | Gln | Pro | Asp | Glu | Glu | Leu | Lys | Pro | Lys |
| | 290 | | | | | 295 | | | | | 300 | | | | |
| Lys | Lys | Val | Phe | Glu | Lys | Leu | Gln | Ala | Asp | Phe | Lys | Ile | Ser | Glu | Glu |
| 305 | | | | | 310 | | | | | 315 | | | | | 320 |
| Cys | Ile | Ala | Gln | Trp | Lys | Gln | Thr | Asn | Phe | Met | Thr | Lys | Leu | Gly | Ser |
| | | | | 325 | | | | | 330 | | | | | 335 | |
| Ile | Ser | Cys | Lys | Ser | Leu | Lys | Gly | Gly | Asn | Ile | Ser |
| | | | 340 | | | | | 345 | | | |

```
<210> SEQ ID NO 7
<211> LENGTH: 2178
```

<212> TYPE: DNA
<213> ORGANISM: Homo sapiens

<400> SEQUENCE: 7

```
ttcagaaagt ggtggaggga agacttcctt tttcccagag acagaaggtt atgcacccag      60
tggcctggga ccattgttct gggcttttt tcccttcgac atggatttgc ttctcactgt     120
gtaccccaac caccaaaacc accctgagat caatgctggt gctcctgcat cagatggctt     180
agagatcctt ccacctctta acacaagcat ctaggtccac tttactcaaa tctggcctca     240
gttgagagca gagtatacca tcagagccca ttctcctgtc tgctgtctgg gacgtggaaa     300
gaaagttagc tctaggggt cttccaggg gcctctgtaa ggactggatg ctcctttccg      360
gaatccaaga gttcaccagg ctgcttctct aatggacgat gatcctcttc ctcctgacgt     420
ctctccctgg cagcacccag atgcagacag cctgtatgta gaagaattg acgtggggga     480
agctgaacca cggactgtgg tgagcggcct ggtacagttc gtgcccaagg aggaactgca     540
ggacaggctg gtagtggtgc tgtgcaacct gaaaccccag aagatgagag gagtcgagtc     600
ccaaggcatg cttctgtgtg cttctatgtg agtgaggact tggagtgggg cacaggacct     660
ggggaggcca ggaagagtag ggaatcagcc catatgatgt ccttccacac accaggtgga     720
agctctgaga acacgtgcct cttccttgct gatgccaaaa gttgatgcat gaaggactta     780
tcgtacaagt actgttaatg aagcattta cctacagtta atttgttaa aatagaaatg      840
gagggctcaa accagtacat acccaagtct tactactagt aaggagtgga gcagggattc     900
aaatcccagt tttgatgtct ataaagtcct cgctacgtta tttatactt cctcccctag      960
aaacacagat tttggtatct tgacacacaa ttttggtata gcctgggtta atgtaaccct    1020
ggtgatatgc agggatgtag caagataaga ggacctcctg gggctctggt actgaggatg    1080
ccctaaatcc catcagggcc cctgtgtaaa ggcccggatt gctttggcct ccacagtcac    1140
tggaacccat ccatagcctc actcttctct tgtcctgtgt cttcccagag aagggataaa    1200
ccgccaggtt gaacctctgg accctccggc aggctctgct cctggtgagc acgtgtttgt    1260
gaagggctat gaaaagggcc aaccagatga ggagctcaag cccaagagga aagtcttcga    1320
gaagttgcag gctgacttca aaatttctga ggagtgcatc gcacagtgga agcaaaccaa    1380
cttcatgacc aagctgggct ccatttcctg taaatcgctg aaagggggga acattagcta    1440
gccagcccag catcttcccc ccttcttcca ccactgagtc atctgctgtc tcttcagtct    1500
gctccaccca tcacccattt acccatctct caggacacgg aagcagcggg tttggactct    1560
ttattcggtg cagaactcgg caaggggcag cttaccctcc ccagaaccca ggatcatcct    1620
gtctggctgc agtgagagac caacccctaa caagggctgg gccacagcag ggagtccagc    1680
cctaccttct tcccttggca gctggagaaa tctggttttca atataactca tttaaaaatt    1740
tatgccacag tccttataat tggaaaaata ctggtgccca ggttttcttg gagttatcca    1800
agcagctgcg cccctagctg ggatctggta cctggactag gctaattaca gcttctcccc    1860
aacaggaaac tgtgggattt gaaaaggaaa gggaagggaa aacagagaac ctagtggtct    1920
accaagtggt tggcaacttt cccaatgtct gcttactctg aggcttggca ctggggggcca    1980
gggcctgccc cagggctcct ggaatttccc ttgatccagc taggctggga cactccctaa    2040
atcagctgcg tgttgttagc atcaggcaga atgaatggca gagagtgatt ctgtcttcat    2100
agagggtggg gtacttctcc ataaggcatc tcagtcaaat ccccatcact gtcataaatt    2160
caaataaaat gtctgaac                                                  2178
```

<210> SEQ ID NO 8
<211> LENGTH: 388
<212> TYPE: PRT
<213> ORGANISM: Homo sapiens
<220> FEATURE:
<221> NAME/KEY: VARIANT
<222> LOCATION: 354, 355, 356, 357, 358, 359, 360, 361, 362, 363, 364,
365, 366, 367, 368, 369, 370, 371, 372, 373, 374, 375, 376, 377,
378, 379, 380, 381, 382, 383, 384, 385, 386, 387, 388
<223> OTHER INFORMATION: Xaa = Any Amino Acid

<400> SEQUENCE: 8

```
Met Gly Asp Ala Pro Ser Pro Glu Glu Lys Leu His Leu Ile Thr Arg
 1               5                  10                  15

Asn Leu Gln Glu Val Leu Gly Glu Glu Lys Leu Lys Glu Ile Leu Lys
             20                  25                  30

Glu Arg Glu Leu Lys Ile Tyr Trp Gly Thr Ala Thr Thr Gly Lys Pro
         35                  40                  45

His Val Ala Tyr Phe Val Pro Met Ser Lys Ile Ala Asp Phe Leu Lys
     50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350
```

Gly Xaa Xaa Xaa Xaa Xaa Xaa Xaa Xaa Xaa Xaa Xaa Xaa
         355                 360                 365

Xaa Xaa Xaa Xaa Xaa Xaa Xaa Xaa Xaa Xaa Xaa Xaa
         370                 375                 380

Xaa Xaa Xaa Xaa
385

<210> SEQ ID NO 9
<211> LENGTH: 1167
<212> TYPE: DNA
<213> ORGANISM: Homo sapiens

<400> SEQUENCE: 9

| | | | | | |
|---|---|---|---|---|---|
| atgggggacg | ctcccagccc | tgaagagaaa | ctgcaccttta | tcacccggaa | cctgcaggag | 60 |
| gttctggggg | aagagaagct | gaaggagata | ctgaaggagc | gggaacttaa | aatttactgg | 120 |
| ggaacggcaa | ccacgggcaa | accacatgtg | gcttactttg | tgcccatgtc | aaagattgca | 180 |
| gacttcttaa | aggcagggtg | tgaggtaaca | attctgtttg | cggacctcca | cgcatacctg | 240 |
| gataacatga | agccccatg | ggaacttcta | gaactccgag | tcagttacta | tgagaatgtg | 300 |
| atcaaagcaa | tgctggagag | cattggtgtg | cccttggaga | agctcaagtt | catcaaaggc | 360 |
| actgattacc | agctcagcaa | agagtacaca | ctagatgtgt | acagactctc | ctccgtggtc | 420 |
| acacagcacg | attccaagaa | ggctggagct | gaggtggtaa | agcaggtgga | gcaccctttg | 480 |
| ctgagtggcc | tcttataccc | cggactgcag | gctttggatg | aagagtattt | aaaagtagat | 540 |
| gcccaatttg | gaggcattga | tcagagaaag | attttcacct | ttgcagagaa | gtacctccct | 600 |
| gcacttggct | attcaaaacg | ggtccatctg | atgaatccta | tggttccagg | attaacaggc | 660 |
| agcaaaatga | gctcttcaga | agaggagtcc | aagattgatc | tccttgatcg | gaaggaggat | 720 |
| gtgaagaaaa | aactgaagaa | ggccttctgt | gagccaggaa | atgtggagaa | caatggggtt | 780 |
| ctgtccttca | tcaagcatgt | cctttttccc | cttaagtccg | agtttgtgat | cctacgagat | 840 |
| gagaaatggg | gtggaaacaa | aacctacaca | gcttacgtgg | acctggaaaa | ggactttgct | 900 |
| gctgaggttg | tacatcctgg | agacctgaag | aattctgttg | aagtcgcact | gaacaagttg | 960 |
| ctggatccaa | tccgggaaaa | gtttaatacc | cctgccctga | aaaaactggc | cagcgctgcc | 1020 |
| tacccagatc | cctcaaagca | gaagccaatg | gccaaaggcc | tgccaagaat | tcagaaccag | 1080 |
| aggaggtcat | cccatcccgg | ctggatatcc | gtgtgggaa | aatcatcact | gtggagaagc | 1140 |
| acccagatgc | agacagcctg | tatgtag | | | | 1167 |

<210> SEQ ID NO 10
<211> LENGTH: 318
<212> TYPE: PRT
<213> ORGANISM: Homo sapiens

<400> SEQUENCE: 10

Met Asn Pro Met Val Pro Gly Leu Thr Gly Ser Lys Met Ser Ser Ser
 1               5                  10                  15

Glu Glu Glu Ser Lys Ile Asp Leu Leu Asp Arg Lys Glu Asp Val Lys
            20                  25                  30

Lys Lys Leu Lys Lys Ala Phe Cys Glu Pro Gly Asn Val Glu Asn Asn
        35                  40                  45

Gly Val Leu Ser Phe Ile Lys His Val Leu Phe Pro Leu Lys Ser Glu
    50                  55                  60

Phe Val Ile Leu Arg Asp Glu Lys Trp Gly Gly Asn Lys Thr Tyr Thr

```
                65                  70                  75                  80
Ala Tyr Val Asp Leu Glu Lys Asp Phe Ala Ala Glu Val Val His Pro
                        85                  90                  95
Gly Asp Leu Lys Asn Ser Val Glu Val Ala Leu Asn Lys Leu Leu Asp
                100                 105                 110
Pro Ile Arg Glu Lys Phe Asn Thr Pro Ala Leu Lys Lys Leu Ala Ser
                115                 120                 125
Ala Ala Tyr Pro Asp Pro Ser Lys Gln Lys Pro Met Ala Lys Gly Pro
            130                 135                 140
Ala Lys Asn Ser Glu Pro Glu Val Ile Pro Ser Arg Leu Asp Ile
145                 150                 155                 160
Arg Val Gly Lys Ile Ile Thr Val Glu Lys His Pro Asp Ala Asp Ser
                    165                 170                 175
Leu Tyr Val Glu Lys Ile Asp Val Gly Glu Ala Glu Pro Arg Thr Val
                180                 185                 190
Val Ser Gly Leu Val Gln Phe Val Pro Lys Glu Glu Leu Gln Asp Arg
            195                 200                 205
Leu Val Val Val Leu Cys Asn Leu Lys Pro Gln Lys Met Arg Gly Val
    210                 215                 220
Glu Ser Gln Gly Met Leu Leu Cys Ala Ser Ile Glu Gly Ile Asn Arg
225                 230                 235                 240
Gln Val Glu Pro Leu Asp Pro Pro Ala Gly Ser Ala Pro Gly Glu His
                245                 250                 255
Val Phe Val Lys Gly Tyr Glu Lys Gly Gln Pro Asp Glu Glu Leu Lys
            260                 265                 270
Pro Lys Lys Lys Val Phe Glu Lys Leu Gln Ala Asp Phe Lys Ile Ser
        275                 280                 285
Glu Glu Cys Ile Ala Gln Trp Lys Gln Thr Asn Phe Met Thr Lys Leu
    290                 295                 300
Gly Ser Ile Ser Cys Lys Ser Leu Lys Gly Gly Asn Ile Ser
305                 310                 315

<210> SEQ ID NO 11
<211> LENGTH: 1736
<212> TYPE: DNA
<213> ORGANISM: Homo sapiens

<400> SEQUENCE: 11
gaaagatttt caccttttgca gagaagtacc tccctgcact tggctattca aaacgggtcc      60
atctgatgaa tcctatggtt ccaggattaa caggcagcaa atgagctct tcagaagagg      120
agtccaagat tgatctcctt gatcggaagg aggatgtgaa gaaaaactg aagaaggcct      180
tctgtgagcc aggaaatgtg gagaacaatg gggttctgtc cttcatcaag catgtccttt      240
ttcccctaa gtccgagttt gtgatcctac gagatgagaa atggggtgga aacaaaacct      300
acacagctta cgtggacctg aaaaggact ttgctgctga ggttgtacat cctggagacc      360
tgaagaattc tgttgaagtc gcactgaaca gttgctgga tccaatccgg gaaaagttta      420
atacccctgc cctgaaaaaa ctggccagcg ctgcctaccc agatccctca agcagaagc      480
caatggccaa aggccctgcc aagaattcag aaccagagga ggtcatccca tcccggctgg      540
atatccgtgt ggggaaaatc atcactgtgg agaagcaccc agatgcagac agcctgtatg      600
tagagaagat tgacgtgggg gaagctgaac cacggactgt ggtgagcggc ctggtacagt      660
tcgtgcccaa ggaggaactg caggacaggc tggtagtggt gctgtgcaac ctgaaacccc      720
```

```
agaagatgag aggagtcgag tcccaaggca tgcttctgtg tgcttctata gaagggataa   780
accgccaggt tgaacctctg gaccctccgg caggctctgc tcctggtgag cacgtgtttg   840
tgaagggcta tgaaaagggc aaccagatg aggagctcaa gcccaagaag aaagtcttcg    900
agaagttgca ggctgacttc aaaatttctg aggagtgcat cgcacagtgg aagcaaacca   960
acttcatgac caagctgggc tccatttcct gtaaatcgct gaaaggggg aacattagct   1020 agccagccca gcatcttccc cccttcttcc accactgagt catctgctgt ctcttcagtc  1080
tgctccatcc atcacccatt tacccatctc tcaggacacg gaagcagcgg gtttggactc  1140
tttattcggt gcagaactcg gcaagggca gcttaccctc cccagaaccc aggatcatcc   1200
tgtctggctg cagtgagaga ccaacccta caagggctg ggccacagca gggagtccag    1260
ccctaccttc ttcccttggc agctggagaa atctggtttc aatataactc atttaaaaat  1320
ttatgccaca gtccttataa ttggaaaaat actggtgccc aggttttctt ggagttatcc   1380
aagcagctgc gcccctagct gggatctggt acctggacta ggctaattac agcttctccc   1440
caacaggaaa ctgtgggatt tgaaaaggaa agggaaggga aaacagagaa cctagtggtc   1500
taccaagtgg ttggcaactt tcccaatgtc tgcttactct gaggcttggc actggggcc   1560 agggcctgcc ccagggctcc tggaatttcc cttgatccag ctaggctggg acactcccta   1620
aatcagctgc gtgttgttag catcaggcag aatgaatggc agagagtgat tctgtcttca   1680
tagagggtgg ggtacttctc cataaggcat ctcagtcaaa tccccatcac tgtcat      1736
```

<210> SEQ ID NO 12
<211> LENGTH: 179
<212> TYPE: PRT
<213> ORGANISM: Homo sapiens

<400> SEQUENCE: 12

```
Met Ala Lys Gly Pro Ala Lys Asn Ser Glu Pro Glu Glu Val Ile Pro
 1               5                  10                  15

Ser Arg Leu Asp Ile Arg Val Gly Lys Ile Ile Thr Val Glu Lys His
             20                  25                  30

Pro Asp Ala Asp Ser Leu Tyr Val Glu Lys Ile Asp Val Gly Glu Ala
         35                  40                  45

Glu Pro Arg Thr Val Val Ser Gly Leu Val Gln Phe Val Pro Lys Glu
     50                  55                  60

Glu Leu Gln Asp Arg Leu Val Val Val Leu Cys Asn Leu Lys Pro Gln
 65                  70                  75                  80

Lys Met Arg Gly Val Glu Ser Gln Gly Met Leu Leu Cys Ala Ser Ile
                 85                  90                  95

Glu Gly Ile Asn Arg Gln Val Glu Pro Leu Asp Pro Pro Ala Gly Ser
            100                 105                 110

Ala Pro Gly Glu His Val Phe Val Lys Gly Tyr Glu Lys Gly Gln Pro
        115                 120                 125

Asp Glu Glu Leu Lys Pro Lys Lys Val Phe Glu Lys Leu Gln Ala
    130                 135                 140

Asp Phe Lys Ile Ser Glu Glu Cys Ile Ala Gln Trp Lys Gln Thr Asn
145                 150                 155                 160

Phe Met Thr Lys Leu Gly Ser Ile Ser Cys Lys Ser Leu Lys Gly Gly
                165                 170                 175

Asn Ile Ser
```

<210> SEQ ID NO 13

<211> LENGTH: 1167
<212> TYPE: DNA
<213> ORGANISM: Homo sapiens

<400> SEQUENCE: 13

```
atgggggacg ctcccagccc tgaagagaaa ctgcacctta tcacccggaa cctgcaggag      60
gttctggggg aagagaagct gaaggagata ctgaaggagc gggaacttaa aatttactgg     120
ggaacggcaa ccacgggcaa accacatgtg gcttactttg tgcccatgtc aaagattgca     180
gacttcttaa aggcagggtg tgaggtaaca attctgtttg cggacctcca cgcatacctg     240
gataacatga aagccccatg gaacttcta gaactccgag tcagttacta tgagaatgtg      300
atcaaagcaa tgctggagag cattggtgtg cccttggaga agctcaagtt catcaaaggc     360
actgattacc agctcagcaa agagtacaca ctagatgtgt acagactctc ctccgtggtc     420
acacagcacg attccaagaa ggctggagct gaggtggtaa agcaggtgga gcaccctttg     480
ctgagtggcc tcttataccc cggactgcag gctttggatg aagagtattt aaaagtagat     540
gcccaatttg gaggcattga tcagagaaag attttcacct ttgcagagaa gtacctccct     600
gcacttggct attcaaaacg ggtccatctg atgaatccta tggttccagg attaacaggc     660
agcaaaatga gctcttcaga agaggagtcc aagattgatc tccttgatcg gaaggaggat     720
gtgaagaaaa aactgaagaa ggccttctgt gagccaggaa atgtggagaa caatggggtt     780
ctgtccttca tcaagcatgt cctttttccc cttaagtccg agtttgtgat cctacgagat     840
gagaaatggg gtggaaacaa aacctacaca gcttacgtgg acctggaaaa ggactttgct     900
gctgaggttg tacatcctgg agacctgaag aattctgttg aagtcgcact gaacaagttg     960
ctggatccaa tccgggaaaa gtttaatacc cctgccctga aaaaactggc cagcgctgcc    1020
tacccagatc cctcaaagca gaagccaatg gccaaaggcc tgccaagaat tcagaaccag    1080
aggaggtcat cccatcccgg ctggatatcc gtgtgggaa atcatcact gtggagaagc      1140
acccagatgc agacagcctg tatgtag                                         1167
```

<210> SEQ ID NO 14
<211> LENGTH: 188
<212> TYPE: PRT
<213> ORGANISM: Homo sapiens
<220> FEATURE:
<221> NAME/KEY: VARIANT
<222> LOCATION: 1, 2, 3, 4, 5, 6, 7, 8
<223> OTHER INFORMATION: Xaa = Any Amino Acid

<400> SEQUENCE: 14

```
Xaa Xaa Xaa Xaa Xaa Xaa Xaa Xaa Pro Met Ala Lys Gly Pro Ala Lys
 1               5                  10                  15

Asn Ser Glu Pro Glu Glu Val Ile Pro Ser Arg Leu Asp Ile Arg Val
             20                  25                  30

Gly Lys Ile Ile Thr Val Glu Lys His Pro Asp Ala Asp Ser Leu Tyr
         35                  40                  45

Val Glu Lys Ile Asp Val Gly Glu Ala Glu Pro Arg Thr Val Val Ser
     50                  55                  60

Gly Leu Val Gln Phe Val Pro Lys Glu Glu Leu Gln Asp Arg Leu Val
 65                  70                  75                  80

Val Val Leu Cys Asn Leu Lys Pro Gln Lys Met Arg Gly Val Glu Ser
                 85                  90                  95

Gln Gly Met Leu Leu Cys Ala Ser Ile Glu Gly Ile Asn Arg Gln Val
            100                 105                 110
```

```
Glu Pro Leu Asp Pro Pro Ala Gly Ser Ala Pro Gly Glu His Val Phe
            115                 120                 125
Val Lys Gly Tyr Glu Lys Gly Gln Pro Asp Glu Leu Lys Pro Lys
    130                 135                 140
Lys Lys Val Phe Glu Lys Leu Gln Ala Asp Phe Lys Ile Ser Glu Glu
145                 150                 155                 160
Cys Ile Ala Gln Trp Lys Gln Thr Asn Phe Met Thr Lys Leu Gly Ser
                165                 170                 175
Ile Ser Cys Lys Ser Leu Lys Gly Gly Asn Ile Ser
            180                 185
```

<210> SEQ ID NO 15
<211> LENGTH: 2262
<212> TYPE: DNA
<213> ORGANISM: Homo sapiens

<400> SEQUENCE: 15

| | | | | | |
|---|---|---|---|---|---|
| gccagacaca | gtggctcaca | cctgtaatct | taacactttg | gaaggctgag | gcaggcggat | 60 |
| cacttgagcc | caaaagttag | agaccaaaac | ccagtctcta | cccaaaaaaa | aaaaaaaaaa | 120 |
| aaaaattagc | caggcatagt | agcacatgcc | tgtagtccca | gctacttggg | aggctgaggt | 180 |
| gagaggatca | cctgagcatg | gggaagttga | gactgcagtg | agccatgatc | gcaccactgc | 240 |
| actccagcct | gggcaacaga | gtgagactct | atgtctcaaa | aaagaaaaa | tgatagaaat | 300 |
| tagattagac | ctattatacc | caaccggtat | atagggtatc | gatagtttct | tacacagctg | 360 |
| ttgggcagag | cctgcagagc | ttagagaagc | ttatctttag | attctcccag | tttccttcta | 420 |
| tgtgcatggg | cctggctctt | agttggccat | ccacttgtgc | gtaatgctaa | gatattggca | 480 |
| ttgatagctt | tgtgcgaccc | ttccagaaaa | aaactcagta | actcagtaaa | atttttttt | 540 |
| ttttttctaa | aagagacaga | gtctggctct | gttgcccagc | ctggtcttga | agtcctgggc | 600 |
| ttaagcaatc | ctcccgtctc | agcctcccaa | agtgctagaa | ttacaggtgt | gagctaccac | 660 |
| acctggccaa | gactcagtaa | attctatgtg | gaatgcatga | atggaaatac | ctaaaggagg | 720 |
| caaagctact | actgctccct | ccccgctagt | ctaataattg | agggagagaa | cagatgaaaa | 780 |
| tcaggtatgt | catgtctgaa | aggttgccaa | cccagtatta | agaagttac | aactcagtgt | 840 |
| ttagactctg | ggattctac | actaaatctt | acctaatctc | agtgtcttaa | cgtggtggga | 900 |
| tcagcagctg | acctgccaca | gggaagaatt | ctacctcatg | gggttcttct | cattcccaga | 960 |
| gccaatggcc | aaaggccctg | ccaagaattc | agaaccagag | gaggtcatcc | catcccggct | 1020 |
| ggatatccgt | gtgggaaaa | tcatcactgt | ggagaagcac | ccagatgcag | acagcctgta | 1080 |
| tgtagagaag | attgacgtgg | gggaagctga | accacggact | gtggtgagcg | cctggtaca | 1140 |
| gttcgtgccc | aaggaggaac | tgcaggacag | gctggtagtg | gtgctgtgca | acctgaaacc | 1200 |
| ccagaagatg | agaggagtcg | agtcccaagg | catgcttctg | tgtgcttcta | tagaagggat | 1260 |
| aaaccgccag | gttgaacctc | tggacccctcc | ggcaggctct | gctcctggtg | agcacgtgtt | 1320 |
| tgtgaagggc | tatgaaaagg | gccaaccaga | tgaggagctc | aagcccaaga | agaaagtctt | 1380 |
| cgagaagttg | caggctgact | tcaaaatttc | tgaggagtgc | atcgcacagt | ggaagcaaac | 1440 |
| caacttcatg | accaagctgg | gctccatttc | ctgtaaatcg | ctgaaagggg | ggaacattag | 1500 |
| ctagccagcc | cagcatcttc | cccccttctt | ccaccactga | gtcatctgct | gtctcttcag | 1560 |
| tctgctccat | ccatcaccca | tttacccatc | tctcaggaca | cggaagcagc | gggtttggac | 1620 |
| tctttattcg | gtgcagaact | cggcaagggg | cagcttaccc | tccccagaac | ccaggatcat | 1680 |

-continued

```
cctgtctggc tgcagtgaga gaccaacccc taacaagggc tgggccacag cagggagtcc      1740
agccctacct tcttcccttg gcagctggag aaatctggtt tcaatataac tcatttaaaa      1800
atttatgcca cagtccttat aattggaaaa atactggtgc ccaggttttc ttggagttat      1860
ccaagcagct gcgcccctag ctgggatctg gtacctggac taggctaatt acagcttctc      1920
cccaacagga aactgtggga tttgaaaagg aaagggaagg gaaaacagag aacctagtgg      1980
tctaccaagt ggttggcaac tttcccaatg tctgcttact ctgaggcttg gcactggggg      2040
ccagggcctg ccccagggct cctggaattt cccttgatcc agctaggctg ggacactccc      2100
taaatcagct gcgtgttgtt agcatcaggc agaatgaatg gcagagagtg attctgtctt      2160
catagagggt ggggtacttc tccataaggc atctcagtca aatccccatc actgtcataa      2220
attcaaataa aatgtctgaa caagggaaaa aaaaaaaaaa aa                         2262
```

<210> SEQ ID NO 16
<211> LENGTH: 685
<212> TYPE: PRT
<213> ORGANISM: Homo sapiens

<400> SEQUENCE: 16

```
Met Asp Gly Ala Gly Ala Glu Glu Val Leu Ala Pro Leu Arg Leu Ala
  1               5                  10                  15

Val Arg Gln Gln Gly Asp Leu Val Arg Lys Leu Lys Glu Asp Lys Ala
             20                  25                  30

Pro Gln Val Asp Val Asp Lys Ala Val Ala Glu Leu Lys Ala Arg Lys
         35                  40                  45

Arg Val Leu Glu Ala Lys Glu Leu Ala Leu Gln Pro Lys Asp Asp Ile
     50                  55                  60

Val Asp Arg Ala Lys Met Glu Asp Thr Leu Lys Arg Arg Phe Phe Tyr
 65                  70                  75                  80

Asp Gln Ala Phe Ala Ile Tyr Gly Gly Val Ser Gly Leu Tyr Asp Phe
                 85                  90                  95

Gly Pro Val Gly Cys Ala Leu Lys Asn Asn Ile Ile Gln Thr Trp Arg
            100                 105                 110

Gln His Phe Ile Gln Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270
```

```
Gly Asn Ser Phe Arg Asn Glu Ile Ser Pro Arg Ser Gly Leu Ile Arg
            275                 280                 285

Val Arg Glu Phe Thr Met Ala Glu Ile Glu His Phe Val Asp Pro Ser
290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
            355                 360                 365

Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
            435                 440                 445

Ala Ile Gly Lys Ala Tyr Lys Lys Asp Ala Lys Leu Val Met Glu Tyr
            450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510

Val Glu Glu Val Val Pro Asn Val Ile Glu Pro Ser Phe Gly Leu Gly
            515                 520                 525

Arg Ile Met Tyr Thr Val Phe Glu His Thr Phe His Val Arg Glu Gly
530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
            595                 600                 605

Glu Ile Gly Val Ala Phe Gly Val Thr Ile Asp Phe Asp Thr Val Asn
610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
            675                 680                 685
```

<210> SEQ ID NO 17
<211> LENGTH: 2058
<212> TYPE: DNA
<213> ORGANISM: Homo sapiens

<400> SEQUENCE: 17

| | | | | | |
|---|---|---|---|---|---|
| atggacggcg | cggggctga | ggaggtgctg | gcacctctga | ggctagcagt | gcgccagcag | 60 |
| ggagatcttg | tgcgaaaact | caaagaagat | aaagcacccc | aagtagacgt | agacaaagca | 120 |
| gtggctgagc | tcaaagcccg | caagagggtt | ctggaagcaa | aggagctggc | gttacagccc | 180 |
| aaagatgata | ttgtagaccg | agcaaaaatg | gaagatacccc | tgaagaggag | gtttttctat | 240 |
| gatcaagctt | ttgctatttta | tggaggtgtt | agtggtctgt | atgactttgg | gccagttggc | 300 |
| tgtgctttga | agaacaatat | tattcagacc | tggaggcagc | actttatcca | agaggaacag | 360 |
| atcctggaga | tcgattgcac | catgctcacc | cctgagccag | ttttaaagac | tctggccat | 420 |
| gtagacaaat | ttgctgactt | catggtgaaa | gacgtaaaaa | atggagaatg | ttttcgtgct | 480 |
| gaccatctat | taaagctca | tttacagaaa | ttgatgtctg | ataagaagtg | ttctgtcgaa | 540 |
| aagaaatcag | aaatggaaag | tgttttggcc | cagcttgata | actatggaca | gcaagaactt | 600 |
| gcggatcttt | ttgtgaacta | taatgtaaaa | tctcccatta | ctggaaatga | tctatcccct | 660 |
| ccagtgtctt | ttaacttaat | gttcaagact | ttcattgggc | ctggaggaaa | catgcctggg | 720 |
| tacttgagac | cagaaactgc | acaggggatt | ttcttgaatt | tcaaacgact | tttggagttc | 780 |
| aaccaaggaa | agttgccttt | tgctgctgcc | cagattggaa | attcttttag | aaatgagatc | 840 |
| tcccctcgat | ctggactgat | cagagtcaga | gaattcacaa | tggcagaaat | tgagcacttt | 900 |
| gtagatccca | gtgagaaaga | ccaccccaag | ttccagaatg | tggcagacct | tcacctttat | 960 |
| ttgtattcag | caaaagccca | ggtcagcgga | cagtccgctc | ggaaaatgcg | cctgggagat | 1020 |
| gctgttgaac | agggtgtgat | taataacaca | gtattaggct | atttcattgg | ccgcatctac | 1080 |
| ctctacctca | cgaaggttgg | aatatctcca | gataaactcc | gcttccggca | gcacatggag | 1140 |
| aatgagatgg | cccattatgc | ctgtgactgt | tgggatgcag | aatccaaaac | atcctacggt | 1200 |
| tggattgaga | ttgttggatg | tgctgatcgt | tcctgttatg | acctctcctg | tcatgcacga | 1260 |
| gccaccaaag | tcccacttgt | agctgagaaa | cctctgaaag | aacccaaaac | agtcaatgtt | 1320 |
| gttcagtttg | aacccagtaa | gggagcaatt | ggtaaggcat | ataagaagga | tgcaaaactg | 1380 |
| gtgatggagt | atcttgccat | ttgtgatgag | tgctacatta | cagaaatgga | gatgctgctg | 1440 |
| aatgagaaag | gggaattcac | aattgaaact | gaagggaaaa | catttcagtt | aacaaaagac | 1500 |
| atgatcaatg | tgaagagatt | ccagaaaaca | ctatatgtgg | aagaagttgt | tccgaatgta | 1560 |
| attgaaccct | ccttcggcct | gggtaggatc | atgtatacgg | tatttgaaca | tacattccat | 1620 |
| gtacgagaag | gagatgaaca | gagaacattc | ttcagtttcc | ctgctgtagt | tgctccattc | 1680 |
| aaatgttccg | tcctcccact | gagccaaaac | aggagttca | tgccatttgt | caaggaatta | 1740 |
| tcggaagccc | tgaccaggca | tggagtatct | cacaaagtag | acgattcctc | tgggtcaatc | 1800 |
| ggaaggcgct | atgccaggac | tgatgagatt | ggcgtggctt | ttggtgtcac | cattgacttt | 1860 |
| gacacagtga | acaagacccc | ccacactgca | actctgaggg | accgtgactc | aatgcggcag | 1920 |
| ataagagcag | agatctctga | gctgccagc | atagtccaag | acctagccaa | tggcaacatc | 1980 |
| acatgggctg | atgtggaggc | caggtatcct | ctgtttgaag | ggcaagagac | tggtaaaaaa | 2040 |
| gagacaatcg | aggaatga | | | | | 2058 |

<210> SEQ ID NO 18

```
<211> LENGTH: 17
<212> TYPE: PRT
<213> ORGANISM: Homo sapiens

<400> SEQUENCE: 18

Pro Gly Tyr Leu Arg Pro Glu Thr Ala Gln Gly Ile Phe Leu Asn Phe
1               5                   10                  15

Lys

<210> SEQ ID NO 19
<211> LENGTH: 16
<212> TYPE: PRT
<213> ORGANISM: Homo sapiens

<400> SEQUENCE: 19

Thr Gly Asn Asp Leu Ser Pro Pro Val Ser Phe Asn Leu Met Phe Lys
1               5                   10                  15

<210> SEQ ID NO 20
<211> LENGTH: 9
<212> TYPE: PRT
<213> ORGANISM: Homo sapiens

<400> SEQUENCE: 20

Asn Val Val Gln Phe Glu Pro Ser Lys
1               5

<210> SEQ ID NO 21
<211> LENGTH: 19
<212> TYPE: PRT
<213> ORGANISM: Homo sapiens

<400> SEQUENCE: 21

Leu Tyr Val Glu Glu Val Val Pro Asn Val Ile Glu Pro Ser Phe Gly
1               5                   10                  15

Leu Gly Arg

<210> SEQ ID NO 22
<211> LENGTH: 20
<212> TYPE: PRT
<213> ORGANISM: Homo sapiens

<400> SEQUENCE: 22

Ala Ile Tyr Gly Gly Val Ser Gly Leu Tyr Asp Phe Gly Pro Val Gly
1               5                   10                  15

Cys Ala Leu Lys
            20

<210> SEQ ID NO 23
<211> LENGTH: 15
<212> TYPE: PRT
<213> ORGANISM: Homo sapiens

<400> SEQUENCE: 23

Gln His Phe Ile Gln Glu Gln Ile Leu Glu Ile Asp Cys Thr
1               5                   10                  15

<210> SEQ ID NO 24

<400> SEQUENCE: 24

000
```

<210> SEQ ID NO 25
<211> LENGTH: 775
<212> TYPE: PRT
<213> ORGANISM: Homo sapiens

<400> SEQUENCE: 25

Met Ala Ala Leu Asp Ser Leu Ser Leu Phe Thr Ser Leu Gly Leu Ser
1               5                   10                  15

Glu Gln Lys Ala Arg Glu Thr Leu Lys Asn Ser Ala Leu Ser Ala Gln
            20                  25                  30

Leu Arg Glu Ala Ala Thr Gln Ala Gln Gln Thr Leu Gly Ser Thr Ile
        35                  40                  45

Asp Lys Ala Thr Gly Ile Leu Leu Tyr Gly Leu Ala Ser Arg Leu Arg
    50                  55                  60

Asp Thr Arg Arg Leu Ser Phe Leu Val Ser Tyr Ile Ala Ser Lys Lys
65                  70                  75                  80

Ile His Thr Glu Pro Gln Leu Ser Ala Ala Leu Glu Tyr Val Arg Ser
                85                  90                  95

His Pro Leu Asp Pro Ile Asp Thr Val Asp Phe Glu Arg Glu Cys Gly
            100                 105                 110

Val Gly Val Ile Val Thr Pro Glu Gln Ile Glu Glu Ala Val Glu Ala
        115                 120                 125

Ala Ile Asn Arg His Arg Pro Gln Leu Leu Val Glu Arg Tyr His Phe
    130                 135                 140

Asn Met Gly Leu Leu Met Gly Glu Ala Arg Ala Val Leu Lys Trp Ala
145                 150                 155                 160

Asp Gly Lys Met Ile Lys Asn Glu Val Asp Met Gln Val Leu His Leu
                165                 170                 175

Leu Gly Pro Lys Leu Glu Ala Asp Leu Glu Lys Lys Phe Lys Val Ala
            180                 185                 190

Lys Ala Arg Leu Glu Glu Thr Asp Arg Arg Thr Ala Lys Asp Val Val
        195                 200                 205

Glu Asn Gly Glu Thr Ala Asp Gln Thr Leu Ser Leu Met Glu Gln Leu
    210                 215                 220

Arg Gly Glu Ala Leu Lys Phe His Lys Pro Gly Glu Asn Tyr Lys Thr
225                 230                 235                 240

Pro Gly Tyr Val Val Thr Pro His Thr Met Asn Leu Leu Lys Gln His
                245                 250                 255

Leu Glu Ile Thr Gly Gly Gln Val Arg Thr Arg Phe Pro Pro Glu Pro
            260                 265                 270

Asn Gly Ile Leu His Ile Gly His Ala Lys Ala Ile Asn Phe Asn Phe
        275                 280                 285

Gly Tyr Ala Lys Ala Asn Asn Gly Ile Cys Phe Leu Arg Phe Asp Asp
    290                 295                 300

Thr Asn Pro Glu Lys Glu Glu Ala Lys Phe Phe Thr Ala Ile Cys Asp
305                 310                 315                 320

Met Val Ala Trp Leu Gly Tyr Thr Pro Tyr Lys Val Thr Tyr Ala Ser
                325                 330                 335

Asp Tyr Phe Asp Gln Leu Tyr Ala Trp Ala Val Glu Leu Ile Arg Arg
            340                 345                 350

Gly Leu Ala Tyr Val Cys His Gln Arg Gly Glu Glu Leu Lys Gly His
        355                 360                 365

Asn Thr Leu Pro Ser Pro Trp Arg Asp Arg Pro Met Glu Glu Ser Leu
    370                 375                 380

```
Leu Leu Phe Glu Ala Met Arg Lys Gly Lys Phe Ser Glu Gly Glu Ala
385                 390                 395                 400

Thr Leu Arg Met Lys Leu Val Met Glu Asp Gly Lys Met Asp Pro Val
            405                 410                 415

Ala Tyr Arg Val Lys Tyr Thr Pro His His Arg Thr Gly Asp Lys Trp
        420                 425                 430

Cys Ile Tyr Pro Thr Tyr Asp Tyr Thr His Cys Leu Cys Asp Ser Ile
    435                 440                 445

Glu His Ile Thr His Ser Leu Cys Thr Lys Glu Phe Gln Ala Arg Arg
450                 455                 460

Ser Ser Tyr Phe Trp Leu Cys Asn Ala Leu Asp Val Tyr Cys Pro Val
465                 470                 475                 480

Gln Trp Glu Tyr Gly Arg Leu Asn Leu His Tyr Ala Val Val Ser Lys
                485                 490                 495

Arg Lys Ile Leu Gln Leu Val Ala Thr Gly Ala Val Arg Asp Trp Asp
            500                 505                 510

Asp Pro Arg Leu Phe Thr Leu Thr Ala Leu Arg Arg Gly Phe Pro
            515                 520                 525

Pro Glu Ala Ile Asn Asn Phe Cys Ala Arg Val Gly Val Thr Val Ala
530                 535                 540

Gln Thr Thr Met Glu Pro His Leu Leu Glu Ala Cys Val Arg Asp Val
545                 550                 555                 560

Leu Asn Asp Thr Ala Pro Arg Ala Met Ala Val Leu Glu Ser Leu Arg
                565                 570                 575

Val Ile Ile Thr Asn Phe Pro Ala Ala Lys Ser Leu Asp Ile Gln Val
            580                 585                 590

Pro Asn Phe Pro Ala Asp Glu Thr Lys Gly Phe His Gln Val Pro Phe
595                 600                 605

Ala Pro Ile Val Phe Ile Glu Arg Thr Asp Phe Lys Glu Glu Pro Glu
610                 615                 620

Pro Gly Phe Lys Arg Leu Ala Trp Gly Gln Pro Val Gly Leu Arg His
625                 630                 635                 640

Thr Gly Tyr Val Ile Glu Leu Gln His Val Val Lys Gly Pro Ser Gly
                645                 650                 655

Cys Val Glu Ser Leu Glu Val Thr Cys Arg Arg Ala Asp Ala Gly Glu
            660                 665                 670

Lys Pro Lys Ala Phe Ile His Trp Val Ser Gln Pro Leu Met Cys Glu
            675                 680                 685

Val Arg Leu Tyr Glu Arg Leu Phe Gln His Lys Asn Pro Glu Asp Pro
690                 695                 700

Thr Glu Val Pro Gly Gly Phe Leu Ser Asp Leu Asn Leu Ala Ser Leu
705                 710                 715                 720

His Val Val Asp Ala Ala Leu Val Asp Cys Ser Val Ala Leu Ala Lys
                725                 730                 735

Pro Phe Asp Lys Phe Gln Phe Glu Arg Leu Gly Tyr Phe Ser Val Asp
            740                 745                 750

Pro Asp Ser His Gln Gly Lys Leu Val Phe Asn Arg Thr Val Thr Leu
            755                 760                 765

Lys Glu Asp Pro Gly Lys Val
770                 775

<210> SEQ ID NO 26
<211> LENGTH: 15
<212> TYPE: PRT
```

<213> ORGANISM: Homo sapiens

<400> SEQUENCE: 26

Asp Val Val Glu Asn Gly Glu Thr Ala Asp Gln Thr Leu Ser Leu
1               5                   10                  15

<210> SEQ ID NO 27
<211> LENGTH: 10
<212> TYPE: PRT
<213> ORGANISM: Homo sapiens

<400> SEQUENCE: 27

Thr Pro Gly Tyr Val Val Thr Pro His Thr
1               5                   10

<210> SEQ ID NO 28
<211> LENGTH: 509
<212> TYPE: PRT
<213> ORGANISM: Homo sapiens

<400> SEQUENCE: 28

Met Ala Glu Arg Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
            325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
            355                 360                 365

Met Phe Asp Pro Lys Gly Arg Lys Val Pro Cys Val Gly Leu Ser Ile
370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
            405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
            485                 490                 495

Glu Ile Lys Arg Arg Thr Gly Gln Pro Leu Cys Ile Cys
            500                 505

<210> SEQ ID NO 29
<211> LENGTH: 183
<212> TYPE: DNA
<213> ORGANISM: Homo sapiens

<400> SEQUENCE: 29
atggcagagc gtgcggcgct ggaggagctg gtgaaacttc agggagagcg cgtgcgaggc     60
ctcaagcagc agaaggccag cgccgagctg atcgaggagg aggtggcgaa actcctgaaa    120
ctgaaggcac agctgggtcc tgatgaaagc aaacagaaat ttgtgctcaa accccaag     180 tag                                                                  183

<210> SEQ ID NO 30
<211> LENGTH: 60
<212> TYPE: PRT
<213> ORGANISM: Homo sapiens

<400> SEQUENCE: 30

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 31
<211> LENGTH: 516
<212> TYPE: DNA
<213> ORGANISM: Homo sapiens

<400> SEQUENCE: 31

```
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat ttgtgctcaa accccccaag     180
gctttggagg agaagatacg gaccacggag acacaggtgc ttgtggcatc tgcacagaag     240
aagctgctag aggaaagact aaagcttgtc tcagaactgt gggatgctgg gatcaaggct     300
gagctgctgt acaagaagaa cccaaagcta ctgaaccagt tacagtactg tgaggaggca     360
ggcatcccac tggtggctat catcggcgag caggaactca aggatgggt catcaagctc      420
cgttcagtga cgagcaggga gaggtggat gtccgaagag aagaccttgt ggaggaaatc      480
aaaaggagaa caggccagcc cctctgcatc tgctga                               516
```

<210> SEQ ID NO 32
<211> LENGTH: 171
<212> TYPE: PRT
<213> ORGANISM: Homo sapiens

<400> SEQUENCE: 32

```
Met Ala Glu Arg Ala Ala Leu Glu Glu Leu Val Lys Leu Gln Gly Glu
  1               5                  10                  15

Arg Val Arg Gly Leu Lys Gln Gln Lys Ala Ser Ala Glu Leu Ile Glu
             20                  25                  30

Glu Glu Val Ala Lys Leu Leu Lys Leu Lys Ala Gln Leu Gly Pro Asp
         35                  40                  45

Glu Ser Lys Gln Lys Phe Val Leu Lys Thr Pro Lys Ala Leu Glu Glu
     50                  55                  60

Lys Ile Arg Thr Thr Glu Thr Gln Val Leu Val Ala Ser Ala Gln Lys
 65                  70                  75                  80

Lys Leu Leu Glu Glu Arg Leu Lys Leu Val Ser Glu Leu Trp Asp Ala
                 85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
        115                 120                 125

Gly Glu Gln Glu Leu Lys Asp Gly Val Ile Lys Leu Arg Ser Val Thr
    130                 135                 140

Ser Arg Glu Glu Val Asp Val Arg Arg Glu Asp Leu Val Glu Glu Ile
145                 150                 155                 160

Lys Arg Arg Thr Gly Gln Pro Leu Cys Ile Cys
                165                 170
```

<210> SEQ ID NO 33
<211> LENGTH: 471
<212> TYPE: PRT
<213> ORGANISM: Homo sapiens

<400> SEQUENCE: 33

```
Met Pro Asn Ser Glu Pro Ala Ser Leu Leu Glu Leu Phe Asn Ser Ile
  1               5                  10                  15

Ala Thr Gln Gly Glu Leu Val Arg Ser Leu Lys Ala Gly Asn Ala Ser
```

```
                    20                  25                  30
        Lys Asp Glu Ile Asp Ser Ala Val Lys Met Leu Val Ser Leu Lys Met
                    35                  40                  45

Ser Tyr Lys Ala Ala Gly Glu Asp Tyr Lys Ala Asp Cys Pro Pro
            50                  55                  60

Gly Asn Pro Ala Pro Thr Ser Asn His Gly Pro Asp Ala Thr Glu Ala
        65                  70                  75                  80

Glu Glu Asp Phe Val Asp Pro Trp Thr Val Gln Thr Ser Ser Ala Lys
                        85                  90                  95

Gly Ile Asp Tyr Asp Lys Leu Ile Val Arg Phe Gly Ser Ser Lys Ile
                    100                 105                 110

Asp Lys Glu Leu Ile Asn Arg Ile Glu Arg Ala Thr Gly Gln Arg Pro
                    115                 120                 125

His His Phe Leu Arg Arg Gly Ile Phe Phe Ser His Arg Asp Met Asn
                    130                 135                 140

Gln Val Leu Asp Ala Tyr Glu Asn Lys Lys Pro Phe Tyr Leu Tyr Thr
        145                 150                 155                 160

Gly Arg Gly Pro Ser Ser Glu Ala Met His Val Gly His Leu Ile Pro
                        165                 170                 175

Phe Ile Phe Thr Lys Trp Leu Gln Asp Val Phe Asn Val Pro Leu Val
                    180                 185                 190

Ile Gln Met Thr Asp Asp Glu Lys Tyr Leu Trp Lys Asp Leu Thr Leu
                    195                 200                 205

Asp Gln Ala Tyr Ser Tyr Ala Val Glu Asn Ala Lys Asp Ile Ile Ala
                    210                 215                 220

Cys Gly Phe Asp Ile Asn Lys Thr Phe Ile Phe Ser Asp Leu Asp Tyr
        225                 230                 235                 240

Met Gly Met Ser Ser Gly Phe Tyr Lys Asn Val Val Lys Ile Gln Lys
                        245                 250                 255

His Val Thr Phe Asn Gln Val Lys Gly Ile Phe Gly Phe Thr Asp Ser
                    260                 265                 270

Asp Cys Ile Gly Lys Ile Ser Phe Pro Ala Ile Gln Ala Ala Pro Ser
                    275                 280                 285

Phe Ser Asn Ser Phe Pro Gln Ile Phe Arg Asp Arg Thr Asp Ile Gln
                    290                 295                 300

Cys Leu Ile Pro Cys Ala Ile Asp Gln Asp Pro Tyr Phe Arg Met Thr
        305                 310                 315                 320

Arg Asp Val Ala Pro Arg Ile Gly Tyr Pro Lys Pro Ala Leu Leu His
                        325                 330                 335

Ser Thr Phe Phe Pro Ala Leu Gln Gly Ala Gln Thr Lys Met Ser Ala
                    340                 345                 350

Ser Asp Pro Asn Ser Ser Ile Phe Leu Thr Asp Thr Ala Lys Gln Ile
                    355                 360                 365

Lys Thr Lys Val Asn Lys His Ala Phe Ser Gly Gly Arg Asp Thr Ile
                    370                 375                 380

Glu Glu His Arg Gln Phe Gly Gly Asn Cys Asp Val Asp Val Ser Phe
        385                 390                 395                 400

Met Tyr Leu Thr Phe Phe Leu Glu Asp Asp Lys Leu Glu Gln Ile
                        405                 410                 415

Arg Lys Asp Tyr Thr Ser Gly Ala Met Leu Thr Gly Glu Leu Lys Lys
                    420                 425                 430

Ala Leu Ile Glu Val Leu Gln Pro Leu Ile Ala Glu His Gln Ala Arg
                    435                 440                 445
```

```
Arg Lys Glu Val Thr Asp Glu Ile Val Lys Glu Phe Met Thr Pro Arg
            450                 455                 460

Lys Leu Ser Phe Asp Phe Gln
465                 470

<210> SEQ ID NO 34
<211> LENGTH: 379
<212> TYPE: PRT
<213> ORGANISM: Homo sapiens

<400> SEQUENCE: 34

Met Ser Ala Lys Gly Ile Asp Tyr Asp Lys Leu Ile Val Arg Phe Gly
  1               5                  10                  15

Ser Ser Lys Ile Asp Lys Glu Leu Ile Asn Arg Ile Glu Arg Ala Thr
             20                  25                  30

Gly Gln Arg Pro His His Phe Leu Arg Arg Gly Ile Phe Phe Ser His
         35                  40                  45

Arg Asp Met Asn Gln Val Leu Asp Ala Tyr Glu Asn Lys Lys Pro Phe
 50                  55                  60

Tyr Leu Tyr Thr Gly Arg Gly Pro Ser Ser Glu Ala Met His Val Gly
 65                  70                  75                  80

His Leu Ile Pro Phe Ile Phe Thr Lys Trp Leu Gln Asp Val Phe Asn
                 85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Ser Tyr Ala Val Glu Asn Ala Lys
        115                 120                 125

Asp Ile Ile Ala Cys Gly Phe Asp Ile Asn Lys Thr Phe Ile Phe Ser
130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
```

```
                340             345             350
His Gln Ala Arg Arg Lys Glu Val Thr Asp Glu Ile Val Lys Glu Phe
            355                 360                 365
Met Thr Pro Arg Lys Leu Ser Phe Asp Phe Gln
        370                 375

<210> SEQ ID NO 35
<211> LENGTH: 424
<212> TYPE: PRT
<213> ORGANISM: Homo sapiens

<400> SEQUENCE: 35

Met Ser Tyr Lys Ala Ala Gly Glu Asp Tyr Lys Ala Asp Cys Pro
  1               5                  10                  15
Pro Gly Asn Pro Ala Pro Thr Ser Asn His Gly Pro Asp Ala Thr Glu
                 20                  25                  30
Ala Glu Glu Asp Phe Val Asp Pro Trp Thr Val Gln Thr Ser Ser Ala
             35                  40                  45
Lys Gly Ile Asp Tyr Asp Lys Leu Ile Val Arg Phe Gly Ser Ser Lys
     50                  55                  60
Ile Asp Lys Glu Leu Ile Asn Arg Ile Glu Arg Ala Thr Gly Gln Arg
 65                  70                  75                  80
Pro His His Phe Leu Arg Arg Gly Ile Phe Phe Ser His Arg Asp Met
                 85                  90                  95
Asn Gln Val Leu Asp Ala Tyr Glu Asn Lys Lys Pro Phe Tyr Leu Tyr
                100                 105                 110
Thr Gly Arg Gly Pro Ser Ser Glu Ala Met His Val Gly His Leu Ile
            115                 120                 125
Pro Phe Ile Phe Thr Lys Trp Leu Gln Asp Val Phe Asn Val Pro Leu
        130                 135                 140
Val Ile Gln Met Thr Asp Asp Glu Lys Tyr Leu Trp Lys Asp Leu Thr
145                 150                 155                 160
Leu Asp Gln Ala Tyr Ser Tyr Ala Val Glu Asn Ala Lys Asp Ile Ile
                165                 170                 175
Ala Cys Gly Phe Asp Ile Asn Lys Thr Phe Ile Phe Ser Asp Leu Asp
            180                 185                 190
Tyr Met Gly Met Ser Ser Gly Phe Tyr Lys Asn Val Val Lys Ile Gln
        195                 200                 205
Lys His Val Thr Phe Asn Gln Val Lys Gly Ile Phe Gly Phe Thr Asp
    210                 215                 220
Ser Asp Cys Ile Gly Lys Ile Ser Phe Pro Ala Ile Gln Ala Ala Pro
225                 230                 235                 240
Ser Phe Ser Asn Ser Phe Pro Gln Ile Phe Arg Asp Arg Thr Asp Ile
                245                 250                 255
Gln Cys Leu Ile Pro Cys Ala Ile Asp Gln Asp Pro Tyr Phe Arg Met
            260                 265                 270
Thr Arg Asp Val Ala Pro Arg Ile Gly Tyr Pro Lys Pro Ala Leu Leu
        275                 280                 285
His Ser Thr Phe Phe Pro Ala Leu Gln Gly Ala Gln Thr Lys Met Ser
    290                 295                 300
Ala Ser Asp Pro Asn Ser Ser Ile Phe Leu Thr Asp Thr Ala Lys Gln
305                 310                 315                 320
Ile Lys Thr Lys Val Asn Lys His Ala Phe Ser Gly Gly Arg Asp Thr
                325                 330                 335
```

```
Ile Glu Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
    370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420

<210> SEQ ID NO 36
<211> LENGTH: 13
<212> TYPE: PRT
<213> ORGANISM: Mus musculus

<400> SEQUENCE: 36

Glu Thr Leu Lys Asn Glu Ala Leu Ser Thr Gln Leu Arg
1               5                   10

<210> SEQ ID NO 37
<211> LENGTH: 28
<212> TYPE: PRT
<213> ORGANISM: Mus musculus

<400> SEQUENCE: 37

Glu Ala Ala Thr Gln Ala His Gln Ile Leu Gly Ser Thr Ile Asp Lys
1               5                   10                  15

Ala Thr Gly Val Leu Leu Tyr Asp Leu Val Ser Arg
            20                  25

<210> SEQ ID NO 38
<211> LENGTH: 41
<212> TYPE: PRT
<213> ORGANISM: Mus musculus

<400> SEQUENCE: 38

Glu Thr Leu Lys Asn Glu Ala Leu Ser Thr Gln Leu Arg Glu Ala Ala
1               5                   10                  15

Thr Gln Ala His Gln Ile Leu Gly Ser Thr Ile Asp Lys Ala Thr Gly
            20                  25                  30

Val Leu Leu Tyr Asp Leu Val Ser Arg
            35                  40

<210> SEQ ID NO 39
<211> LENGTH: 27
<212> TYPE: PRT
<213> ORGANISM: Mus musculus

<400> SEQUENCE: 39

Asp Phe Glu Gln Glu Cys Gly Val Gly Val Val Thr Pro Glu Gln
1               5                   10                  15

Ile Glu Glu Ala Val Glu Ser Thr Ile Asn Lys
            20                  25

<210> SEQ ID NO 40
<211> LENGTH: 11
<212> TYPE: PRT
<213> ORGANISM: Mus musculus
```

```
<400> SEQUENCE: 40

Phe Asn Met Gly Leu Leu Met Gly Glu Ala Arg
1               5                   10

<210> SEQ ID NO 41
<211> LENGTH: 17
<212> TYPE: PRT
<213> ORGANISM: Mus musculus

<400> SEQUENCE: 41

Met Ile Lys Asn Glu Val Asp Met Gln Val Leu His Leu Leu Gly Pro
1               5                   10                  15

Lys

<210> SEQ ID NO 42
<211> LENGTH: 14
<212> TYPE: PRT
<213> ORGANISM: Mus musculus

<400> SEQUENCE: 42

Asn Glu Val Asp Met Gln Val Leu His Leu Leu Gly Pro Lys
1               5                   10

<210> SEQ ID NO 43
<211> LENGTH: 15
<212> TYPE: PRT
<213> ORGANISM: Mus musculus

<400> SEQUENCE: 43

Thr Pro Gly Tyr Val Ile Thr Pro Tyr Thr Met Asp Leu Leu Lys
1               5                   10                  15

<210> SEQ ID NO 44
<211> LENGTH: 12
<212> TYPE: PRT
<213> ORGANISM: Mus musculus

<400> SEQUENCE: 44

Phe Asp Asp Thr Asn Pro Glu Lys Glu Glu Ala Lys
1               5                   10

<210> SEQ ID NO 45
<211> LENGTH: 15
<212> TYPE: PRT
<213> ORGANISM: Mus musculus

<400> SEQUENCE: 45

Val Glu Glu Leu Lys Gly His Asn Pro Leu Pro Ser Pro Trp Arg
1               5                   10                  15

<210> SEQ ID NO 46
<211> LENGTH: 15
<212> TYPE: PRT
<213> ORGANISM: Mus musculus

<400> SEQUENCE: 46

Asp Arg Pro Lys Glu Glu Ser Leu Leu Leu Phe Glu Ala Met Arg
1               5                   10                  15

<210> SEQ ID NO 47
<211> LENGTH: 30
<212> TYPE: PRT
<213> ORGANISM: Mus musculus
```

```
<400> SEQUENCE: 47

Val Glu Glu Leu Lys Gly His Asn Pro Leu Pro Ser Pro Trp Arg Asp
1               5                   10                  15

Arg Pro Lys Glu Glu Ser Leu Leu Leu Phe Glu Ala Met Arg
            20                  25                  30

<210> SEQ ID NO 48
<211> LENGTH: 14
<212> TYPE: PRT
<213> ORGANISM: Mus musculus

<400> SEQUENCE: 48

Leu Val Met Glu Asp Gly Lys Met Asp Pro Val Ala Tyr Arg
1               5                   10

<210> SEQ ID NO 49
<211> LENGTH: 11
<212> TYPE: PRT
<213> ORGANISM: Mus musculus

<400> SEQUENCE: 49

Val Tyr Cys Pro Val Gln Trp Glu Tyr Gly Arg
1               5                   10

<210> SEQ ID NO 50
<211> LENGTH: 11
<212> TYPE: PRT
<213> ORGANISM: Mus musculus

<400> SEQUENCE: 50

Ile Leu Gln Leu Val Ala Ala Gly Ala Val Arg
1               5                   10

<210> SEQ ID NO 51
<211> LENGTH: 28
<212> TYPE: PRT
<213> ORGANISM: Mus musculus

<400> SEQUENCE: 51

Asp Val Leu Asn Asp Ala Ala Pro Arg Ala Met Ala Val Leu Glu Pro
1               5                   10                  15

Leu Gln Val Val Ile Thr Asn Phe Pro Ala Pro Lys
            20                  25

<210> SEQ ID NO 52
<211> LENGTH: 38
<212> TYPE: PRT
<213> ORGANISM: Mus musculus

<400> SEQUENCE: 52

Gly Phe His Gln Val Pro Phe Ala Ser Thr Val Phe Ile Glu Arg Ser
1               5                   10                  15

Asp Phe Lys Glu Glu Ser Glu Pro Gly Tyr Lys Arg Leu Ala Ser Gly
            20                  25                  30

Gln Pro Val Gly Leu Arg
        35

<210> SEQ ID NO 53
<211> LENGTH: 15
<212> TYPE: PRT
<213> ORGANISM: Mus musculus
```

```
<400> SEQUENCE: 53

Ala Phe Ile His Trp Val Ser Gln Pro Leu Val Cys Glu Ile Arg
1               5                   10                  15

<210> SEQ ID NO 54
<211> LENGTH: 19
<212> TYPE: PRT
<213> ORGANISM: Mus musculus

<400> SEQUENCE: 54

Leu Gly Tyr Phe Ser Val Asp Pro Asp Ser His Gln Gly Gln Ile Val
1               5                   10                  15

Phe Asn Arg

<210> SEQ ID NO 55
<211> LENGTH: 15
<212> TYPE: PRT
<213> ORGANISM: Mus musculus

<400> SEQUENCE: 55

Thr Pro Gly Tyr Val Ile Thr Pro Tyr Thr Met Asp Leu Leu Lys
1               5                   10                  15

<210> SEQ ID NO 56
<211> LENGTH: 10
<212> TYPE: PRT
<213> ORGANISM: Mus musculus

<400> SEQUENCE: 56

Ala Ile Asn Phe Asn Phe Gly Tyr Ala Lys
1               5                   10

<210> SEQ ID NO 57
<211> LENGTH: 12
<212> TYPE: PRT
<213> ORGANISM: Mus musculus

<400> SEQUENCE: 57

Phe Asp Asp Thr Asn Pro Glu Lys Glu Glu Ala Lys
1               5                   10

<210> SEQ ID NO 58
<211> LENGTH: 18
<212> TYPE: PRT
<213> ORGANISM: Mus musculus

<400> SEQUENCE: 58

Phe Phe Thr Ala Ile Tyr Asp Met Val Thr Trp Leu Gly Tyr Thr Pro
1               5                   10                  15

Tyr Lys

<210> SEQ ID NO 59
<211> LENGTH: 30
<212> TYPE: PRT
<213> ORGANISM: Mus musculus

<400> SEQUENCE: 59

Phe Asp Asp Thr Asn Pro Glu Lys Glu Glu Ala Lys Phe Phe Thr Ala
1               5                   10                  15

Ile Tyr Asp Met Val Thr Trp Leu Gly Tyr Thr Pro Tyr Lys
            20                  25                  30
```

```
<210> SEQ ID NO 60
<211> LENGTH: 15
<212> TYPE: PRT
<213> ORGANISM: Mus musculus

<400> SEQUENCE: 60

Asp Arg Pro Lys Glu Glu Ser Leu Leu Leu Phe Glu Ala Met Arg
1               5                   10                  15

<210> SEQ ID NO 61
<211> LENGTH: 11
<212> TYPE: PRT
<213> ORGANISM: Mus musculus

<400> SEQUENCE: 61

Val Tyr Cys Pro Val Gln Trp Glu Tyr Gly Arg
1               5                   10

<210> SEQ ID NO 62
<211> LENGTH: 10
<212> TYPE: PRT
<213> ORGANISM: Mus musculus

<400> SEQUENCE: 62

Leu Asn Leu His Tyr Ala Val Val Ser Lys
1               5                   10

<210> SEQ ID NO 63
<211> LENGTH: 21
<212> TYPE: PRT
<213> ORGANISM: Mus musculus

<400> SEQUENCE: 63

Val Tyr Cys Pro Val Gln Trp Glu Tyr Gly Arg Leu Asn Leu His Tyr
1               5                   10                  15

Ala Val Val Ser Lys
            20

<210> SEQ ID NO 64
<211> LENGTH: 11
<212> TYPE: PRT
<213> ORGANISM: Mus musculus

<400> SEQUENCE: 64

Ile Leu Gln Leu Val Ala Ala Gly Ala Val Arg
1               5                   10

<210> SEQ ID NO 65
<211> LENGTH: 19
<212> TYPE: PRT
<213> ORGANISM: Mus musculus

<400> SEQUENCE: 65

Ala Met Ala Val Leu Glu Pro Leu Gln Val Val Ile Thr Asn Phe Pro
1               5                   10                  15

Ala Pro Lys

<210> SEQ ID NO 66
<211> LENGTH: 15
<212> TYPE: PRT
<213> ORGANISM: Mus musculus

<400> SEQUENCE: 66

Pro Leu Asp Ile Arg Val Pro Asn Phe Pro Ala Asp Glu Thr Lys
```

```
                1               5                   10                  15
```

<210> SEQ ID NO 67
<211> LENGTH: 34
<212> TYPE: PRT
<213> ORGANISM: Mus musculus

<400> SEQUENCE: 67

```
Ala Met Ala Val Leu Glu Pro Leu Gln Val Val Ile Thr Asn Phe Pro
 1               5                   10                  15

Ala Pro Lys Pro Leu Asp Ile Arg Val Pro Asn Phe Pro Ala Asp Glu
            20                  25                  30

Thr Lys
```

<210> SEQ ID NO 68
<211> LENGTH: 36
<212> TYPE: PRT
<213> ORGANISM: Mus musculus

<400> SEQUENCE: 68

```
Ser Asp Phe Lys Glu Glu Ser Glu Pro Gly Tyr Lys Arg Leu Ala Ser
 1               5                   10                  15

Gly Gln Pro Val Gly Leu Arg His Thr Gly Tyr Val Ile Glu Leu Gln
            20                  25                  30

Asn Ile Val Arg
        35
```

<210> SEQ ID NO 69
<211> LENGTH: 15
<212> TYPE: PRT
<213> ORGANISM: Mus musculus

<400> SEQUENCE: 69

```
Ala Phe Ile His Trp Val Ser Gln Pro Leu Val Cys Glu Ile Arg
 1               5                   10                  15
```

<210> SEQ ID NO 70
<211> LENGTH: 19
<212> TYPE: PRT
<213> ORGANISM: Mus musculus

<400> SEQUENCE: 70

```
Leu Gly Tyr Phe Ser Val Asp Pro Asp Ser His Gln Gly Gln Ile Val
 1               5                   10                  15

Phe Asn Arg
```

<210> SEQ ID NO 71
<211> LENGTH: 13
<212> TYPE: PRT
<213> ORGANISM: Mus musculus

<400> SEQUENCE: 71

```
Lys Ala Thr Gly Val Leu Leu Tyr Asp Leu Val Ser Arg
 1               5                   10
```

<210> SEQ ID NO 72
<211> LENGTH: 10
<212> TYPE: PRT
<213> ORGANISM: Mus musculus

<400> SEQUENCE: 72

```
Ser Phe Leu Val Ser Tyr Ile Ala Asn Lys
 1               5                   10
```

-continued

```
1               5                   10
```

<210> SEQ ID NO 73
<211> LENGTH: 27
<212> TYPE: PRT
<213> ORGANISM: Mus musculus

<400> SEQUENCE: 73

```
Asp Phe Glu Gln Glu Cys Gly Val Gly Val Val Thr Pro Glu Gln
1               5                   10                  15

Ile Glu Glu Ala Val Glu Ser Thr Ile Asn Lys
            20                  25
```

<210> SEQ ID NO 74
<211> LENGTH: 17
<212> TYPE: PRT
<213> ORGANISM: Mus musculus

<400> SEQUENCE: 74

```
Met Ile Lys Asn Glu Val Asp Met Gln Val Leu His Leu Leu Gly Pro
1               5                   10                  15

Lys
```

<210> SEQ ID NO 75
<211> LENGTH: 28
<212> TYPE: PRT
<213> ORGANISM: Mus musculus

<400> SEQUENCE: 75

```
Glu Ala Ala Thr Gln Ala His Gln Ile Leu Gly Ser Thr Ile Asp Lys
1               5                   10                  15

Ala Thr Gly Val Leu Leu Tyr Asp Leu Val Ser Arg
            20                  25
```

<210> SEQ ID NO 76
<211> LENGTH: 13
<212> TYPE: PRT
<213> ORGANISM: Homo sapiens

<400> SEQUENCE: 76

```
Glu Thr Leu Lys Asn Ser Ala Leu Ser Ala Gln Leu Arg
1               5                   10
```

<210> SEQ ID NO 77
<211> LENGTH: 28
<212> TYPE: PRT
<213> ORGANISM: Homo sapiens

<400> SEQUENCE: 77

```
Glu Ala Ala Thr Gln Ala Gln Gln Thr Leu Gly Ser Thr Ile Asp Lys
1               5                   10                  15

Ala Thr Gly Ile Leu Leu Tyr Gly Leu Ala Ser Arg
            20                  25
```

<210> SEQ ID NO 78
<211> LENGTH: 41
<212> TYPE: PRT
<213> ORGANISM: Homo sapiens

<400> SEQUENCE: 78

```
Glu Thr Leu Lys Asn Ser Ala Leu Ser Ala Gln Leu Arg Glu Ala Ala
1               5                   10                  15
```

```
Thr Gln Ala Gln Gln Thr Leu Gly Ser Thr Ile Asp Lys Ala Thr Gly
            20                  25                  30

Ile Leu Leu Tyr Gly Leu Ala Ser Arg
        35                  40

<210> SEQ ID NO 79
<211> LENGTH: 27
<212> TYPE: PRT
<213> ORGANISM: Homo sapiens

<400> SEQUENCE: 79

Asp Phe Glu Arg Glu Cys Gly Val Gly Val Ile Val Thr Pro Glu Gln
1               5                   10                  15

Ile Glu Glu Ala Val Glu Ala Ala Ile Asn Arg
            20                  25

<210> SEQ ID NO 80
<211> LENGTH: 15
<212> TYPE: PRT
<213> ORGANISM: Homo sapiens

<400> SEQUENCE: 80

Thr Pro Gly Tyr Val Val Thr Pro His Thr Met Asn Leu Leu Lys
1               5                   10                  15

<210> SEQ ID NO 81
<211> LENGTH: 15
<212> TYPE: PRT
<213> ORGANISM: Homo sapiens

<400> SEQUENCE: 81

Gly Glu Glu Leu Lys Gly His Asn Thr Leu Pro Ser Pro Trp Arg
1               5                   10                  15

<210> SEQ ID NO 82
<211> LENGTH: 15
<212> TYPE: PRT
<213> ORGANISM: Homo sapiens

<400> SEQUENCE: 82

Asp Arg Pro Met Glu Glu Ser Leu Leu Leu Phe Glu Ala Met Arg
1               5                   10                  15

<210> SEQ ID NO 83
<211> LENGTH: 30
<212> TYPE: PRT
<213> ORGANISM: Homo sapiens

<400> SEQUENCE: 83

Gly Glu Glu Leu Lys Gly His Asn Thr Leu Pro Ser Pro Trp Arg Asp
1               5                   10                  15

Arg Pro Met Glu Glu Ser Leu Leu Leu Phe Glu Ala Met Arg
            20                  25                  30

<210> SEQ ID NO 84
<211> LENGTH: 11
<212> TYPE: PRT
<213> ORGANISM: Homo sapiens

<400> SEQUENCE: 84

Ile Leu Gln Leu Val Ala Thr Gly Ala Val Arg
1               5                   10
```

```
<210> SEQ ID NO 85
<211> LENGTH: 28
<212> TYPE: PRT
<213> ORGANISM: Homo sapiens

<400> SEQUENCE: 85

Asp Val Leu Asn Asp Thr Ala Pro Arg Ala Met Ala Val Leu Glu Ser
1               5                   10                  15

Leu Arg Val Ile Ile Thr Asn Phe Pro Ala Ala Lys
            20                  25

<210> SEQ ID NO 86
<211> LENGTH: 38
<212> TYPE: PRT
<213> ORGANISM: Homo sapiens

<400> SEQUENCE: 86

Gly Phe His Gln Val Pro Phe Ala Pro Ile Val Phe Ile Glu Arg Thr
1               5                   10                  15

Asp Phe Lys Glu Glu Pro Glu Pro Gly Phe Lys Arg Leu Ala Trp Gly
            20                  25                  30

Gln Pro Val Gly Leu Arg
        35

<210> SEQ ID NO 87
<211> LENGTH: 15
<212> TYPE: PRT
<213> ORGANISM: Homo sapiens

<400> SEQUENCE: 87

Ala Phe Ile His Trp Val Ser Gln Pro Leu Met Cys Glu Val Arg
1               5                   10                  15

<210> SEQ ID NO 88
<211> LENGTH: 19
<212> TYPE: PRT
<213> ORGANISM: Homo sapiens

<400> SEQUENCE: 88

Leu Gly Tyr Phe Ser Val Asp Pro Asp Ser His Gln Gly Lys Leu Val
1               5                   10                  15

Phe Asn Arg

<210> SEQ ID NO 89
<211> LENGTH: 15
<212> TYPE: PRT
<213> ORGANISM: Homo sapiens

<400> SEQUENCE: 89

Thr Pro Gly Tyr Val Val Thr Pro His Thr Met Asn Leu Leu Lys
1               5                   10                  15

<210> SEQ ID NO 90
<211> LENGTH: 18
<212> TYPE: PRT
<213> ORGANISM: Homo sapiens

<400> SEQUENCE: 90

Phe Phe Thr Ala Ile Cys Asp Met Val Ala Trp Leu Gly Tyr Thr Pro
1               5                   10                  15

Tyr Lys
```

<210> SEQ ID NO 91
<211> LENGTH: 30
<212> TYPE: PRT
<213> ORGANISM: Homo sapiens

<400> SEQUENCE: 91

Phe Asp Asp Thr Asn Pro Glu Lys Glu Ala Lys Phe Phe Thr Ala
1               5                   10                  15

Ile Tyr Asp Met Val Thr Trp Leu Gly Tyr Thr Pro Tyr Lys
            20                  25                  30

<210> SEQ ID NO 92
<211> LENGTH: 15
<212> TYPE: PRT
<213> ORGANISM: Homo sapiens

<400> SEQUENCE: 92

Asp Arg Pro Met Glu Glu Ser Leu Leu Leu Phe Glu Ala Met Arg
1               5                   10                  15

<210> SEQ ID NO 93
<211> LENGTH: 11
<212> TYPE: PRT
<213> ORGANISM: Homo sapiens

<400> SEQUENCE: 93

Ile Leu Gln Leu Val Ala Thr Gly Ala Val Arg
1               5                   10

<210> SEQ ID NO 94
<211> LENGTH: 19
<212> TYPE: PRT
<213> ORGANISM: Homo sapiens

<400> SEQUENCE: 94

Ala Met Ala Val Leu Glu Ser Leu Arg Val Ile Ile Thr Asn Phe Pro
1               5                   10                  15

Ala Ala Lys

<210> SEQ ID NO 95
<211> LENGTH: 15
<212> TYPE: PRT
<213> ORGANISM: Homo sapiens

<400> SEQUENCE: 95

Ser Leu Asp Ile Gln Val Pro Asn Phe Pro Ala Asp Glu Thr Lys
1               5                   10                  15

<210> SEQ ID NO 96
<211> LENGTH: 34
<212> TYPE: PRT
<213> ORGANISM: Homo sapiens

<400> SEQUENCE: 96

Ala Met Ala Val Leu Glu Ser Leu Arg Val Ile Ile Thr Asn Phe Pro
1               5                   10                  15

Ala Ala Lys Ser Leu Asp Ile Gln Val Pro Asn Phe Pro Ala Asp Glu
            20                  25                  30

Thr Lys

<210> SEQ ID NO 97
<211> LENGTH: 36
<212> TYPE: PRT

<213> ORGANISM: Homo sapiens

<400> SEQUENCE: 97

Thr Asp Phe Lys Glu Glu Pro Glu Pro Gly Phe Lys Arg Leu Ala Trp
1               5                   10                  15

Gly Gln Pro Val Gly Leu Arg His Thr Gly Tyr Val Ile Glu Leu Gln
            20                  25                  30

His Val Val Lys
        35

<210> SEQ ID NO 98
<211> LENGTH: 15
<212> TYPE: PRT
<213> ORGANISM: Homo sapiens

<400> SEQUENCE: 98

Ala Phe Ile His Trp Val Ser Gln Pro Leu Met Cys Glu Val Arg
1               5                   10                  15

<210> SEQ ID NO 99
<211> LENGTH: 19
<212> TYPE: PRT
<213> ORGANISM: Homo sapiens

<400> SEQUENCE: 99

Leu Gly Tyr Phe Ser Val Asp Pro Asp Ser His Gln Gly Lys Leu Val
1               5                   10                  15

Phe Asn Arg

<210> SEQ ID NO 100
<211> LENGTH: 13
<212> TYPE: PRT
<213> ORGANISM: Homo sapiens

<400> SEQUENCE: 100

Lys Ala Thr Gly Ile Leu Leu Tyr Gly Leu Ala Ser Arg
1               5                   10

<210> SEQ ID NO 101
<211> LENGTH: 10
<212> TYPE: PRT
<213> ORGANISM: Homo sapiens

<400> SEQUENCE: 101

Ser Phe Leu Val Ser Tyr Ile Ala Ser Lys
1               5                   10

<210> SEQ ID NO 102
<211> LENGTH: 27
<212> TYPE: PRT
<213> ORGANISM: Homo sapiens

<400> SEQUENCE: 102

Asp Phe Glu Arg Glu Cys Gly Val Gly Val Ile Val Thr Pro Glu Gln
1               5                   10                  15

Ile Glu Glu Ala Val Glu Ala Ala Ile Asn Arg
            20                  25

<210> SEQ ID NO 103
<211> LENGTH: 28
<212> TYPE: PRT
<213> ORGANISM: Homo sapiens -continued

<400> SEQUENCE: 103

Glu Ala Ala Thr Gln Ala Gln Gln Thr Leu Gly Ser Thr Ile Asp Lys
1               5                   10                  15

Ala Thr Gly Ile Leu Leu Tyr Gly Leu Ala Ser Arg
            20                  25

<210> SEQ ID NO 104
<211> LENGTH: 86
<212> TYPE: PRT
<213> ORGANISM: Homo sapiens

<400> SEQUENCE: 104

Met Pro Thr Val Ser Val Lys Arg Asp Leu Leu Phe Gln Ala Leu Gly
1               5                   10                  15

Arg Thr Tyr Thr Asp Glu Glu Phe Asp Glu Leu Cys Phe Glu Phe Gly
            20                  25                  30

Leu Glu Leu Asp Glu Ile Lys Asp Leu Glu Leu Leu Cys Pro Arg Cys
        35                  40                  45

Ser Leu Ser Thr Asp His Gln His Arg Cys Val Trp Pro Ile Lys Lys
50                  55                  60

Ala Ala Ser Tyr Gln Glu Lys Thr Gly Ala Ile Gln Cys Thr Val Glu
65                  70                  75                  80

Gly Glu Ser Gly Thr Asn
                85

<210> SEQ ID NO 105
<211> LENGTH: 501
<212> TYPE: PRT
<213> ORGANISM: Homo sapiens

<400> SEQUENCE: 105

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu

```
                195                 200                 205
Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala Glu Asp Ser Asn Thr His Arg His Leu Thr Glu Phe Val Gly
                275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
                340                 345                 350

Ala Met Leu Arg Glu Ala Gly Val Glu Met Gly Asp Glu Asp Leu
                355                 360                 365

Ser Thr Pro Asn Glu Lys Leu Leu Gly His Leu Val Lys Glu Lys Tyr
370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 106
<211> LENGTH: 471
<212> TYPE: PRT
<213> ORGANISM: Homo sapiens

<400> SEQUENCE: 106

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
                20                  25                  30

Lys Asp Glu Ile Asp Ser Ala Val Lys Met Leu Val Ser Leu Lys Met
                35                  40                  45

Ser Tyr Lys Ala Ala Ala Gly Glu Asp Tyr Lys Ala Asp Cys Pro Pro
50                  55                  60
```

-continued

```
Gly Asn Pro Ala Pro Thr Ser Asn His Gly Pro Asp Ala Thr Glu Ala
 65                  70                  75                  80

Glu Glu Asp Phe Val Asp Pro Trp Thr Val Gln Thr Ser Ser Ala Lys
                 85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
    450                 455                 460

Lys Leu Ser Phe Asp Phe Gln
465                 470
```

-continued

```
<210> SEQ ID NO 107
<211> LENGTH: 424
<212> TYPE: PRT
<213> ORGANISM: Homo sapiens

<400> SEQUENCE: 107
```

| | | | | | | | | | | | | | | | |
|---|---|---|---|---|---|---|---|---|---|---|---|---|---|---|---|
| Met | Ser | Tyr | Lys | Ala | Ala | Gly | Glu | Asp | Tyr | Lys | Ala | Asp | Cys | Pro | |
| 1 | | | | 5 | | | | | 10 | | | | | 15 | |
| Pro | Gly | Asn | Pro | Ala | Pro | Thr | Ser | Asn | His | Gly | Pro | Asp | Ala | Thr | Glu |
| | | | 20 | | | | | 25 | | | | | 30 | | |
| Ala | Glu | Glu | Asp | Phe | Val | Asp | Pro | Trp | Thr | Val | Gln | Thr | Ser | Ser | Ala |
| | | | 35 | | | | | 40 | | | | | 45 | | |
| Lys | Gly | Ile | Asp | Tyr | Asp | Lys | Leu | Ile | Val | Arg | Phe | Gly | Ser | Ser | Lys |
| | 50 | | | | | 55 | | | | | 60 | | | | |
| Ile | Asp | Lys | Glu | Leu | Ile | Asn | Arg | Ile | Glu | Arg | Ala | Thr | Gly | Gln | Arg |
| 65 | | | | | 70 | | | | | 75 | | | | | 80 |
| Pro | His | His | Phe | Leu | Arg | Arg | Gly | Ile | Phe | Phe | Ser | His | Arg | Asp | Met |
| | | | | 85 | | | | | 90 | | | | | 95 | |
| Asn | Gln | Val | Leu | Asp | Ala | Tyr | Glu | Asn | Lys | Lys | Pro | Phe | Tyr | Leu | Tyr |
| | | | 100 | | | | | 105 | | | | | 110 | | |
| Thr | Gly | Arg | Gly | Pro | Ser | Ser | Glu | Ala | Met | His | Val | Gly | His | Leu | Ile |
| | | | 115 | | | | | 120 | | | | | 125 | | |
| Pro | Phe | Ile | Phe | Thr | Lys | Trp | Leu | Gln | Asp | Val | Phe | Asn | Val | Pro | Leu |
| | 130 | | | | | 135 | | | | | 140 | | | | |
| Val | Ile | Gln | Met | Thr | Asp | Asp | Glu | Lys | Tyr | Leu | Trp | Lys | Asp | Leu | Thr |
| 145 | | | | | 150 | | | | | 155 | | | | | 160 |
| Leu | Asp | Gln | Ala | Tyr | Ser | Tyr | Ala | Val | Glu | Asn | Ala | Lys | Asp | Ile | Ile |
| | | | | 165 | | | | | 170 | | | | | 175 | |
| Ala | Cys | Gly | Phe | Asp | Ile | Asn | Lys | Thr | Phe | Ile | Phe | Ser | Asp | Leu | Asp |
| | | | 180 | | | | | 185 | | | | | 190 | | |
| Tyr | Met | Gly | Met | Ser | Ser | Gly | Phe | Tyr | Lys | Asn | Val | Val | Lys | Ile | Gln |
| | | | 195 | | | | | 200 | | | | | 205 | | |
| Lys | His | Val | Thr | Phe | Asn | Gln | Val | Lys | Gly | Ile | Phe | Gly | Phe | Thr | Asp |
| | 210 | | | | | 215 | | | | | 220 | | | | |
| Ser | Asp | Cys | Ile | Gly | Lys | Ile | Ser | Phe | Pro | Ala | Ile | Gln | Ala | Ala | Pro |
| 225 | | | | | 230 | | | | | 235 | | | | | 240 |
| Ser | Phe | Ser | Asn | Ser | Phe | Pro | Gln | Ile | Phe | Arg | Asp | Arg | Thr | Asp | Ile |
| | | | | 245 | | | | | 250 | | | | | 255 | |
| Gln | Cys | Leu | Ile | Pro | Cys | Ala | Ile | Asp | Gln | Asp | Pro | Tyr | Phe | Arg | Met |
| | | | 260 | | | | | 265 | | | | | 270 | | |
| Thr | Arg | Asp | Val | Ala | Pro | Arg | Ile | Gly | Tyr | Pro | Lys | Pro | Ala | Leu | Leu |
| | | | 275 | | | | | 280 | | | | | 285 | | |
| His | Ser | Thr | Phe | Phe | Pro | Ala | Leu | Gln | Gly | Ala | Gln | Thr | Lys | Met | Ser |
| | 290 | | | | | 295 | | | | | 300 | | | | |
| Ala | Ser | Asp | Pro | Asn | Ser | Ser | Ile | Phe | Leu | Thr | Asp | Thr | Ala | Lys | Gln |
| 305 | | | | | 310 | | | | | 315 | | | | | 320 |
| Ile | Lys | Thr | Lys | Val | Asn | Lys | His | Ala | Phe | Ser | Gly | Gly | Arg | Asp | Thr |
| | | | | 325 | | | | | 330 | | | | | 335 | |
| Ile | Glu | Glu | His | Arg | Gln | Phe | Gly | Gly | Asn | Cys | Asp | Val | Asp | Val | Ser |
| | | | 340 | | | | | 345 | | | | | 350 | | |
| Phe | Met | Tyr | Leu | Thr | Phe | Phe | Leu | Glu | Asp | Asp | Lys | Leu | Glu | Gln | |
| | | | 355 | | | | | 360 | | | | | 365 | | |
| Ile | Arg | Lys | Asp | Tyr | Thr | Ser | Gly | Ala | Met | Leu | Thr | Gly | Glu | Leu | Lys |
| | 370 | | | | | 375 | | | | | 380 | | | | |

```
Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420

<210> SEQ ID NO 108
<211> LENGTH: 401
<212> TYPE: PRT
<213> ORGANISM: Homo sapiens

<400> SEQUENCE: 108

Ser Asn His Gly Pro Asp Ala Thr Glu Ala Glu Asp Phe Val Asp
1               5                   10                  15

Pro Trp Thr Val Gln Thr Ser Ser Ala Lys Gly Ile Asp Tyr Asp Lys
                20                  25                  30

Leu Ile Val Arg Phe Gly Ser Ser Lys Ile Asp Lys Glu Leu Ile Asn
                35                  40                  45

Arg Ile Glu Arg Ala Thr Gly Gln Arg Pro His His Phe Leu Arg Arg
50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

Glu Ala Met His Val Gly His Leu Ile Pro Phe Ile Phe Thr Lys Trp
                100                 105                 110

Leu Gln Asp Val Phe Asn Val Pro Leu Val Ile Gln Met Thr Asp Asp
            115                 120                 125

Glu Lys Tyr Leu Trp Lys Asp Leu Thr Leu Asp Gln Ala Tyr Ser Tyr
    130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
                180                 185                 190

Val Lys Gly Ile Phe Gly Phe Thr Asp Ser Asp Cys Ile Gly Lys Ile
            195                 200                 205

Ser Phe Pro Ala Ile Gln Ala Ala Pro Ser Phe Ser Asn Ser Phe Pro
    210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
                260                 265                 270

Leu Gln Gly Ala Gln Thr Lys Met Ser Ala Ser Asp Pro Asn Ser Ser
            275                 280                 285

Ile Phe Leu Thr Asp Thr Ala Lys Gln Ile Lys Thr Lys Val Asn Lys
    290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335
```

-continued

```
Leu Glu Asp Asp Asp Lys Leu Glu Gln Ile Arg Lys Asp Tyr Thr Ser
            340                 345                 350

Gly Ala Met Leu Thr Gly Glu Leu Lys Lys Ala Leu Ile Glu Val Leu
        355                 360                 365

Gln Pro Leu Ile Ala Glu His Gln Ala Arg Arg Lys Glu Val Thr Asp
    370                 375                 380

Glu Ile Val Lys Glu Phe Met Thr Pro Arg Lys Leu Ser Phe Asp Phe
385                 390                 395                 400

Gln
```